US008895761B2

(12) United States Patent
Muehlebach et al.

(10) Patent No.: US 8,895,761 B2
(45) Date of Patent: *Nov. 25, 2014

(54) 4-PHENYLPYRANE-3,5-DIONES, 4-PHENYLTHIOPYRANE-3,5-DIONES AND 2-PHENYLCYCLOHEXANE-1,3,5-TRIONES AS HERBICIDES

(75) Inventors: Michel Muehlebach, Stein (CH); Christopher John Mathews, Bracknell (GB); James Nicholas Scutt, Bracknell (GB); Stephane Andre Marie Jeanmart, Bracknell (GB); Mangala Govenkar, Goa (IN)

(73) Assignees: Syngenta Limited, Guildford, Surrey (GB); Syngenta Crop Protection, LLC, Greensboro, NC (US)

( * ) Notice: Subject to any disclaimer, the term of this patent is extended or adjusted under 35 U.S.C. 154(b) by 93 days.

This patent is subject to a terminal disclaimer.

(21) Appl. No.: 12/747,395

(22) PCT Filed: Dec. 11, 2008

(86) PCT No.: PCT/EP2008/010513
§ 371 (c)(1),
(2), (4) Date: Jun. 10, 2010

(87) PCT Pub. No.: WO2009/074314
PCT Pub. Date: Jun. 18, 2009

(65) Prior Publication Data
US 2010/0279872 A1 Nov. 4, 2010

(30) Foreign Application Priority Data
Dec. 13, 2007 (IN) .................. 2616/DEL/2007

(51) Int. Cl.
| C07D 307/62 | (2006.01) |
| C07D 335/02 | (2006.01) |
| C07D 303/00 | (2006.01) |
| C07D 409/14 | (2006.01) |
| C07C 49/747 | (2006.01) |
| C07D 409/10 | (2006.01) |
| C07D 309/28 | (2006.01) |
| C07D 493/10 | (2006.01) |
| C07D 405/10 | (2006.01) |

(52) U.S. Cl.
CPC ............ *C07D 493/10* (2013.01); *C07D 409/14* (2013.01); *C07C 49/747* (2013.01); *C07D 409/10* (2013.01); *C07D 309/28* (2013.01); *C07D 335/02* (2013.01); *C07D 405/10* (2013.01)
USPC .............. 549/317; 549/28; 549/332

(58) Field of Classification Search
USPC .......................... 549/317, 28, 332
See application file for complete search history.

(56) References Cited

U.S. PATENT DOCUMENTS

| 4,175,135 A | 11/1979 | Haines |
| 4,209,532 A | 6/1980 | Wheeler |
| 4,409,153 A | 10/1983 | Hodakowski |
| 4,489,012 A | 12/1984 | Hodakowski |
| 4,526,723 A | 7/1985 | Wheeler et al. |
| 4,659,372 A | 4/1987 | Wheeler et al. |
| 5,801,120 A | 9/1998 | Lee et al. |
| 6,458,965 B1 | 10/2002 | Lieb et al. |
| 6,894,005 B1 | 5/2005 | Maetzke et al. |
| 8,058,210 B2 | 11/2011 | Lieb et al. |
| 8,084,649 B2 | 12/2011 | Muehlebach et al. |
| 8,680,299 B2 * | 3/2014 | Scutt .......................... 549/332 |
| 2003/0176464 A1 | 9/2003 | Fischer et al. |
| 2003/0216260 A1 | 11/2003 | Ruther et al. |
| 2004/0102516 A1 | 5/2004 | Fischer et al. |
| 2005/0164883 A1 | 7/2005 | Maetzke et al. |
| 2006/0166829 A1 | 7/2006 | Fischer et al. |
| 2010/0113270 A1 | 5/2010 | Mathews et al. |
| 2010/0210466 A1 | 8/2010 | Muehlebach et al. |
| 2011/0152095 A1 | 6/2011 | Scutt et al. |
| 2012/0040826 A1 | 2/2012 | Jeanmart et al. |

FOREIGN PATENT DOCUMENTS

| CA | 2322158 | 8/2000 |
| CA | 2325526 | 9/2000 |
| CA | 2382432 | 2/2002 |
| CA | 2382435 | 2/2002 |
| CA | 2456776 | 2/2004 |
| DE | 2813341 | 4/1983 |
| EP | 1481970 | 12/2004 |
| WO | 9943649 | 9/1999 |
| WO | 9947525 | 9/1999 |
| WO | 9948869 | 9/1999 |
| WO | 0037437 | 6/2000 |
| WO | 0117972 A2 | 3/2001 |
| WO | 0117972 A3 | 3/2001 |
| WO | 0117973 A2 | 3/2001 |
| WO | 0117973 A3 | 3/2001 |
| WO | 2001017972 | 3/2001 |
| WO | 0174770 | 10/2001 |
| WO | 03013249 | 2/2003 |

(Continued)

OTHER PUBLICATIONS

Dorwald F. A. Side Reactions in Organic Synthesis, 2005, Wiley: VCH, Weinheim p. IX of Preface p. 1-15.*

Office Action dated Jul. 14, 2011 mailed in U.S. Appl. No. 12/519015; relating to Syngenta docket No. 71369; [Preliminary_STN_12519015_07052011 (2011)].

Muehlebach, M., et al., "Discovery and SAR of pinoxaden: a new broad spectrum, postemergence cereal herbicide," in Pesticide Chemistry, Crop Protection, Public Health, Environmental Safety, ed. H. Ohkawa et al., Jun. 2007, pp. 101-110.

(Continued)

*Primary Examiner* — Nizal Chandrakumar
(74) *Attorney, Agent, or Firm* — R. Kody Jones

(57) ABSTRACT

Pyrandione, thiopyrandione and cyclohexanetrione compounds, which are suitable for use as herbicides.

24 Claims, No Drawings

(56) References Cited

FOREIGN PATENT DOCUMENTS

| | | |
|---|---|---|
| WO | 03048138 | 6/2003 |
| WO | 2004111042 | 12/2004 |
| WO | 2005123667 | 12/2005 |
| WO | 2006034315 | 3/2006 |
| WO | 2006034446 | 3/2006 |
| WO | 2008071405 | 6/2008 |
| WO | WO 2008071405 * 6/2008 ........... C07D 49/403 | |
| WO | 2008110307 | 9/2008 |
| WO | 2008110308 | 9/2008 |

OTHER PUBLICATIONS

Wenger, J., and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

Wenger, et al.: "Chapter 11: Acetyl-CoA Carboxylase Inhibitors", in Modern Crop Protection Compounds, Second Edition, Jan. 2012, pp. 447-477.

* cited by examiner

4-PHENYLPYRANE-3,5-DIONES, 4-PHENYLTHIOPYRANE-3,5-DIONES AND 2-PHENYLCYCLOHEXANE-1,3,5-TRIONES AS HERBICIDES

This application is a 371 of International Application No. PCT/EP2008/010513 filed Dec. 11, 2008, which claims priority to IN 2616/Del/2007 filed Dec. 13, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 01/74770.

Novel pyrandione, thiopyrandione and cyclohexanetrione compounds having herbicidal and growth-inhibiting properties have now been found.

The present invention accordingly relates to compounds of formula I

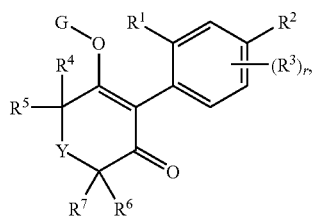

wherein
$R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_1$haloalkoxy, $C_1$-$C_4$alkylthio, $C_1$-$C_4$alkylsulfinyl, $C_1$-$C_4$alkylsulfonyl, nitro or cyano;
$R^2$ is optionally substituted aryl or optionally substituted heteroaryl;
r is 0, 1, 2 or 3;
$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylsulfinyl, $C_1$-$C_6$alkylsulfonyl, cyano or nitro; or the substituents
$R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;
$R^4$, $R^5$, $R^6$ and $R^7$, independently of each other, are hydrogen, $C_1$-$C_4$alkyl, $C_1$-$C_4$haloalkyl, $C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or
$R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or
$R^4$ and $R^7$ are joined to form a 4-8 membered saturated or unsaturated ring unsubstituted or substituted by $C_1$-$C_2$alkyl, $C_1$-$C_2$alkoxy, $C_1$-$C_2$alkoxy$C_1$-$C_2$alkyl, hydroxy, halogen, phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl;
Y is O, C=O, $S(O)_m$ or $S(O)_nNR^8$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;
m is 0 or 1 or 2 and n is 0 or 1;
$R^8$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by $R^9$; benzylcarbonyl or benzylcarbonyl substituted by $R^9$; pyridylcarbonyl or pyridylcarbonyl substituted by $R^9$; phenoxycarbonyl or phenoxycarbonyl substituted by $R^9$; benzyloxycarbonyl or benzyloxycarbonyl substituted by $R^9$;
$R^9$ is $C_1$-$C_6$haloalkyl, $C_1$-$C_6$alkoxycarbonyl, nitro, cyano, formyl, carboxyl or halogen, and
G is hydrogen, an agriculturally acceptable cation or a latentiating group.

In the substituent definitions of the compounds of the formula I, the alkyl substituents and alkyl moieties of alkoxy, alkylthio etc. having 1 to 6 carbon atoms are preferably methyl, ethyl, propyl, butyl, pentyl and hexyl, in the form of their straight and branched isomers. Higher alkyl groups of up to 10 carbon atoms comprise preferably octyl, nonyl and decyl, in form of their straight and branched isomers. The alkenyl and alkynyl radicals having 2 to 6 carbon atoms as well as up to 10 carbon atoms can be straight or branched and can contain more than 1 double or triple bond. Examples are vinyl, allyl, propargyl, butenyl, butynyl, pentenyl and pentynyl. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred halogens are fluorine, chlorine and bromine. Preferred examples of aryls are phenyl and naphthyl. Preferred examples of heteroaryls are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl and pyridazinyl, and, where appropriate, N-oxides and salts thereof. These aryls and heteroaryls can be substituted by one or more substituents, where preferred substituents are halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_1$haloalkylsulfonyl, nitro or cyano. The group G denotes hydrogen, an agriculturally acceptable cation (such as an alkali metal cation, alkaline earth metal cation, sulfonium cation (preferably tri($C_1$-$C_6$) alkylsulfonium cation, ammonium cation, $C_1$-$C_6$alkylammonium cation, di($C_1$-$C_6$alkyl)ammonium cation, tri($C_1$-$C_6$alkyl)ammonium cation or tetra($C_1$-$C_6$) alkylammonium cation), or a latentiating group. These latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^c$)—$R^d$, —$SO_2$—$R^e$, —P($X^e$)($R^f$)—$R^9$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_5$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, amino, $C_1$-$C_3$alkylamino, di($C_1$-$C_3$alkyl)amino, $C_1$-$C_3$alkoxy or $C_3$-$C_7$cycloalkylamino, di($C_3$-$C_7$cycloalkyl)amino or $C_3$-$C_7$cycloalkoxy or $R^c$ and $R^d$ may join together to form a 3-7 membered ring, optionally containing one heteroatom selected from O or S and optionally substituted by 1 or 2 $C_1$-$C_3$alkyl groups.

$R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_5$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, nitro, amino, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di($C_3$-$C_7$cycloalkyl)amino or $C_3$-$C_7$cycloalkoxy, $C_1$-$C_{10}$alkoxy, $C_1$-$C_{10}$haloalkoxy, $C_1$-$C_5$alkylamino or di($C_2$-$C_8$alkyl)amino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, tri($C_3$-$C_5$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, amino, hydroxyl, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di($C_3$-$C_7$cycloalkyl)amino or $C_3$-$C_7$cycloalkoxy, $C_1$-$C_{10}$haloalkoxy, $C_1$-$C_5$alkylamino or di($C_2$-$C_8$alkyl)amino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_8$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In a preferred group of compounds of the formula I, $R^1$ is halogen, $C_1$-$C_4$alkyl, $C_1$-$C_4$haloalkyl, $C_2$-$C_4$alkenyl or $C_2$-$C_4$ alkynyl.

In another preferred group of compounds of the formula I, $R^2$ is aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_1$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_{1-6}$alkyl)aminocarbonylamino, formyl, $C_1$-$C_6$alkylcarbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino;

Preferably, $R^2$ in the compounds of formula I is aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

More preferably, $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl and thiadiazolyl, and N-oxides and salts thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In even more preferred compounds of the formula I, $R^2$ is phenyl or pyridyl or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

In an especially preferred group of compounds, $R^2$ is phenyl substituted at the para-position by halogen (in particular chlorine or fluorine) and is optionally further substituted by halogen, nitro, $C_1$-$C_2$alkyl, $C_1$-$C_2$haloalkyl, $C_1$-$C_2$alkoxy or $C_1$-$C_2$haloalkoxy.

Preferably, $R^3$ is hydrogen (r is 0), halogen or $C_1$-$C_6$alkyl, especially hydrogen.

Preferably, $R^3$, if r is 1, is halogen or $C_1$-$C_3$alkyl.

Preferred are those compounds of the formula I, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

More preferably, $R^4$, $R^5$, $R^6$ and $R^7$, independently of each other, are hydrogen, $C_1$-$C_2$alkyl, $C_1$-$C_2$haloalkyl or $C_1$-$C_2$alkoxy$C_1$-$C_2$alkyl.

It is also preferred that $R^4$ and $R^7$ are joined to form a 4-8 membered saturated or unsaturated ring which is unsubstituted or substituted by $C_1$-$C_2$alkyl, $C_1$-$C_2$alkoxy or $C_1$-$C_2$alkoxy$C_1$-$C_2$alkyl, while $R^5$ and $R^6$ independently of each other are hydrogen or $C_1$-$C_2$alkyl.

Preferred meanings of Y are O, C=O and S.

Y is O is especially preferred.

Preferably, G denotes $C(X^a)$—$R^a$ or $C(X^b)$—$X^c$—$R^b$, and the meanings of $X^a$, $R^a$, $X^b$, $X^c$ and $R^b$ are as defined above. Even more preferably, the latentiating group G is selected from the groups $C(X^a)$—$R^a$, $C(X^b)$—$X^c$—$R^b$, wherein $X^a$, $X^b$ and $X^c$ are oxygen, $R^a$ is $C_1$-$C_6$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl and $R^b$ is $C_1$-$C_6$alkyl, $C_3$-$C_6$alkenyl, $C_3$-$C_6$alkynyl, $C_3$-$C_6$cycloalkyl or $C_1$-$C_4$alkoxy$C_1$-$C_4$alkyl.

More important groups G comprise hydrogen, an alkali metal or alkaline earth metal cation as an agriculturally acceptable cation, where hydrogen is particularly preferred.

In a preferred group of compounds of the formula (I), $R^1$ is $C_1$-$C_4$alkyl, $R^2$ is phenyl or phenyl substituted by halogen or $C_1$-$C_2$alkyl, $R^3$ is hydrogen, $R^4$, $R^5$, $R^6$ and $R^7$, independently of each other, are $C_1$-$C_2$alkyl, Y is O and G is hydrogen, or $R^1$ is $C_1$-$C_4$alkyl, $R^2$ is phenyl or phenyl substituted by halogen or $C_1$-$C_2$alkyl, $R^3$ is hydrogen, $R^5$ and $R^6$, independently of each other, are hydrogen or $C_1$-$C_2$alkyl, $R^4$ and $R^7$ are joined to form a 4-8 membered saturated or unsaturated ring which is unsubstituted or substituted by $C_1$-$C_2$alkyl, $C_1$-$C_2$alkoxy or $C_1$-$C_2$alkoxy$C_1$-$C_2$alkyl, Y is O and G is hydrogen.

In another preferred group of compounds of the formula (I), $R^1$ is $C_1$-$C_2$alkyl, $R^2$ is phenyl substituted by halogen, $C_1$-$C_2$alkoxy or $C_1$-$C_2$haloalkyl, $R^3$ is $C_1$-$C_2$alkyl, r is 1, $R^4$, $R^5$, $R^6$ and $R^7$, independently of each other, are hydrogen, $C_1$-$C_2$alkyl, $C_1$-$C_4$haloalkyl or $C_1$-$C_2$alkoxy$C_1$-$C_2$alkyl, or $R^4$ and $R^7$ are joined to form an ethylene group, Y is O and G is hydrogen, or $R^1$ is $C_1$-$C_4$alkyl, $R^2$ is phenyl or phenyl substituted by halogen or $C_1$-$C_2$alkyl, $R^3$ is $C_1$-$C_2$alkyl, $R^5$ and $R^6$, independently of each other, are hydrogen or $C_1$-$C_2$alkyl, $R^4$ and $R^7$ are joined to form a 4-8 membered saturated or unsaturated ring which is unsubstituted or substituted by $C_1$-$C_2$alkyl, $C_1$-$C_2$alkoxy or $C_1$-$C_2$alkoxy$C_1$-$C_2$alkyl, Y is O and G is hydrogen.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms:

Also, when substituents contain double bonds, cis- and trans-isomers can exist. This invention covers all such isomers and tautomers and mixtures thereof in all proportions. These isomers, too, are within the scope of the claimed compounds of the formula I.

A compound of formula (I) wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$,

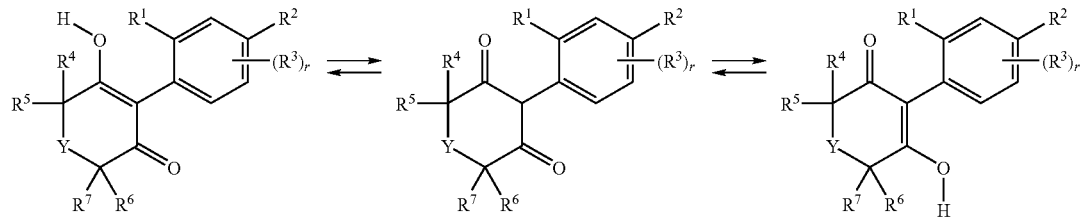

Furthermore, when Y is C=O and $R^4$ is hydrogen, further compounds of formula I may exist in different tautomeric forms:

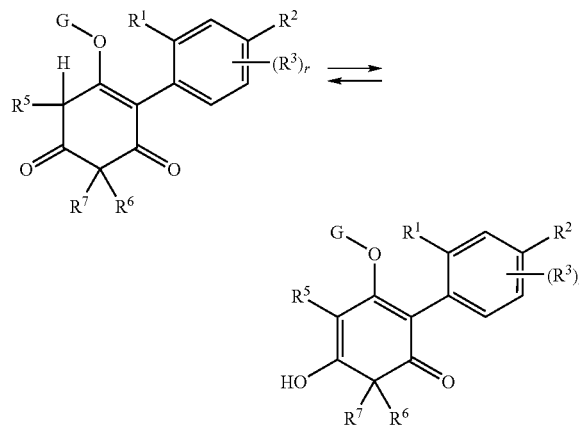

wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base. Where substituents $R^4$ and $R^5$ are not equal to substituents $R^6$ and $R^7$, these reactions may produce, in addition to a compound of formula (I), a second compound of formula (IA). This invention covers both a compound of formula (I) and a compound of formula (IA), together with mixtures of these compounds in any ratio.

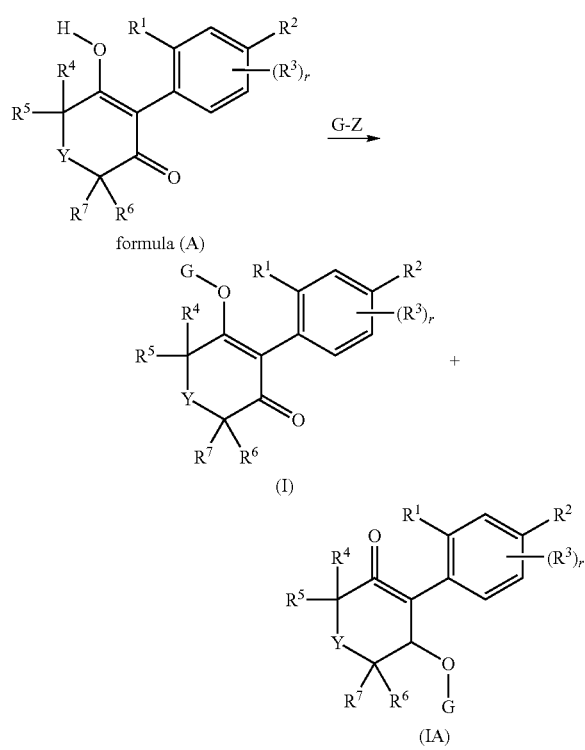

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo [5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is $S(O)_m$ and m is 1 or 2 may be prepared from compounds of formula (A) wherein Y is S by oxidation, according to a procedure analogous to that of E. Fehnel and A. Paul, J. Am. Chem. Soc., (1955), 77, 4241-4244.

A compound of formula (A), wherein Y is O, S or C=O may be prepared via the cyclisation of a compound of formula (B), preferably in the presence of an acid or base, and optionally in the presence of a suitable solvent, by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tent-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

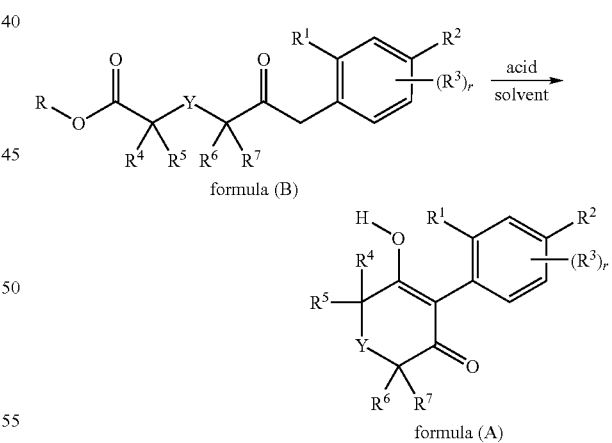

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl (preferably methyl) may be prepared from a compound of formula (C), wherein R is alkyl (preferably methyl), through a Krapcho decarboxylation procedure under known conditions using known reagents (see for example G. Quallich, P. Morrissey, Synthesis, (1993), (1), 51-53).

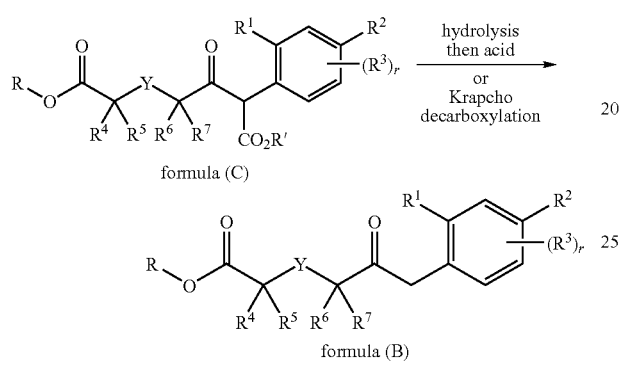

formula (C)

formula (B)

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature of between −80° C. and 30° C.:

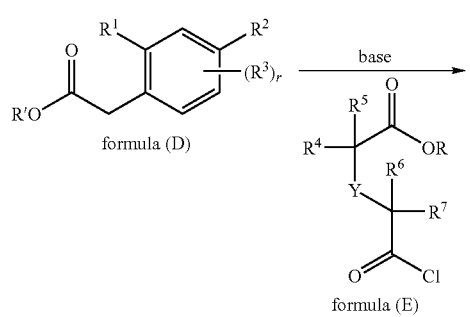

formula (D)

formula (E)

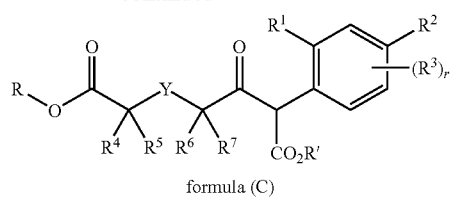

formula (C)

Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

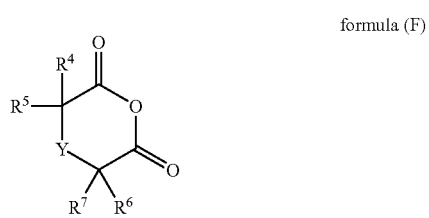

formula (F)

Compounds of formula (E) and formula (F) are known (see, for example T. Terasawa and T. Okada, J. Org. Chem., (1977), 42 (7), 1163-1169 and G. Bennett, W. Houlihan, R. Mason, and R. Engstrom, J. Med. Chem., (1976), 19 (5), 709-14) or may be made by similar methods from commercially available starting materials.

Using similar procedures to those outlined above, and starting from a halogenated phenylacetic acid ester of formula (G) (wherein Hal is chlorine, bromine or iodine), a compound of formula (H) may be prepared. In turn, this may be converted into a compound of formula (A) where $R^2$ is an aryl or heteroaryl, by reaction with a coupling partner such as an aryl or heteroaryl boronic acid, $R^2$—$B(OH)_2$, or a suitable salt or ester thereof, under palladium-catalysed conditions, preferably Suzuki-Miyaura conditions.

The compound of the formula H has been particularly designed as an intermediate for the synthesis of the compounds of the formula (I).

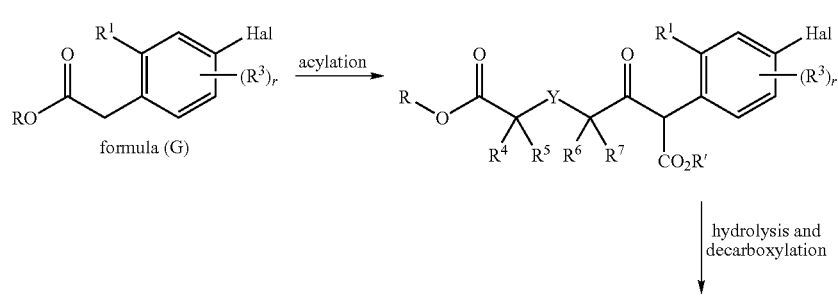

formula (G)

hydrolysis and decarboxylation

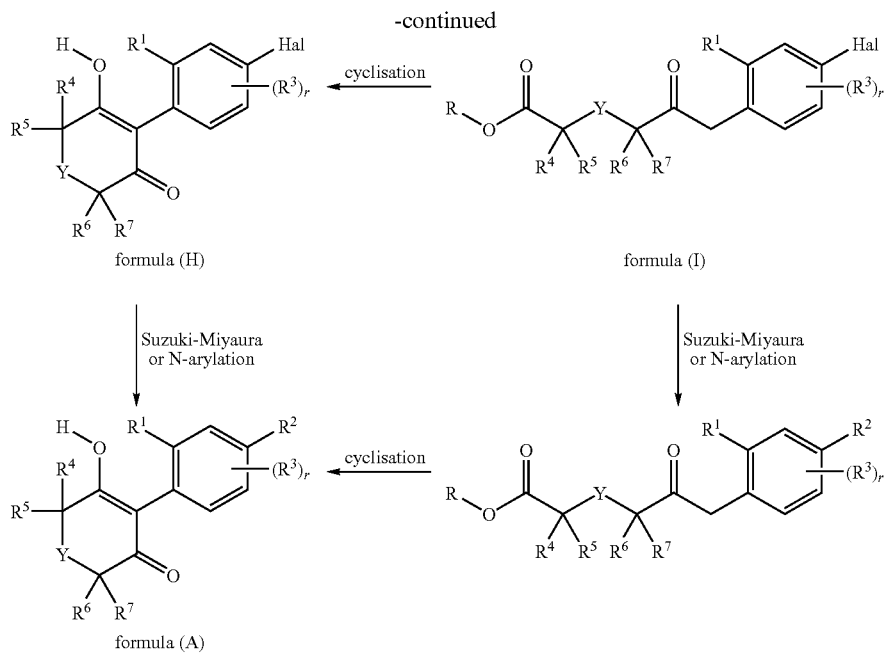

formula (A)

Conditions suitable for effecting the Suzuki-Miyaura cross-coupling of an aryl halide of formula (H) with an aryl- or heteroarylboronic acid of formula $R^2$—$B(OH)_2$, or a suitable salt or ester thereof, are known in the literature (see, for example K. Billingsley and S. Buchwald, J. Am. Chem. Soc., (2007), 129, 3358-3366; H. Stefani, R. Cella and A. Vieira, Tetrahedron, (2007), 63, 3623-3658; N. Kudo, M. Perseghini and G. Fu, Angew. Chem. Int. Ed., (2006), 45, 1282-1284; A. Roglans, A. Pla-Quintana and M. Moreno-Mañas, Chem. Rev., (2006), 106, 4622-4643; J-H Li, Q-M Zhu and Y-X Xie, Tetrahedron (2006), 10888-10895; S, Nolan et al., J. Org. Chem., (2006), 71, 685-692; M. Lysén and K. Köhler, Synthesis, (2006), 4, 692-698; K. Anderson and S. Buchwald, Angew. Chem. Int. Ed., (2005), 44, 6173-6177; Y. Wang and D. Sauer, Org. Lett., (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem., (2003), 68, 5534-5539; A. Suzuki, Journal of Organometallic Chemistry, (2002), 653, 83; G. Molander and C-S Yun, Tetrahedron, (2002), 58, 1465-1470; G. Zou, Y. K. Reddy and J. Falck, Tetrahedron Lett., (2001), 42, 4213-7215; S. Darses, G. Michaud and J-P. Genêt, Eur. J. Org. Chem., (1999), 1877-1883; M. Beavers et al., WO2005/012243; J. Org. Chem. (1994), 59, 6095-6097; A. Collier and G. Wagner, Synthetic Communications, (2006), 36; 3713-3721).

Alternatively, a compound of formula (A) may be prepared by a Suzuki-Miyaura cross-coupling of a compound of formula (I), wherein Hal is chlorine, bromine, iodine or a pseudohalogen such as $C_1$-$C_4$haloalkylsulfonate, especially triflate, with an aryl or heteroaryl boronic acid, of formula $R^2$—$B(OH)_2$, or a suitable salt or ester thereof, followed by cyclisation under conditions previously described for a compound of formula (B).

In a further approach, a compound of formula (A) wherein $R^2$ is an azine N-oxide such as a pyridine N-oxide, a pyrimidine N-oxide, pyridazine N-oxide or pyrazine N-oxide, may be prepared from a compound of formula (H) by reaction with a suitable azine-N-oxide under conditions described by L. Campeau, S. Rousseaux and K. Fagnou, J. Am. Chem. Soc., (2005), 127, 18020 and by J-P. Leclerc and K. Fagnou, Angew. Chem. Int. Ed., (2006), 45, 7781-7786. The resulting N-oxide may be treated with known reagents under known conditions (for example reduction with hydrogen or ammonium formate in the presence of a suitable catalyst) to afford additional compounds of formula (I).

Additional compounds of formula (A), wherein $R^2$ is a heteroaromatic ring linked to the phenyl ring through a nitrogen atom, may be obtained by an Ullmann-type coupling (this reaction is also known in the literature as an N-arylation) of a compound of formula (H), or a compound of formula (I), with an N—H containing heteroaromatic compound, $R^2$—H, in the presence of a suitable catalyst, a suitable ligand, a suitable base and in a suitable solvent as described by, for example, M. Taillefer, N. Xia and A. Ouali, Angew. Chem. Int. Ed., (2007), 46 (6), 934-936; H. Zhang, Q. Cai, D. Ma, J. Org. Chem., (2005), 70, 5164-5173; J. Antilla, J. Baskin, T. Barder and S. Buchwald, J. Org. Chem., (2004), 69, 5578-5587 and A. Thomas and S. Ley, Angew. Chem. Int. Ed., 2003, 42, 5400-5449 and references therein.

In a further approach, a compound of formula (A) wherein Y is O, S or C═O, may be prepared by reaction of a compound of formula (J) with an aryllead tricarboxylate, in the presence of a suitable ligand and in a suitable solvent. Similar reactions are described in the literature (for example see, J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (K). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

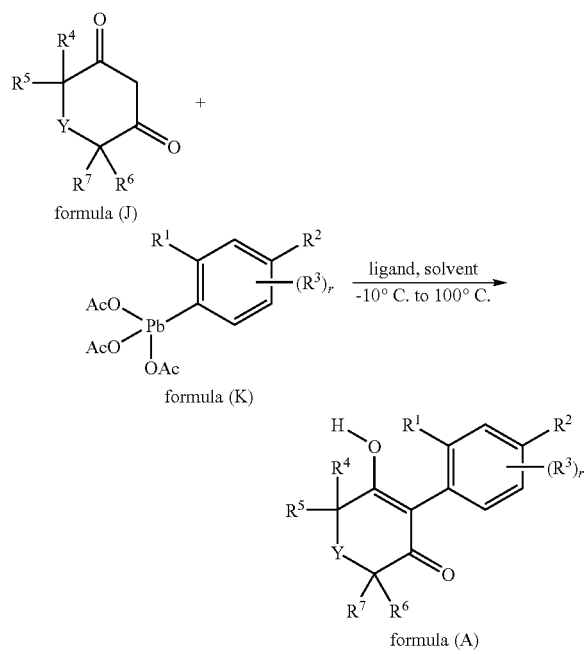

formula (J)

formula (K)

formula (A)

Compounds of formula (J), wherein Y is O, are known compounds or may be prepared by routes analogous to those described in the literature (see, for example, M. Morgan and E. Heyningen, J. Am. Chem. Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem., (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854). Compounds of formula (J), wherein Y is S, are known compounds or may be prepared by routes analogous to those described in the literature (see, for example, E. Fehnel and A. Paul, J. Am. Chem. Soc., (1955), 77, 4241-4244; E. Er and P. Margaretha, Helvetica Chimica Acta (1992), 75(7), 2265-69; H. Gayer et al., DE 3318648 A1). Compounds of formula (J), wherein Y is C═O, are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et at., Chem. Ber., (1986), 119, 3394-3404 and references therein).

A compound of formula (K) may be prepared from a compound of formula (L) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

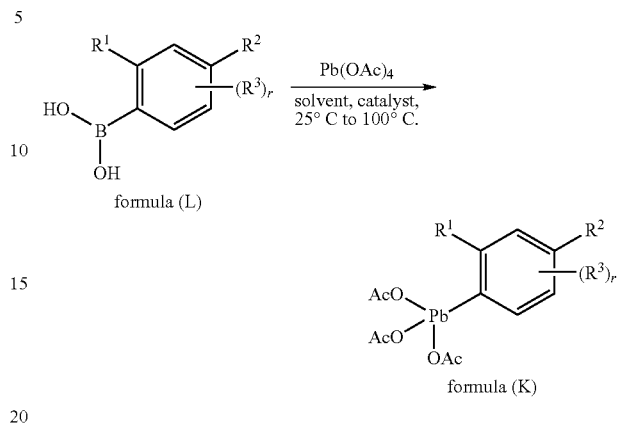

formula (L)

formula (K)

An aryl boronic acid of formula (L) may be prepared from an aryl halide of formula (M), wherein Hal is bromine or iodine by known methods (see, for example, W. Thompson and J. Gaudino, J. Org. Chem., (1984), 49, 5237-5243 and R. Hawkins et al., J. Am. Chem. Soc., (1960), 82, 3053-3059). Thus an aryl halide of formula (M) may be treated with an alkyl lithium or alkyl magnesium halide at low temperature, and the aryl magnesium or aryl lithium reagent obtained is allowed to react with a trialkyl borate, $B(OR'')_3$, preferably trimethylborate, to give an aryl dialkylboronate which may be hydrolysed to the desired boronic acid of formula (L) under acidic conditions. Alternatively the same overall transformation of compound (M) to compound (L) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

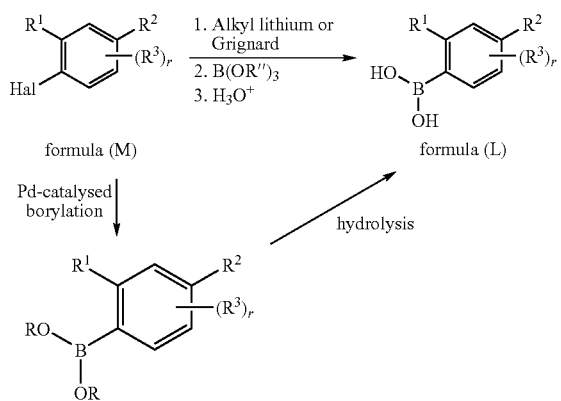

formula (M)

formula (L)

Aryl halides of formula (M) are known compounds or may be made by known methods from known compounds. For example, an aryl halide of formula (M) may be prepared from an aniline of formula (N) by known methods, for example the Sandmeyer reaction, via the corresponding diazonium salt (see, for example, J. March, Advanced Organic Chemistry, 3rd Edition, John Wiley and Sons, pages 647-648 and references therein. For additional examples see also W. Denney et al., J. Med. Chem., (1991), 34, 217-222; P. Knochel et al., Synthesis, (2007), No. 1, 81-84). Additionally, a compound of formula (N) may be converted directly to a compound of formula (L) via a palladium-catalysed borylation of an intermediate aryl diazonium salt under known conditions using known reagents (see for example D. M. Willis, R. M. Strongin, Tetrahedron Lett. (2000), 41, 8683-8686), followed by hydrolysis of the intermediate boronate ester.

can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected sol-

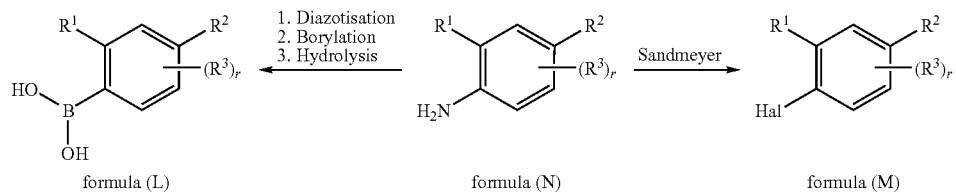

Anilines of formula (N) are known compounds, or may be made from known compounds by known methods. For example, an aniline of formula (N) may be prepared from an nitrobenzene of formula (O) (wherein Hal is chlorine, bromine, iodine, or a pseudohalogen such as $C_1$-$C_4$haloalkysulfonate, especially triflate) by reaction with an aryl- or heteroaryl-boronic acid, $R^2$—$B(OH)_2$, or a suitable salt or ester thereof, under Suzuki-Miyaura conditions, or with an N—H containing heteroaromatic ring, $R^2$—H, under N-arylation conditions, followed by reduction of the nitro group by standard methods. Alternatively, a compound of formula (O) may first be reduced to an aniline, and the aniline cross-coupled under Suzuki-Miyaura conditions (see, for example A. Maj, L. Delaude, A. Demonceau and A. Noels, Tetrahedron, (2007), 63, 2657-2663; F. Bellina, A. Carpita and R. Rossi, Synthesis (2004), 15, 2419-2440 and A. Suzuki, Journal of Organometallic Chemistry, (2002), 653, 83-90)

vent, with a compound of formula (P), a compound of formula (L) and a base. Also suitable are bidendate ligands, for example 1, 1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (P). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

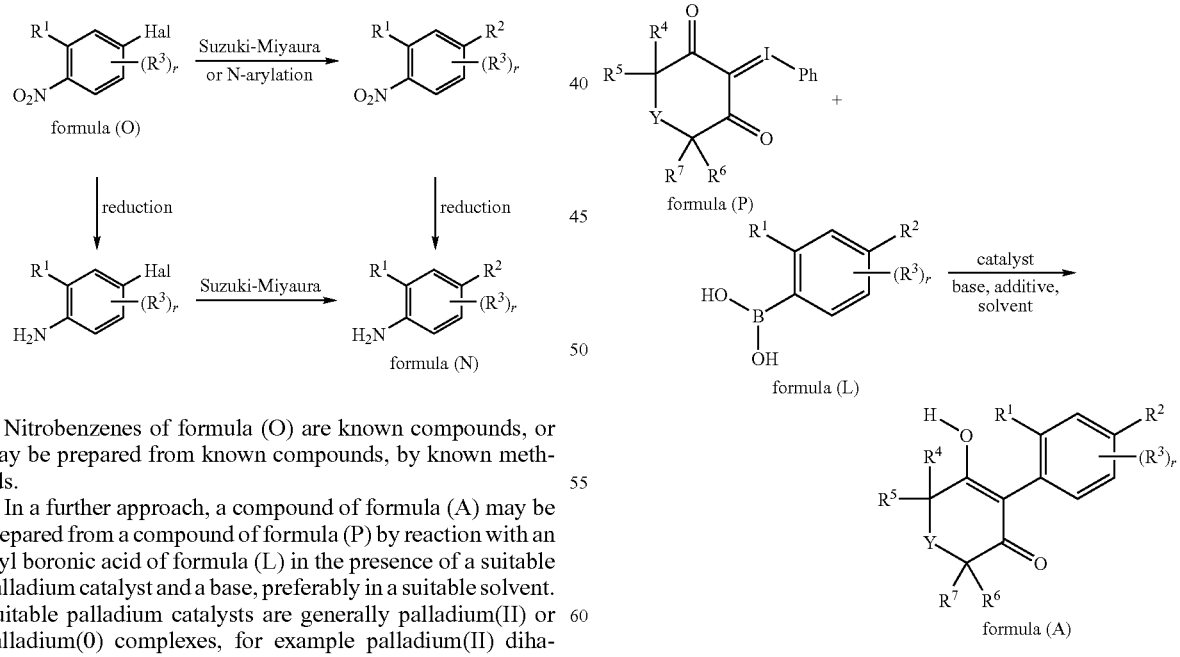

Nitrobenzenes of formula (O) are known compounds, or may be prepared from known compounds, by known methods.

In a further approach, a compound of formula (A) may be prepared from a compound of formula (P) by reaction with an aryl boronic acid of formula (L) in the presence of a suitable palladium catalyst and a base, preferably in a suitable solvent. Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)-palladium(0). The palladium catalyst A compound of formula (P) may be prepared from a compound of formula (J) by treatment with (diacetoxy)iodobenzene according to the procedures of K. Schank and C. Lick, Synthesis, (1983), 392-395, or of Z Yang et al., Org. Lett., (2002), 4 (19), 3333-3336:

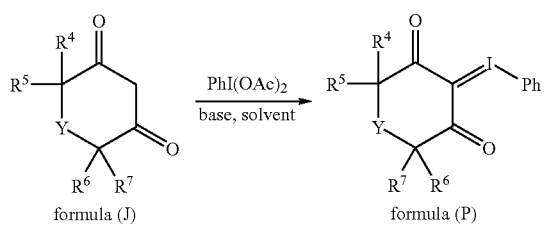

In a further approach a compound of formula (A) may be prepared via the rearrangement of a compound of formula (Q), in the presence of a reagent which promotes rearrangement, such as a metal alkoxide (preferably in an amount equal to or greater than 100% with respect to compound of formula (Q)) or cyanide anion (for example 0.001-25% potassium cyanide, 0.001-25% sodium cyanide), or a cyanohydrin (preferably 0.001-25% acetone cyanohydrin with respect to a compound of formula (Q)). This reaction is optionally performed in a suitable solvent (for example acetonitrile) at a suitable temperature (typically 25-100° C.) and with a suitable base (such as triethylamine).

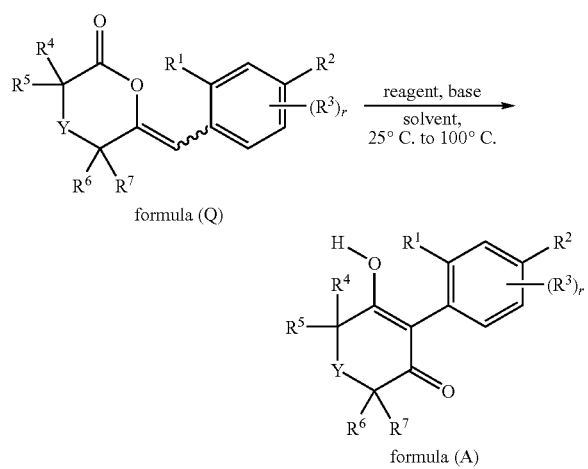

A compound of formula (Q) may be prepared from a compound of formula (R) by treatment with a catalyst which promotes lactonisation (such as palladium(II) dichloride, gold(I) chloride or silver carbonate), preferably 0.001-50% silver carbonate with respect to compound of formula (R), in the presence of a suitable solvent (for example acetonitrile) at a suitable temperature (typically 25° C. to 150° C.), and optionally under microwave irradiation. Similar lactonisations are known in the literature (see for example P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

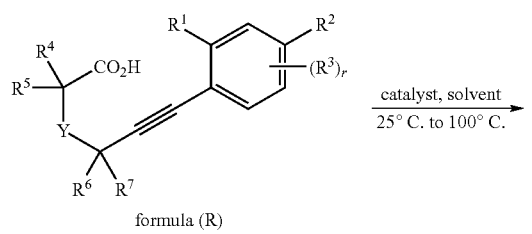

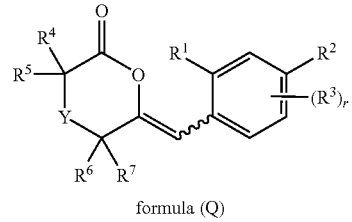

A compound of formula (R) may be prepared by the hydrolysis of a compound of formula (S) where R' is alkyl (preferably methyl or ethyl), and a compound of formula (S) may be prepared from a compound of formula (T) by Sonogashira coupling with a compound of formula (M) in the presence of a suitable palladium catalyst (for example bis(triphenylphosphine)palladium(II) dichloride, tetrakis(triphenylphosphine)palladium(0) or palladium acetate in the presence of a suitable ligand), in an amount typically 0.001-25% of compound of formula (T), optionally in the presence of a suitable copper co-catalyst (for example copper(I) iodide in an amount typically 0.001-50% of compound of formula (T), a suitable base (such as diethylamine, triethylamine, piperidine or pyrrolidine) which may also be used as the solvent, or optionally in an alternative solvent such as 1,4-dioxane, N,N-dimethylacetamide or N,N-dimethylformamide, and optionally under microwave irradiation. Similar Sonogashira couplings are known in the literature (see for example see, J. Vara Prasad, F. Boyer, L. Chupak, M. Dermyer, Q. Ding, K. Gavardinas, S. Hagen, M. Huband, W. Jiao, T. Kaneko, S, N. Maiti, M. Melnick, K. Romero, M. Patterson, X. Wu, Bioorganic and Medicinal Chemistry Letters (2006), 16(20), 5392-5397, N. Leadbeater and B. Tominack, Tetrahedron Lett., (2003), 8653-8656, Z. Gan and R. Roy, Canadian Journal of Chemistry (2002), 80 (8), 908-916 and K. Sonogashira, J. Organomet. Chem., (2002), 653, 46-49 and references therein).

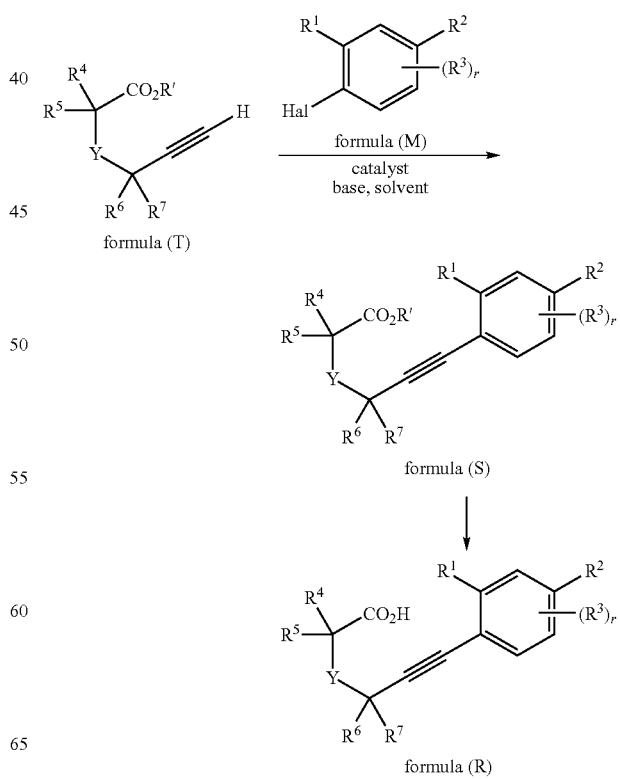

Compounds of formula (T) are known compounds or may be prepared by routes analogous to those described in the literature (see, for example, I. Drizin et al, WO2001/066544; M. Yamamoto, Journal of Chemical Research, Synopses (1991), (7), 165; P. Machin, U.S. Pat. No. 4,774,253; M. Morgan and E. Heyningen, J. Am. Chem. Soc., (1957), 79, 422-424; N. Petiniot, A. J. Anciaux, A. F. Noels, A. J. Hubert, P. Teyssie, Tetrahedron letters, 1978, 14, 1239-42, and A. F. Noels, A. Demonceau, N. Petiniot, A. J. Hubert, P. Teyssie, Tetrahedron (1982), 38(17), 2733-9).

In a further approach, a compound of formula (A) may be prepared from a compound of formula (I) or (1A) (wherein G is $C_{1-4}$ alkyl) by hydrolysis, preferably in the presence of an acid catalyst such as hydrochloric acid and optionally in the presence of a suitable solvent such as tetrahydrofuran. A compound of formula (I) or (1A) (wherein G is preferably $C_{1-4}$ alkyl) may be prepared by reacting a compound of formula (U) (wherein G is preferably $C_{1-4}$ alkyl, and Hal is a halogen, preferably bromine or iodine), with an aryl boronic acid of formula (L) in the presence of a suitable palladium catalyst (for example 0.001-50% palladium(II) acetate with respect to compound (U)) and a base (for example 1 to 10 equivalents potassium phosphate with respect to compound (U)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990).

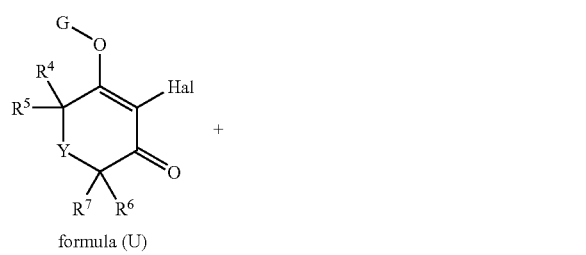

formula (U)

+

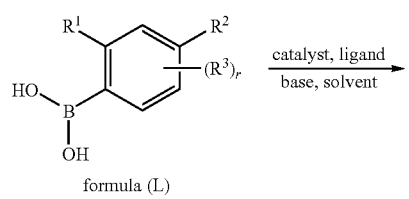

formula (L)

catalyst, ligand
base, solvent
→

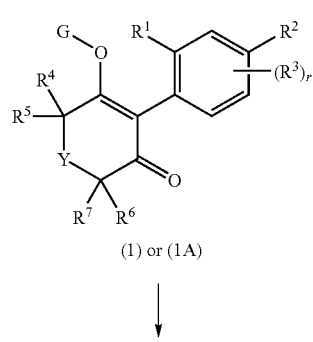

(1) or (1A)

↓

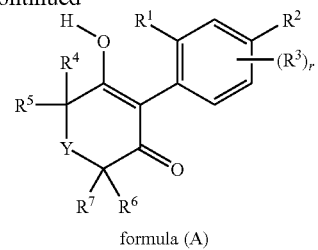

formula (A)

A compound of formula (U) may be prepared by halogenating a compound of formula (J), followed by alkylation of the resulting halide of formula (V) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (U) may be prepared by alkylating a compound of formula (J) with an alkylating agent such as $C_{1-4}$ alkyl halide or a tri-$C_{1-4}$-alkylorthoformate, and halogenating the resulting enone of formula (W) under known conditions (see for example Y. Song, B. Kim and J.-N. Heo, Tetrahedron Letters (2005), 46(36), 5987-5990).

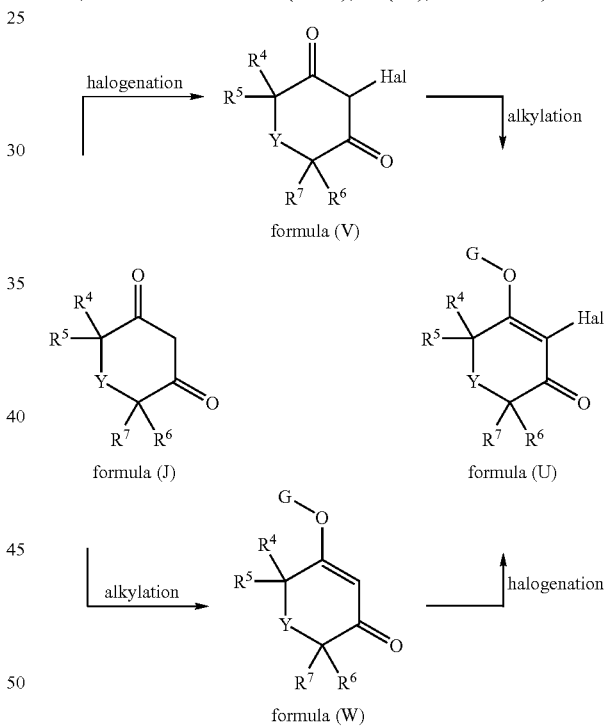

In a further approach, a compound of formula (A) may be prepared by reacting a compound of formula (J) with a compound of formula (M) in the presence of a suitable palladium catalyst (for example 0.001-50% palladium(II) acetate with respect to compound (J)) and a base (for example 1 to 10 equivalents potassium phosphate with respect to compound (J)) and preferably in the presence of a suitable ligand (for example 0.001-50% (2-dicyclohexylphosphino)-2',4',6'-triisopropylbiphenyl with respect to compound (J)), and in a suitable solvent (for example dioxane), preferably between 25° C. and 200° C. and optionally under microwave heating. Similar couplings are known in the literature (see for example, J. Fox, X. Huang, A. Chieffi, S. Buchwald, J. Am. Chem. Soc. (2000), 122, 1360-1370; B. Hong et al. WO 2005/000233). Alternatively, a compound of formula (A)

may be prepared by reacting a compound of formula (J) with a compound of formula (M) in the presence of a suitable copper catalyst (for example 0.001-50% copper(I) iodide with respect to compound (J)) and a base (for example 1 to 10 equivalents cesium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang, N. Wu, H. Wu, M. He, Synlett, (2005), 18, 2731-2734, X. Xie, G. Cai, D. Ma, Organic Letters (2005), 7(21), 4693-4695).

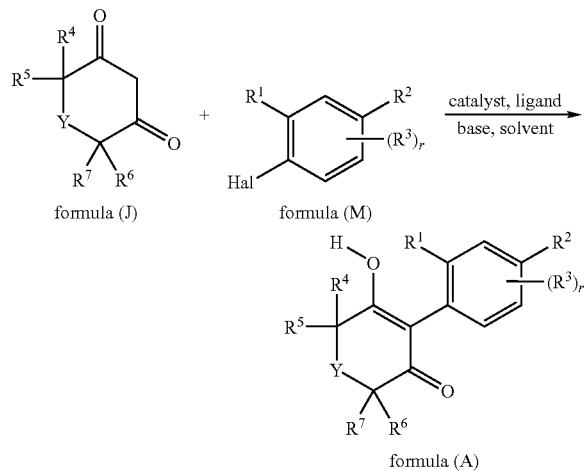

In a further approach, a compound of formula (A) may be prepared from a compound of formula (X) by cross coupling with an aryl- or heteroaryl-halide, $R^2$—Hal, where Hal is preferably chlorine, bromine, iodine or a pseudohalide such as $C_1$-$C_4$haloalkylsulfonate, especially triflate, under Suzuki-Miyaura conditions described previously, or with an N—H containing heteroaromatic compound, $R^2$—H, under copper-catalysed conditions as described, for example, by P. Lam et al., Tetrahedron Lett., (1998), 39 (19), 2941-2944, and P. Lam, G. Vincent, C. G. Clark, S. Deudon, P. K. Jadhav, Tetrahedron Lett., (2001), 42, 3415-3418). The compound of the formula X has been particularly designed as an intermediate for the synthesis of the compounds of the formula (I).

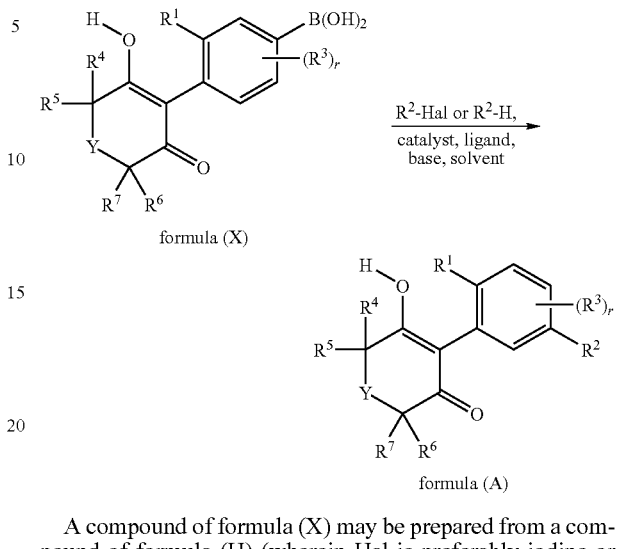

A compound of formula (X) may be prepared from a compound of formula (H) (wherein Hal is preferably iodine or bromine) by treatment with a suitable base (such as sodium hydride or potassium hydride), in a suitable solvent (such as tetrahydrofuran or diethyl ether) followed by a metal-halogen exchange reaction (preferably by treatment with an alkyllithium reagent such as n-butyllithium, sec-butyllithium or tert-butyllithium, or an organomagnesium reagent such as isopropyl magnesium chloride) and subsequent treatment with a trialkylborate, $B(OR'')_3$, (preferably trimethylborate) to give an arylboronate of formula (Y). A compound of formula (Y) may be hydrolysed under acidic conditions to give a boronic acid of formula (X). Alternatively a compound of formula (X) may be prepared from a compound of formula (H) (wherein Hal is preferably iodine, bromine, chlorine or a pseudohalide such as a $C_1$-$C_4$haloalkylsulfonate, especially triflate) under known palladium-catalysed borylation conditions similar to those referenced for the preparation of compound (L).

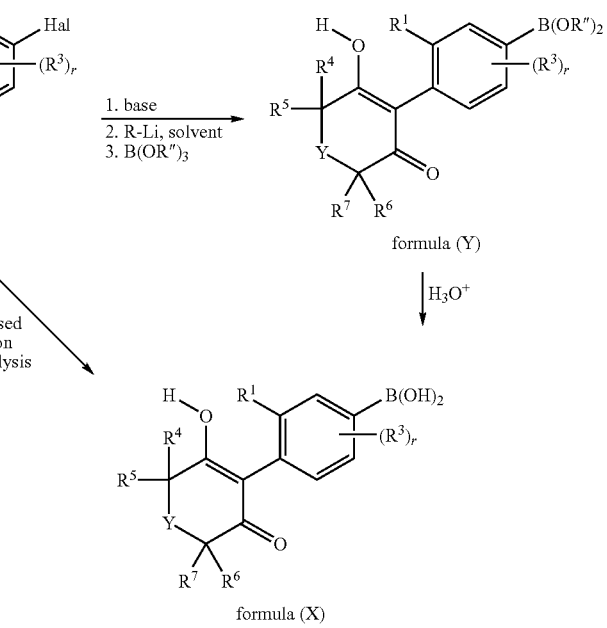

A compound of formula (H) may be prepared as described previously. Alternatively, a compound of formula (H) may be prepared from a compound of formula (J) by reaction with a compound of formula (Z) under conditions similar to those used for the preparation of a compound of formula (A) from a compound of formula (K).

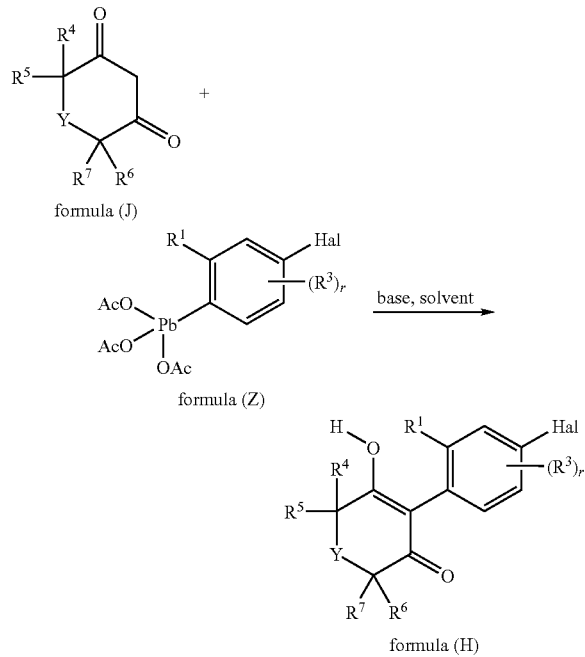

A compound of formula (Z) may be prepared from a compound of formula (Y) by methods similar to those described above for the preparation of a compound of formula (K) from a compound of formula (L).

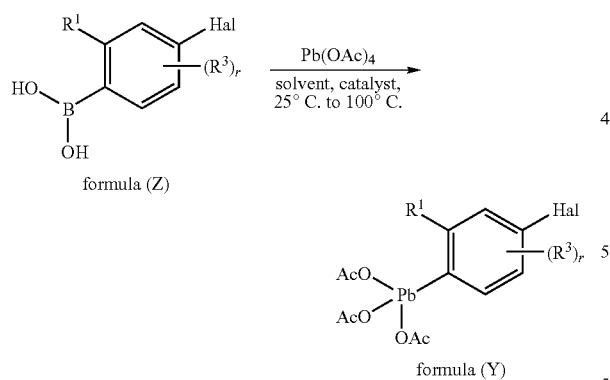

Compounds of formula (Z) are known compounds (see, for example, R. Gross et al J. Med. Chem., (2005), 48, 5780-5793, S. Marcuccio et al., WO99/12940, and W.-W. Liao and T. Muller, Synlett (2006), 20, 3469-3473), or may be made by known methods from known compounds, as described, for example, for the preparation of compounds of formula (L).

In a further approach, a compound of formula (A), wherein Y is oxygen, may be prepared by treating a compound of formula (AA) with a reagent or catalyst that promotes rearrangement, such as a suitable Brönsted or Lewis acid, optionally in the presence of a suitable solvent.

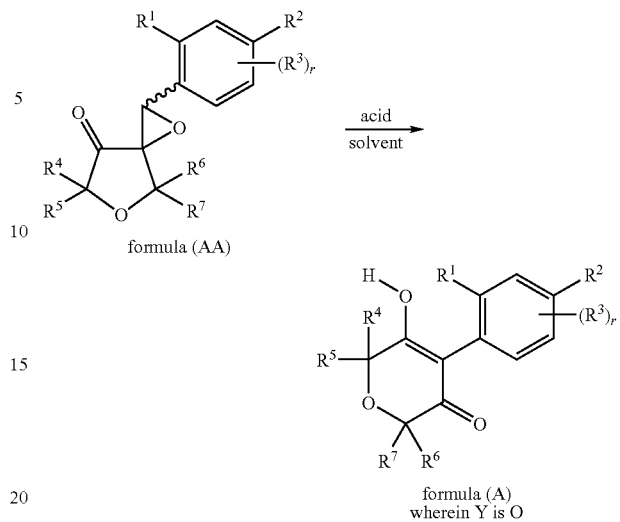

Suitable acids include Brönsted acids such as sulfuric acid, hydrogen chloride and p-toluenesulfonic acid, and suitable Lewis acids such as boron trifluoride etherate and lithium perchlorate (see for example M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400). Sulfuric acid is especially preferred. Suitable solvents are those chosen to be compatible with the acid used, and include dichloromethane, dichloroethane, diethyl ether, acetic acid, toluene or benzene.

A compound of formula (AA) may be prepared by the epoxidation of a compound of formula (BB), optionally in the presence of a suitable solvent.

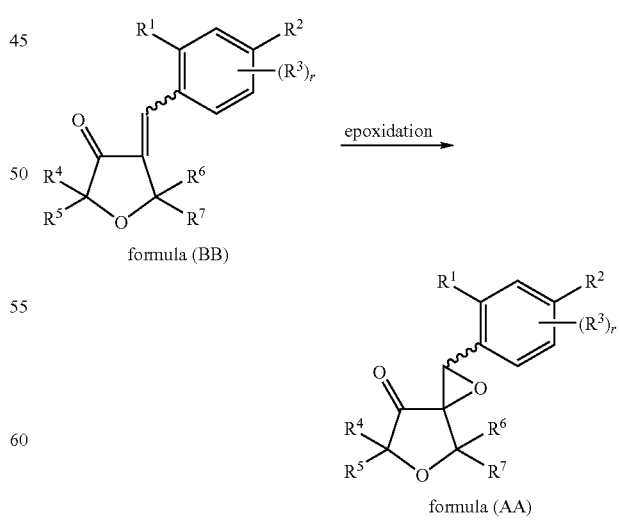

Epoxidation may be effected by treatment of a compound of formula (BB) with a suitable oxidising agent such as dimethyldioxirane, sodium hypochlorite, hydrogen peroxide or tert-butyl peroxide (in combination with a suitable base such as an alkali metal hydroxide or carbonate, alkaline earth metal hydroxide or carbonate, or an organic base such as 1,8-diazabicyclo[5.4.0]-undec-7-ene), in a suitable solvent (such as methanol, ethanol or dichloromethane) and at a suitable temperature. Similar reactions are known in the literature (see for example, A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; and K. Drauz, S. M. Roberts, T. Geller and A. Dhanda, U.S. Pat. No. 6,538,105 (B1). Preferably, epoxidation is carried out using hydrogen peroxide and a metal hydroxide (especially lithium hydroxide or sodium hydroxide), in methanol at a temperature of between −10° C. and 60° C.

A compound of formula (BB) may be prepared from a compound of formula (CC) by condensation with a benzaldehyde of formula (DD), in the presence of a suitable base and optionally in the presence of a suitable solvent (see for example, A. Lagrange, S. Forestier, G. Lang and B. Luppi, EP368717 A1; D. C. Rowlands, U.S. Pat. No. 2,776,239, US19570101; and E. Tamate, Nippon Kagaku Zasshi (1957), 78, 1293-7).

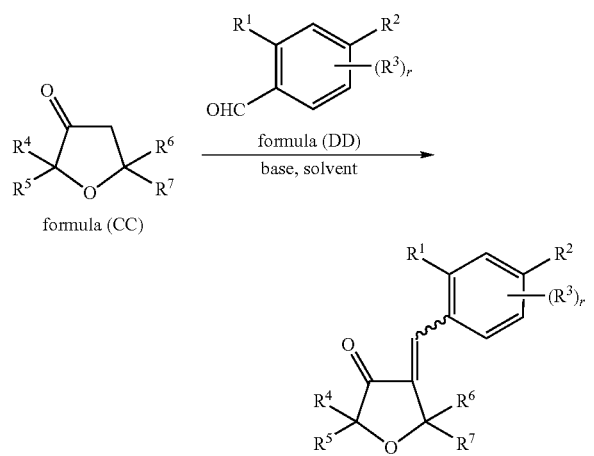

Preferably the base is a metal hydroxide, such as sodium hydroxide or potassium hydroxide, or a metal alkoxide such as sodium methoxide, sodium ethoxide or potassium tert-butoxide. Preferably the solvent is dimethoxyethane, dioxane, tetrahydrofuran, diethyl ether or an alkyl alcohol, such as methanol or ethanol.

Compounds of formula (CC) are known (see for example M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods.

A compound of formula (DD) may be prepared by formylation of a compound of formula (M) wherein Hal is chlorine, bromine or iodine (preferably bromine or iodine).

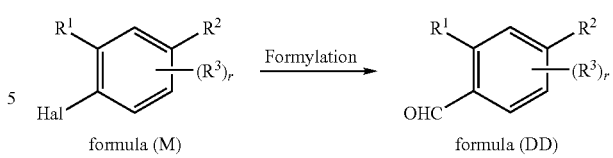

Suitable conditions for effecting the formylation of aryl halides are known, and include, for example, the treatment of an aryl halide with a suitable organometallic reagent (such as isopropyl magnesium chloride, n-butyllithium, sec-butyllithium or tert-butyllithium), or by treatment with a suitable alkali metal or alkali earth metal (such as lithium or magnesium) in a suitable solvent (such as diethyl ether, dimethoxyethane or tetrahydrofuran). The resulting arylmetal reagent is then reacted with a suitable formylating agent such as N,N-dimethylformamide or N-formylmorpholine. Alternatively a compound of formula (DD) may be prepared from a compound of formula (M) (wherein Hal can also be a pseudohalogen such as triflate) by treatment with a carbonylating agent (such as carbon monoxide) in the presence of a suitable catalyst, base, and reducing agent (see for example L. Ashfield and C. Barnard, Org. Process Res. Dev., 11 (1), 39-43, 2007).

The approach described above also permits an additional route to a compound of formula (H), and therefore to a compound of formula (I) by methods described previously. Thus a compound of formula (H), wherein Hal is chlorine, bromine, or iodine may be prepared by the treatment of a compound of formula (EE) with a suitable Brönsted acid (such as sulfuric acid, hydrogen chloride and p-toluenesulfonic acid), or a suitable Lewis acids (such as boron trifluoride etherate and lithium perchlorate), and optionally in a suitable solvent (such as dichloromethane, dichloroethane, diethyl ether, acetic acid, toluene or benzene). Sulfuric acid is especially preferred.

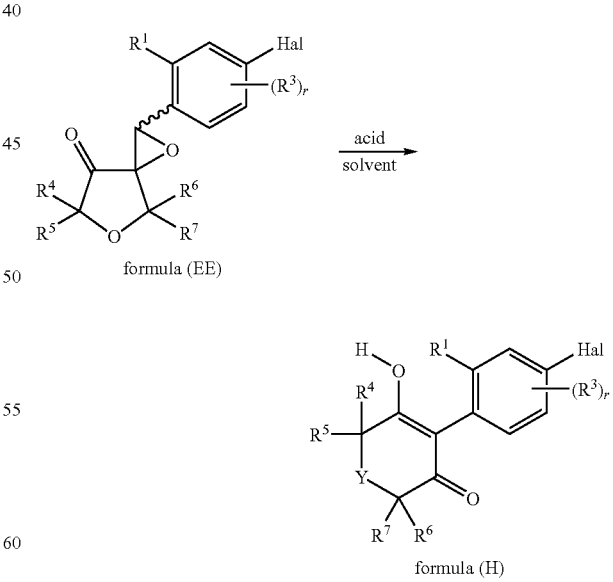

A compound of formula (EE) may be prepared from a compound of formula (FF), itself prepared by the condensation of a benzaldehyde of formula (GG) with a compound of formula (CC) under conditions described previously.

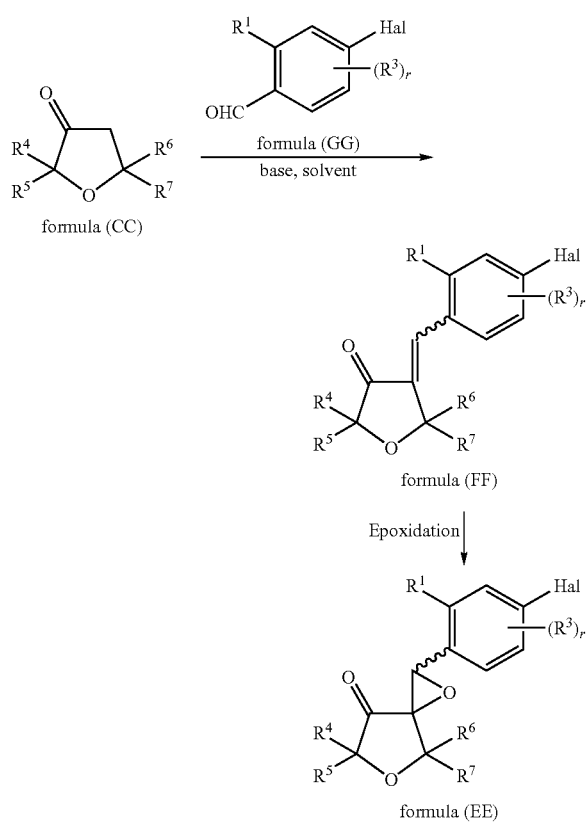

A compound of formula (GG) may be prepared by known methods from known compounds. For example, a compound of formula (GG), wherein Hal is chlorine or bromine, may be prepared by the formylation of an aryl iodide of formula (HH), under conditions described previously for the preparation of a compound of formula (DD). Compounds of formula (HH) are known compounds or may be made by known methods, for example by the iodination of a known aniline of formula (II) under Sandmeyer, or related, conditions.

The compounds of the formulae (B), (H), (X), (AA) and (EE) are novel and have been specifically designed for use as intermediates in the synthesis of the compounds of the formula (I).

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, antifoams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH).

Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:

(% = percent by weight):

Emulsifiable concentrates:

| | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |

Dusts:

| | |
|---|---|
| active ingredient: | 0.1 to 10%, preferably 0.1 to 5% |
| solid carrier: | 99.9 to 90%, preferably 99.9 to 99% |

Suspension concentrates:

| | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

Wettable powders:

| | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

Granules:

| | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include cereals, cotton, soybeans, sugar beet, sugar cane, plantation crops, rape, maize and rice, and for non-selective weed control. The compositions according to the invention are particularly useful for the selective control of grasses and weeds in cereals, maize and rice, especially cereals and rice, and more particularly rice. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 40 below:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifos, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIH-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), compound of formula 1+2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide (CAS RN 372137-35-4), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+ clopyralid, 2,4-D, compound of formula (I)+dicamba, compound of formula (I)+difenzoquat, compound of formula (I)+ difenzoquat metilsulfate, compound of formula (I)+ diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+dicamba, compound of formula (I)+diquat, compound of formula (I)+diquat dibromide, compound of formula (I)+esprocarb, compound of formula (I)+ethoxysulfuron, compound of formula (I)+fenoxaprop-P, compound of formula (I)+fenoxaprop-P-ethyl, compound of formula (I)+fentrazamide, compound of formula (I)+florasulam, compound of formula (I)+glufosinate-ammonium, compound of formula (I)+glyphosate, compound of formula (I)+halosulfuron, compound of formula (I)+halosulfuron-methyl, compound of formula (I)+imazosulfuron, compound of formula (I)+MCPA, compound of formula (I)+mefenacet, compound of formula (I)+mesotrione, compound of formula (I)+metamifop, compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, where the mixtures comprising a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula (I)+fentrazamide, compound of formula (I)+florasulam, compound of formula (I)+halosulfuron, compound of formula (I)+halosulfuron-methyl, compound of formula (I)+imazosulfuron, compound of formula (I)+MCPA, compound of formula (I)+mefenacet, compound of formula (I)+mesotrione, compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl are particularly preferred.

The compounds of formula (I) according to the invention can also be used in combination with safeners. Preferably, in these mixtures, the compound of the formula (I) is one of those compounds listed in Tables 1 to 40 below. The following mixtures with safeners, especially, come into consideration:

compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide (CAS RN 129531-12-0), compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecoprop and compound of the formula (I)+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Preferred compositions according to the present invention contain in addition to comprising the compound of formula I, a further herbicide as mixing partner and a safener.

The following Examples illustrate the invention further but do not limit the invention.

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 and P1, are drawn as an arbitrary single enol tautomer, but it should be inferred that this description covers both the diketone form and any possible enols which could arise through tautomerism. Furthermore, some of the compounds shown below, and in Table A, Table B, Table C and Table D, are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

PREPARATION EXAMPLES

Example 1

Preparation of (1R*,5S*)-3-(4'-chloro-3-ethylbiphenyl-4-yl)-1-methyl-8-oxabicyclo[3.2.1]octane-2,4-dione

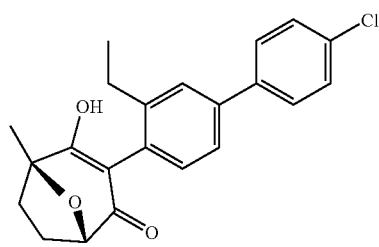

Step 1: Preparation of (1R*,5S*)-2,3,4,4-tetrachloro-1-methyl-8-oxabicyclo[3.2.1]octa-2,6-diene

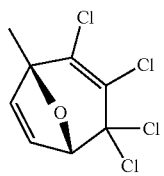

Pentachlorocyclopropane (100 g, 0.467 mol) is added to a suspension of potassium hydroxide (31.4 g, 0.56 mol) in 1,4-dioxane (3600 ml) and the mixture is stirred at room temperature for 30 minutes and then heated to 65° C. for a further 30 minutes. 2-Methylfuran (38.36 g, 0.467 mol) is added to the reaction mixture, the temperature is raised to 85-90° C. and the mixture is stirred for 16 hours. The reaction mixture is cooled to room temperature, filtered through a plug of diatomaceous earth and the filtrate evaporated under reduced pressure to give (1R*,5S*)-2,3,4,4-tetrachloro-1-methyl-8-oxabicyclo[3.2.1]octa-2,6-diene (83 g), used without further purification in the next step.

Step 2: Preparation of (1R*,5S*)-3,4-dichloro-5-methyl-8-oxabicyclo[3.2.1]octa-3,6-dien-2-one

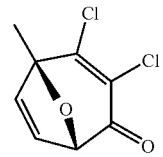

Silver nitrate (166 g, 0.982 mol) is added to a stirred mixture of (1R*,5S*)-2,3,4,4-tetrachloro-1-methyl-8-oxabicyclo[3.2.1]octa-2,6-diene (83 g, 0.32 mol), acetone (1500 ml) and water (1500 ml) and the mixture is heated at 65° C. for 16 hours. The reaction mixture is cooled to room temperature, and a saturated solution of aqueous sodium bicarbonate is added to adjust the pH to 7-8. The mixture is filtered through a plug of diatomaceous earth, and the filtrate is concentrated under reduced pressure to remove most of the acetone. The aqueous mixture is extracted with ethyl acetate (3×500 ml) and the organic extracts are combined, dried over anhydrous sodium sulfate, filtered and the filtrate is evaporated. The residue is purified by column chromatography on silica gel to give (1R*,5S*)-3,4-dichloro-5-methyl-8-oxabicyclo[3.2.1]octa-3,6-dien-2-one (29.5 g) as a yellow oil.

Step 3: Preparation of 3-chloro-1-methyl-4-oxo-spiro(1,3-dioxolane-2,2'-[8]oxa-bicyclo[3.2.1]oct-6-ene)

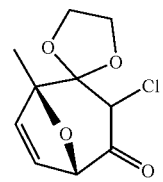

Sodium (4.41 g, 0.19 mol) is added cautiously to ethylene glycol (99.75 g) and the mixture is stirred at 35-40° C. under an atmosphere of nitrogen until the sodium is completely dissolved. A solution of (1R*,5S*)-3,4-dichloro-5-methyl-8-oxabicyclo[3.2.1]octa-3,6-dien-2-one (28 g, 0.136 mol) in tetrahydrofuran (200 ml) is added dropwise over 30 minutes, and once the addition is complete, the mixture is stirred for 90 minutes at room temperature. The reaction mixture is neutralised by addition of 10% aqueous sodium dihydrogen phosphate, and extracted with ethyl acetate (3×100 ml). The organic extracts are combined, dried over anhydrous sodium sulfate, filtered and the filtrate is evaporated. The residue is purified by column chromatography on silica gel to give 3-chloro-1-methyl-4-oxo-spiro(1,3-dioxolane-2,2'-[8]oxabicyclo[3.2.1]oct-6-ene) (24.5 g) as a gum.

Step 4: Preparation of (1R*,5S*)-1-methyl-4-oxo-spiro(1,3-dioxolane-2,2'-[8]oxa-bicyclo[3.2.1]oct-6-ene)

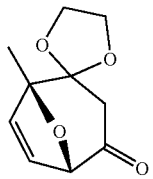

Zinc powder (13.88 g, 0.212 mol) is added to a solution of 3-chloro-1-methyl-4-oxo-spiro(1,3-dioxolane-2,2'-[8]oxabicyclo[3.2.1]oct-6-ene) (24.5 g, 0.106 mol) in acetic acid (122.5 ml) and the reaction mixture is stirred at room temperature for 24 hours. The mixture is diluted with water (612.5 ml) and extracted with ethyl acetate (3×150 ml). The organic extracts are combined, dried over anhydrous sodium sulfate, filtered and the filtrate is evaporated to give (1R*,5S*)-1-methyl-4-oxo-spiro(1,3-dioxolane-2,2'-[8]oxabicyclo[3.2.1]oct-6-ene) (20 g) as a yellow oil, used without further purification in the next step.

Step 5: Preparation of (1R*,5S*)-1-methyl-8-oxabicyclo[3.2.1]oct-6-ene-2,4-dione

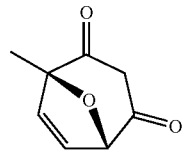

Concentrated hydrochloric acid (50 ml) is added, in three portions, to a mixture of (1R*,5S*)-1-methyl-4-oxo-spiro(1,3-dioxolane-2,2'-[8]oxabicyclo[3.2.1]oct-6-ene) (20 g, 0.102 mol) in acetone (500 ml) and water (250 ml) and the reaction mixture is stirred at 65-70° C. for 48 hours. The mixture is cooled to room temperature, most of the acetone is removed by evaporation under reduced pressure and the resulting aqueous solution is extracted with ethyl acetate (3×100 ml). The organic extracts are combined, dried over anhydrous sodium sulfate, filtered and the filtrate is evaporated. The residue is purified by column chromatography on silica gel to give (1R*,5S*)-1-methyl-8-oxabicyclo[3.2.1]oct-6-ene-2,4-dione (10.0 g) as a yellow oil.

Step 6: Preparation of (1R*,5S*)-1-methyl-8-oxabicyclo[3.2.1]octane-2,4-dione

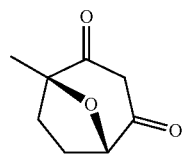

To a solution of (1R*,5S*)-1-methyl-8-oxabicyclo[3.2.1]oct-6-ene-2,4-dione (12.0 g, 0.079 mol) in ethyl acetate (100 ml) is added 10% palladium on carbon (2.4 g), followed by stirring under a 1 bar hydrogen atmosphere for 24 hours. The reaction mixture is then filtered through diatomaceous earth and concentrated under reduced pressure. The residue is purified by column chromatography on silica gel to afford (1R*,5S*)-1-methyl-8-oxabicyclo[3.2.1]octane-2,4-dione (6.90 g) as pale yellow solid.

Step 7: Preparation of (1R*,5S*)-3-(4'-chloro-3-ethylbiphenyl-4-yl)-1-methyl-8-oxabicyclo[3.2.1]octane-2,4-dione

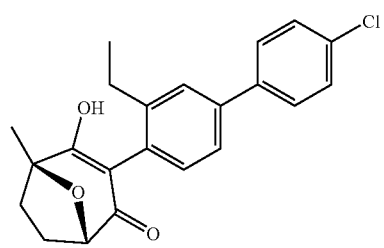 [SMILES: CCc1cc(-c2ccc(Cl)cc2)ccc1C1=C(O)[C@@]2(C)CC[C@H](O2)C1=O]

(1R*,5S*)-1-Methyl-8-oxabicyclo[3.2.1]octane-2,4-dione (0.20 g, 1.30 mmol) and 4-dimethylaminopyridine (0.792 g, 6.49 mmol) are added to a mixture of chloroform (4 ml) and toluene (1 ml). The reaction mixture is flushed with nitrogen for 15 minutes at ambient temperature. 4'-Chloro-3-ethylbiphen-4-yllead triacetate (0.856 g, 1.43 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(4'-chloro-3-ethylbiphenyl-4-yl)-1-methyl-8-oxabicyclo[3.2.1]octane-2,4-dione as a white solid (0.16 g).

Example 2

Preparation of (1R*,5S*-3-(3,5-dimethylbiphenyl-4-yl)-1-methyl-8-oxabicyclo[3.2.1]octane-2,4-dione

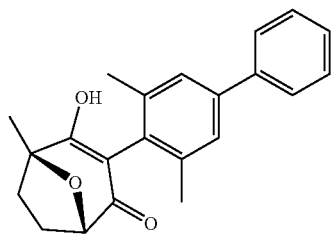 [SMILES: Cc1cc(-c2ccccc2)cc(C)c1C1=C(O)[C@@]2(C)CC[C@H](O2)C1=O]

(1R*,5S*)-1-Methyl-8-oxabicyclo[3.2.1]octane-2,4-dione (0.20 g, 1.30 mmol) and 4-dimethylaminopyridine (0.792 g, 6.49 mmol) are added to a mixture of chloroform (4 ml) and toluene (1 ml). The reaction mixture is flushed with nitrogen for 15 minutes at ambient temperature. 3,5-Dimethylbiphen- 4-yllead triacetate (0.805 g, 1.43 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(3,5-dimethyl-biphenyl-4-yl)-1-methyl-8-oxabicyclo[3.2.1]octane-2,4-dione as a white solid (0.139 g).

Example 3

Preparation of (1R*,5S*)-3-(4'-chloro-3,5-diethylbiphenyl-4-yl)-1-methyl-8-oxabicyclo[3.2.1]octane-2,4-dione

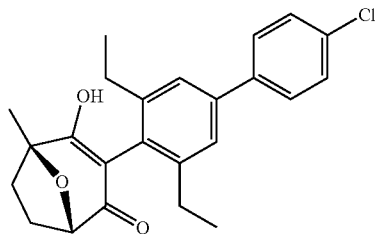 [SMILES: CCc1cc(-c2ccc(Cl)cc2)cc(CC)c1C1=C(O)[C@@]2(C)CC[C@H](O2)C1=O]

(1R*,5S*)-1-Methyl-8-oxabicyclo[3.2.1]octane-2,4-dione (0.20 g, 1.30 mmol) and 4-dimethylamino-pyridine (0.792 g, 6.49 mmol) are added to a mixture of chloroform (4 ml) and toluene (1 ml). The reaction mixture is flushed with nitrogen for 15 minutes at ambient temperature. 4'-Chloro-3,5-diethylbiphen-4-yllead triacetate (0.896 g, 1.43 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(4'-chloro-3,5-diethyl-biphenyl-4-yl)-1-methyl-8-oxabicyclo[3.2.1]octane-2,4-dione as a white solid (0.064 g).

Example 4

Preparation of (1R*,5S*)-3-(4'-chloro-3-methylbiphenyl-4-yl)-1-methyl-8-oxabicyclo[3.2.1]octane-2,4-dione

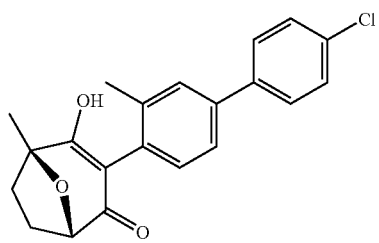 [SMILES: Cc1cc(-c2ccc(Cl)cc2)ccc1C1=C(O)[C@@]2(C)CC[C@H](O2)C1=O]

(1R*,5S*)-1-Methyl-8-oxabicyclo[3.2.1]octane-2,4-dione (0.20 g, 1.298 mmol) and 4-dimethylaminopyridine (0.792 g, 6.49 mmol) are added to a mixture of chloroform (4 ml) and toluene (1 ml). The reaction mixture is flushed with nitrogen for 15 minutes at ambient temperature. 4-Chloro-3-methylbiphen-4-yllead triacetate (0.836 g, 1.428 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(3,5-dimethyl-biphenyl-4-yl)-1-methyl-8-oxabicyclo[3.2.1]octane-2,4-dione as a white solid (0.142 g).

Example 5

Preparation of 4-(3-ethyl-4'-fluorobiphenyl-4-yl)-2,2,6-trimethylpyran-3,5-dione

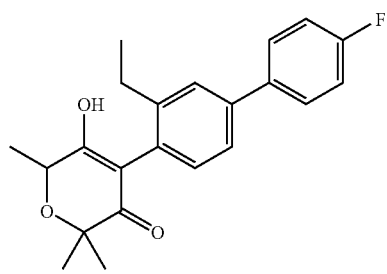 [SMILES: CCc1cc(-c2ccc(F)cc2)ccc1C1=C(O)C(C)OC(C)(C)C1=O]

Step 1: Preparation of 2-(1,1-dimethylprop-2-ynyloxy)propionic acid methyl ester

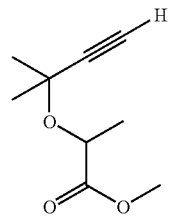

To a mixture of sodium hydride (23.8 g, 0.595 mol) in tetrahydrofuran (400 ml) cooled to 0° C., is added a solution of 2-methyl-3-butyne-2-ol (50 g, 0.595 mol) in tetrahydrofuran (50 ml). The reaction mixture is stirred at 0° C. for 1 hour. A solution of methyl-2-bromo-propionate (99.36 g, 0.595 mol) in tetrahydrofuran (100 ml) is added to the reaction mixture slowly at 0° C. The reaction mixture is stirred at 0° C. for 2 hours and allowed to come to ambient temperature and stirred for 1 hour. The reaction mixture is cooled to 10° C. and quenched with ice cold water. The mixture is extracted with diethyl ether (3×200 ml), the organic phases are combined, washed with water, and dried over anhydrous sodium sulfate. The mixture is filtered and the filtrate is evaporated under reduced pressure to give 2-(1,1-dimethylprop-2-ynyloxy)

propionic acid methyl ester (90 g) as a colorless oil, used without further purification in the next step.

Step 2: Preparation of 2-(1,1-dimethyl-2-oxopropoxy)propionic acid methyl ester

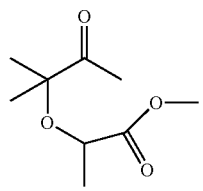

A mixture of mercury (II) acetate (7.76 g, 0.024 mol), sulfuric acid (9 ml, 0.09 mol) and water (450 ml) is heated at 60° C. 2-(1,1-dimethylprop-2-ynyloxy)propionic acid methyl ester (90 g, 0.529 mol) is added carefully at 60° C. The reaction mixture is maintained at 60° C. for 8 hours and cooled to ambient temperature. The aqueous phase is extracted with diethyl ether (3×250 ml), the organic phases are combined, washed with water, and dried over anhydrous sodium sulfate. The mixture is filtered, and the filtrate is evaporated under reduced pressure. The residue is purified by column chromatography on silica gel to give 2-(1,1-dimethyl-2-oxopropoxy)propionic acid methyl ester (24 g) as a colorless oil.

Step 3: Preparation of 2,2,6-trimethylpyran-3,5-dione

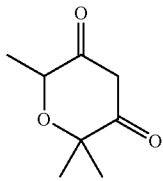

To a mixture of potassium tert-butoxide (28.5 g, 0.254 mol) in tetrahydrofuran (200 ml) cooled to 0° C., is added a solution of 2-(1,1-dimethyl-2-oxopropoxy)propionic acid methyl ester (24 g, 0.127 mol) in tetrahydrofuran (50 ml). The reaction mixture is stirred at 0° C. for 3 hours. The reaction mixture is quenched with ice cold water, and the aqueous phase is extracted with diethyl ether (3×200 ml). The organic phases are combined, washed with water, and dried over anhydrous sodium sulfate. The mixture is filtered, and the filtrate is evaporated under reduced pressure. The residue is purified by column chromatography on silica gel to give 2,2,6-trimethylpyran-3,5-dione (7.5 g) as a white solid.

Step 4: Preparation of 4-(4-bromo-2-ethylphenyl)-2,2,6-trimethylpyran-3,5-dione

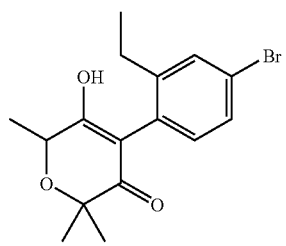 [SMILES: CCc1cc(Br)ccc1C1=C(O)C(C)OC(C)(C)C1=O]

2,2,6-Trimethylpyran-3,5-dione (1 g, 6.4 mmol) and 4-dimethylaminopyridine (3.9 g, 32 mmol) are added to a mixture of chloroform (20 ml) and toluene (5 ml). The reaction mixture is flushed with nitrogen for 15 minutes at ambient temperature. 4-Bromo-2-ethylphenyllead triacetate (4.3 g, 7.57 mmol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with chloroform (2×25 ml), the organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6-trimethylpyran-3,5-dione as a white solid (0.5 g).

Step 5: Preparation of 4-(3-ethyl-4'-fluorobiphenyl-4-yl)-2,2,6-trimethylpyran-3,5-dione

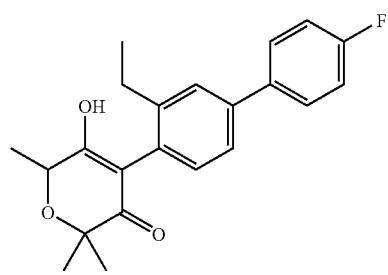 [SMILES: CCc1cc(-c2ccc(F)cc2)ccc1C1=C(O)C(C)OC(C)(C)C1=O]

To a mixture of 4-(4-bromo-2-ethylphenyl)-2,2,6-trimethylpyran-3,5-dione (0.5 g, 1.48 mmol), cesium fluoride (0.70 g, 4.4 mmol), 4-fluorophenylboronic acid (0.31 g, 2.23 mmol) and [1,1'-bis(diphenylphosphino)ferrocene]dichloropalladium(II) (0.19 g, 0.23 mmol) is added degassed dimethoxyethane (15 ml) and the resulting suspension is stirred under nitrogen for 45 minutes then heated at 80° C. for 24 hours. After cooling to room temperature the reaction mixture is acidified with 1N aqueous hydrochloric acid. The mixture is extracted with ethyl acetate (3×25 ml) and then all organic fractions are combined, dried over anhydrous sodium sulphate and concentrated under reduced pressure. The residue is purified by column chromatography on silica gel to afford 4-(3-ethyl-4'-fluorobiphenyl-4-yl)-2,2,6-trimethylpyran-3,5-dione (0.27 g) as a white solid.

Example 6

Preparation of (1R*,5S*)-3-(4-bromo-2-ethylphenyl)-1-methyl-8-oxabicyclo[3.2.1]octane-2,4-dione

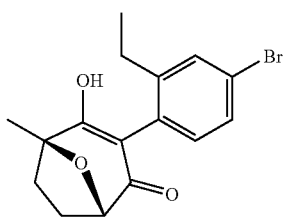 [SMILES: CCc1cc(Br)ccc1C1=C(O)[C@@]2(C)CC[C@H](O2)C1=O]

(1R*,5S*)-1-Methyl-8-oxabicyclo[3.2.1]octane-2,4-dione (6 g, 38.96 mmol) and 4-dimethylaminopyridine (23.76 g, 194.75 mmol) are added to a mixture of chloroform (120 ml) and toluene (30 ml). The reaction mixture is flushed with nitrogen for 15 minutes at ambient temperature. 4-Bromo-2-ethylphenyllead triacetate (24.3 g, 42.85 mmol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases separated. The aqueous phase is extracted with dichloromethane (2×50 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(4-bromo-2-ethylphenyl)-1-methyl-8-oxabicyclo[3.2.1]octane-2,4-dione as a white solid (6 g).

This compound, together with the arylbromides described below, may be converted into additional compounds in Table A, using appropriate aryl- and heteroarylboronic acids under the Suzuki-Miyaura conditions described in Step 5 of Example 5.

Example 7

Preparation of (1R*,5S*)-3-(4-bromo-2,6-dimethylphenyl)-1-methyl-8-oxabicyclo[3.2.1]octane-2,4-dione

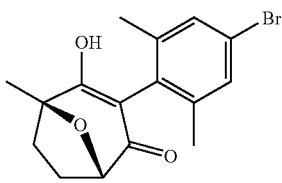 [SMILES: Cc1cc(Br)cc(C)c1C1=C(O)[C@@]2(C)CC[C@H](O2)C1=O]

(1R*,5S*)-1-Methyl-8-oxabicyclo[3.2.1]octane-2,4-dione (6 g, 0.039 mol) and 4-dimethylaminopyridine (24 g, 0.196 mol) are added to a mixture of chloroform (120 ml) and toluene (30 ml). The reaction mixture is flushed with nitrogen for 15 minutes at ambient temperature. 4-Bromo-2,6-dimethylphenyllead triacetate (24 g, 0.042 mol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×100 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(4-bromo-2,6-dimethylphenyl)-1-methyl-8-oxabicyclo[3.2.1]octane-2,4-dione as a white solid (1 g).

Example 8

Preparation of (1R*,5S*)-3-(4-bromo-2,6-diethylphenyl)-1-methyl-8-oxabicyclo[3.2.1]octane-2,4-dione

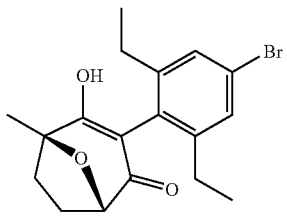 [SMILES: CCc1cc(Br)cc(CC)c1C1=C(O)[C@@]2(C)CC[C@H](O2)C1=O]

(1R*,5S*)-1-Methyl-8-oxabicyclo[3.2.1]octane-2,4-dione (1 g, 6.5 mmol) and 4-dimethylamino-pyridine (3.96 g, 32.5 mmol) are added to a mixture of chloroform (20 ml) and toluene (5 ml). The reaction mixture is flushed with nitrogen for 15 minutes at ambient temperature. 4-Bromo-2,6-diethylphenyllead triacetate (4.25 g, 7.14 mmol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×25 ml), the organic phases are combined, washed with water, and dried over anhydrous sodium sulfate. The mixture is filtered, and the filtrate is evaporated under reduced pressure. The residue is purified by column chromatography on silica gel to give (1R*,5S*)-3-(4-bromo-2,6-diethylphenyl)-1-methyl-8-oxabicyclo[3.2.1]octane-2,4-dione as a white solid (0.1 g).

Example 9

Preparation of (1S*,5S*)-3-(4-bromo-2-ethylphenyl)-1-ethoxymethyl-8-oxabicyclo[3.2.1]octane-2,4-dione

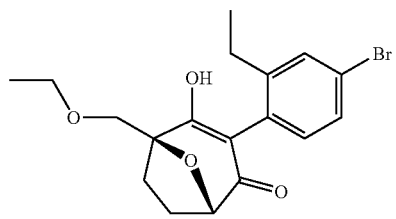 [SMILES: CCOC[C@]12CC[C@H](O1)C(=O)C(c1ccc(Br)cc1CC)=C2O]

Step 1: Preparation of (1S*,5S*)-2,3,4,4-tetrachloro-1-ethoxymethyl-8-oxabicyclo-[3.2.1]octa-2,6-diene

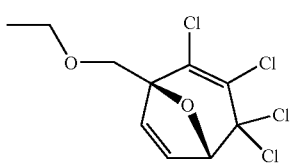 [SMILES: CCOC[C@]12C=C[C@H](O1)C(Cl)(Cl)C(Cl)=C2Cl]

Pentachlorocyclopropane (25 g, 0.116 mol) is added to a suspension of potassium hydroxide (7.8 g, 0.139 mol) in 1,4-dioxane (900 ml) and the mixture is stirred at room temperature for 30 minutes and then heated to 65° C. for a further 30 minutes. 2-Ethoxymethylfuran (17.5 g, 0.139 mol) is added to the reaction mixture, the temperature is raised to 85-90° C. and the mixture is stirred for 16 hours. The reaction mixture is cooled to room temperature, filtered through a plug of diatomaceous earth and the filtrate is evaporated under reduced pressure to give (1S*,5S*)-2,3,4,4-tetrachloro-1-ethoxymethyl-8-oxabicyclo[3.2.1]octa-2,6-diene (23 g), used without further purification in the next step.

Step 2: Preparation of (1S*,5S*)-3,4-dichloro-5-ethoxymethyl-8-oxabicyclo[3.2.1]octa-3,6-dien-2-one

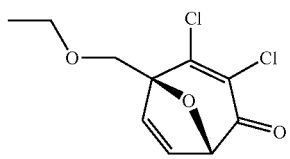

Silver nitrate (26 g, 0.154 mol) is added to a stirred mixture of (1S*,5S*)-2,3,4,4-tetrachloro-1-ethoxymethyl-8-oxabicyclo[3.2.1]octa-2,6-diene (23.5 g, 0.077 mol), acetone (450 ml) and water (450 ml) and the mixture is heated at 65° C. for 16 hours. The reaction mixture is cooled to room temperature, and a saturated solution of aqueous sodium bicarbonate is added to adjust the pH to 7-8. The mixture is filtered through a plug of diatomaceous earth, and the filtrate is concentrated under reduced pressure to remove most of the acetone. The aqueous mixture is extracted with ethyl acetate (3×250 ml) and the organic extracts are combined, dried over anhydrous sodium sulfate, filtered and the filtrate is evaporated. The residue is purified by column chromatography on silica gel to give (1S*,5S*)-3,4-dichloro-5-ethoxymethyl-8-oxabicyclo[3.2.1]octa-3,6-dien-2-one (6 g) as a yellow oil.

Step 3: Preparation of 3-chloro-1-ethoxymethyl-4-oxo-spiro(1,3-dioxolane-2,2'-[8]oxabicyclo[3.2.1]oct-6-ene)

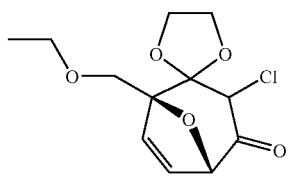 [SMILES: CCOC[C@]12C=C[C@H](O1)C(=O)C(Cl)C21OCCO1]

Sodium (0.83 g, 0.036 mol) is added cautiously to ethylene glycol (69 g) and the mixture is stirred at 35-40° C. under an atmosphere of nitrogen until the sodium is completely dissolved. A solution of (1S*,5S*)-3,4-dichloro-5-ethoxymethyl-8-oxabicyclo[3.2.1]octa-3,6-dien-2-one (6 g, 0.024 mol) in tetrahydrofuran (45 ml) is added dropwise over 30 minutes, and once the addition is complete, the mixture is stirred for 90 minutes at room temperature. The reaction mixture is neutralised by addition of 10% aqueous sodium dihydrogen phosphate, and extracted with ethyl acetate (3×75 ml). The organic extracts are combined, dried over anhydrous sodium sulfate, filtered and the filtrate is evaporated. The residue is purified by column chromatography on silica gel to give 3-chloro-1-ethoxymethyl-4-oxo-spiro(1,3-dioxolane-2,2'-[8]oxabicyclo[3.2.1]oct-6-ene) (6 g) as a gum.

Step 4: Preparation of (1S*,5S*)-1-ethoxymethyl-4-oxo-spiro(1,3-dioxolane-2,2'-[8]oxabicyclo[3.2.1]oct-6-ene)

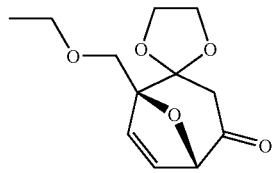 [SMILES: CCOC[C@]12C=C[C@H](O1)C(=O)CC21OCCO1]

Zinc powder (6.25 g, 0.048 mol) is added to a solution of 3-chloro-1-ethoxymethyl-4-oxo-spiro(1,3-dioxolane-2,2'-[8]oxabicyclo[3.2.1]oct-6-ene) (6 g, 0.024 mol) in acetic acid (30 ml) and the reaction mixture is stirred at room temperature for 24 hours. The mixture is diluted with water (300 ml) and extracted with ethyl acetate (3×100 ml). The organic extracts are combined, dried over anhydrous sodium sulfate, filtered and the filtrate is evaporated to give (1S*,5S*)-1-ethoxymethyl-4-oxo-spiro(1,3-dioxolane-2,2'-[8]oxabicyclo[3.2.1]oct-6-ene) (6 g) as a yellow oil, used without further purification in the next step.

Step 5: Preparation of (1S*,5S*)-1-ethoxymethyl-8-oxabicyclo[3.2.1]oct-6-ene-2,4-dione

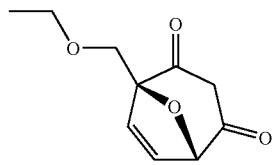

Concentrated hydrochloric acid (18 ml) is added, in three portions, to a mixture of (1S*,5S*)-1-ethoxymethyl-4-oxo-spiro(1,3-dioxolane-2,2'-[8]oxabicyclo[3.2.1]oct-6-ene) (6 g, 0.025 mol) in acetone (80 ml) and water (40 ml) and the reaction mixture is stirred at 65-70° C. for 48 hours. The mixture is cooled to room temperature, most of the acetone is removed by evaporation under reduced pressure and the resulting aqueous solution is extracted with ethyl acetate (3×100 ml). The organic extracts are combined, dried over anhydrous sodium sulfate, filtered and the filtrate is evaporated. The residue is purified by column chromatography on silica gel to give (1S*,5S*)-1-ethoxymethyl-8-oxabicyclo[3.2.1]oct-6-ene-2,4-dione (2.8 g) as a yellow oil.

Step 6: Preparation of (1S*,5S*)-1-ethoxymethyl-8-oxabicyclo[3.2.1]octane-2,4-dione

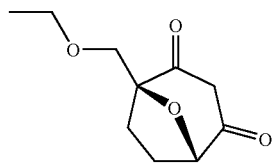

To a solution of (1S*,5S*)-1-ethoxymethyl-8-oxabicyclo[3.2.1]oct-6-ene-2,4-dione (2.8 g, 0.014 mol) in ethyl acetate (10 ml) is added 10% palladium on carbon (0.056 g), followed by stirring under a 1 bar hydrogen atmosphere for 24 hours. The reaction mixture is then filtered through diatomaceous earth and the filtrate is concentrated under reduced pressure. The residue is purified by column chromatography on silical gel to afford (1S*,5S*)-1-ethoxymethyl-8-oxabicyclo[3.2.1]octane-2,4-dione (2.3 g) as a pale yellow solid.

Step 7: Preparation of (1S*,5S*)-3-(4-bromo-2-ethylphenyl)-1-ethoxymethyl-8-oxabicyclo[3.2.1]octane-2,4-dione

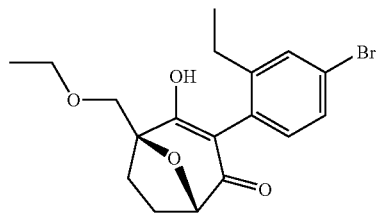 [SMILES: CCOC[C@]12CC[C@H](O1)C(=O)C(c1ccc(Br)cc1CC)=C2O]

(1S*,5S*)-1-Ethoxymethyl-8-oxabicyclo[3.2.1]octane-2,4-dione (0.8 g, 4.04 mmol) and 4-dimethylaminopyridine (2.4 g, 19.67 mmol) are added to a mixture of chloroform (16 ml) and toluene (4 ml). The reaction mixture is flushed with nitrogen for 15 minutes at ambient temperature. 4-Bromo-2-ethylphenyllead triacetate (2.49 g, 4.38 mmol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×25 ml), the organic phases are combined, washed with water, and dried over anhydrous sodium sulfate. The mixture is filtered, and the filtrate is evaporated under reduced pressure. The residue is purified by column chromatography on silica gel to give (1S*,5S*)-3-(4-bromo-2-ethylphenyl)-1-ethoxymethyl-8-oxabicyclo[3.2.1]octane-2,4-dione as white solid (0.45 g).

Example 10

Preparation of 4-(4-bromo-2-ethylphenyl)-2,2,6,6-tetramethylpyran-3,5-dione

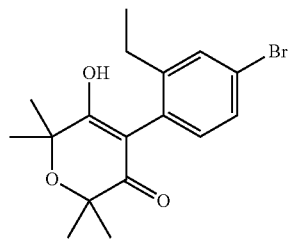 [SMILES: CCc1cc(Br)ccc1C1=C(O)C(C)(C)OC(C)(C)C1=O]

Step I:

2,2,6,6-Tetramethylpyran-3,5-dione (8 g, 0.047 mol) and 4-dimethylaminopyridine (24 g, 0.196 mol) are added to a mixture of chloroform (160 ml) and toluene (40 ml). The reaction mixture is flushed with nitrogen for 15 minutes at ambient temperature. 4-Bromo-2-ethyl-phenyllead triacetate (29.4 g, 0.051 mol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×100 ml), the organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6,6-tetramethylpyran-3,5-dione as a white solid (10 g).

Example 11

Preparation of 4-(4-bromo-2-ethylphenyl)-2-ethyl-2,6,6-trimethylpyran-3,5-dione

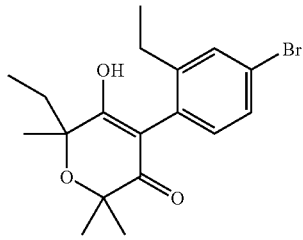 [SMILES: CCc1cc(Br)ccc1C1=C(O)C(C)(CC)OC(C)(C)C1=O]

Step 1: Preparation of 2,5-dimethylhept-3-yne-2,5-diol

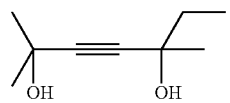

A solution of 2-methyl-3-butyne-2-ol (15 g, 0.178 mol) in tetrahydrofuran (150 ml) is cooled to −78° C. under a nitrogen atmosphere and n-butyl lithium (1.6 molar solution in hexanes, 244 ml, 0.39 mol) is added slowly over 1.5-2.0 hours. The reaction mixture is stirred for 1 hour at −78° C. and to this mixture a solution of 2-butanone (24 ml, 0.266 mol) in tetrahydrofuran (24 ml) is added. The reaction mixture is stirred at −78° C. for one hour and allowed to come to ambient temperature and stirred at ambient temperature for 2-3 hours. The reaction mixture is cooled to 10° C., quenched with ice cold water. The aqueous phase is extracted with dichloromethane (3×150 ml). The organic phases are combined, washed with water, and dried over anhydrous sodium sulfate. The mixture is filtered, and the filtrate is evaporated under reduced pressure. The residue is purified by column chromatography on silica gel to give 2,5-dimethylhept-3-yne-2,5-diol (15 g) as colourless oil.

Step 2: Preparation of a mixture of 2-ethyl-2,5,5-trimethyldihydrofuran-3-one and 5-ethyl-2,2,5-trimethyldihydrofuran-3-one

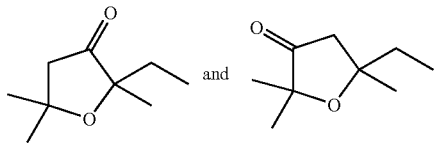

A mixture of mercury (II) acetate (1.5 g, 0.0047 mol), sulfuric acid (1.5 ml), water (150 ml) and 2,5-dimethylhept-3-yne-2,5-diol (15 g, 0.096 mol) is heated at 80° C. The reaction mixture is maintained at 80° C. for 4 hours and allowed to cool to ambient temperature. The mixture is extracted with diethyl ether (3×150 ml), and the organic phases are combined, washed with water, and dried over anhydrous sodium sulfate. The mixture is filtered, and the filtrate is evaporated under reduced pressure to give a mixture of 2-ethyl-2,5,5-trimethyl-dihydrofuran-3-one and 5-ethyl-2,2,5-trimethyldihydrofuran-3-one (15 g), used without further purification in the next step.

Step 3: Preparation of a mixture of 4-[1-(4-bromo-2-ethylphenyl)methylidene]-2-ethyl-2,5,5-trimethyldihydrofuran-3-one and 4-[1-(4-bromo-2-ethylphenyl)methylidene]-5-ethyl-2,2,5-trimethyldihydrofuran-3-one

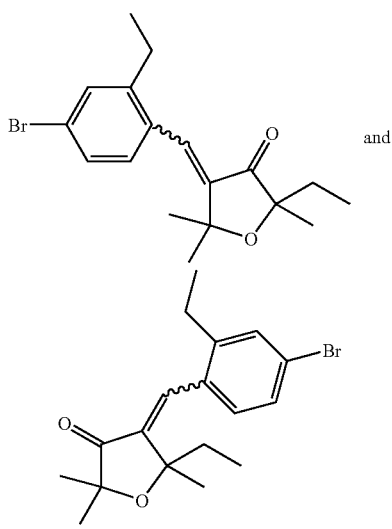

Sodium methoxide (7 g, 0.13 mol) is added to a solution of mixture of 2-ethyl-2,5,5-trimethyldihydrofuran-3-one and 5-ethyl-2,2,5-trimethyldihydrofuran-3-one (10 g, 0.064 mol) in dimethoxyethane (50 ml) at 0° C. The reaction mixture is stirred for 15 minutes at 0° C. and to this mixture is added a solution of 4-bromo-2-ethylbenzaldehyde (12.23 g, 0.057 mol) in dimethoxyethane (18 ml). The reaction mixture is stirred at 0° C. for 1 hour, acidified to pH 1 with 2N aqueous hydrochloric acid and extracted with diethyl ether (3×100 ml). The organic phases are combined, washed with water, and dried over anhydrous sodium sulfate. The mixture is filtered, and the filtrate is evaporated under reduced pressure to give a mixture of 4-[1-(4-bromo-2-ethylphenyl)methylidene]-2-ethyl-2,5,5-trimethyl-dihydrofuran-3-one and 4-[1-(4-bromo-2-ethylphenyl)methylidene]-5-ethyl-2,2,5-trimethyldihydrofuran-3-one (19 g), used without further purification in the next step.

Step 4: Preparation of a mixture of 2-(4-bromo-2-ethylphenyl)-6-ethyl-4,4,6-trimethyl-1,5-dioxospiro[2.4]heptane-7-one and 2-(4-bromo-2-ethylphenyl)-4-ethyl-4,6,6-trimethyl-1,5-dioxospiro[2.4]heptane-7-one

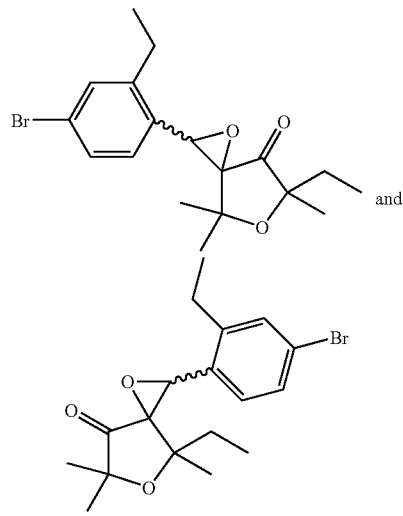

To a solution of a mixture of 4-[1-(4-bromo-2-ethylphenyl)methylidene]-2-ethyl-2,5,5-trimethyldihydrofuran-3-one and 4-[1-(4-bromo-2-ethylphenyl)methylidene]-5-ethyl-2,2,5-trimethyldihydrofuran-3-one (19 g, 0.056 mol) in methanol (760 ml) is added a 50% solution of aqueous hydrogen peroxide (9.8 ml, 0.169 mol) and a 2N solution of aqueous sodium hydroxide (11.26 ml, 0.022 mol) at ambient temperature. The reaction mixture is stirred at ambient temperature for 12-15 hours. The reaction mixture is quenched with a saturated solution of aqueous sodium metabisulfite, evaporated under reduced pressure to remove most of the solvent and extracted with dichloromethane (3×200 ml). The organic phases are combined, washed with water, and dried over anhydrous sodium sulfate. The mixture is filtered, and the filtrate is evaporated under reduced pressure to give a mixture of 2-(4-bromo-2-ethylphenyl)-6-ethyl-4,4,6-trimethyl-1,5-dioxospiro[2.4]heptane-7-one and 2-(4-bromo-2-ethylphenyl)-4-ethyl-4,6,6-trimethyl-1,5-dioxospiro[2.4]-heptane-7-one (15 g) as yellow solid, used without further purification in the next step.

Step 5: Preparation of 4-(4-bromo-2-ethylphenyl)-2-ethyl-2,6,6-trimethylpyran-3,5-dione

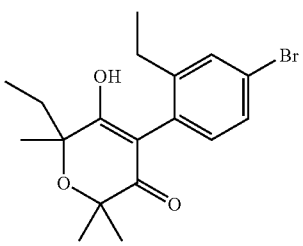 [SMILES: CCc1cc(Br)ccc1C1=C(O)C(C)(CC)OC(C)(C)C1=O]

To an ice cold solution of a mixture of 2-(4-bromo-2-ethylphenyl)-6-ethyl-4,4,6-trimethyl-1,5-dioxospiro[2.4]heptane-7-one and 2-(4-bromo-2-ethylphenyl)-4-ethyl-4,6,6-trimethyl-1,5-dioxospiro[2.4]heptane-7-one (15 g, 0.041 mol) in dichloromethane (7.5 ml) is added concentrated sulphuric acid (45 ml), dropwise, over 50-60 minutes, maintaining the temperature of the reaction mixture at 5-10° C. The reaction mixture is maintained at 5-10° C. for 10-15 minutes, quenched into crushed ice (225 g) and the aqueous phase is extracted with dichloromethane (3×100 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2-ethyl-2,6,6-trimethylpyran-3,5-dione (3.5 g) as a white solid.

Example 12

Preparation of 4-(4-bromo-2-ethylphenyl)-2,2-dimethyl-1-oxa-spiro[5,5]-undecane-3,5-dione

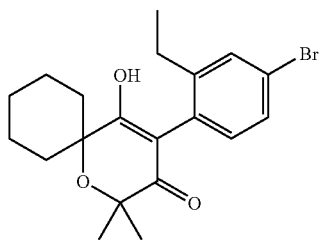 [SMILES: CCc1cc(Br)ccc1C1=C(O)C2(CCCCC2)OC(C)(C)C1=O]

Step 1: Preparation of 1-(3-hydroxy-3-methylbut-1-ynyl)cyclohexanol

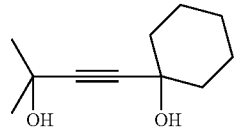

A solution of 2-methyl-3-butyne-2-ol (25 g, 0.297 mol) in tetrahydrofuran (250 ml) is cooled to −78° C. under a nitrogen atmosphere and to this solution, n-butyl lithium (1.6 molar solution in hexanes, 410 ml, 0.65 mol) is added slowly over 1.5-2.0 hours. The reaction mixture is stirred for 1 hour at −78° C. and a solution of cyclohexanone (46.2 ml, 0.44 mol) in tetrahydrofuran (46 ml) is added. The reaction mixture is stirred at −78° C. for one hour and allowed to come to ambient temperature and stirred at ambient temperature for 2-3 hours. The reaction mixture is cooled to 10° C. and quenched with ice cold water. The mixture is extracted with dichloromethane (3×250 ml), the organic phases are combined, washed with water, and dried over anhydrous sodium sulfate. The mixture is filtered, and the filtrate is evaporated under reduced pressure. The residue is purified by column chromatography on silica gel to give 1-(3-hydroxy-3-methylbut-1-ynyl)cyclohexanol (20 g) as a colourless oil.

Step 2: Preparation of a mixture of 2,2-dimethyl-1-oxaspiro[4.5]decan-4-one and 2,2-dimethyl-1-oxaspiro[4.5]decan-3-one

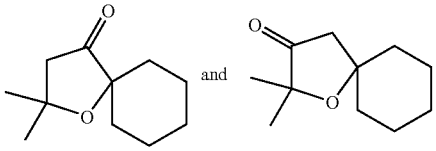

A mixture of mercury (II) acetate (1.8 g, 0.0056 mol), sulfuric acid (1.8 ml, 0.018 mol), water (180 ml) and 1-(3-hydroxy-3-methylbut-1-ynyl)cyclohexanol (18 g, 0.099 mol) is heated at 80° C. The reaction mixture is maintained at 80° C. for 4 hours and allowed to come to ambient temperature. The aqueous phase is extracted with diethyl ether (3×200 ml), the organic phases are combined, washed with water, and dried over anhydrous sodium sulfate. The mixture is filtered, and the filtrate is evaporated under reduced pressure to give a mixture of 2,2-dimethyl-1-oxaspiro[4.5]decan-4-one and 2,2-dimethyl-1-oxaspiro[4.5]decan-3-one (16 g), used without further purification in the next step.

Step 3: Preparation of a mixture of 3-[1-(4-bromo-2-ethylphenyl)methylidene]-2,2-dimethyl-1-oxaspiro[4.5]decan-4-one and 4-[1-(4-bromo-2-ethylphenyl)methyl-idene]-2,2-dimethyl-1-oxaspiro[4.5]decan-3-one Sodium methoxide (5.4 g, 0.1 mol) is added to a solution of a mixture of 2,2-dimethyl-1-oxaspiro[4.5]decan-4-one and 2,2-dimethyl-1-oxaspiro[4.5]decan-3-one (9 g, 0.049 mol) in dimethoxyethane (45 ml) at 0° C. The reaction mixture is stirred for 15 minutes at 0° C. and to this mixture is added a solution of 4-bromo-2-ethyl benzaldehyde (9.4 g, mol) in dimethoxyethane (14 ml). The reaction mixture is stirred at 0° C. for 1 hour, acidified to pH 1 with 2N aqueous hydrochloric acid and extracted with diethyl ether (3×100 ml). The organic phases are combined, washed with water, and dried over anhydrous sodium sulfate. The mixture is filtered, and the filtrate is evaporated under reduced pressure to give a mixture of 3-[1-(4-bromo-2-ethylphenyl)methylidene]-2,2-dimethyl-1-oxaspiro[4.5]-decan-4-one and 4-[1-(4-bromo-2-ethylphenyl)methylidene]-2,2-dimethyl-1-oxa-spiro[4.5]decan-3-one (20 g), used without further purification in the next step.

Step 4: Preparation of a mixture of 2-(4-bromo-2-ethylphenyl)-12,12-dimethyl-1,11-dioxadispiro [2.1.5.2]dodecan-4-one and 2-(4-bromo-2-ethylphenyl)-11,11-dimethyl-1,10-dioxadispiro[2.0.5.3] dodecan-12-one

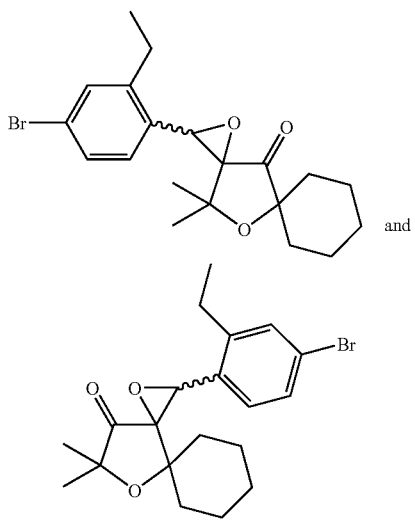

and

To a solution of a mixture of 3-[1-(4-bromo-2-ethylphenyl) methylidene]-2,2-dimethyl-1-oxaspiro[4.5]decan-4-one and 4-[1-(4-bromo-2-ethylphenyl)methylidene]-2,2-dimethyl-1-oxaspiro[4.5]decan-3-one (20 g, 0.053 mol) in methanol (800 ml) is added a 50% solution of aqueous hydrogen peroxide (9.24 ml, 0.159 mol) and a 2N aqueous solution of sodium hydroxide (10.6 ml, 0.02 mol) at ambient temperature. The reaction mixture is stirred at ambient temperature for 12-15 hours. The reaction mixture is quenched with a saturated solution of sodium metabisulfite, evaporated under reduced pressure to remove most of the solvent and extracted with dichloromethane (3×200 ml). The organic phases are combined, washed with water, and dried over anhydrous sodium sulfate. The mixture is filtered, and the filtrate is evaporated under reduced pressure to give mixture of 2-(4-bromo-2-ethylphenyl)-12,12-dimethyl-1,11-dioxadispiro[2.1.5.2] dodecan-4-one and 2-(4-bromo-2-ethylphenyl)-11,11-dimethyl-1,10-dioxadispiro[2.0.5.3]dodecan-12-one (15 g) used without further purification in the next step.

Step 5: Preparation of 4-(4-bromo-2-ethylphenyl)-2, 2-dimethyl-1-oxaspiro[5.5]-undecane-3,5-dione

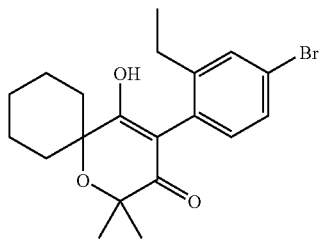 [SMILES: CCc1cc(Br)ccc1C1=C(O)C2(CCCCC2)OC(C)(C)C1=O]

To an ice cold solution of mixture of 2-(4-bromo-2-ethylphenyl)-12,12-dimethyl-1,11-dioxadispiro[2.1.5.2]dodecan-4-one and 2-(4-bromo-2-ethylphenyl)-11,11-dimethyl-1,10-dioxadispiro[2.0.5.3]dodecan-12-one (15 g, 0.038 mol) in dichloromethane (7.5 ml) is added concentrated sulphuric acid (45 ml), dropwise, over 50-60 minutes, maintaining the temperature of the reaction mixture at 5-10° C. The reaction mixture is maintained at 5-10° C. for 10-15 minutes, quenched into crushed ice (225 g) and extracted with dichloromethane (3×100 ml). The organic phases are combined, washed with water and dried over anhydrous sodium sulfate. The mixture is filtered and the filtrate is evaporated under reduced pressure. The residue is purified by column chromatography on silica gel to give 4-(4-bromo-2-ethylphenyl)-2, 2-dimethyl-1-oxaspiro[5.5]undecane-3,5-dione (3 g) as a white solid.

Example 13

Preparation of 4-(4-bromo-2-ethylphenyl)-2-methoxymethyl-2,6,6-tri-methylpyran-3,5-dione

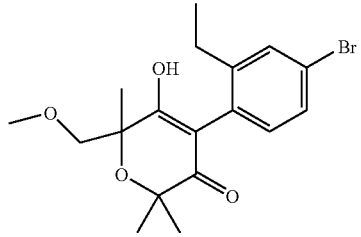 [SMILES: CCc1cc(Br)ccc1C1=C(O)C(C)(COC)OC(C)(C)C1=O]

Step 1: Preparation of 1-methoxy-2,5-dimethylhex-3-yne-2,5-diol

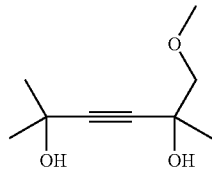

A solution of 2-methyl-3-butyne-2-ol (25 g, 0.3 mol) in tetrahydrofuran (250 ml) is cooled to −78° C. under a nitrogen atmosphere and to this solution, n-butyl lithium (1.6 molar solution in hexanes, 372 ml, 0.59 mol) is added slowly over 1.5-2.0 hours. The reaction mixture is stirred for 1 hour at −78° C. and a solution of methoxyacetone (38 g, 0.43 mol) in tetrahydrofuran (50 ml) is added. The reaction mixture is stirred at −78° C. for one hour, allowed to come to ambient temperature, and stirred for 2-3 hours. The reaction mixture is cooled to 10° C. and quenched with ice cold water. The mixture is extracted with ethyl acetate (3×250 ml), and the organic phases are combined, washed with water, and dried over anhydrous sodium sulfate. The mixture is filtered, and the filtrate is evaporated under reduced pressure. The residue is purified by column chromatography on silica gel to give 1-methoxy-2,5-dimethylhex-3-yne-2,5-diol (15 g) as a colourless oil.

Step 2: Preparation of a mixture of 2-methoxymethyl-2,5,5-trimethyldihydrofuran-3-one and 5-methoxymethyl-2,2,5-trimethyldihydrofuran-3-one

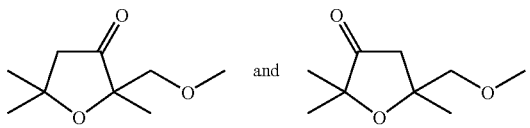

A mixture of mercury (II) oxide (0.6 g, 0.0027 mol), trifluoroacetic acid (0.2 ml, 0.0027 mol), boron trifluoride-diethyl etherate (0.6 ml, 0.0047 mol) and methanol (15 ml) is stirred for 10 minutes at ambient temperature under a nitrogen atmosphere. A solution of 1-methoxy-2,5-dimethylhex-3-yne-2,5-diol (15 g, 0.087 mol) in methanol (60 ml) is added to the reaction mixture and the mixture is heated at 60° C. The reaction mixture is maintained at 60° C. for 3 hours then allowed to cool to ambient temperature and quenched with water. The aqueous layer is extracted with diethyl ether (3×150 ml), the organic phases are combined, washed with water, and dried over anhydrous sodium sulfate. The mixture is filtered, and the filtrate is evaporated under reduced pressure to give a mixture of 2-methoxymethyl-2,5,5-trimethyldihydrofuran-3-one and 5-methoxymethyl-2,2,5-trimethyldihydrofuran-3-one (6 g) as a colourless oil, used in the next step without further purification.

Step 3: Preparation of a mixture of 3-[1-(4-bromo-2-ethylphenyl)methylidene]-2-methoxymethyl-2,5,5-trimethyldihydrofuran-3-one and 4-[1-(4-bromo-2-ethylphenyl)-methylidene]-5-methoxymethyl-2,2,5-trimethyldihydrofuran-3-one

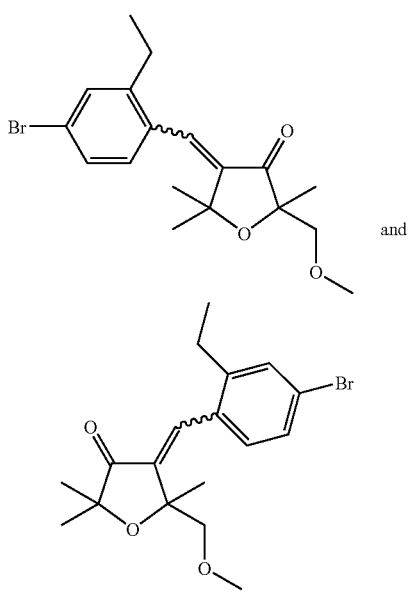

Sodium methoxide (2 g, 0.035 mol) is added to a solution of a mixture of 2-methoxymethyl-2,5,5-trimethyldihydrofuran-3-one and 5-methoxymethyl-2,2,5-tri-methyldihydrofuran-3-one (3 g, 0.0174 mol) in dimethoxyethane (15 ml) at 0° C. The reaction mixture is stirred for 15 minutes at 0° C. and a solution of 4-bromo-2-ethyl benzaldehyde (3.31 g, 0.0156 mol) in dimethoxyethane (5 ml) is added. The reaction mixture is stirred at 0° C. for 1 hour, acidified to pH 1 with 2N aqueous hydrochloric acid and extracted with diethyl ether (3×50 ml). The organic phases are combined, washed with water, and dried over anhydrous sodium sulfate. The mixture is filtered, and the filtrate is evaporated under reduced pressure to give a mixture of 3-[1-(4-bromo-2-ethylphenyl)methylidene]-2-methoxymethyl-2,5,5-trimethyl-dihydrofuran-3-one and 4-[1-(4-bromo-2-ethylphenyl)methylidene]-5-methoxymethyl-2,2,5-trimethyldihydrofuran-3-one (7 g) which is used in the next step without further purification.

Step 4: Preparation of a mixture of 2-(4-bromo-2-ethylphenyl)-6-methoxymethyl-4,4,6-trimethyl-1,5-dioxaspiro[2.4]heptan-7-one and 2-(4-bromo-2-ethylphenyl)-4-methoxymethyl-4,6,6-trimethyl-1,5-dioxaspiro[2.4]heptan-7-one

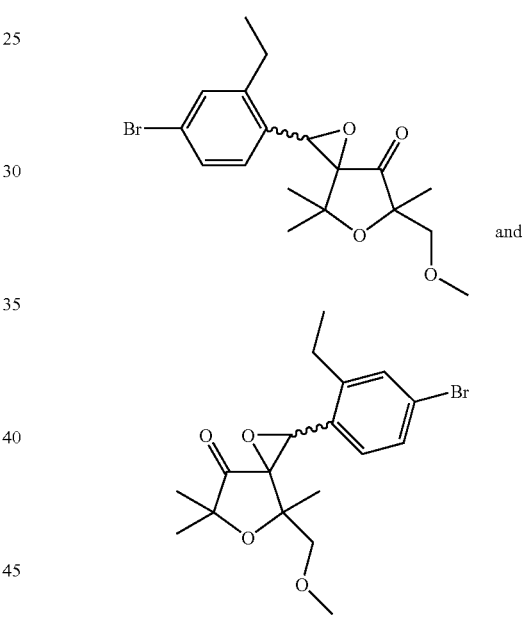

To a solution of a mixture of 3-[1-(4-bromo-2-ethylphenyl)methylidene]-2-methoxymethyl-2,5,5-trimethyldihydrofuran-3-one and 4-[1-(4-bromo-2-ethyl-phenyl)methylidene]-5-methoxymethyl-2,2,5-trimethyldihydrofuran-3-one (7 g, 0.019 mol) in methanol (280 ml) is added 50% aqueous solution of hydrogen peroxide (3.3 ml, 0.057 mol) and 2N aqueous solution of sodium hydroxide (3.8 ml, 0.0076 mol) at ambient temperature. The reaction mixture is stirred at ambient temperature for 12-15 hours. The reaction mixture is quenched with a saturated solution of sodium metabisulfite, evaporated under reduced pressure to remove most of the solvent and extracted with dichloromethane (3×75 ml). The organic phases are combined, washed with water, and dried over anhydrous sodium sulfate. The mixture is filtered, and the filtrate is evaporated under reduced pressure to give a mixture of 2-(4-bromo-2-ethylphenyl)-6-methoxymethyl-4,4,6-trimethyl-1,5-dioxaspiro[2.4]heptan-7-one and 2-(4-bromo-2-ethylphenyl)-4-methoxymethyl-4,6,6-trimethyl-1, 5-dioxa-spiro[2.4]heptan-7-one (5 g) as a yellow solid, used in the next step without further purification.

Step 5: Preparation of 4-(4-bromo-2-ethylphenyl)-2-methoxymethyl-2,6,6-trimethylpyran-3,5-dione

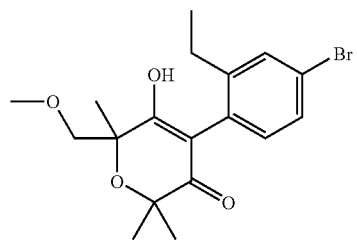 [SMILES: CCc1cc(Br)ccc1C1=C(O)C(C)(COC)OC(C)(C)C1=O]

To an ice cold solution of a mixture of 2-(4-bromo-2-ethylphenyl)-6-methoxymethyl-4,4,6-trimethyl-1,5-dioxaspiro[2.4]heptan-7-one and 2-(4-bromo-2-ethylphenyl)-4-methoxymethyl-4,6,6-trimethyl-1,5-dioxaspiro[2.4]heptan-7-one (5 g, 0.013 mol) in dichloromethane (2.5 ml) is added concentrated sulphuric acid (15 ml), dropwise over 50-60 minutes, maintaining the temperature of the reaction mixture at 5-10° C. The reaction mixture is maintained at 5-10° C. for 10-15 minutes, quenched into crushed ice (75 g) and extracted with dichloromethane (3×50 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2-methoxymethyl-2,6,6-trimethylpyran-3,5-dione (1.82 g) as a white solid.

Example 14

Preparation of 9-(4-bromo-2-ethylphenyl)-7,7-dimethyl-6-oxaspiro-[4.5]decane-8,10-dione

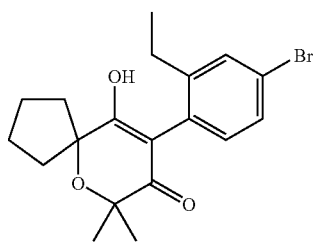 [SMILES: CCc1cc(Br)ccc1C1=C(O)C2(CCCC2)OC(C)(C)C1=O]

Step 1: Preparation of 1-(3-hydroxy-3-methylbut-1-ynyl)cyclopentanol

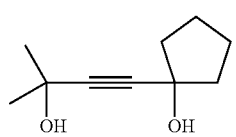

A solution of 2-methyl-3-butyne-2-ol (25 g, 0.297 mol) in tetrahydrofuran (250 ml) is cooled to −78° C. under a nitrogen atmosphere and n-butyl lithium (1.6 molar solution in hexanes, 410 ml, 0.65 mol) is added slowly over 1.5-2.0 hours. The reaction mixture is stirred for 1 hour at −78° C. and a solution of cyclopentanone (39 ml, 0.44 mol) in tetrahydrofuran (39 ml) is added. The reaction mixture is stirred at −78° C. for one hour and allowed to come to ambient temperature and stirred for 2-3 hours. The reaction mixture is cooled to 10° C. and quenched with ice cold water. The mixture is extracted with dichloromethane (3×250 ml), and the organic phases are combined, washed with water, and dried over anhydrous sodium sulfate. The mixture is filtered, and the filtrate is evaporated under reduced pressure. The residue is purified by column chromatography on silica gel to give 1-(3-hydroxy-3-methylbut-1-ynyl)-cyclopentanol (17 g) as colourless oil.

Step 2: Preparation of a mixture of 2,2-dimethyl-1-oxaspiro[4.4]nonan-4-one and 2,2-dimethyl-1-oxaspiro[4.4]nonan-3-one

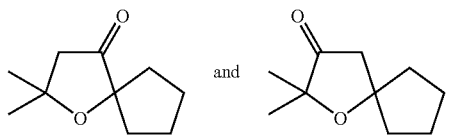

A mixture of mercury (II) acetate (1.5 g, 0.0047 mol), sulfuric acid (1.5 ml), water (150 ml) and 1-(3-hydroxy-3-methylbut-1-ynyl)cyclopentanol (15 g, 0.082 mol) is heated at 80° C. The reaction mixture is maintained at 80° C. for 4 hours and allowed to come to ambient temperature. The mixture is extracted with diethyl ether (3×150 ml), and the organic phases are combined, washed with water, and dried over anhydrous sodium sulfate. The mixture is filtered, and the filtrate is evaporated under reduced pressure to give a mixture of 2,2-di-methyl-1-oxaspiro[4.4]nonan-4-one and 2,2-dimethyl-1-oxaspiro[4.4]nonan-3-one (15 g) as colourless oil, used without further purification in the next step.

Step 3: Preparation of a mixture of 3-[1-(4-bromo-2-ethylphenyl)methylidene]-2,2-dimethyl-1-oxaspiro[4.4]nonan-4-one and 4-[1-(4-bromo-2-ethylphenyl)methylidene]-2,2-dimethyl-1-oxaspiro[4.4]nonan-3-one

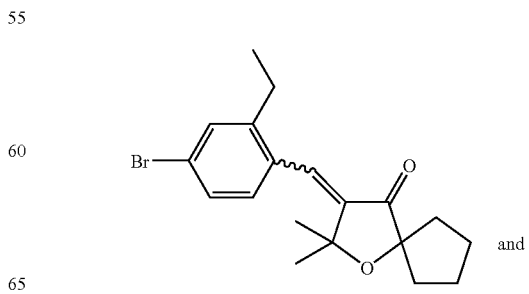

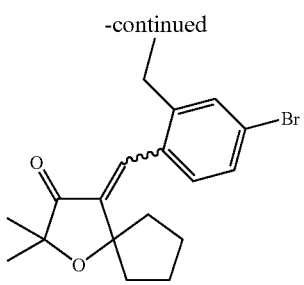

Sodium methoxide (3.27 g, 0.06 mol) is added to a solution of mixture of 2,2-dimethyl-1-oxaspiro[4.4]nonan-4-one and 2,2-dimethyl-1-oxaspiro[4.4]nonan-3-one (5 g, 0.0297 mol) in dimethoxyethane (25 ml) at 0° C. The reaction mixture is stirred for 15 minutes at 0° C. and to this mixture is added a solution of 4-bromo-2-ethyl benzaldehyde (5.6 g, 0.0267 mol) in dimethoxyethane (8.4 ml). The reaction mixture is stirred at 0° C. for 1 hour, acidified to pH 1 with 2N aqueous hydrochloric acid and extracted with diethyl ether (3×50 ml). The organic phases are combined, washed with water, and dried over anhydrous sodium sulfate. The mixture is filtered and the filtrate is evaporated under reduced pressure to give mixture of 3-[1-(4-bromo-2-ethylphenyl)methylidene]-2,2-dimethyl-1-oxaspiro[4.4]nonan-4-one and 4-[1-(4-bromo-2-ethylphenyl)methylidene]-2,2-dimethyl-1-oxaspiro[4.4]nonan-3-one (10 g) which is used in the next step without further purification.

Step 4: Preparation of a mixture of 2-(4-bromo-2-ethylphenyl)-11,11-dimethyl-1,10-dioxadispiro[2.1.4.2]undecan-4-one and 2-(4-bromo-2-ethylphenyl)-10,10-dimethyl-1,9-dioxadispiro[2.0.4.3]undecan-11-one

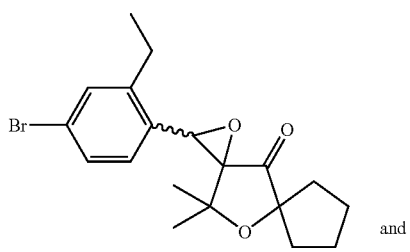

To a solution of a mixture of 3-[1-(4-bromo-2-ethylphenyl)methylidene]-2,2-dimethyl-1-oxaspiro[4.4]nonan-4-one and 4-[1-(4-bromo-2-ethylphenyl)methylidene]-2,2-dimethyl-1-oxaspiro[4,4]nonan-3-one (10 g, 0.027 mol) in methanol (400 ml) is added a 50% solution of aqueous hydrogen peroxide (4.79 ml, 0.082 mol) and a 2N aqueous solution of sodium hydroxide (5.48 ml, 0.011 mol) at ambient temperature. The reaction mixture is stirred at ambient temperature for 12-15 hours. The reaction mixture is quenched with a saturated solution of aqueous sodium metabisulfite, evaporated under reduced pressure to remove most of the solvent and extracted with dichloromethane (3×100 ml). The organic phases are combined, washed with water, and dried over anhydrous sodium sulfate. The mixture is filtered, and the filtrate is evaporated under reduced pressure to give mixture of 2-(4-bromo-2-ethylphenyl)-11,11-dimethyl-1,10-dioxadispiro[2.1.4.2]undecan-4-one and 2-(4-bromo-2-ethylphenyl)-10,10-dimethyl-1,9-dioxadispiro[2.0.4.3]undecan-11-one (7 g) as a yellow solid, used without further purification in the next step.

Step 5: Preparation of 9-(4-bromo-2-ethylphenyl)-7,7-dimethyl-6-oxaspiro[4.5]-decane-8,10-dione

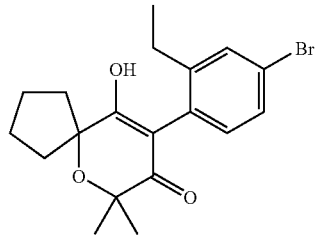 [SMILES: CCc1cc(Br)ccc1C1=C(O)C2(CCCC2)OC(C)(C)C1=O]

To an ice cold solution of a mixture of 2-(4-bromo-2-ethylphenyl)-11,11-dimethyl-1,10-dioxadispiro[2.1.4.2]undecan-4-one and 2-(4-bromo-2-ethylphenyl)-10,10-dimethyl-1,9-dioxadispiro[2.0.4.3]undecan-11-one (7 g, 0.0185 mol) in dichloromethane (3.5 ml) is added concentrated sulphuric acid (21 ml), dropwise over 50-60 minutes, maintaining the temperature of the reaction mixture at 5-10° C. The reaction mixture is maintained at 5-10° C. for 10-15 minutes, quenched into crushed ice (100 g) and extracted with dichloromethane (3×75 ml). The organic phases are combined, washed with water, and dried over anhydrous sodium sulfate. The mixture is filtered and the filtrate is evaporated under reduced pressure. The residue is purified by column chromatography on silica gel to give 9-(4-bromo-2-ethyl-phenyl)-7,7-dimethyl-6-oxaspiro[4.5]decane-8,10-dione (1.1 g) as a white solid.

Example 15

Preparation of 4-(4-bromo-2-ethylphenyl)-2,6-diethyl-2,6-dimethylypran-3,5-dione

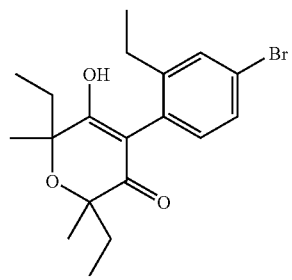 [SMILES: CCc1cc(Br)ccc1C1=C(O)C(C)(CC)OC(C)(CC)C1=O]

Step 1: Preparation of
3,6-dimethyloct-4-yne-3,6-diol

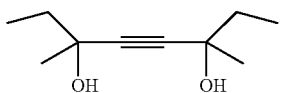

A solution of 3-methyl-1-pentyn-3-ol (30 g, 0.3 mol) in tetrahydrofuran (250 ml) is cooled to −78° C. under a nitrogen atmosphere and n-butyl lithium (1.6 molar solution in hexanes, 383 ml, 0.611 mol) is added slowly over 1.5-2.0 hours. The reaction mixture is stirred for 1 hour at −78° C. and a solution of 2-butanone (41 ml, 0.458 mol) in tetrahydrofuran (50 ml) is added. The reaction mixture is stirred at −78° C. for one hour, allowed to come to ambient temperature and stirred for 2-3 hours. The reaction mixture is cooled to 10° C. and quenched with ice cold water. The aqueous phase is extracted with dichloromethane (3×200 ml). The organic phases are combined, washed with water, and dried over anhydrous sodium sulfate. The mixture is filtered, and the filtrate is evaporated under reduced pressure. The residue is purified by column chromatography on silica gel to give 3,6-dimethyloct-4-yne-3,6-diol (27 g) as a colourless oil.

Step 2: Preparation of
2,5-diethyl-2,5-dimethyldihydrofuran-3-one

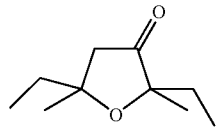

A mixture of mercury (II) acetate (2.7 g, 0.0084 mol), sulfuric acid (2.7 ml, 0.027 mol), water (270 ml) and 3,6-dimethyl-oct-4-yne-3,6-diol (27.0 g, 0.159 mol) is heated at 80° C. The reaction mixture is maintained at 80° C. for 4 hours and allowed to cool to ambient temperature. The mixture is extracted with diethyl ether (3×150 ml), the organic phases are combined, washed with water, and dried over anhydrous sodium sulfate. The mixture is filtered and the filtrate is evaporated under reduced pressure to give 2,5-diethyl-2,5-di-methyldihydrofuran-3-one (20 g) as a colourless oil.

Step 3: Preparation of 4-[1-(4-bromo-2-ethylphenyl)
methylidene]-2,5-diethyl-2,5-dimethyldihydrofuran-3-one

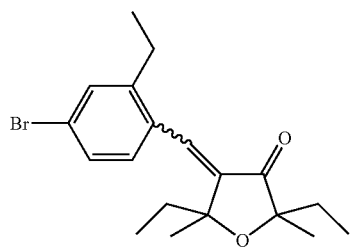 [SMILES: CCc1cc(Br)ccc1C=C1C(=O)C(C)(CC)OC1(C)CC]

Sodium methoxide (5.08 g, 0.094 mol) is added to a solution of 2,5-diethyl-2,5-dimethyldihydrofuran-3-one (8 g, 0.047 mol) in dimethoxyethane (40 ml) at 0° C. The reaction mixture is stirred for 15 minutes at 0° C. and a solution of 4-bromo-2-ethyl benzaldehyde (8.96 g, 0.042 mol) in dimethoxyethane (8 ml) is added. The reaction mixture is stirred at 0° C. for 1 hour, acidified to pH 1 with 2N aqueous hydrochloric acid and extracted with diethyl ether (3×75 ml). The organic phases are combined, washed with water, and dried over anhydrous sodium sulfate. The mixture is filtered, and the filtrate is evaporated under reduced pressure to give 4-[1-(4-bromo-2-ethylphenyl)methylidene]-2,5-diethyl-2,5-dimethyldihydrofuran-3-one (17 g), used without further purification in the next step.

Step 4: Preparation of 2-(4-bromo-2-ethylphenyl)-4,
6-diethyl-4,6-dimethyl-1,5-dioxaspiro[2.4]heptan-7-
one

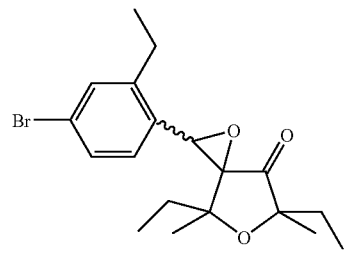 [SMILES: CCc1cc(Br)ccc1C1OC12C(=O)C(C)(CC)OC2(C)CC]

To a solution of 4-[1-(4-bromo-2-ethylphenyl)methylidene]-2,5-diethyl-2,5-dimethyldihydrofuran-3-one (20 g, 0.055 mol) in methanol (800 ml) is added a solution of 50% aqueous hydrogen peroxide (9.58 ml, 0.165 mol) and a solution of 2N aqueous sodium hydroxide (10.98 ml, 0.02 mol) at ambient temperature. The reaction mixture is stirred at ambient temperature for 12-15 hours. The reaction mixture is quenched with a solution of saturated aqueous sodium metabisulfite, evaporated under reduced pressure to remove most of the solvent and extracted with dichloromethane (3×100 ml). The organic phases are combined, washed with water, and dried over anhydrous sodium sulfate. The mixture is filtered, and the filtrate is evaporated under reduced pressure to give 2-(4-bromo-2-ethylphenyl)-4,6-diethyl-4,6-dimethyl-1,5-dioxaspiro[2.4]heptan-7-one (15 g), used without further purification in the next step.

Step 5: Preparation of 4-(4-bromo-2-ethylphenyl)-2,
6-diethyl-2,6-dimethylpyran-3,5-dione

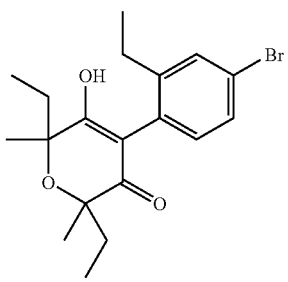 [SMILES: CCc1cc(Br)ccc1C1=C(O)C(C)(CC)OC(C)(CC)C1=O]

To an ice cold solution of 2-(4-bromo-2-ethylphenyl)-4,6-diethyl-4,6-dimethyl-1,5-dioxaspiro[2.4]heptan-7-one (15 g, 0.0397 mol) in dichloromethane (7.5 ml) is added concentrated sulphuric acid (45 ml), dropwise over 50-60 minutes, maintaining the temperature of the reaction mixture at 5-10° C. The reaction mixture is maintained at 5-10° C. for 10-15 minutes, quenched into crushed ice (225 g) and extracted with dichloromethane (3×100 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,6-diethyl-2,6-dimethylpyran-3,5-dione (2 g) as a white solid.

Additional compounds in Table A are prepared by analogous procedures, from appropriate starting materials. It should be noted that certain compounds of the invention exist as a mixture of atropisomers, or other isomers noted above, under the conditions used to obtain the $^1$H NMR data. Where this has occurred, the characterising data are reported for the mixture of atropisomers, or other isomers, present at ambient temperature in the specified solvent. 1H nmr data are obtained in deuterated chloroform (CDCl$_3$), deuterated methanol (CD$_3$OD) or deuterated dimethyl sulfoxide (DMSO-d$_6$). In some cases mixed solvent systems are used, and recorded as such (for example as CDCl$_3$/CD$_3$OD).

Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: H$_2$O with 0.05% TFA
Solvent B: CH$_3$CN with 0.05% TFA

TABLE A

| Compound Number | Structure | $^1$H NMR (CDCl$_3$ unless stated) or other physical data |
|---|---|---|
| A-1 | 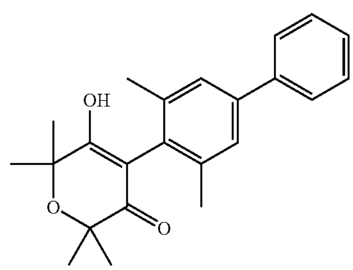 [SMILES: Cc1cc(-c2ccccc2)cc(C)c1C1=C(O)C(C)(C)OC(C)(C)C1=O] | $\delta_H$ 7.61 (d, 2H), 7.49 (t, 2H), 7.42-7.38 (m, 3H), 5.60 (s, 1H), 2.23 (s, 6H), 1.68 (s, 6H), 1.56 (s, 6H). |
| A-2 | 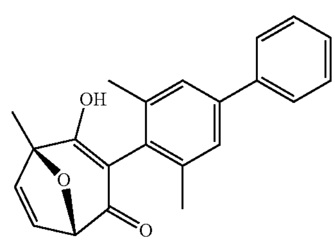 [SMILES: Cc1cc(-c2ccccc2)cc(C)c1C1=C(O)[C@@]2(C)C=C[C@H](O2)C1=O] | $\delta_H$ 757-7.25 (m, 7H), 5.87 (br. s, 1H), 4.87 and 4.7 (2 × d, 1H), 2.6-2.4 (m, 1H), 2.23 and 2.22 (2 × s, 3H), 2.07 (s, 3H), 2.04-1.94 (m, 3H), 1.67 and 1.59 (2 × s, 3H). |
| A-3 | 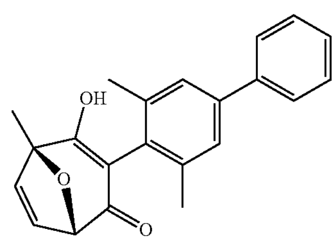 [SMILES: Cc1cc(-c2ccccc2)cc(C)c1C1=C(O)[C@@]2(C)C=C[C@H](O2)C1=O] | $\delta_H$ 7.56-7.25 (m, 7H), 6.41 (dd, 1H), 6.24 (dd, 1H), 5.76 (s, 1H), 5.43 (dd, 1H), 2.32 (s, 3H), 1.94 (s, 3H), 1.76 (s, 3H). |
| A-4 | 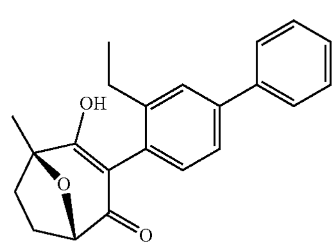 [SMILES: CCc1cc(-c2ccccc2)ccc1C1=C(O)[C@@]2(C)CC[C@H](O2)C1=O] | $\delta_H$ 7.59-7.04 (m, 8H), 5.9-5.7 (m, 1H), 4.87 and 4.70 (d and m, 1H), 2.6-2.4 (m, 3H), 2.1-1.95 (m, 3H), 1.68 and 1.59 (2 × s, 3H), 1.18 and 1.13 (2 × t, 3H). |

TABLE A-continued

| Compound Number | Structure | ¹H NMR (CDCl₃ unless stated) or other physical data |
|---|---|---|
| A-5 | 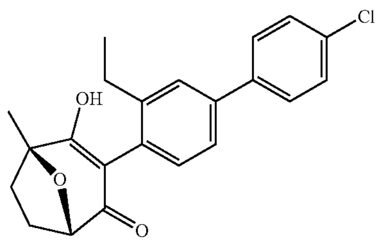 [SMILES: CCc1cc(-c2ccc(Cl)cc2)ccc1C1=C(O)[C@@]2(C)CC[C@H](O2)C1=O] | $\delta_H$ 7.52-7.4 (m, 6H), 7.17 and 7.05 (2 × d, 1H), 5.85 (br. s, 1H), 4.85 and 4.7 (2 × d, 1H), 2.6-2.3 (m, 3H), 2.1-1.9 (m, 3H), 1.67 and 1.58 (2 × s, 3H), 1.25 and 1.17 (2 × t, 3H). |
| A-6 | 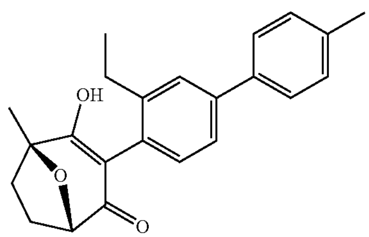 | $\delta_H$ 7.53-7.02 (m, 7H), 5.9-5.7 (br. s, 1H), 4.86 and 4.70 (m, 1H), 2.6-2.3 (m, 6H), 2.2-1.9 (m, 3H), 1.55 (s, 3H), 1.15 and 1.12 (2 × t, 3H). |
| A-7 | 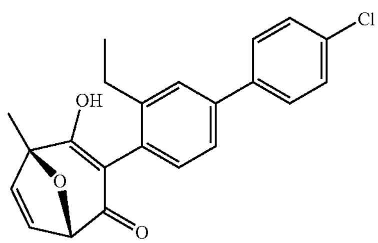 [SMILES: CCc1cc(-c2ccc(Cl)cc2)ccc1C1=C(O)[C@@]2(C)C=C[C@H](O2)C1=O] | $\delta_H$ 7.5-7.33 (m, 7H), 6.4 (dd, 1H), 6.25 (d, 1H), 5.42 (s, 1H), 5.4 (d, 1H), 2.5 (m, 2H), 1.73 (s, 3H), 1.18 (t, 3H). |
| A-8 | 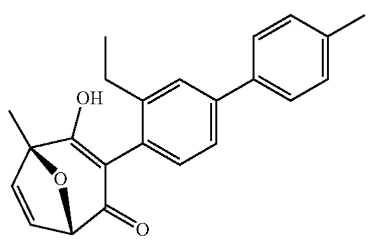 | $\delta_H$ 7.48-7.22 (m, 7H), 6.4 (m, 1H), 6.25 (d, 1H), 5.41 (s, 1H), 5.39 (s, 1H), 2.52 (m, 2H), 2.38 (s, 3H), 1.73 (s, 3H), 1.15 (t, 3H). |
| A-9 | 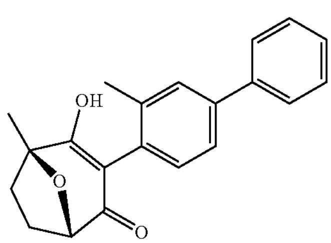 [SMILES: Cc1cc(-c2ccccc2)ccc1C1=C(O)[C@@]2(C)CC[C@H](O2)C1=O] | $\delta_H$ 7.6-7.1 (m, 8H), 5.9-5.7 (br. s, 1H), 4.8-4.6 (m, 1H), 2.26 (s, 3H), 1.9-2.2 (m, 4H), 1.6 (s, 3H). |
| A-10 | 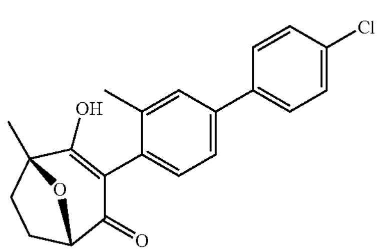 [SMILES: Cc1cc(-c2ccc(Cl)cc2)ccc1C1=C(O)[C@@]2(C)CC[C@H](O2)C1=O] | $\delta_H$ 7.5-7.0 (m, 7H), 5.9-5.7 (br. s, 1H), 4.86 and 4.7 (2 × d, 1H), 2.5-2.4 (m, 1H), 2.16 and 2.11 (2 × s, 3H), 2.1-1.9 (m, 3H), 1.56 (s, 3H). |

TABLE A-continued

| Compound Number | Structure | ¹H NMR (CDCl₃ unless stated) or other physical data |
|---|---|---|
| A-11 | 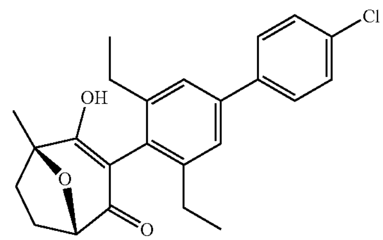 [SMILES: CCc1cc(-c2ccc(Cl)cc2)cc(CC)c1C1=C(O)[C@@]2(C)CC[C@H](O2)C1=O] | $\delta_H$ 7.52-7.3 (m, 6H), 5.6 (br. s, 1H), 4.87 and 4.7 (2 × d, 1H), 2.6-2.45 (m, 3H), 2.4-2.3 (m, 2H), 2.2-1.9 (m, 3H), 1.67 and 1.61 (2 × s, 3H), 1.17 and 1.16 (2 × t, 6H). |
| A-12 | 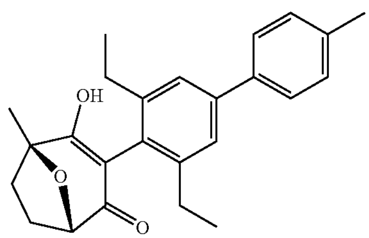 | $\delta_H$ 7.24-7.5 (m, 6H), 5.7 (br. s, 1H), 4.87 and 4.7 (2 × d, 1H), 2.6-1.9 (m, 11H), 1.67 and 1.58 (2 × s, 3H), 1.27-1.08 (m, 6 H). |
| A-13 | 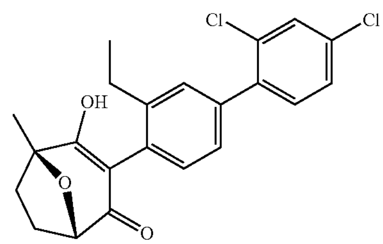 [SMILES: CCc1cc(-c2ccc(Cl)cc2Cl)ccc1C1=C(O)[C@@]2(C)CC[C@H](O2)C1=O] | $\delta_H$ 7.49 (s, 1H), 7.4-7.04 (m, 5H), 6.0 (m, 1H), 4.8 and 4.7 (2 × d, 1H), 2.6-2.3 (m, 3H), 2.1-1.9 (m, 3H), 1.55 (s, 3H), 1.2-1.1 (m, 3H). |
| A-14 | 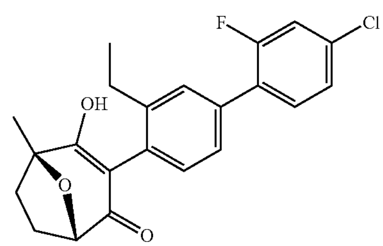 [SMILES: CCc1cc(-c2ccc(Cl)cc2F)ccc1C1=C(O)[C@@]2(C)CC[C@H](O2)C1=O] | $\delta_H$ 7.47-7.35 (m, 3H), 7.23-7.05 (m, 3H), 5.92-5.81 (m, 1H), 4.86 and 4.7 (2 × d, 1H), 2.6-2.3 (m, 3H), 2.2-1.9 (m, 3H), 1.68 and 1.58 (2 × s, 3H), 1.16 and 1.11 (2 × t, 3H). |
| A-15 | 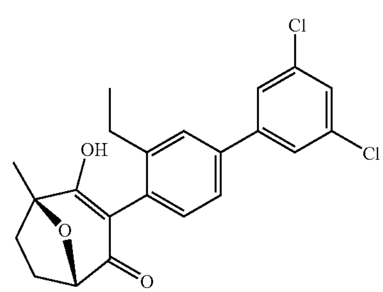 [SMILES: CCc1cc(-c2cc(Cl)cc(Cl)c2)ccc1C1=C(O)[C@@]2(C)CC[C@H](O2)C1=O] | $\delta_H$ 7.5-7.0 (m, 6H), 5.75 and 5.85 (2 × br. s, 1H), 4.86 and 4.7 (2 × d, 1H), 2.6-2.35 (m, 3H), 2.1-1.9 (m, 3H), 1.58 (s, 3H), 1.2-1.1 (m, 3H). |
| A-16 | 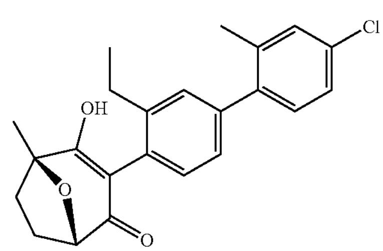 [SMILES: CCc1cc(-c2ccc(Cl)cc2C)ccc1C1=C(O)[C@@]2(C)CC[C@H](O2)C1=O] | $\delta_H$ 7.87 and 7.02 (2 × d, 1H), 7.27-7.14 (m, 5H), 5.6 (br. s., 1H), 5.06 and 4.87 (2 × d, 1H), 2.68-2.32 (m, 3H), 2.28 (s, 3H), 2.13-1.94 (m, 3H), 1.6 and 1.59 (2 × s, 3H), 1.16 and 1.1 (2 × t, 3H). |

TABLE A-continued

| Compound Number | Structure | $^1$H NMR (CDCl$_3$ unless stated) or other physical data |
|---|---|---|
| A-17 | 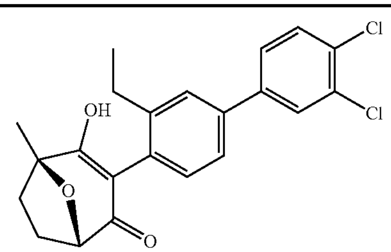 | δ$_H$ 7.67-7.65 (m, 1H), 7.52-7.39 (m, 4H), 7.19 and 7.06 (2 × d, 1H), 5.6 (br. s., 1H), 4.85 4.7 (2 × d, 1H), 2.7-2.38 (m, 3H), 2.12-1.95 (m, 3H), 1.52 (s, 3H), 1.18 and 1.12 (2 × t, 3H). |
| A-18 | 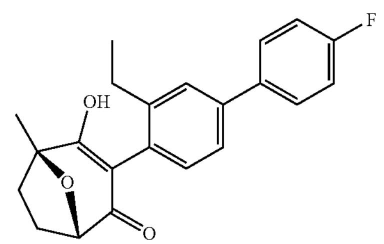 [SMILES: CCc1cc(-c2ccc(F)cc2)ccc1C1=C(O)[C@@]2(C)CC[C@H](O2)C1=O] | δ$_H$ 7.56-7.36 (m, 4 H), 7.15-7.10 (m, 3H), 5.66 (br. s, 1H), 4.93 and 4.86 (2 × d, 1H), 2.7-2.3 (m, 4H), 2.1-1.9 (m, 2H), 1.58 and 1.53 (2 × s, 3H), 1.25-1.1 (m, 3H). |
| A-19 | 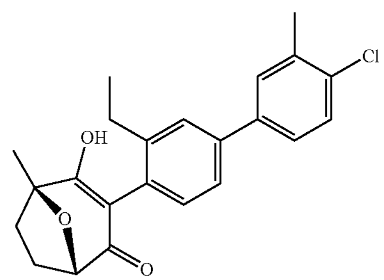 [SMILES: CCc1cc(-c2ccc(Cl)c(C)c2)ccc1C1=C(O)[C@@]2(C)CC[C@H](O2)C1=O] | δ$_H$ 7.49-7.32 (m, 5H), 7.1 7.02 (2 × d, 1H), 6.1 (br. s, 1H), 4.78 (br. s, 1H), 2.6-2.3 (m, 7 H), 2.1-1.9 (m, 2H), 1.66 (s, 3H), 1.16 and 1.11 (2 × t, 3H). |
| A-20 | 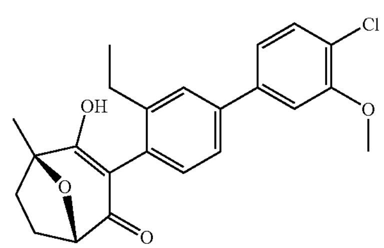 | δ$_H$ (CDCl$_3$/CD$_3$OD) 7.55-7.25 (m, 3H), 7.2-7.0 (m, 3H), 4.82 (br. s, 1H), 3.98 (s, 3H), 2.8-2.5 (m, 1H), 2.5-2.35 (m, 2H), 2.15-1.85 (m, 3H), 1.59 (3H, s), 1.22-1.06 (m, 3H). |
| A-21 | 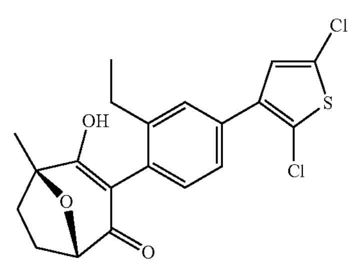 [SMILES: CCc1cc(-c2cc(Cl)sc2Cl)ccc1C1=C(O)[C@@]2(C)CC[C@H](O2)C1=O] | δ$_H$ (CDCl$_3$/CD$_3$OD) 7.44-7.34 (m, 2H), 7.15 and 7.06 (2 × d, 1H), 6.91 (s, 1H), 4.79 (br. s, 1H), 2.7-2.5 (m, 1H), 2.5-2.35 (m, 2H), 2.15-1.9 (m, 3H), 1.59 (s, 3H), 1.18 and 1.13 (2 × t, 3H). |
| A-22 | 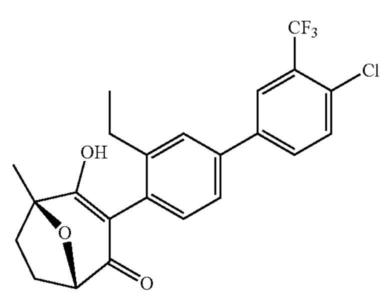 [SMILES: CCc1cc(-c2ccc(Cl)c(C(F)(F)F)c2)ccc1C1=C(O)[C@@]2(C)CC[C@H](O2)C1=O] | δ$_H$ (CDCl$_3$/CD$_3$OD) 7.87 (s,1H), 7.67 (d, 1H), 7.52 (d, 1H), 7.47-7.35 (m, 2H), 7.17 and 7.05 (2 × d, 1H), 4.79 (br. s, 1H), 2.7-2.5 (m, 1H), 2.5-2.35 (m, 2H), 2.15-1.9 (m, 3H), 1.59 (s, 3H), 1.18 and 1.13 (2 × t, 3 H). |

TABLE A-continued

| Compound Number | Structure | ¹H NMR (CDCl₃ unless stated) or other physical data |
|---|---|---|
| A-23 | 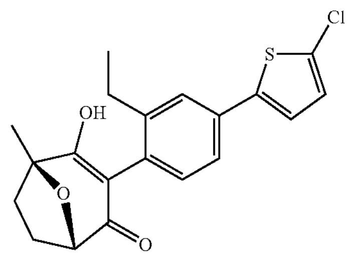 [SMILES: CCc1cc(-c2ccc(Cl)s2)ccc1C1=C(O)[C@@]2(C)CC[C@H](O2)C1=O] | $\delta_H$ (CDCl₃/CD₃OD) 7.34 (d, 2H), 7.08 (s, 1H), 7.01 (d, 1H), 6.96 (s, 1H), 4.79 (br. s, 1H), 2.7-2.5 (m, 1H), 2.5-2.3 (m, 2H), 2.15-1.9 (m, 3H), 1.59 (s, 3H), 1.2-1.07 (m, 3H). |
| A-24 | 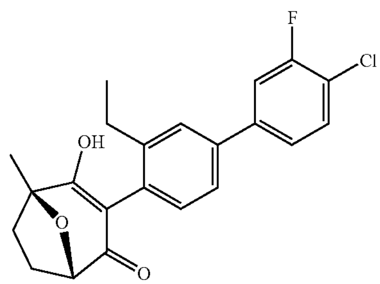 [SMILES: CCc1cc(-c2ccc(Cl)c(F)c2)ccc1C1=C(O)[C@@]2(C)CC[C@H](O2)C1=O] | $\delta_H$ (CDCl₃/CD₃OD) 7.50-7.31 (m, 5H), 7.17 and 7.08 (2 × d, 1H), 4.81 (br. s, 1H), 2.7-2.5 (m, 1H), 2.5-2.35 (m, 2H), 2.15-1.9 (m, 3H), 1.59 (s, 3H), 1.18 and 1.13 (2 × t, 3H). |
| A-25 | 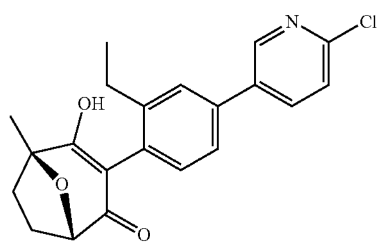 [SMILES: CCc1cc(-c2ccc(Cl)nc2)ccc1C1=C(O)[C@@]2(C)CC[C@H](O2)C1=O] | $\delta_H$ (CDCl₃/CD₃OD) 8.4 (s, 1H), 7.84 (dd, 1H), 7.4-7.3 (m, 3H), 7.2 and 7.1 (2 × d, 1H), 4.8 (br. s, 1H), 2.7-2.5 (m, 1H), 2.5-2.35 (m, 2H), 2.15-1.9 (m, 3H), 1.59 (s, 3H), 1.18 and 1.13 (2 × t, 3H). |
| A-26 | 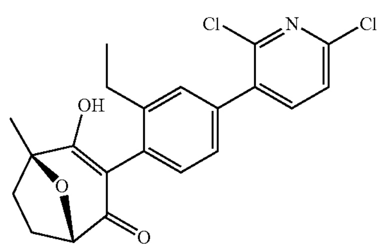 [SMILES: CCc1cc(-c2ccc(Cl)nc2Cl)ccc1C1=C(O)[C@@]2(C)CC[C@H](O2)C1=O] | $\delta_H$ (CDCl₃/CD₃OD) 7.69 (d, 1H), 7.34 (d, 1H), 7.32-7.24 (m, 2H), 7.2 and 7.1 (2 × d, 1H), 4.8 (br. s, 1H), 2.8-2.5 (m, 1H), 2.5-2.35 (m, 2H), 2.15-1.9 (m, 3H), 1.59 (s, 3H), 1.16 and 1.11 (2 × t, 3H). |
| A-27 | 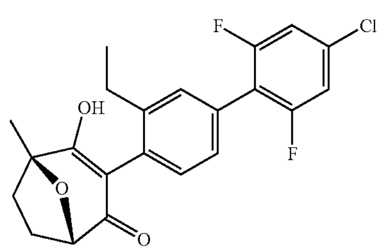 [SMILES: CCc1cc(-c2c(F)cc(Cl)cc2F)ccc1C1=C(O)[C@@]2(C)CC[C@H](O2)C1=O] | $\delta_H$ (CDCl₃/CD₃OD) 7.35-7.15 (m, 3H), 7.1-6.99 (m, 2H), 4.78 (br. s, 1H), 2.8-2.5 (m, 1H), 2.5-2.35 (m, 2H), 2.15-1.9 (m, 3H), 1.59 (s, 3H), 1.16 and 1.11 (2 × t, 3H). |
| A-28 | 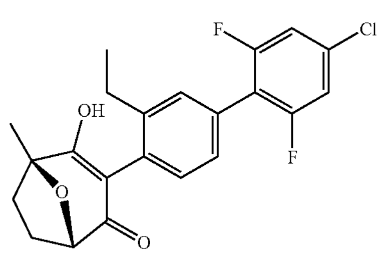 [SMILES: CCc1cc(-c2c(F)cc(Cl)cc2F)ccc1C1=C(O)[C@@]2(C)CC[C@H](O2)C1=O] | $\delta_H$ (CDCl₃/CD₃OD) 7.39-7.16 (m, 3H), 7.1-6.98 (m, 2H), 4.78 (br. s, 1H), 2.8-2.5 (m, 1H), 2.5-2.35 (m, 2H), 2.15-1.9 (m, 3H), 1.59 (s, 3H), 1.16 and 1.11 (2 × t, 3H). |

TABLE A-continued

| Compound Number | Structure | ¹H NMR (CDCl₃ unless stated) or other physical data |
|---|---|---|
| A-29 | 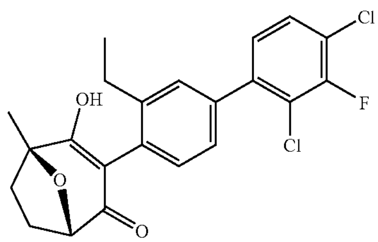 [SMILES: CCc1cc(-c2ccc(Cl)c(F)c2Cl)ccc1C1=C(O)[C@@]2(C)CC[C@H](O2)C1=O] | $\delta_H$ (CDCl₃/CD₃OD) 7.44-7.08 (m, 5H), 4.8 (br. s, 1H), 2.75-2.54 (m, 1H), 2.54-2.35 (m, 2H), 2.15-1.9 (m, 3H), 1.59 (s, 3H), 1.16 and 1.11 (2 × t, 3 H). |
| A-30 | 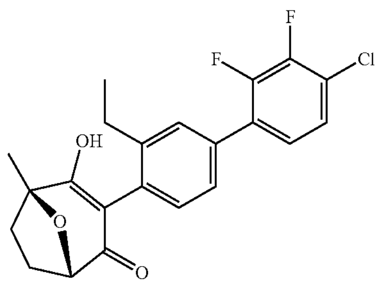 [SMILES: CCc1cc(-c2ccc(Cl)c(F)c2F)ccc1C1=C(O)[C@@]2(C)CC[C@H](O2)C1=O] | $\delta_H$ (CDCl₃/CD₃OD) 7.4-7.04 (m, 5H), 4.78 (br. s, 1H), 2.75-2.54 (m, 1H), 2.54-2.35 (m, 2H), 2.15-1.9 (m, 3H), 1.59 (s, 3H), 1.16 and 1.11 (2 × t, 3H). |
| A-31 | 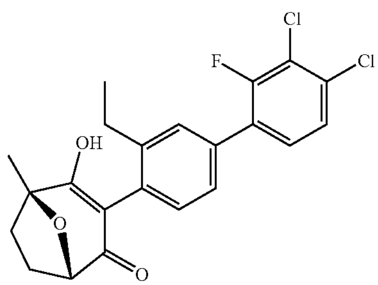 | $\delta_H$ (CDCl₃/CD₃OD) 7.6-7.08 (m, 5H), 4.78 (br. s, 1H), 2.95-2.5 (m, 1H), 2.5-2.35 (m, 2H), 2.2-1.9 (m, 3H), 1.59 (s, 3H), 1.16 and 1.11 (2 × t, 3H). |
| A-32 | 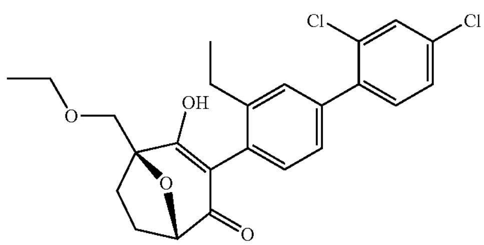 [SMILES: CCOC[C@]12CC[C@H](O1)C(=O)C(c1ccc(-c3ccc(Cl)cc3Cl)cc1CC)=C2O] | LC-MS (ES−): 448, 446 (M − H)⁻ |
| A-33 | 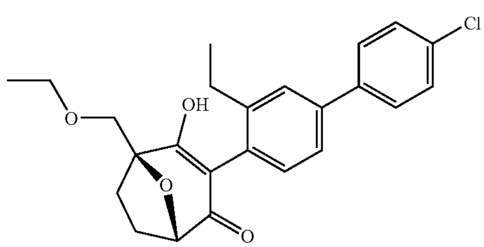 [SMILES: CCOC[C@]12CC[C@H](O1)C(=O)C(c1ccc(-c3ccc(Cl)cc3)cc1CC)=C2O] | LC-MS (ES−): 414, 412 (M − H)⁻ |
| A-34 | 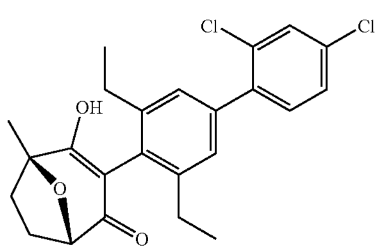 [SMILES: CCc1cc(-c2ccc(Cl)cc2Cl)cc(CC)c1C1=C(O)[C@@]2(C)CC[C@H](O2)C1=O] | $\delta_H$ 7.49 (s, 1H), 7.3 (d, 2H), 7.2 (t, 2H), 5.9 and 5.8 (2 × s, 1H), 4.87 and 4.73 (2 × d, 1H), 2.57-2.42 (m, 3H), 2.39-2.18 (m, 3H), 2.15-1.93 (m, 2H), 1.67 and 1.59 (2 × s, 3H), 1.16-1.06 (m, 6H). |

TABLE A-continued

| Compound Number | Structure | $^1$H NMR (CDCl$_3$ unless stated) or other physical data |
|---|---|---|
| A-35 | 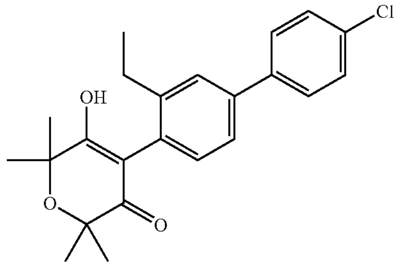 [SMILES: CCc1cc(-c2ccc(Cl)cc2)ccc1C1=C(O)C(C)(C)OC(C)(C)C1=O] | $\delta_H$ 7.60-6.7 (m, 7H), 5.6 (s, 1H), 2.52-2.3 (2H, m), 1.7-1.4 (m, 12H), 1.2-1.1 (m, 3H). |
| A-36 | 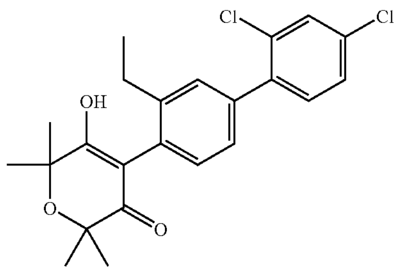 [SMILES: CCc1cc(-c2ccc(Cl)cc2Cl)ccc1C1=C(O)C(C)(C)OC(C)(C)C1=O] | $\delta_H$ 7.50-7.13 (m, 6H), 5.75 (s, 1H), 2.51-2.30 (m, 2H), 1.63 (2 × s, 6H), 1.47 (s, 6H), 1.17-1.12 (m, 3H). |
| A-37 | 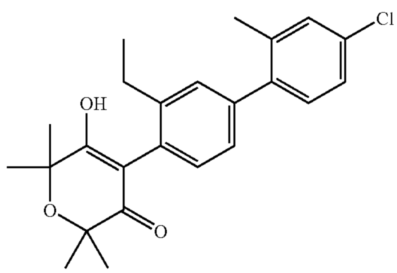 [SMILES: CCc1cc(-c2ccc(Cl)cc2C)ccc1C1=C(O)C(C)(C)OC(C)(C)C1=O] | $\delta_H$ 7.30-6.67 (m, 6H), 5.65 (s, 1H), 2.50-2.35 (m, 2H), 2.3 (s, 3H), 1.62-1.42 (m, 12H), 1.18-1.11 (m, 3H). |
| A-38 | 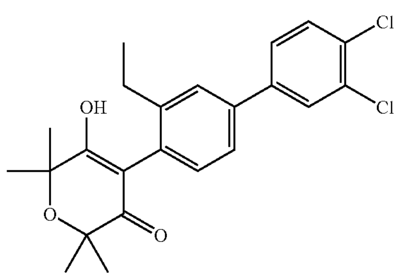 [SMILES: CCc1cc(-c2ccc(Cl)c(Cl)c2)ccc1C1=C(O)C(C)(C)OC(C)(C)C1=O] | $\delta_H$ (DMSO-d6): 10.42 (s, 1H), 7.96 (s, 1H), 7.7 (s, 2H), 7.58 (d, 1H), 7.5 (dd, 1H), 7.0 (d, 1H), 2.4 (q, 2H), 1.5 (s, 6H), 1.35 (s, 6H), 1.07 (t, 3H). |
| A-39 | 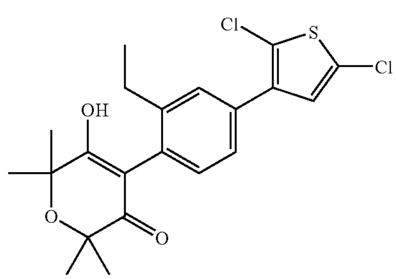 [SMILES: CCc1cc(-c2cc(Cl)sc2Cl)ccc1C1=C(O)C(C)(C)OC(C)(C)C1=O] | $\delta_H$ 7.49 (d, 1H), 7.43 (dd, 1H), 7.13 (d, 1H), 6.92 (s, 1H), 5.62 (s, 1H), 2.55-2.40 (m, 2H), 1.61 (s, 6H), 1.50 (s, 3H), 1.49 (s, 3H), 1.15 (t, 3H). |

TABLE A-continued

| Compound Number | Structure | ¹H NMR (CDCl₃ unless stated) or other physical data |
|---|---|---|
| A-40 | 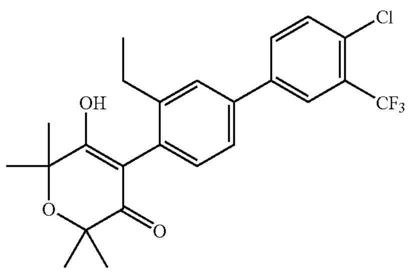 [SMILES: CCc1cc(-c2ccc(Cl)c(C(F)(F)F)c2)ccc1C1=C(O)C(C)(C)OC(C)(C)C1=O] | $\delta_H$ 7.89 (d, 1H), 7.69 (dd, 1H), 7.58 (d, 1H), 7.51 (d, 1H), 7.45 (dd, 1H), 7.18 (d, 1H), 5.63 (s, 1H), 2.57-2.45 (m, 2H), 1.61 (s, 6H), 1.50 (s, 3H), 1.49 (s, 3H), 1.16 (t, 3H). |
| A-41 | 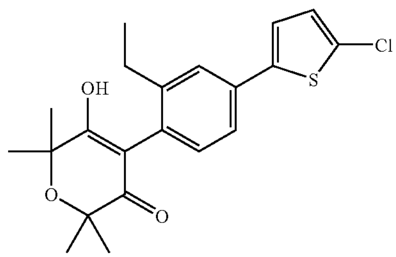 [SMILES: CCc1cc(-c2ccc(Cl)s2)ccc1C1=C(O)C(C)(C)OC(C)(C)C1=O] | $\delta_H$ 7.46 (s, 1 H), 7.40 (dd, 1 H), 7.10 (d, 1 H), 7.08 (d, 1 H), 6.90 (d, 1 H), 5.64 (s, 1 H), 2.51-2.41 (m, 2 H), 1.60 (s, 6 H), 1.49 (s, 3 H), 1.48 (s, 3 H), 1.14 (t, 3 H). |
| A-42 | 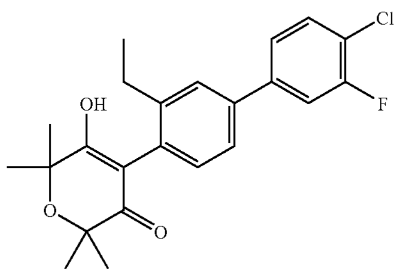 | $\delta_H$ 7.51 (d, 1H), 7.46 (d, 1H), 7.45 (dd, 1H), 7.38 (dd, 1H), 7.33 (dd, 1H), 7.17 (d, 1H), 5.54 (s, 1H), 2.58-2.44 (m, 2H), 1.62 (s, 6H), 1.50 (s, 3H), 1.49 (s, 3H), 1.16 (t, 3H). |
| A-43 | 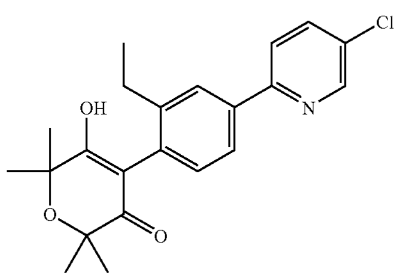 | $\delta_H$ 7.96 (d, 1H), 7.76 (dd, 1H), 7.34 (d, 1H), 7.29 (d, 1H), 7.26 (dd, 1H), 7.20 (d, 1H), 5.6 (s, 1H), 2.66-2.42 (m, 2H), 1.66 (s, 6H), 1.51 (s, 6H), 1.16 (t, 3H). |
| A-44 | 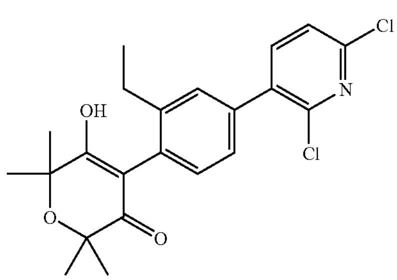 [SMILES: CCc1cc(-c2ccc(Cl)nc2Cl)ccc1C1=C(O)C(C)(C)OC(C)(C)C1=O] | $\delta_H$ 7.67 (d, 1H), 7.42 (d, 1 H), 7.37 (d, 1H), 7.36 (dd, 1 H), 7.18 (d, 1 H), 5.67 (s, 1 H), 2.57-2.45 (m, 2 H), 1.63 (s, 6 H), 1.51 (s, 3 H), 1.50 (s, 3 H), 1.16 (t, 3 H). |

TABLE A-continued

| Compound Number | Structure | ¹H NMR (CDCl₃ unless stated) or other physical data |
|---|---|---|
| A-45 | 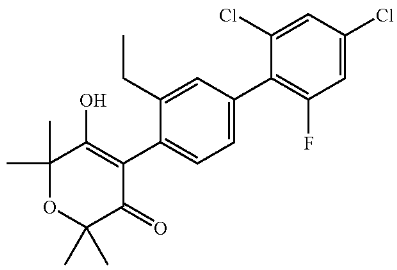 [SMILES: CCc1cc(-c2c(F)cc(Cl)cc2Cl)ccc1C1=C(O)C(C)(C)OC(C)(C)C1=O] | δ_H 7.33 (d, 1H), 7.28-7.24 (m, 2H), 7.19-7.15 (m, 1H), 7.13 (dd, 1H), 5.76-5.69 (m, 1H), 2.59-2.40 (m, 2H), 1.62 (s, 6H), 1.51 (s, 3H), 1.50 (s, 3H), 1.15 (t, 3H). |
| A-46 | 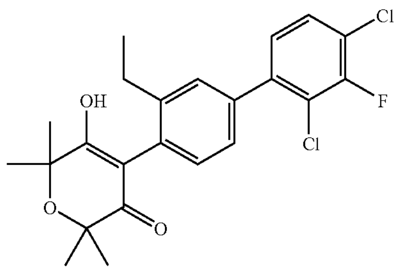 [SMILES: CCc1cc(-c2ccc(Cl)c(F)c2Cl)ccc1C1=C(O)C(C)(C)OC(C)(C)C1=O] | δ_H 7.39 (s, 1H), 7.36 (dd, 1H), 7.34 (dd, 1H), 7.16 (d, 1H), 7.12 (dd, 1H), 5.64 (s, 1H), 2.55-2.45 (m, 2H), 1.63 (s, 6H), 1.51 (s, 3H), 1.50 (s, 3H), 1.15 (t, 3H). |
| A-47 | 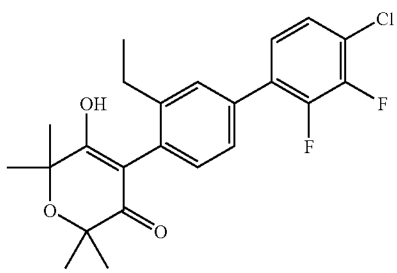 [SMILES: CCc1cc(-c2ccc(Cl)c(F)c2F)ccc1C1=C(O)C(C)(C)OC(C)(C)C1=O] | δ_H 7.49 (s, 1H), 7.43 (dt, 1H), 7.25 (s, 1H), 7.18 (d, 2H), 5.55 (s, 1H), 2.56-2.45 (m, 2H), 1.62 (s, 6H), 1.51 (s, 3H), 1.50 (s, 3H), 1.16 (t, 3H). |
| A-48 | 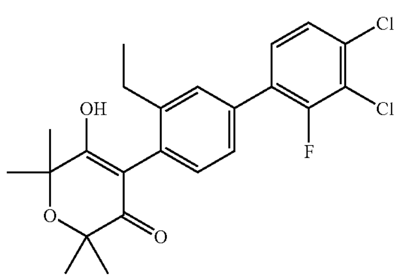 [SMILES: CCc1cc(-c2ccc(Cl)c(Cl)c2F)ccc1C1=C(O)C(C)(C)OC(C)(C)C1=O] | δ_H 7.47 (s, 1H), 7.41 (ddd, 1H), 7.34 (t, 1H), 7.30 (t, 1H), 7.17 (d, 1H), 5.66 (s, 1H), 2.55-2.45 (m, 2H), 1.62 (s, 6H), 1.50 (s, 3H), 1.49 (s, 3H), 1.15 (t, 3H). |
| A-49 | 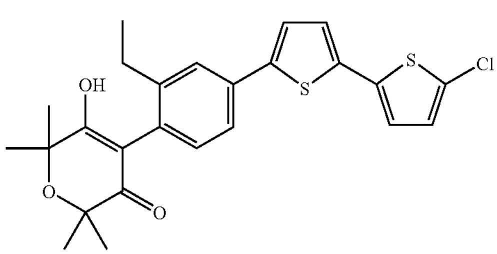 [SMILES: CCc1cc(-c2ccc(-c3ccc(Cl)s3)s2)ccc1C1=C(O)C(C)(C)OC(C)(C)C1=O] | δ_H 7.55 (s, 1H), 7.49 (d, 1H), 7.24 (d, 1H), 7.10 (d, 1H), 7.08 (d, 1H), 6.97 (d, 1H), 6.86 (d, 1H), 5.54 (s, 1H), 2.54-2.43 (m, 2H), 1.61 (s, 6H), 1.50 (s, 3H), 1.49 (s, 3H), 1.16 (t, 3H). |

TABLE A-continued

| Compound Number | Structure | ¹H NMR (CDCl₃ unless stated) or other physical data |
|---|---|---|
| A-50 | 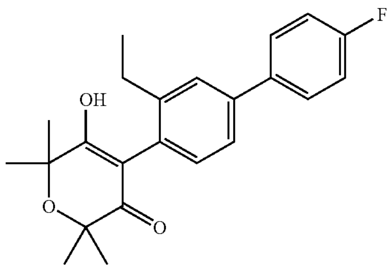 | $\delta_H$ (DMSO-d₆) 10.34 (s, 1H), 7.74-7.70 (m, 2H), 7.49 (s, 1H), 7.43-7.41 (dd,1H), 7.29 (t, 2H), 6.99 (d, 1H), 2.4 (m, 2H), 1.52 (s, 6H), 1.34 (s, 6H), 1.07 (t, 3H). |
| A-51 | 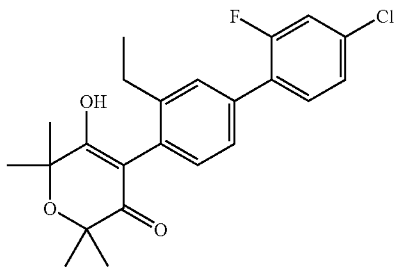 [SMILES: CCc1cc(-c2ccc(Cl)cc2F)ccc1C1=C(O)C(C)(C)OC(C)(C)C1=O] | $\delta_H$ (DMSO-d₆) 10.44 (s, 1H), 7.7-6.7 (m, 6H), 2.4 (m, 2H), 1.52 (s, 3H), 1.36 (s, 6H), 1.23 (s, 3H), 1.14-1.06 (m, 3H). |
| A-52 | 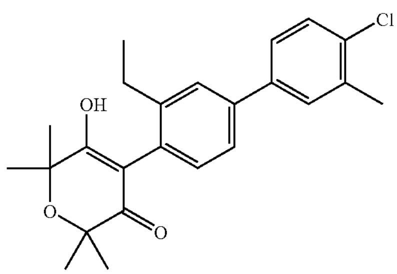 | $\delta_H$ (DMSO-d₆) 10.36 (s, 1H), 7.69 (d, 1H), 7.55-7.43 (m, 4H), 7.0 (d, 1H), 2.4 (m, 5H), 1.52 (s, 6H), 1.35 (s, 6H), 1.07 (t, 3H). |
| A-53 | 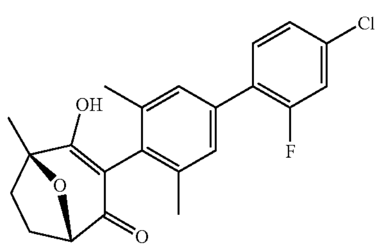 [SMILES: Cc1cc(-c2ccc(Cl)cc2F)cc(C)c1C1=C(O)[C@@]2(C)CC[C@H](O2)C1=O] | $\delta_H$ (DMSO-d₆) 11.25 (s, 1H), 7.57-7.51 (m, 2H), 7.38 (dd, 1H), 7.17 (d, 2H), 4.86 (s, 1H), 2.4-2.3 (m, 2H), 2.07 (s, 3H), 1.96 (s, 3H), 1.92-1.86 (m, 2H), 1.4 (s, 3H). |
| A-54 | 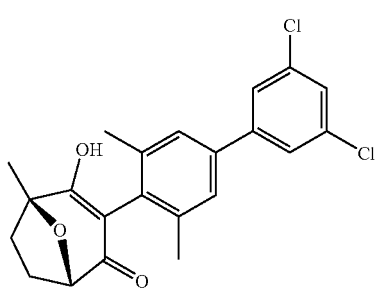 [SMILES: Cc1cc(-c2cc(Cl)cc(Cl)c2)cc(C)c1C1=C(O)[C@@]2(C)CC[C@H](O2)C1=O] | LC-MS (ES−): 403, 401 (M − H)⁻ |
| A-55 | 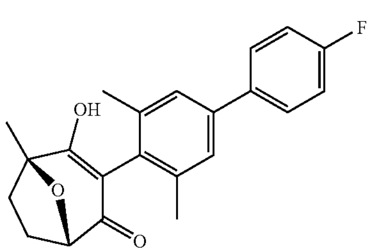 [SMILES: Cc1cc(-c2ccc(F)cc2)cc(C)c1C1=C(O)[C@@]2(C)CC[C@H](O2)C1=O] | LC-MS (ES−): 351 (M − H)⁻ |

TABLE A-continued

| Compound Number | Structure | ¹H NMR (CDCl₃ unless stated) or other physical data |
|---|---|---|
| A-56 | 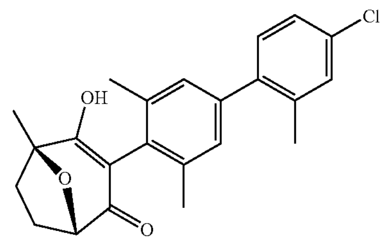 [SMILES: Cc1cc(Cl)ccc1-c1cc(C)c(C2=C(O)[C@@]3(C)CC[C@H](O3)C2=O)c(C)c1] | $\delta_H$ 7.3-7.0 (m, 6H), 5.6 (br. s, 1H), 5.1-4.7 (m, 1H), 2.6-2.3 (m, 3H), 2.28 (s, 3H), 2.15-1.9 (m, 3H), 1.6 (s, 3H), 1.18-1.08 (m, 3H). |
| A-57 | 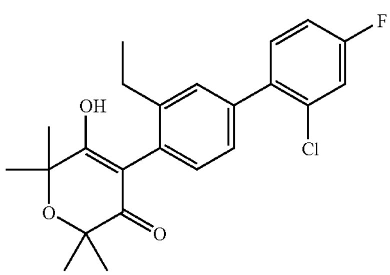 | $\delta_H$ 7.40 (s, 1H), 7.35 (m, 2H), 7.25 (dd, 1H), 7.15 (d, 1H), 7.05 (dt, 1H), 5.80 (s, 1H), 2.50 (m, 2H), 1.60 (s, 6H), 1.50 (2 × s, 6H), 1.15 (t, 3H). |
| A-58 | 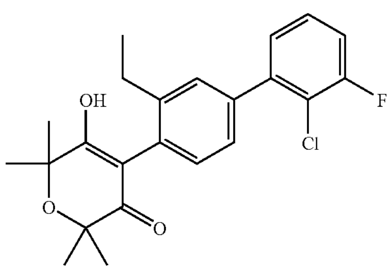 | $\delta_H$ 7.40 (s, 1H), 7.35 (dd, 1H), 7.30 (m, 1H), 7.20-7.10 (m, 3H), 5.75 (s, 1H), 2.50 (m, 2H), 1.65 (s, 6H), 1.50 (2 × s, 6H), 1.15 (3H, t). |
| A-59 | 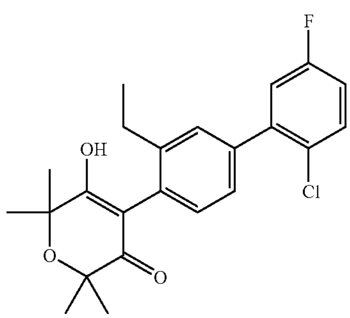 | $\delta_H$ 7.45 (m, 2H), 7.35 (dd, 1H), 7.15 (d, 1H), 7.10 (dd, 1H), 7.00 (m, 1H), 5.70 (s, 1H), 2.50 (m, 2H), 1.65 (s, 6H), 1.50 (2 × s, 6H), 1.15 (t, 3H). |
| A-60 | 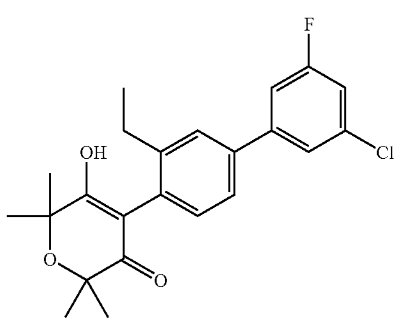 | $\delta_H$ 7.50 (s, 1H), 7.45 (dd, 1H), 7.35 (s, 1H), 7.20 (m, 1H), 7.15 (d, 1H), 7.10 (m, 1H), 5.55 (s, 1H), 2.50 (m, 2H), 1.60 (s, 6H), 1.50 (2 × s, 6H), 1.15 (t, 3H). |

| Compound Number | Structure | ¹H NMR (CDCl₃ unless stated) or other physical data |
|---|---|---|
| A-61 | 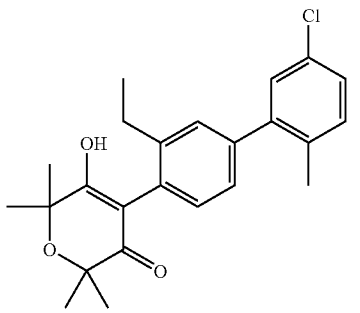 | $\delta_H$ 7.30-7.15 (m, 5H), 7.10 (d, 1H), 5.65 (s, 1H), 2.50 (m, 2H), 2.25 (s, 3H), 1.65 (s, 6H), 1.50 (2 × s, 6H), 1.15 (t, 3H). |
| A-62 | 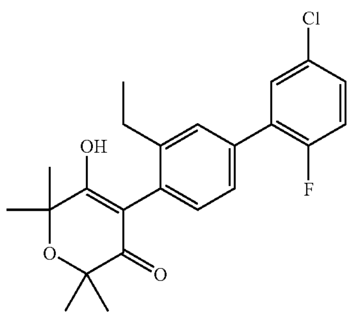 [SMILES: CCc1cc(-c2cc(Cl)ccc2F)ccc1C1=C(O)C(C)(C)OC(C)(C)C1=O] | $\delta_H$ 7.50 (s, 1H), 7.45 (m, 2H), 7.30 (m, 1H), 7.20-7.05 (m, 2H), 5.60 (s, 1H), 2.50 (m, 2H), 1.60 (s, 6H), 1.50 (2 × s, 6H), 1.15 (t, 3H). |
| A-63 | 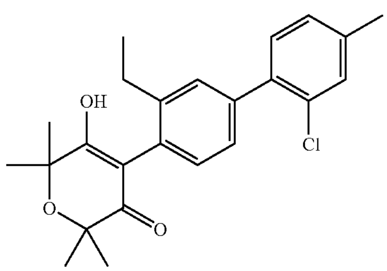 | $\delta_H$ 7.40 (s, 1H), 7.35 (dd, 1H), 7.30 (s, 1H), 7.25 (d, 1H), 7.15-7.10 (m, 2H), 5.80 (br. s, 1H), 2.50 (m, 2H), 2.40 (s, 3H), 1.60 (s, 6H), 1.50 (2 × s, 6H), 1.15 (t, 3H). |
| A-64 | 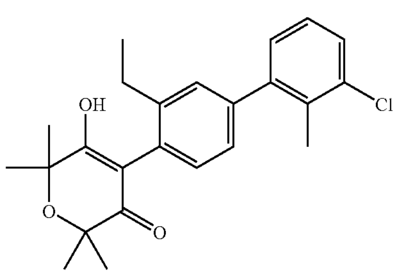 [SMILES: CCc1cc(-c2cccc(Cl)c2C)ccc1C1=C(O)C(C)(C)OC(C)(C)C1=O] | $\delta_H$ 7.40 (dd, 1H), 7.25 (d, 1H), 7.20-7.10 (m, 4H), 5.75 (s, 1H), 2.50 (m, 2H), 2.30 (s, 3H), 1.60 (s, 6H), 1.50 (2 × s, 6H), 1.15 (t, 3H). |
| A-65 | 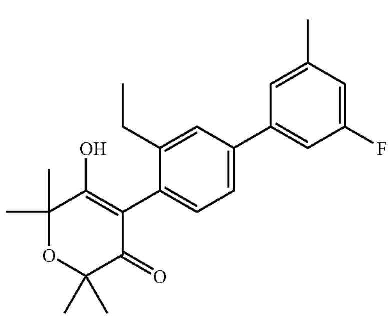 [SMILES: CCc1cc(-c2cc(C)cc(F)c2)ccc1C1=C(O)C(C)(C)OC(C)(C)C1=O] | $\delta_H$ 7.50 (s, 1H), 7.45 (dd, 1H), 7.20 (s, 1H), 7.15 (d, 1H), 7.10 (d, 1H), 6.90 (d, 1H), 5.60 (s, 1H), 2.50 (m, 2H), 2.45 (s, 3H), 1.60 (s, 6H), 1.50 (2 × s, 6H), 1.15 (t, 3H). |

TABLE A-continued

| Compound Number | Structure | ¹H NMR (CDCl₃ unless stated) or other physical data |
|---|---|---|
| A-66 | 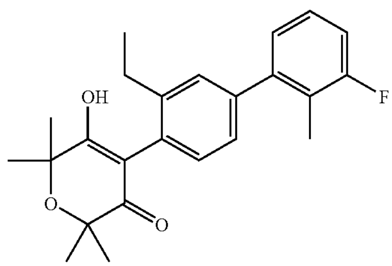 [SMILES: CCc1cc(-c2cccc(F)c2C)ccc1C1=C(O)C(C)(C)OC(C)(C)C1=O] | $\delta_H$ 7.30 (s, 1H), 7.25-7.20 (m, 2H), 7.15 (d, 1H), 7.05-7.00 (m, 2H), 5.65 (br. s, 1H), 2.50 (m, 2H), 2.20 (d, 3H), 1.65 (s, 6H), 1.50 (2 × s, 6H), 1.15 (t, 3H). |
| A-67 | 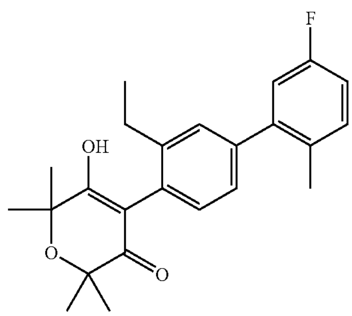 [SMILES: CCc1cc(-c2cc(F)ccc2C)ccc1C1=C(O)C(C)(C)OC(C)(C)C1=O] | $\delta_H$ 7.30 (s, 1H), 7.25-7.20 (m, 2H), 7.15 (d, 1H), 7.00-6.90 (m, 2H), 5.60 (s, 1H), 2.50 (m, 2H), 2.25 (s, 3H), 1.65 (s, 6H), 1.50 (2 × s, 6H), 1.15 (t, 3H). |
| A-68 | 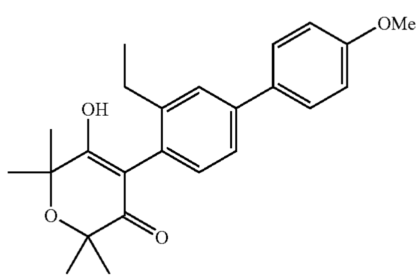 [SMILES: CCc1cc(-c2ccc(OC)cc2)ccc1C1=C(O)C(C)(C)OC(C)(C)C1=O] | $\delta_H$ 7.55 (m, 3H), 7.45 (dd, 1H), 7.15 (d, 1H), 7.00 (d, 2H), 5.65 (br. s, 1H), 3.85 (s, 3H), 2.50 (m, 2H), 1.60 (s, 6H), 1.50 (2 × s, 6H), 1.15 (t, 3H). |
| A-69 | 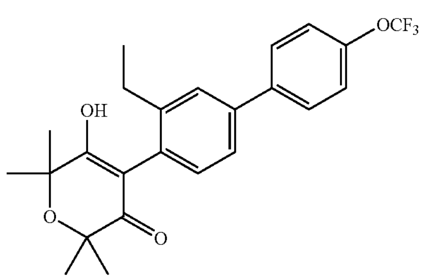 [SMILES: CCc1cc(-c2ccc(OC(F)(F)F)cc2)ccc1C1=C(O)C(C)(C)OC(C)(C)C1=O] | $\delta_H$ 7.60 (d, 2H), 7.50 (s, 1H), 7.45 (dd, 1H), 7.30 (d, 2H), 7.15 (d, 1H), 5.60 (br. s, 1H), 2.50 (m, 2H), 1.60 (s, 6H), 1.50 (2 × s, 6H), 1.15 (t, 3H). |
| A-70 | 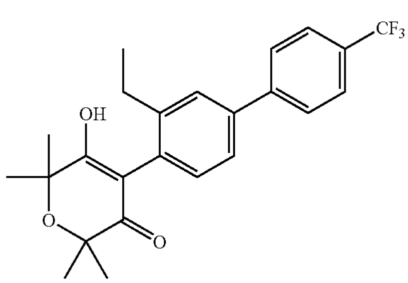 [SMILES: CCc1cc(-c2ccc(C(F)(F)F)cc2)ccc1C1=C(O)C(C)(C)OC(C)(C)C1=O] | $\delta_H$ 7.70 (s, 4H), 7.55 (d, 1H), 7.50 (dd, 1H), 7.20 (d, 1H), 5.60 (br. s, 1H), 2.50 (m, 2H), 1.60 (s, 6H), 1.50 (2 × s, 6H), 1.15 (t, 3H). |

TABLE A-continued

| Compound Number | Structure | $^1$H NMR (CDCl$_3$ unless stated) or other physical data |
|---|---|---|
| A-71 | 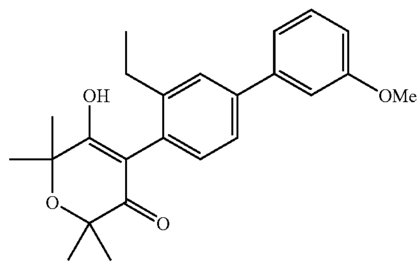 [SMILES: CCc1cc(-c2cccc(OC)c2)ccc1C1=C(O)C(C)(C)OC(C)(C)C1=O] | δ$_H$ 7.55 (d, 1H), 7.50 (dd, 1H), 7.35 (t, 1H), 7.20 (dd, 1H), 7.15-7.10 (m, 2H), 6.90 (dd, 1H), 5.65 (br. s, 1H), 3.90 (s, 3H), 2.50 (m, 2H), 1.60 (s, 6H), 1.50 (2 × s, 6H), 1.15 (t, 3H). |
| A-72 | 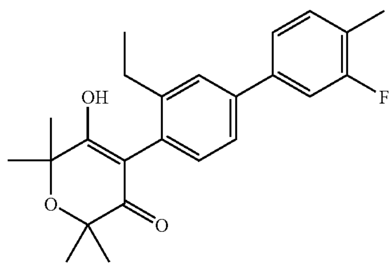 | δ$_H$ 7.55 (s, 1H), 7.45 (dd, 1H), 7.30-7.20 (m, 3H), 7.15 (d, 1H), 6.60 (s, 1H), 2.50 (m, 2H), 2.30 (s, 3H), 1.60 (s, 6H), 1.50 (2 × s, 6H), 1.15 (t, 3H). |
| A-73 | 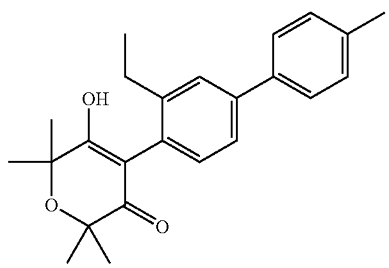 | δ$_H$ 7.55 (s, 1H), 7.50 (d, 2H), 7.45 (d, 1H), 7.35 (d, 2H), 7.15 (d, 1H), 5.65 (s, 1H), 2.50 (m, 2H), 2.40 (s, 3H), 1.65 (s, 6H), 1.50 (2 × s, 6H), 1.15 (t, 3H). |
| A-74 | 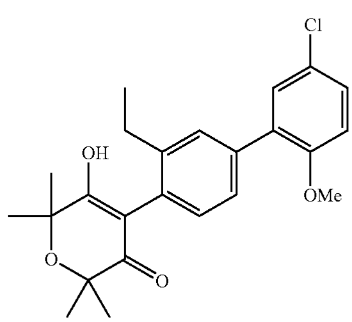 [SMILES: CCc1cc(-c2cc(Cl)ccc2OC)ccc1C1=C(O)C(C)(C)OC(C)(C)C1=O] | δ$_H$ 7.45 (s, 1H), 7.40 (dd, 1H), 7.30-7.25 (m, 2H), 7.10 (d, 1H), 6.90 (d, 1H), 5.80 (br. s, 1H), 3.80 (s, 3H), 2.50 (m, 2H), 1.60 (s, 6H), 1.50 (2 × s, 6H), 1.15 (t, 3H). |
| A-75 | 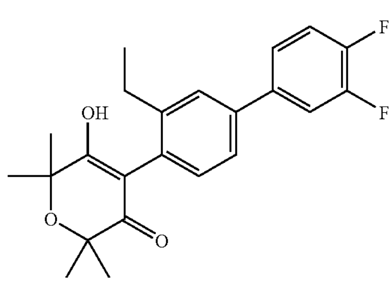 [SMILES: CCc1cc(-c2ccc(F)c(F)c2)ccc1C1=C(O)C(C)(C)OC(C)(C)C1=O] | δ$_H$ 7.50 (s, 1H), 7.45-7.35 (m, 2H), 7.30 (m, 1H), 7.25 (m, 1H), 7.15 (m, 1H), 5.80 (br. s, 1H), 2.50 (q, 2H), 1.55 (br., 12H), 1.15 (t, 3H). |

TABLE A-continued

| Compound Number | Structure | ¹H NMR (CDCl₃ unless stated) or other physical data |
|---|---|---|
| A-76 | 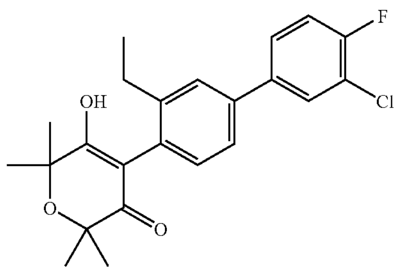 [SMILES: CCc1cc(-c2ccc(F)c(Cl)c2)ccc1C1=C(O)C(C)(C)OC(C)(C)C1=O] | δ$_H$ 7.60 (dd, 1H), 7.50 (s, 1H), 7.45-7.40 (m, 2H), 7.20 (t, 1H), 7.15 (d, 1H), 5.60 (br. s, 1H), 2.50 (m, 2H), 1.65 (s, 6H), 1.50 (2 × s, 6H), 1.15 (t, 3H). |
| A-77 | 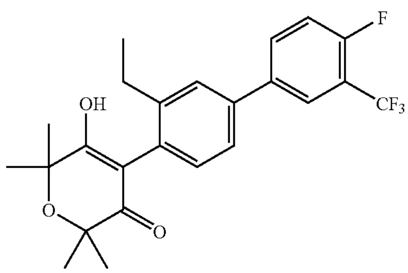 [SMILES: CCc1cc(-c2ccc(F)c(C(F)(F)F)c2)ccc1C1=C(O)C(C)(C)OC(C)(C)C1=O] | δ$_H$ 7.80 (m, 1H), 7.75 (m, 1H), 7.50 (s, 1H), 7.45 (dd, 1H), 7.30 (t, 1H), 7.15 (d, 1H), 5.60 (br. s, 1H), 2.50 (m, 2H), 1.65 (s, 6H), 1.50 (2 × s, 6H), 1.15 (t, 3H). |
| A-78 | 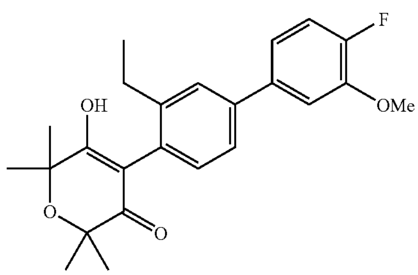 [SMILES: CCc1cc(-c2ccc(F)c(OC)c2)ccc1C1=C(O)C(C)(C)OC(C)(C)C1=O] | δ$_H$ 7.50 (s, 1H), 7.45 (dd, 1H), 7.15-7.05 (m, 4H), 5.60 (br., 1H), 3.95 (s, 3H), 2.50 (m, 2H), 1.65 (br. s, 6H), 1.50 (br. s, 6H), 1.15 (t, 3H). |
| A-79 | 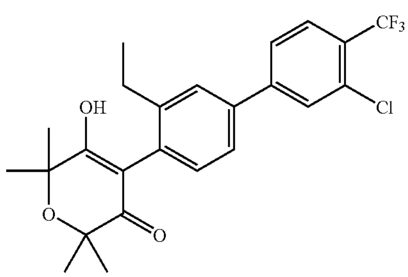 [SMILES: CCc1cc(-c2ccc(C(F)(F)F)c(Cl)c2)ccc1C1=C(O)C(C)(C)OC(C)(C)C1=O] | δ$_H$ 7.75 (d, 1H), 7.70 (s, 1H), 7.55 (d, 1H), 7.50 (s, 1H), 7.45 (d, 1H), 7.20 (d, 1H), 5.55 (s, 1H), 2.50 (m, 2H), 1.60 (s, 6H), 1.50 (2 × s, 6H), 1.15 (t, 3H). |
| A-80 | 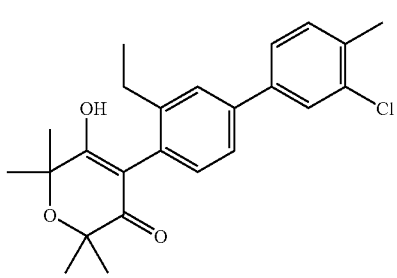 [SMILES: CCc1cc(-c2ccc(C)c(Cl)c2)ccc1C1=C(O)C(C)(C)OC(C)(C)C1=O] | δ$_H$ 7.60 (s, 1H), 7.50 (s, 1H), 7.45 (dd, 1H), 7.40 (dd, 1H), 7.30 (d, 1H), 7.15 (d, 1H), 5.60 (br., 1H), 2.50 (m, 2H), 2.40 (s, 3H), 1.60 (s, 6H), 1.50 (2 × s, 6H), 1.15 (t, 3H). |

TABLE A-continued

| Compound Number | Structure | ¹H NMR (CDCl₃ unless stated) or other physical data |
|---|---|---|
| A-81 | 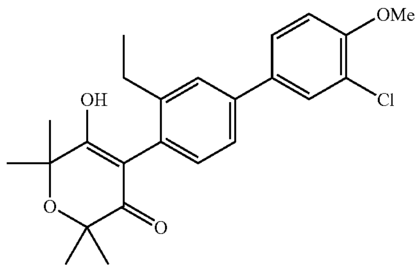 [SMILES: CCc1cc(-c2ccc(OC)c(Cl)c2)ccc1C1=C(O)C(C)(C)OC(C)(C)C1=O] | δ$_H$ 7.60 (d, 1H), 7.50 (s, 1H), 7.45-7.40 (m, 2H), 7.15 (d, 1H), 7.00 (d, 1H), 5.60 (br. s, 1H), 3.95 (s, 3H), 2.50 (m, 2H), 1.60 (s, 6H), 1.50 (2 × s, 6H), 1.15 (t, 3H). |
| A-82 | 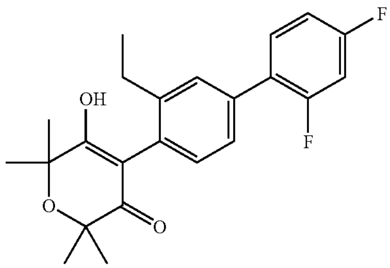 [SMILES: CCc1cc(-c2ccc(F)cc2F)ccc1C1=C(O)C(C)(C)OC(C)(C)C1=O] | δ$_H$ 7.50 (s, 1H), 7.45-7.40 (m, 2H), 7.15 (d, 1H), 7.00-6.90 (m, 2H), 5.70 (br. s, 1H), 2.50 (m, 2H), 1.60 (s, 6H), 1.50 (2 × s, 6H), 1.15 (t, 3H). |
| A-83 | 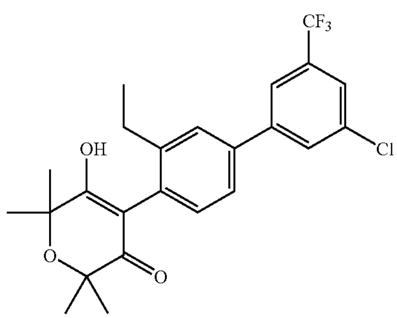 [SMILES: CCc1cc(-c2cc(Cl)cc(C(F)(F)F)c2)ccc1C1=C(O)C(C)(C)OC(C)(C)C1=O] | δ$_H$ 7.75 (s, 1H), 7.70 (s, 1H), 7.60 (s, 1H), 7.50 (s, 1H), 7.45 (d, 1H), 7.20 (d, 1H), 5.60 (br. s, 1H), 2.50 (m, 2H), 1.65 (s, 6H), 1.50 (2 × s, 6H), 1.15 (t, 3H). |
| A-84 | 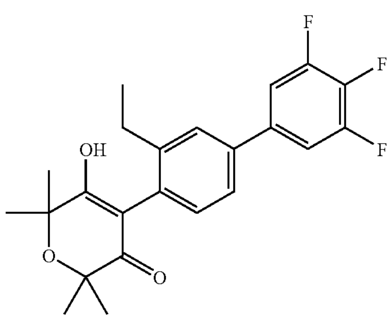 [SMILES: CCc1cc(-c2cc(F)c(F)c(F)c2)ccc1C1=C(O)C(C)(C)OC(C)(C)C1=O] | δ$_H$ 7.45 (s, 1H), 7.40 (dd, 1H), 7.20-7.15 (m, 3H), 5.55 (s, 1H), 2.50 (q, 2H), 1.60 (s, 6H), 1.50 (2 × s, 6H), 1.15 (t, 3H). |
| A-85 | 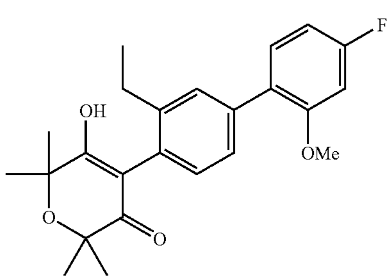 [SMILES: CCc1cc(-c2ccc(F)cc2OC)ccc1C1=C(O)C(C)(C)OC(C)(C)C1=O] | δ$_H$ 7.45 (s, 1H), 7.40 (dd, 1H), 7.30 (d, 1H), 7.10 (d, 1H), 6.85-6.80 (m, 2H), 5.95 (br., 1H), 3.80 (s, 3H), 2.50 (m, 2H), 1.60 (br. s, 6H), 1.50 (br. s, 6H), 1.15 (t, 3H). |

TABLE A-continued

| Compound Number | Structure | $^1$H NMR (CDCl$_3$ unless stated) or other physical data |
|---|---|---|
| A-86 | 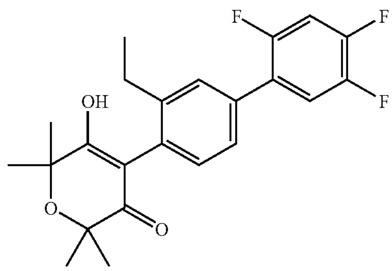 [SMILES: CCc1cc(-c2cc(F)c(F)cc2F)ccc1C1=C(O)C(C)(C)OC(C)(C)C1=O] | δ$_H$ 7.45 (s, 1H), 7.40 (d, 1H), 7.30 (m, 1H), 7.15 (d, 1H), 7.05 (m, 1H), 5.70 (br. s, 1H), 2.50 (m, 2H), 1.60 (s, 6H), 1.50 (2 × s, 6H), 1.15 (t, 3H). |
| A-87 | 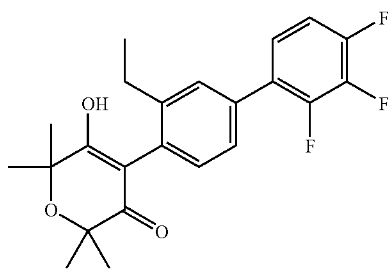 [SMILES: CCc1cc(-c2ccc(F)c(F)c2F)ccc1C1=C(O)C(C)(C)OC(C)(C)C1=O] | δ$_H$ 7.50 (s, 1H), 7.40 (d, 1H), 7.15 (m, 2H), 7.05 (m, 1H), 5.65 (br. s, 1H), 2.50 (m, 2H), 1.65 (s, 6H), 1.50 (2 × s, 6H), 1.15 (t, 3H). |
| A-88 | 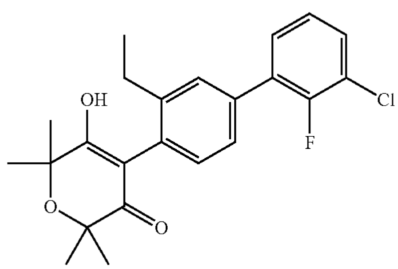 [SMILES: CCc1cc(-c2cccc(Cl)c2F)ccc1C1=C(O)C(C)(C)OC(C)(C)C1=O] | δ$_H$ 7.50 (s, 1H), 7.45-7.30 (m, 3H), 7.15 (m, 2H), 5.70 (br., 1H), 2.50 (m, 2H), 1.65 (s, 6H), 1.50 (2 × s, 6H), 1.15 (t, 3H). |
| A-89 | 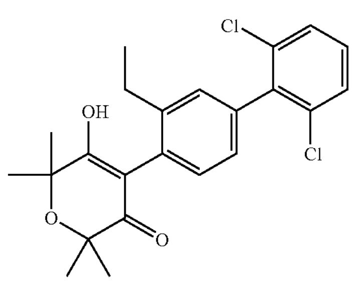 [SMILES: CCc1cc(-c2c(Cl)cccc2Cl)ccc1C1=C(O)C(C)(C)OC(C)(C)C1=O] | δ$_H$ 7.40 (d, 2H), 7.25-7.15 (m, 4H), 6.05 (br., 1H), 2.50 (m, 2H), 1.65 (br., 6H), 1.50 (br., 6H), 1.15 (t, 3H). |
| A-90 | 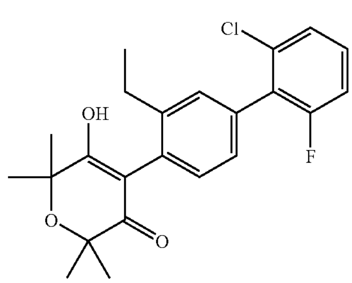 [SMILES: CCc1cc(-c2c(F)cccc2Cl)ccc1C1=C(O)C(C)(C)OC(C)(C)C1=O] | δ$_H$ 7.35 (s, 1H), 7.30 (m, 3H), 7.15 (d, 1H), 7.10 (dt, 1H), 6.00 (br., 1H), 2.50 (br., 2H), 1.70-1.50 (br., 12H), 1.15 (t, 3H). |

TABLE A-continued

| Compound Number | Structure | ¹H NMR (CDCl₃ unless stated) or other physical data |
|---|---|---|
| A-91 | 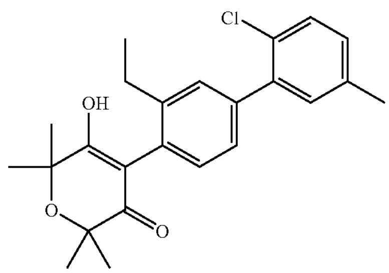 | $\delta_H$ 7.40 (s, 1H), 7.35 (d, 2H), 7.20 (s, 1H), 7.10 (m, 2H), 6.05 (br. s, 1H), 2.50 (br., 2H), 2.35 (s, 3H), 1.65 (br., 6H), 1.50 (br., 6H), 1.15 (t, 3H). |
| A-92 | 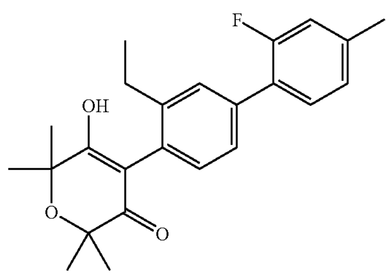 | $\delta_H$ 7.25 (s, 1H), 7.20 (m, 2H), 7.10 (d, 1H), 7.00-6.90 (m, 2H), 5.80 (br., 1H), 2.50 (m, 2H), 2.30 (s, 3H), 1.60 (s, 6H), 1.50 (2 × s, 6H), 1.15 (t, 3H). |
| A-93 | 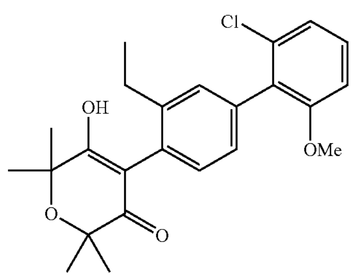 [SMILES: CCc1cc(-c2c(Cl)cccc2OC)ccc1C1=C(O)C(C)(C)OC(C)(C)C1=O] | $\delta_H$ 7.25 (m, 2H), 7.20 (d, 1H), 7.15-7.05 (m, 2H), 6.90 (d, 1H), 5.8 (br. s, 1H), 3.75 (s, 3H), 2.50 (m, 2H), 1.60 (br., 6H), 1.50 (2 × s, 6H), 1.15 (t, 3H). |
| A-94 | 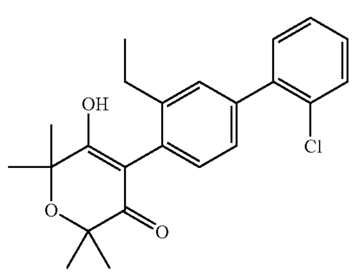 [SMILES: CCc1cc(-c2ccccc2Cl)ccc1C1=C(O)C(C)(C)OC(C)(C)C1=O] | $\delta_H$ (DMSO-d₆) 10.44 (s, 1H), 7.57 (d, 1H), 7.46-7.37 (m, 3H), 7.31 (d, 1H), 7.26 (dd, 1H), 7.01 (d, 1H), 2.4 (q, 2H), 1.53 (s, 6H), 1.35 (s, 6H), 1.07 (t, 3H). |
| A-95 | 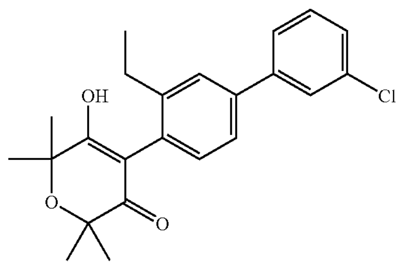 [SMILES: CCc1cc(-c2cccc(Cl)c2)ccc1C1=C(O)C(C)(C)OC(C)(C)C1=O] | $\delta_H$ (DMSO-d₆) 10.39 (s, 1H), 7.74 (t, 1H), 7.66 (d, 1H), 7.55 (d, 1H), 7.51-7.46 (dd, 2H), 7.42 (d, 1H), 7.01 (d, 1H), 2.4 (q, 2H), 1.52 (s, 6H), 1.35 (s, 6H), 1.08 (t, 3H). |

TABLE A-continued

| Compound Number | Structure | ¹H NMR (CDCl₃ unless stated) or other physical data |
|---|---|---|
| A-96 | 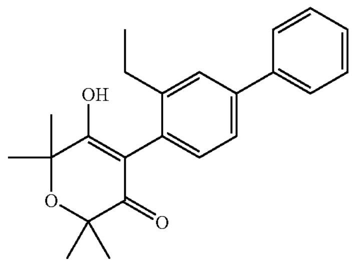 [SMILES: CCc1cc(-c2ccccc2)ccc1C1=C(O)C(C)(C)OC(C)(C)C1=O] | δ$_H$ 7.62-7.55 (m, 3H), 7.52-7.42 (m, 3H), 7.39-7.33 (m, 1H), 7.15 (d, 1H), 5.66 (s, 1H), 2.5 (m, 2H), 1.6-1.4 (m, 12H), 1.16 (t, 3H). |
| A-97 | 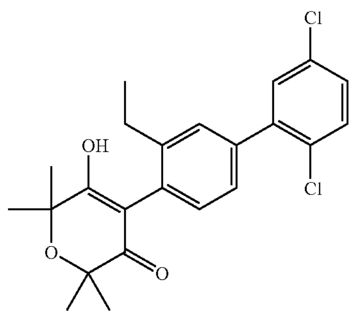 [SMILES: CCc1cc(-c2cc(Cl)ccc2Cl)ccc1C1=C(O)C(C)(C)OC(C)(C)C1=O] | δ$_H$ 7.48-7.26 (m, 5H), 7.15 (d, 1H), 5.8 (s, 1H), 2.5-2.3 (m, 2H), 1.63 (s, 3H), 1.62 (s, 3H), 1.51 (s, 3H), 1.48 (s, 3H), 1.2-1.13 (m, 3H). |
| A-98 | 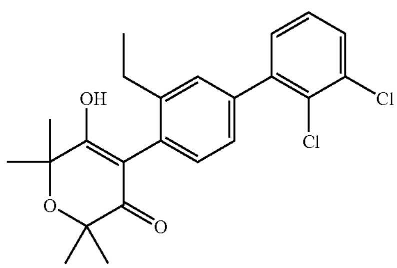 [SMILES: CCc1cc(-c2cccc(Cl)c2Cl)ccc1C1=C(O)C(C)(C)OC(C)(C)C1=O] | δ$_H$ 7.47 (t, 1H), 7.39 (d, 1H), 7.32 (dd, 1H), 7.26-7.24 (m, 2H), 7.15 (d, 1H), 5.8 (s, 1H), 2.5 (m, 2H), 1.6-1.5 (m, 12H), 1.15 (t, 3H). |
| A-99 | 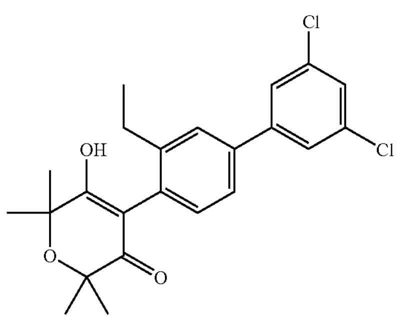 | δ$_H$ 7.5 (d, 1H), 7.46-7.42 (m, 3H), 7.35 (t, 1H), 7.17 (d, 1H) 5.8 (br. s, 1H) 2.5 (m, 2H), 1.6 (s, 3H), 1.55 (s, 6H), 1.5 (s, 3H), 1.16 (t, 3H). |
| A-100 | 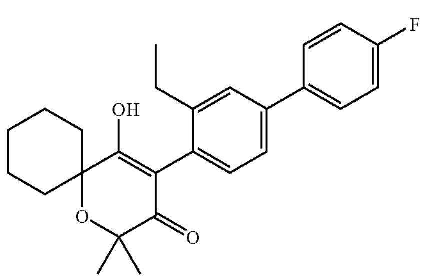 [SMILES: CCc1cc(-c2ccc(F)cc2)ccc1C1=C(O)C2(CCCCC2)OC(C)(C)C1=O] | δ$_H$ (DMSO-d₆) 10.28 (s, 1H), 7.74-7.69 (m, 2H), 7.48 (d, 1H), 7.42 (dd, 1H), 7.3 (t, 2H), 6.98 (d, 1H), 2.4 (q, 2H), 1.9-1.2 (m, 16 H), 1.06 (t, 3H). |

TABLE A-continued

| Compound Number | Structure | ¹H NMR (CDCl₃ unless stated) or other physical data |
|---|---|---|
| A-101 | 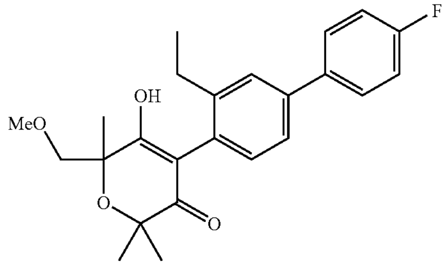 [SMILES: CCc1cc(-c2ccc(F)cc2)ccc1C1=C(O)C(C)(COC)OC(C)(C)C1=O] | LC-MS (ES−): 397 (M − H)⁻ |
| A-102 | 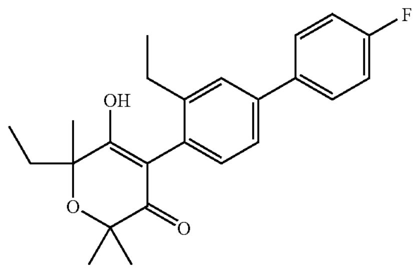 [SMILES: CCc1cc(-c2ccc(F)cc2)ccc1C1=C(O)C(C)(CC)OC(C)(C)C1=O] | LC-MS (ES−): 381 (M − H)⁻ |
| A-103 | 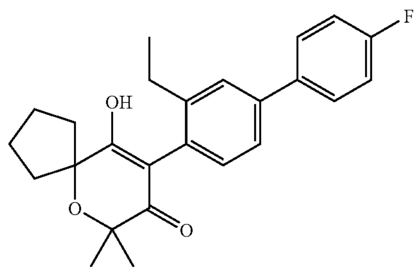 [SMILES: CCc1cc(-c2ccc(F)cc2)ccc1C1=C(O)C2(CCCC2)OC(C)(C)C1=O] | $\delta_H$ (DMSO-d₆) 10.38 (br., 1H), 7.81-7.77 (m, 2H), 7.56 (s, 1H), 7.5 (dd, 1H), 7.36 (t, 2H), 7.06 (d, 1H), 2.47 (q, 2H), 2.3-1.6 (m, 8 H), 1.4 (s, 3H), 1.39 (s, 3H), 1.14 (t, 3H). |
| A-104 | 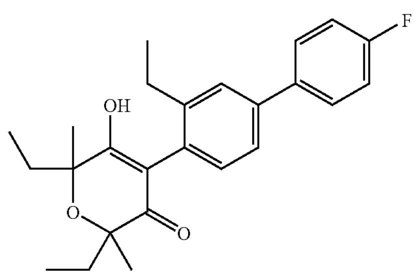 [SMILES: CCc1cc(-c2ccc(F)cc2)ccc1C1=C(O)C(C)(CC)OC(C)(CC)C1=O] | LC-MS (ES+): 397 (M + H)⁺ |
| A-105 | 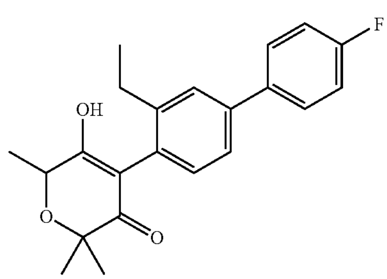 [SMILES: CCc1cc(-c2ccc(F)cc2)ccc1C1=C(O)C(C)OC(C)(C)C1=O] | $\delta_H$ 7.56-7.51 (m, 2H), 7.5 (d, 1H), 7.42 (dd, 1H), 7.16-7.09 (m, 3H), 5.71 and 5.62 (2 × d, 1H), 4.76 and 4.44 (2 × q, 1H), 2.6-2.4 (m, 2H), 1.62 and 1.45 (2 × d, 3H), 1.54 and 1.48 (2 × s, 3H), 1.47 (s, 3H), 1.17-1.13 (m, 3H). |

TABLE A-continued

| Compound Number | Structure | $^1$H NMR (CDCl$_3$ unless stated) or other physical data |
|---|---|---|
| A-106 | 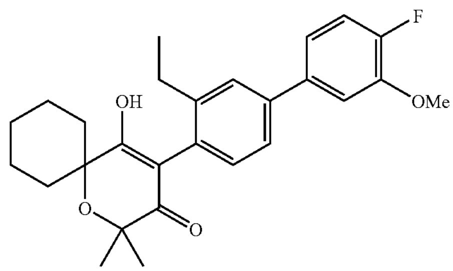 [SMILES: CCc1cc(-c2ccc(F)c(OC)c2)ccc1C1=C(O)C2(CCCCC2)OC(C)(C)C1=O] | δ$_H$ 7.50 (s, 1H), 7.40 (d, 1H), 7.15-7.05 (m, 4H), 5.55 (br., 1H), 3.95 (s, 3H), 2.50 (m, 2H), 2.00-1.30 (m, 16H), 1.15 (t, 3H). |
| A-107 | 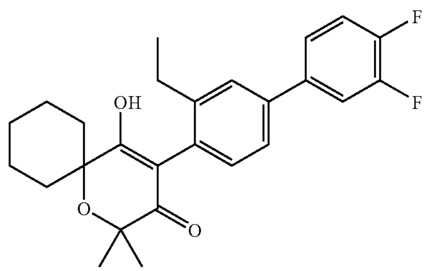 [SMILES: CCc1cc(-c2ccc(F)c(F)c2)ccc1C1=C(O)C2(CCCCC2)OC(C)(C)C1=O] | δ$_H$ 7.50 (s, 1H), 7.40 (m, 2H), 7.30 (m, 1H), 7.20 (m, 1H), 7.10 (d, 1H), 5.50 (br., 1H), 2.50 (m, 2H), 2.00-1.30 (m, 16H), 1.15 (t, 3H). |
| A-108 | 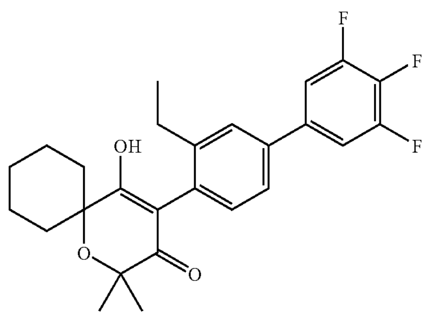 [SMILES: CCc1cc(-c2cc(F)c(F)c(F)c2)ccc1C1=C(O)C2(CCCCC2)OC(C)(C)C1=O] | δ$_H$ 7.45 (s, 1H), 7.40 (d, 1H), 7.20-7.10 (m, 3H), 5.50 (br., 1H), 2.50 (m, 2H), 2.00-1.30 (m, 16H), 1.15 (t, 3H). |
| A-109 | 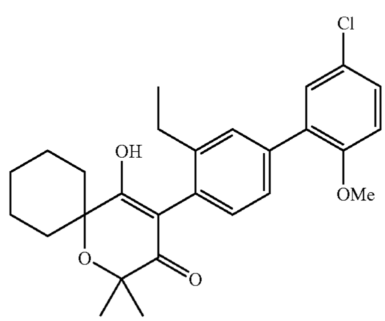 [SMILES: CCc1cc(-c2cc(Cl)ccc2OC)ccc1C1=C(O)C2(CCCCC2)OC(C)(C)C1=O] | δ$_H$ 7.45 (s, 1H), 7.40 (d, 1H), 7.30 (2H, m), 7.10 (1H, d), 6.90 (1H, d), 5.70 (1H, br.), 3.90 (3H, s), 2.50 (2H, m), 2.00-1.30 (16H, m), 1.15 (3H, t). |
| A-110 | 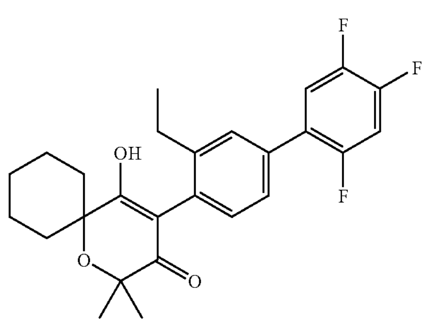 [SMILES: CCc1cc(-c2cc(F)c(F)cc2F)ccc1C1=C(O)C2(CCCCC2)OC(C)(C)C1=O] | δ$_H$ 7.45 (s, 1H), 7.40 (d, 1H), 7.25 (m, 1H), 7.15 (d, 1H), 7.05 (m, 1H), 5.60 (br., 1H), 2.50 (m, 2H), 2.00-1.30 (m, 16H), 1.15 (t, 3H). |

TABLE A-continued

| Compound Number | Structure | ¹H NMR (CDCl₃ unless stated) or other physical data |
|---|---|---|
| A-111 | 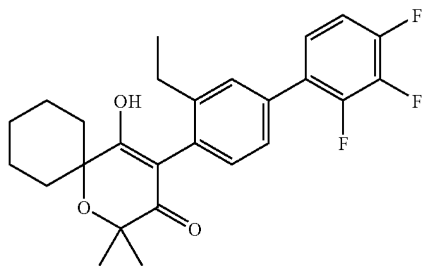 [SMILES: CCc1cc(-c2ccc(F)c(F)c2F)ccc1C1=C(O)C2(CCCCC2)OC(C)(C)C1=O] | δ$_H$ 7.45 (s, 1H), 7.40 (d, 1H), 7.15 (m, 2H), 7.05 (m, 1H), 5.60 (br., 1H), 2.50 (m, 2H), 2.00-1.30 (m, 16H), 1.15 (t, 3H). |
| A-112 | 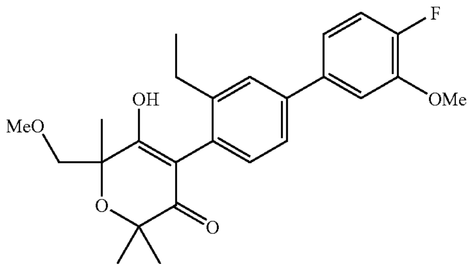 [SMILES: CCc1cc(-c2ccc(F)c(OC)c2)ccc1C1=C(O)C(C)(COC)OC(C)(C)C1=O] | LC-MS (ES−): 427 (M − H)⁻ |
| A-113 | 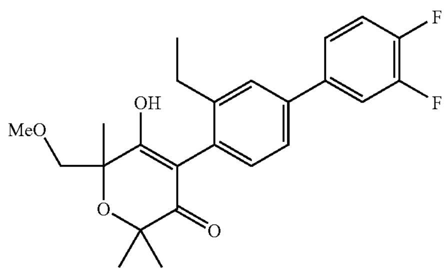 [SMILES: CCc1cc(-c2ccc(F)c(F)c2)ccc1C1=C(O)C(C)(COC)OC(C)(C)C1=O] | LC-MS (ES−): 415 (M − H)⁻ |
| A-114 | 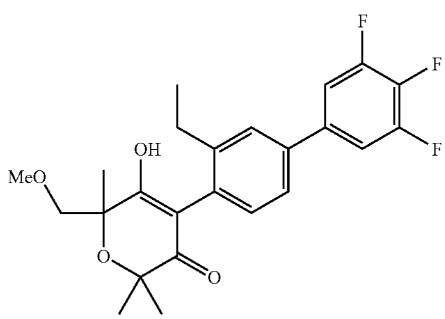 [SMILES: CCc1cc(-c2cc(F)c(F)c(F)c2)ccc1C1=C(O)C(C)(COC)OC(C)(C)C1=O] | LC-MS (ES−): 433 (M − H)⁻ |
| A-115 | 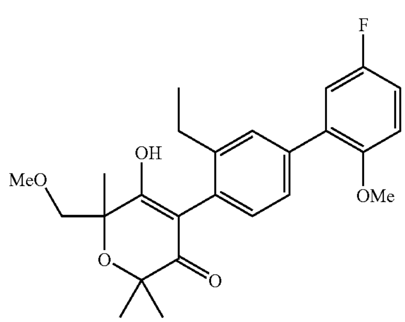 | LC-MS (ES−): 445, 443 (M − H)⁻ |

TABLE A-continued

| Compound Number | Structure | ¹H NMR (CDCl₃ unless stated) or other physical data |
|---|---|---|
| A-116 | 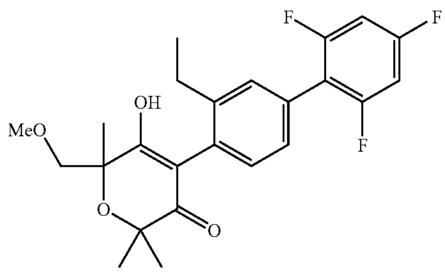 [SMILES: CCc1cc(-c2c(F)cc(F)cc2F)ccc1C1=C(O)C(C)(COC)OC(C)(C)C1=O] | LC-MS (ES−): 433 (M − H)⁻ |
| A-117 | 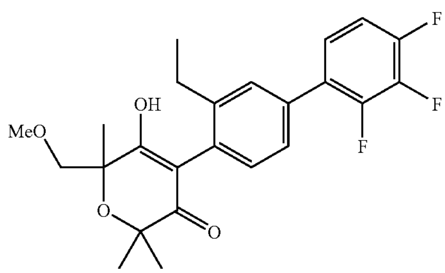 [SMILES: CCc1cc(-c2ccc(F)c(F)c2F)ccc1C1=C(O)C(C)(COC)OC(C)(C)C1=O] | LC-MS (ES−): 433 (M − H)⁻ |
| A-118 | 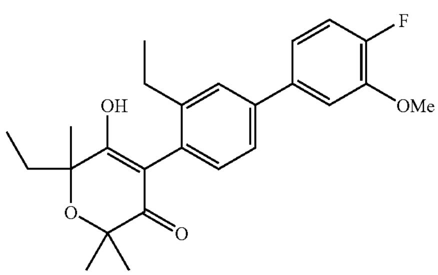 [SMILES: CCc1cc(-c2ccc(F)c(OC)c2)ccc1C1=C(O)C(C)(CC)OC(C)(C)C1=O] | LC-MS (ES−): 411 (M − H)⁻ |
| A-119 | 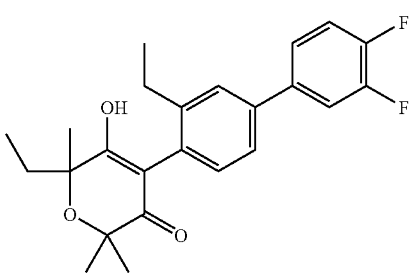 [SMILES: CCc1cc(-c2ccc(F)c(F)c2)ccc1C1=C(O)C(C)(CC)OC(C)(C)C1=O] | LC-MS (ES−): 399 (M − H)⁻ |
| A-120 | 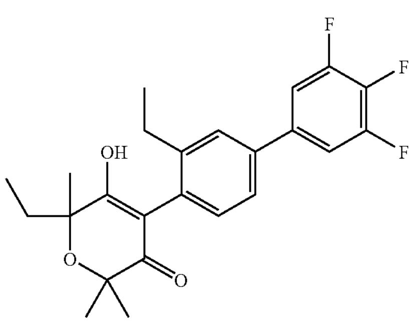 [SMILES: CCc1cc(-c2cc(F)c(F)c(F)c2)ccc1C1=C(O)C(C)(CC)OC(C)(C)C1=O] | LC-MS (ES−): 417 (M − H)⁻ |

TABLE A-continued

| Compound Number | Structure | ¹H NMR (CDCl₃ unless stated) or other physical data |
|---|---|---|
| A-121 | 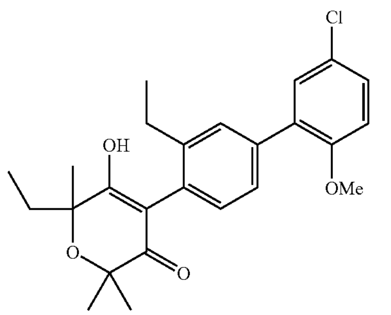 [SMILES: CCc1cc(-c2cc(Cl)ccc2OC)ccc1C1=C(O)C(C)(CC)OC(C)(C)C1=O] | LC-MS (ES−): 429, 427 (M − H)⁻ |
| A-122 | 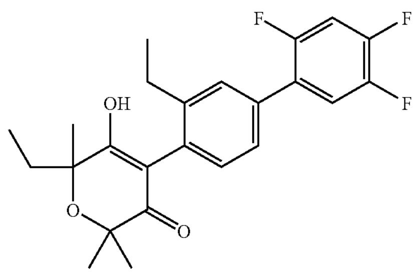 [SMILES: CCc1cc(-c2cc(F)c(F)cc2F)ccc1C1=C(O)C(C)(CC)OC(C)(C)C1=O] | LC-MS (ES−): 417 (M − H)⁻ |
| A-123 | 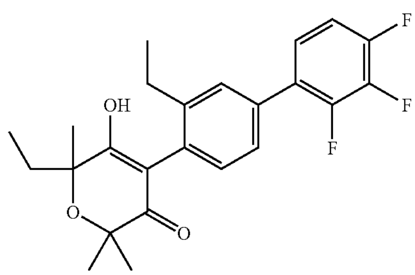 [SMILES: CCc1cc(-c2ccc(F)c(F)c2F)ccc1C1=C(O)C(C)(CC)OC(C)(C)C1=O] | LC-MS (ES−): 417 (M − H)⁻ |
| A-124 | 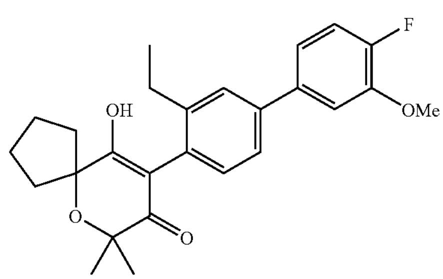 [SMILES: CCc1cc(-c2ccc(F)c(OC)c2)ccc1C1=C(O)C2(CCCC2)OC(C)(C)C1=O] | δ_H 7.50 (s, 1H), 7.45 (d, 1H), 7.20-7.05 (m, 4H), 5.65 and 5.60 (2 × s, 1H), 3.95 (s, 3H), 2.50 (m, 2H), 2.30-1.70 (m, 8H), 1.60 (s, 3H), 1.50 (2 × s, 3H), 1.15 (t, 3H). |
| A-125 | 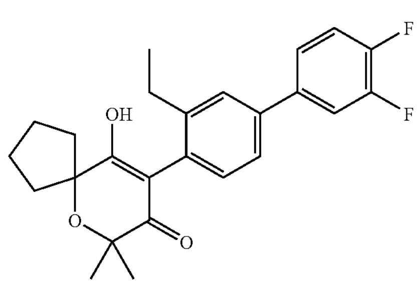 [SMILES: CCc1cc(-c2ccc(F)c(F)c2)ccc1C1=C(O)C2(CCCC2)OC(C)(C)C1=O] | δ_H 7.50 (s, 1H), 7.45-7.35 (m, 2H), 7.30 (br., 1H), 7.20 (m, 1H), 7.15 (d, 1H), 5.60 and 5.55 (2 × s, 1H), 2.50 (m, 2H), 2.30-1.75 (m, 8H), 1.60 (s, 3H), 1.50 (2 × s, 3H), 1.15 (t, 3H). |

TABLE A-continued

| Compound Number | Structure | ¹H NMR (CDCl₃ unless stated) or other physical data |
|---|---|---|
| A-126 | 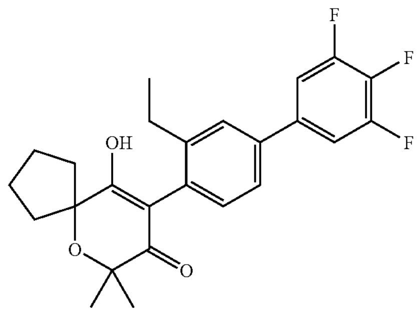 [SMILES: CCc1cc(-c2cc(F)c(F)c(F)c2)ccc1C1=C(O)C2(CCCC2)OC(C)(C)C1=O] | δ$_H$ 7.45 (s, 1H), 7.40 (d, 1H), 7.25-7.15 (m, 3H), 5.60 (br., 1H), 2.50 (m, 2H), 2.30-1.70 (m, 8H), 1.60 (s, 3H), 1.55 (2 × s, 3H), 1.15 (t, 3H). |
| A-127 | 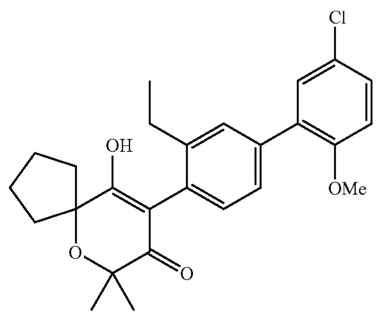 [SMILES: CCc1cc(-c2cc(Cl)ccc2OC)ccc1C1=C(O)C2(CCCC2)OC(C)(C)C1=O] | δ$_H$ 7.45 (s, 1H), 7.40 (d, 1H), 7.30 (m, 2H), 7.10 (d, 1H), 6.90 (d, 1H), 5.85 and 5.75 (2 × s, 1H), 3.80 (s, 3H), 2.50 (m, 2H), 2.30-1.75 (m, 8H), 1.60 (s, 3H), 1.50 (2 × s, 3H), 1.15 (t, 3H). |
| A-128 | 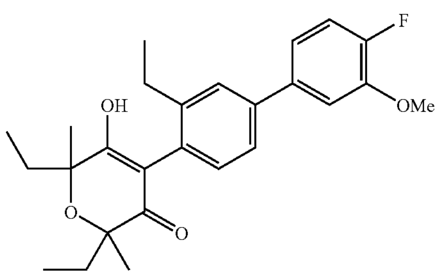 [SMILES: CCc1cc(-c2ccc(F)c(OC)c2)ccc1C1=C(O)C(C)(CC)OC(C)(CC)C1=O] | LC-MS (ES−): 425 (M − H)⁻ |
| A-129 | 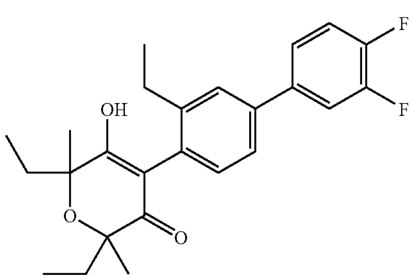 [SMILES: CCc1cc(-c2ccc(F)c(F)c2)ccc1C1=C(O)C(C)(CC)OC(C)(CC)C1=O] | LC-MS (ES−): 413 (M − H)⁻ |
| A-130 | 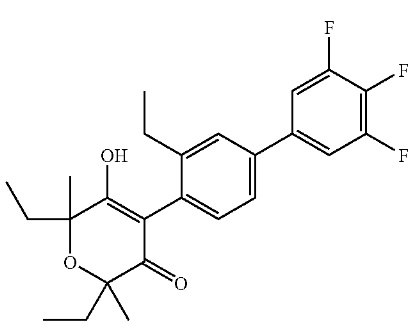 [SMILES: CCc1cc(-c2cc(F)c(F)c(F)c2)ccc1C1=C(O)C(C)(CC)OC(C)(CC)C1=O] | LC-MS (ES−): 431 (M − H)⁻ |

TABLE A-continued

| Compound Number | Structure | ¹H NMR (CDCl₃ unless stated) or other physical data |
|---|---|---|
| A-131 | 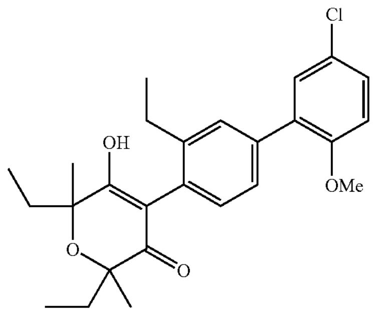 [SMILES: CCc1cc(-c2cc(Cl)ccc2OC)ccc1C1=C(O)C(C)(CC)OC(C)(CC)C1=O] | LC-MS (ES−): 443, 441 (M − H)⁻ |
| A-132 | 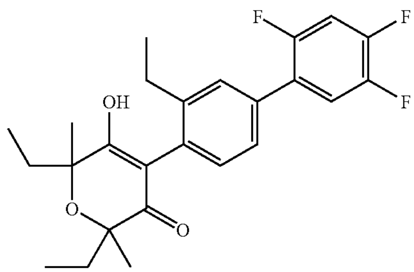 [SMILES: CCc1cc(-c2cc(F)c(F)cc2F)ccc1C1=C(O)C(C)(CC)OC(C)(CC)C1=O] | LC-MS (ES−): 431 (M − H)⁻ |
| A-133 | 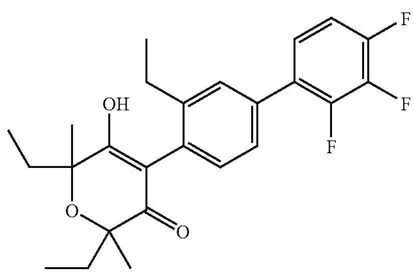 [SMILES: CCc1cc(-c2ccc(F)c(F)c2F)ccc1C1=C(O)C(C)(CC)OC(C)(CC)C1=O] | LC-MS (ES−): 431 (M − H)⁻ |
| A-134 | 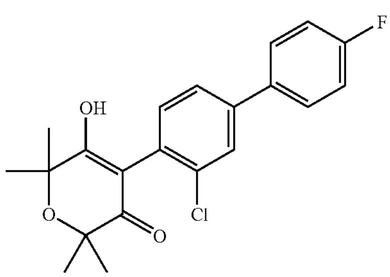 [SMILES: CC1(C)OC(C)(C)C(O)=C(c2ccc(-c3ccc(F)cc3)cc2Cl)C1=O] | LC-MS (ES−): 375, 373 (M − H)⁻ |
| A-135 | 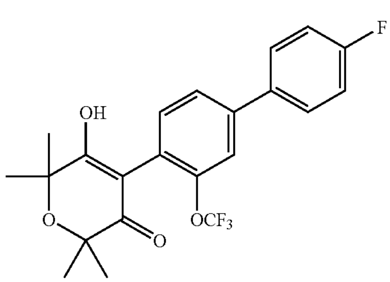 [SMILES: CC1(C)OC(C)(C)C(O)=C(c2ccc(-c3ccc(F)cc3)cc2OC(F)(F)F)C1=O] | $\delta_H$ 7.56-7.52 (m, 4H), 7.33 (d, 1H), 7.16 (t, 2H), 5.72 (s, 1H), 1.6 (s, 6H), 1.57 (s, 6H). |

Example 16

Preparation of 4-(4-bromo-2-ethylphenyl)-2,2,6,6-tetramethylthiopyran-3,5-dione

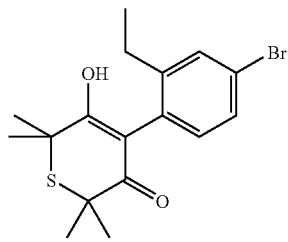 [SMILES: CCc1cc(Br)ccc1C1=C(O)C(C)(C)SC(C)(C)C1=O]

2,2,6,6-Tetramethylthiopyran-3,5-dione (10 g, 0.053 mol) (described in Helvetica Chimica Acta, 1992, 75(7), 2265-69) and 4-dimethylaminopyridine (32 g, 0.26 mol) are added to a mixture of chloroform (200 ml) and toluene (50 ml). The reaction mixture is flushed with nitrogen for 15 minutes at ambient temperature. 4-Bromo-2-ethylphenyllead triacetate (34 g, 0.06 mol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The aqueous phase is extracted with dichloromethane (2×100 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6,6-tetramethylthiopyran-3,5-dione as a white solid (8 g).

Example 17

Preparation of 4-(4-bromo-2-ethylphenyl)-2,2,6,6-tetramethyl-1-oxo-dihydrothiopyran-3,5-dione

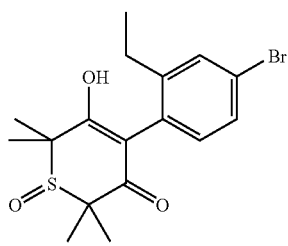 [SMILES: CCc1cc(Br)ccc1C1=C(O)C(C)(C)S(=O)C(C)(C)C1=O]

A solution of 3-chloroperbenzoic acid (2.45 g, 0.0142 mol) in dichloromethane (40 ml) is added to a pre-cooled solution (0° C.) of 4-(4-bromo-2-ethylphenyl)-2,2,6,6-tetramethyl-thiopyran-3,5-dione (3.5 g, 0.0095 mol) in dichloromethane (100 ml). The reaction mixture is stirred at 0° C. for one hour and then allowed to come to room temperature. The reaction mixture is stirred at room temperature for one hour, diluted with water (100 ml) and separated. The organic phase is collected, and the aqueous layer is extracted with dichloromethane (2×50 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6,6-tetramethyl-1-oxo-dihydrothiopyran-3,5-dione as a white solid (2.0 g).

Example 18

Preparation of 4-(4-bromo-2-ethylphenyl)-2,2,6,6-tetramethyl-1,1-dioxo-dihydrothiopyran-3,5-dione

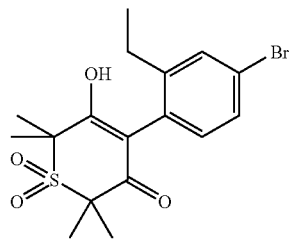 [SMILES: CCc1cc(Br)ccc1C1=C(O)C(C)(C)S(=O)(=O)C(C)(C)C1=O]

A solution of 3-chloroperbenzoic acid (6.54 g, 0.038 mol) in dichloromethane (40 ml) is added to a pre-cooled solution (0° C.) of 4-(4-bromo-2-ethylphenyl)-2,2,6,6-tetramethyl-thiopyran-3,5-dione (3.5 g, 0.0095 mol) in dichloromethane (100 ml). The reaction mixture is stirred at 0° C. for one hour and then allowed to come to room temperature. The reaction mixture is stirred at room temperature for one hour, diluted with water (100 ml) and separated. The organic phase is collected, and the aqueous layer is extracted with dichloromethane (2×50 ml). The organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6,6-tetramethyl-1,1-dioxo-dihydrothiopyran-3,5-dione as a white solid (2.57 g).

The compounds prepared in Examples 16-18 may be converted into compounds B-1 to B-21 in Table B, using appropriate arylboronic acids under the Suzuki-Miyaura conditions described in Step 5 of Example 5.

TABLE B

| Compound Number | Structure | 1H nmr (CDCl₃ unless stated) or other physical data |
|---|---|---|
| B-1 | 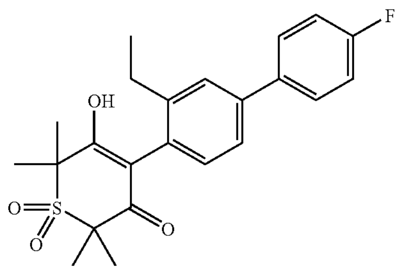 [SMILES: CCc1cc(-c2ccc(F)cc2)ccc1C1=C(O)C(C)(C)S(=O)(=O)C(C)(C)C1=O] | $\delta_H$ (DMSO-d₆): 7.75-7.71(m, 2H), 7.5(d, 1H), 7.44(dd, 1H), 7.29(t, 2H), 6.8(d, 1H), 2.35(q, 2H), 1.65 and 1.63 (2 × s, 12H), 1.03(t, 3H). |
| B-2 | 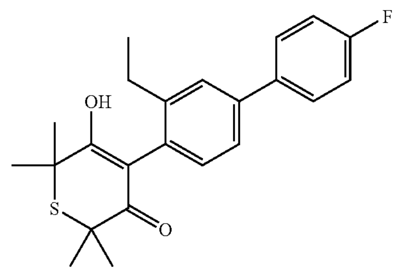 [SMILES: CCc1cc(-c2ccc(F)cc2)ccc1C1=C(O)C(C)(C)SC(C)(C)C1=O] | LC-MS (ES−): 383 (M − H)⁻ |
| B-3 | 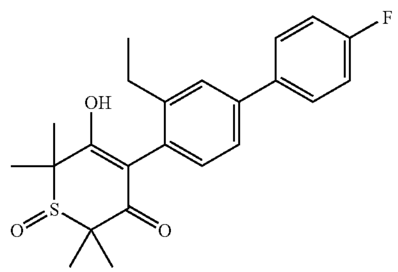 [SMILES: CCc1cc(-c2ccc(F)cc2)ccc1C1=C(O)C(C)(C)S(=O)C(C)(C)C1=O] | LC-MS (ES−): 399 (M − H)⁻ |
| B-4 | 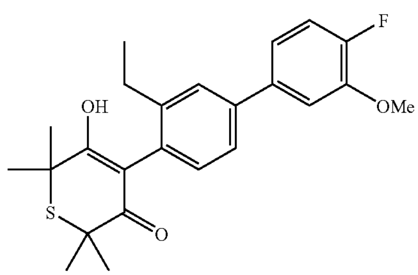 | $\delta_H$ 7.50(s, 1H), 7.45(d, 1H), 7.20-7.10(m, 4H), 5.45(br, 1H), 3.95(s, 3H), 2.50(m, 2H), 1.75 (2 × s, 6H), 1.60(s, 6H), 1.15(t, 3H). |
| B-5 | 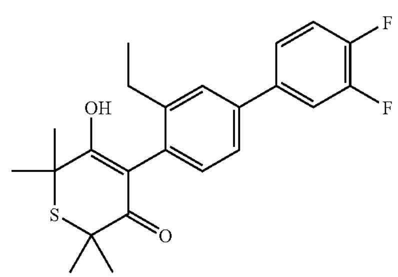 | $\delta_H$ 7.50(s, 1H), 7.45-7.35(m, 2H), 7.30(m, 1H), 7.25(m, 1H), 7.10(d, 1H), 5.40(br, 1H), 2.50(m, 2H), 1.70(2 × s, 6H), 1.60(s, 6H), 1.20(t, 3H). |

TABLE B-continued

| Compound Number | Structure | 1H nmr (CDCl₃ unless stated) or other physical data |
|---|---|---|
| B-6 | 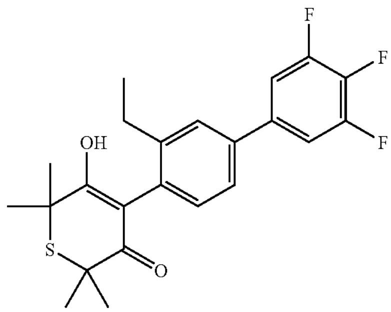 | $\delta_H$ 7.45(s, 1H), 7.40(d, 1H), 7.20(m, 2H), 7.15 (d, 1H), 5.35(s, 1H), 2.50(m, 2H), 1.70(2 × s, 6H), 1.6(2 × s, 6H), 1.20(t, 3H). |
| B-7 | 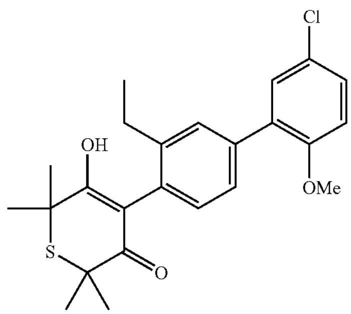 | $\delta_H$ 7.45(s, 1H), 7.40(d, 1H), 7.30(m, 2H), 7.10 (d, 1H), 6.90(d, 1H), 5.60(br, 1H), 3.80(s, 3H), 2.50(m, 2H), 1.75(2 × s, 6H), 1.60(s, 6H), 1.15(t, 3H). |
| B-8 | 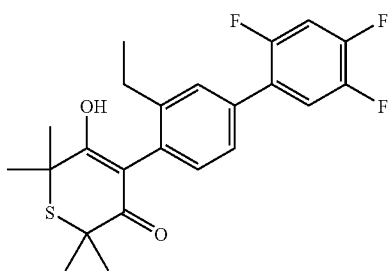 [SMILES: CCc1cc(-c2cc(F)c(F)cc2F)ccc1C1=C(O)C(C)(C)SC(C)(C)C1=O] | $\delta_H$ 7.45(s, 1H), 7.40(d, 1H), 7.30(m, 1H), 7.15 (d, 1H), 7.05(m, 1H), 5.40(s, 1H), 2.50(m, 2H), 1.70(2 × s, 6H), 1.60(s, 6H), 1.15(t, 3H). |
| B-9 | 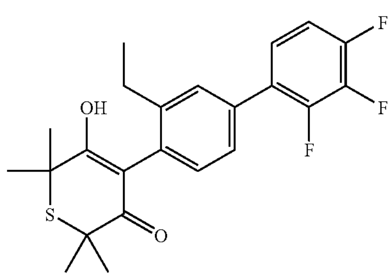 | $\delta_H$ 7.50(s, 1H), 7.40(d, 1H), 7.20-7.10(m, 2H), 7.05(m, 1H), 5.40(s, 1H), 2.50(m, 2H), 1.70 (2 × s, 6H), 1.60(s, 6H), 1.15(t, 3H). |
| B-10 | 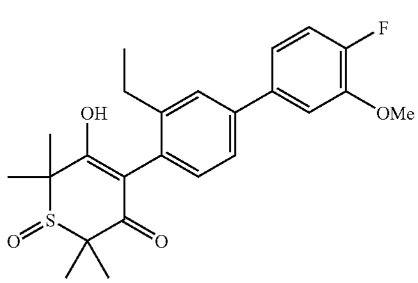 | LC-MS (ES−): 429 (M − H)⁻ |

TABLE B-continued

| Compound Number | Structure | 1H nmr (CDCl₃ unless stated) or other physical data |
|---|---|---|
| B-11 | 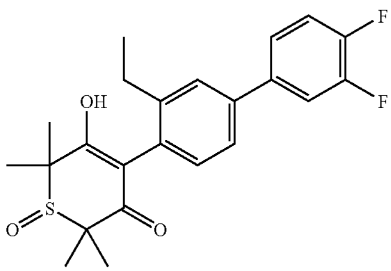 | $\delta_H$ LC-MS (ES−): 417 (M − H)⁻ |
| B-12 | 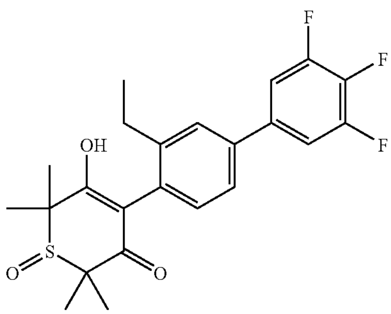 | $\delta_H$ LC-MS (ES−): 436 (M − H)⁻ |
| B-13 | 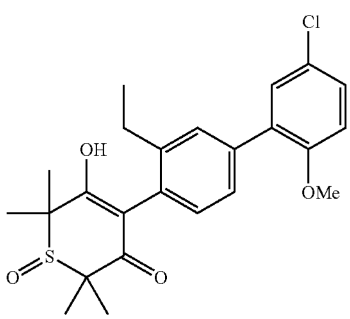 | LC-MS (ES−): 447, 445 (M − H)⁻ |
| B-14 | 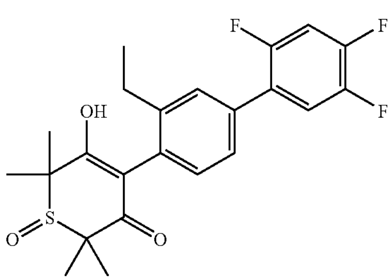 [SMILES: CCc1cc(-c2cc(F)c(F)cc2F)ccc1C1=C(O)C(C)(C)S(=O)C(C)(C)C1=O] | LC-MS (ES−): 436 (M − H)⁻ |
| B-15 | 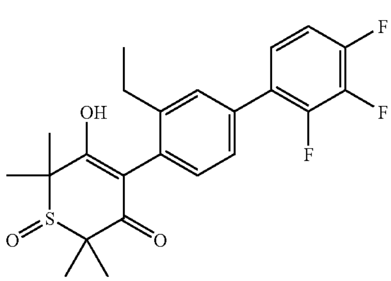 [SMILES: CCc1cc(-c2ccc(F)c(F)c2F)ccc1C1=C(O)C(C)(C)S(=O)C(C)(C)C1=O] | LC-MS (ES−): 436 (M − H)⁻ |

TABLE B-continued

| Compound Number | Structure | 1H nmr (CDCl₃ unless stated) or other physical data |
|---|---|---|
| B-16 | 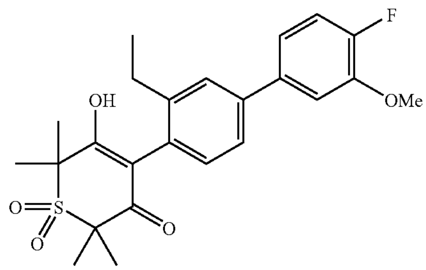 [SMILES: CCc1cc(-c2ccc(F)c(OC)c2)ccc1C1=C(O)C(C)(C)S(=O)(=O)C(C)(C)C1=O] | $\delta_H$ 7.50(s, 1H), 7.45(d, 1H), 7.20-7.10(m, 4H), 3.95(s, 3H), 2.50(m, 2H), 1.80(br, 12H), 1.15 (t, 3H). |
| B-17 | 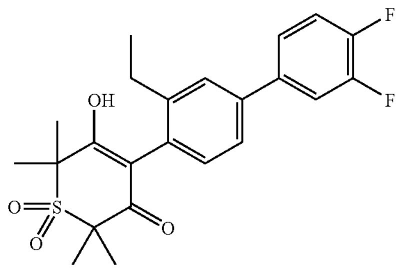 | $\delta_H$ 7.50(s, 1H), 7.45(d, 1H), 7.40(m, 1H), 7.30 (br, 1H), 7.20(m, 1H), 7.15(d, 1H), 5.80(s, 1H), 2.50(m, 2H), 1.90(2 × s, 6H), 1.70(s, 6H), 1.15(t, 3H). |
| B-18 | 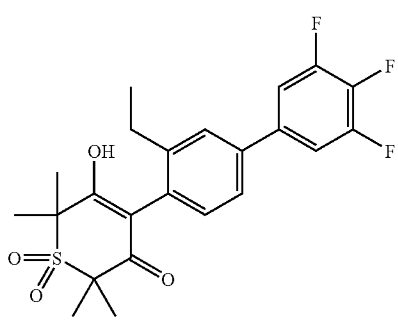 [SMILES: CCc1cc(-c2cc(F)c(F)c(F)c2)ccc1C1=C(O)C(C)(C)S(=O)(=O)C(C)(C)C1=O] | $\delta_H$ 7.50(s, 1H), 7.45(d, 1H), 7.20-7.10(m, 3H), 5.80(br, 1H), 2.50(m, 2H), 1.90(2 × s, 6H), 1.70(s, 6H), 1.15(t, 3H). |
| B-19 | 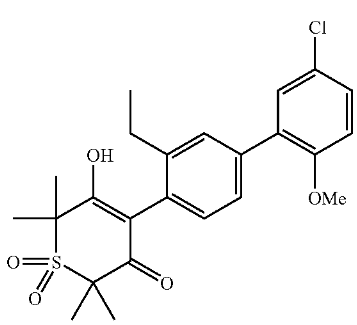 [SMILES: CCc1cc(-c2cc(Cl)ccc2OC)ccc1C1=C(O)C(C)(C)S(=O)(=O)C(C)(C)C1=O] | $\delta_H$ 7.50(s, 1H), 7.45(d, 1H), 7.30(m, 2H), 7.10 (d, 1H), 6.90(m, 1H), 3.80(m, 3H), 2.45(q, 2H), 1.90(br, 12H), 1.15(t, 3H). |

TABLE B-continued

| Compound Number | Structure | 1H nmr (CDCl₃ unless stated) or other physical data |
|---|---|---|
| B-20 | 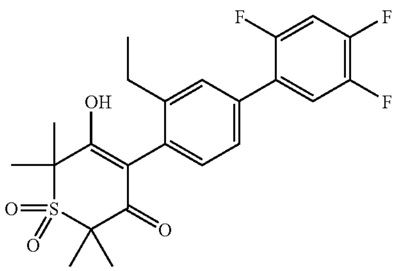 [SMILES: CCc1cc(-c2cc(F)c(F)cc2F)ccc1C1=C(O)C(C)(C)S(=O)(=O)C(C)(C)C1=O] | $\delta_H$ 7.50(s, 1H), 7.40(d, 1H), 7.25(m, 1H), 7.20 (d, 1H), 7.05(m, 1H), 2.50(m, 2H), 1.90-1.70 (br, 12H), 1.15(t, 3H). |
| B-21 | 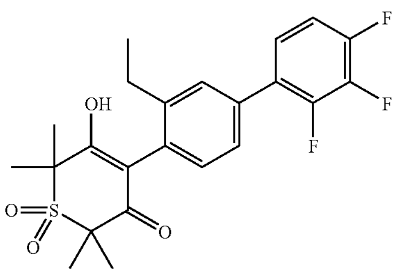 [SMILES: CCc1cc(-c2ccc(F)c(F)c2F)ccc1C1=C(O)C(C)(C)S(=O)(=O)C(C)(C)C1=O] | $\delta_H$ 7.50(s, 1H), 7.45(d, 1H), 7.15(m, 2H), 7.05 (m, 1H), 5.90(br, 1H), 2.45(m, 2H), 1.90(2 × s, 6H), 1.75(s, 6H)m 1.15(t, 3H). |

Example 19

Preparation of 6-(3,5-dimethylbiphenyl-4-yl)-2,2,4,4-tetramethylcyclohexane-1,3,5-trione

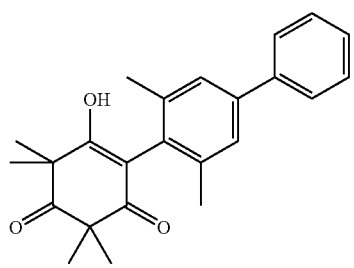 [SMILES: Cc1cc(-c2ccccc2)cc(C)c1C1=C(O)C(C)(C)C(=O)C(C)(C)C1=O]

To a mixture of 2,2,4,4-tetramethylcyclohexane-1,3,5-trione (182 mg, 1 mmol) and 4-dimethylaminopyridine (610 mg, 5 mmol) under an atmosphere of nitrogen, is added dry chloroform (5.6 ml), followed by stirring at room temperature until dissolution is complete. To this solution is then added dry toluene (2 ml), and 3,5-dimethylbiphenyllead triacetate (0.5 M solution in dry chloroform, 2.4 ml, 1.2 mmol). This solution is then heated under reflux for 1 hour. The reaction mixture is cooled to room temperature, acidified to pH 1 with 2N aqueous hydrochloric acid, filtered and the filtrate is extracted with dichloromethane (2×40 ml). The organic extracts are combined, dried over anhydrous magnesium sulfate, filtered and the filtrate is evaporated under reduced pressure. The residue is further purified by column chromatography on silica gel to give 6-(3,5-dimethylbiphenyl-4-yl)-2,2,4,4-tetramethylcyclohexane-1,3,5-trione (166 mg).

Example 20

Preparation of 4-(4-bromo-2-ethylphenyl)-2,2,6,6-tetramethylcyclohexane-1,3,5-trione

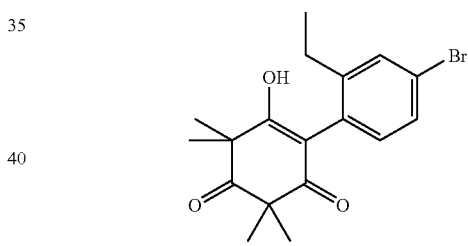

2,2,6,6-Tetramethylcyclohexane-1,3,5-trione (5 g, 0.027 mol) and 4-dimethylamino-pyridine (16.47 g, 0.135 mol) are added to a mixture of chloroform (100 ml) and toluene (25 ml). The reaction mixture is flushed with nitrogen for 15 minutes at ambient temperature. 4-Bromo-2-ethylphenyllead triacetate (17.16 g, 0.03 mol) is added in one portion and the reaction mixture is stirred and heated to 80° C. (pre-heated oil bath) under an atmosphere of nitrogen for 1 hour. The reaction mixture is cooled to room temperature, acidified to pH 1 with 2N aqueous hydrochloric acid, filtered through a plug of diatomaceous earth and the two phases are separated. The organic phase is collected, and the aqueous phase is extracted with dichloromethane (2×75 ml). the organic phases are combined, washed with water, and dried over anhydrous sodium sulfate. The mixture is filtered, and the filtrate is evaporated under reduced pressure. The residue is purified by column chromatography on silica gel to give 4-(4-bromo-2-ethylphenyl)-2,2,6,6-tetramethyl-cyclohexane-1,3,5-trione as a white solid (3.5 g).

This compound may be converted into compounds C-2 to C-8 in Table C, using appropriate arylboronic acids under the Suzuki-Miyaura conditions described in Step 5 of Example 5.

TABLE C

| Compound Number | Structure | $^1$H nmr (CDCl$_3$ unless stated) or other physical data |
|---|---|---|
| C-1 | 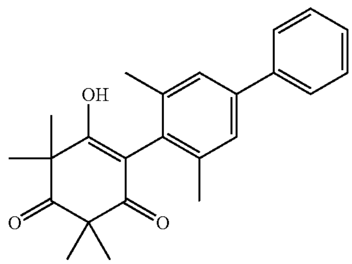 [SMILES: Cc1cc(-c2ccccc2)cc(C)c1C1=C(O)C(C)(C)C(=O)C(C)(C)C1=O] | $\delta_H$ 7.60(d, 2H), 7.45(t, 2H), 7.38-7.34(m, 3H), 5.73(s, 1H), 2.18(s, 6H), 1.57(s, 6H), 1.47(s, 6H). |
| C-2 | 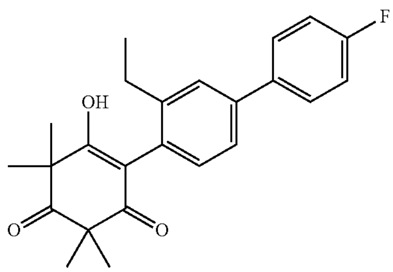 [SMILES: CCc1cc(-c2ccc(F)cc2)ccc1C1=C(O)C(C)(C)C(=O)C(C)(C)C1=O] | $\delta_H$ (DMSO-d$_6$) 10.32(s, 1H), 7.75-7.71(m, 2H), 7.5(d, 1H), 7.44(dd, 1H), 7.3(t, 2H), 7.02(d, 1H), 2.4(m, 2H), 1.46(s, 6H), 1.3(br s, 6H), 1.17(t, 3H). |
| C-3 | 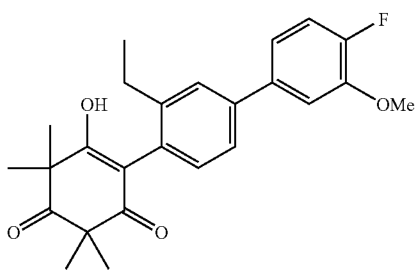 [SMILES: CCc1cc(-c2ccc(F)c(OC)c2)ccc1C1=C(O)C(C)(C)C(=O)C(C)(C)C1=O] | $\delta_H$ 7.50(s, 1H), 7.45(d, 1H), 7.20-7.10(m, 4H), 5.85(br, 1H), 3.95(s, 3H), 2.50(m, 2H), 1.60 (s, 6H), 1.45(2 × s, 6H), 1.15(t, 3H). |
| C-4 | 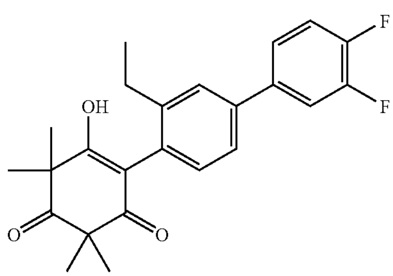 [SMILES: CCc1cc(-c2ccc(F)c(F)c2)ccc1C1=C(O)C(C)(C)C(=O)C(C)(C)C1=O] | $\delta_H$ 7.50(s, 1H), 7.45(d, 1H), 7.40(m, 1H), 7.30 (br, 1H), 7.25(m, 1H), 7.15(d, 1H), 5.80(s, 1H), 2.50(m, 2H), 1.60(s, 6H), 1.45(2 × s, 6H), 1.15(t, 3H). |
| C-5 | 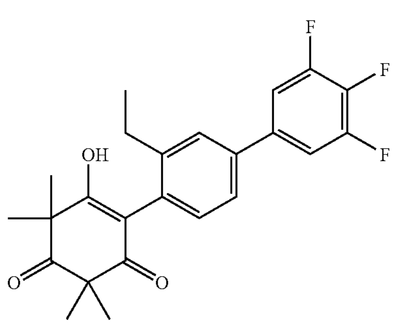 [SMILES: CCc1cc(-c2cc(F)c(F)c(F)c2)ccc1C1=C(O)C(C)(C)C(=O)C(C)(C)C1=O] | $\delta_H$ 7.50(s, 1H), 7.40(d, 1H), 7.20(m, 3H), 5.80 (br, 1H), 2.50(m, 2H), 1.60(s, 6H), 1.50(2 × s, 6H), 1.10(t, 3H). |

TABLE C-continued

| Compound Number | Structure | ¹H nmr (CDCl₃ unless stated) or other physical data |
|---|---|---|
| C-6 | 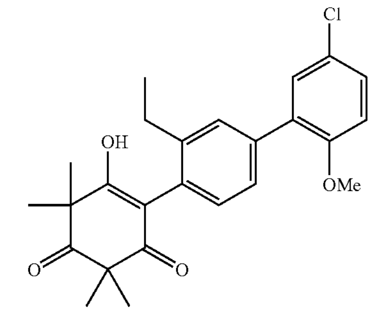 | $\delta_H$ 7.50(s, 1H), 7.45(d, 1H), 7.35(s, 1H), 7.30 (m, 1H), 7.10(d, 1H), 6.90(d, 1H), 6.00(br, 1H), 3.80(s, 3H), 2.50(m, 2H), 1.60(s, 6H), 1.45(2 × s, 6H), 1.15(t, 3H). |
| C-7 | 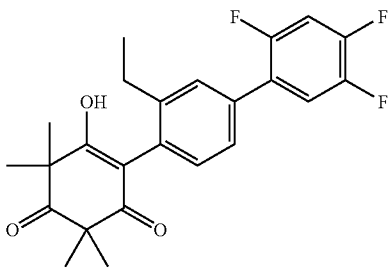 [SMILES: CCc1cc(-c2cc(F)c(F)cc2F)ccc1C1=C(O)C(C)(C)C(=O)C(C)(C)C1=O] | $\delta_H$ 7.50(s, 1H), 7.40(d, 1H), 7.30(m, 1H), 7.20 (d, 1H), 7.05(m, 1H), 5.80(br, 1H), 2.50(m, 2H), 1.60(s, 6H), 1.45(2 × s, 6H), 1.15(t, 3H). |
| C-8 | 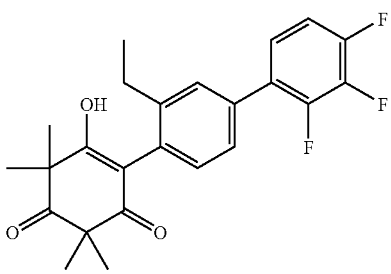 | $\delta_H$ 7.50(s, 1H), 7.40(d, 1H), 7.20(m, 3H), 5.90(br, 1H), 2.50(m, 2H), 1.60(s, 6H), 1.45 (2 × s, 6H), 1.15(t, 3H). |

The compounds of the following Tables 1 to 40 may be obtained in an analogous manner.

Table 1:

This table covers 1134 compounds of the type T-1:

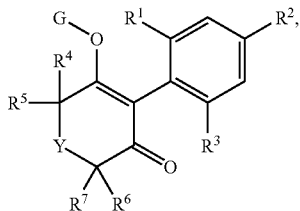

wherein Y is O, $R^4$, $R^5$, $R^6$ and $R^7$ are hydrogen, G is hydrogen and $R^1$, $R^2$ and $R^3$ are as defined below:

| Compound Number | $R^1$ | $R^2$ | $R^3$ |
|---|---|---|---|
| 1.001 | CH₃ | phenyl | H |
| 1.002 | CH₃ | 2-fluorophenyl | H |
| 1.003 | CH₃ | 3-fluorophenyl | H |
| 1.004 | CH₃ | 4-fluorophenyl | H |
| 1.005 | CH₃ | 2-chlorophenyl | H |
| 1.006 | CH₃ | 3-chlorophenyl | H |
| 1.007 | CH₃ | 4-chlorophenyl | H |
| 1.008 | CH₃ | 2-bromophenyl | H |
| 1.009 | CH₃ | 3-bromophenyl | H |
| 1.010 | CH₃ | 4-bromophenyl | H |
| 1.011 | CH₃ | 4-tert-butyl | H |
| 1.012 | CH₃ | 2-iodophenyl | H |
| 1.013 | CH₃ | 3-iodophenyl | H |
| 1.014 | CH₃ | 4-iodophenyl | H |
| 1.015 | CH₃ | 2-methylphenyl | H |
| 1.016 | CH₃ | 3-methylphenyl | H |
| 1.017 | CH₃ | 4-methylphenyl | H |
| 1.018 | CH₃ | 2-cyanophenyl | H |
| 1.019 | CH₃ | 3-cyanophenyl | H |
| 1.020 | CH₃ | 4-cyanophenyl | H |
| 1.021 | CH₃ | 2-methoxyphenyl | H |
| 1.022 | CH₃ | 3-methoxyphenyl | H |
| 1.023 | CH₃ | 4-methoxyphenyl | H |
| 1.024 | CH₃ | 2-difluoromethoxyphenyl | H |
| 1.025 | CH₃ | 3-difluoromethoxyphenyl | H |
| 1.026 | CH₃ | 4-difluoromethoxyphenyl | H |
| 1.027 | CH₃ | 2-difluoromethylphenyl | H |
| 1.028 | CH₃ | 3-difluoromethylphenyl | H |
| 1.029 | CH₃ | 4-difluoromethylphenyl | H |
| 1.030 | CH₃ | 2-trifluoromethylphenyl | H |

-continued

| Compound Number | R¹ | R² | R³ |
|---|---|---|---|
| 1.031 | $CH_3$ | 3-trifluoromethylphenyl | H |
| 1.032 | $CH_3$ | 4-trifluoromethylphenyl | H |
| 1.033 | $CH_3$ | 2-trifluoromethoxyphenyl | H |
| 1.034 | $CH_3$ | 3-trifluoromethoxyphenyl | H |
| 1.035 | $CH_3$ | 4-trifluoromethoxyphenyl | H |
| 1.036 | $CH_3$ | 4-methylthiophenyl | H |
| 1.037 | $CH_3$ | 4-methylsulfinylphenyl | H |
| 1.038 | $CH_3$ | 4-methylsulfonylphenyl | H |
| 1.039 | $CH_3$ | 4-trifluoromethylthiophenyl | H |
| 1.040 | $CH_3$ | 4-trifluoromethylsulfinylphenyl | H |
| 1.041 | $CH_3$ | 4-trifluoromethylsulfonylphenyl | H |
| 1.042 | $CH_3$ | 2,3-difluorophenyl | H |
| 1.043 | $CH_3$ | 2,4-difluorophenyl | H |
| 1.044 | $CH_3$ | 2,5-difluorophenyl | H |
| 1.045 | $CH_3$ | 2,6-difluorophenyl | H |
| 1.046 | $CH_3$ | 3,4-difluorophenyl | H |
| 1.047 | $CH_3$ | 3,5-difluorophenyl | H |
| 1.048 | $CH_3$ | 2,3-dichlorophenyl | H |
| 1.049 | $CH_3$ | 2,4-dichlorophenyl | H |
| 1.050 | $CH_3$ | 2,5-dichlorophenyl | H |
| 1.051 | $CH_3$ | 2,6-dichlorophenyl | H |
| 1.052 | $CH_3$ | 3,4-dichlorophenyl | H |
| 1.053 | $CH_3$ | 3,5-dichlorophenyl | H |
| 1.054 | $CH_3$ | 4-chloro-2-cyanophenyl | H |
| 1.055 | $CH_3$ | 4-chloro-3-cyanophenyl | H |
| 1.056 | $CH_3$ | 4-chloro-2-fluorophenyl | H |
| 1.057 | $CH_3$ | 4-chloro-3-fluorophenyl | H |
| 1.058 | $CH_3$ | 4-chloro-2-methoxyphenyl | H |
| 1.059 | $CH_3$ | 4-chloro-3-methoxyphenyl | H |
| 1.060 | $CH_3$ | 4-chloro-2-methylphenyl | H |
| 1.061 | $CH_3$ | 4-chloro-3-methylphenyl | H |
| 1.062 | $CH_3$ | 4-chloro-2-difluoromethoxyphenyl | H |
| 1.063 | $CH_3$ | 4-chloro-3-difluoromethoxyphenyl | H |
| 1.064 | $CH_3$ | 4-chloro-2-trifluoromethoxyphenyl | H |
| 1.065 | $CH_3$ | 4-chloro-3-trifluoromethoxyphenyl | H |
| 1.066 | $CH_3$ | 4-chloro-2-difluoromethylphenyl | H |
| 1.067 | $CH_3$ | 4-chloro-3-difluoromethylphenyl | H |
| 1.068 | $CH_3$ | 4-chloro-2-trifluoromethylphenyl | H |
| 1.069 | $CH_3$ | 4-chloro-3-trifluoromethylphenyl | H |
| 1.070 | $CH_3$ | 4-chloro-2,3-difluorophenyl | H |
| 1.071 | $CH_3$ | 4-chloro-2,5-difluorophenyl | H |
| 1.072 | $CH_3$ | 4,-chloro-2,6-difluorophenyl | H |
| 1.073 | $CH_3$ | 2,4-dichloro-3-fluorophenyl | H |
| 1.074 | $CH_3$ | 2,4-dichloro-5-fluorophenyl | H |
| 1.075 | $CH_3$ | 2,4-dichloro-6-fluorophenyl | H |
| 1.076 | $CH_3$ | 2,3,4-trichlorophenyl | H |
| 1.077 | $CH_3$ | 2,3,5-trichlorophenyl | H |
| 1.078 | $CH_3$ | 2,3,6-trichlorophenyl | H |
| 1.079 | $CH_3$ | 2,4,5-trichlorophenyl | H |
| 1.080 | $CH_3$ | 2,4,6-trichlorophenyl | H |
| 1.081 | $CH_3$ | 2,3,4-trifluorophenyl | H |
| 1.082 | $CH_3$ | 2,3,5-trifluorophenyl | H |
| 1.083 | $CH_3$ | 2,3,6-trifluorophenyl | H |
| 1.084 | $CH_3$ | 2,4,5-trifluorophenyl | H |
| 1.085 | $CH_3$ | 2,4,6-trifluorophenyl | H |
| 1.086 | $CH_3$ | 2-fluoro-4-trifluoromethylphenyl | H |
| 1.087 | $CH_3$ | 3-fluoro-4-trifluoromethylphenyl | H |
| 1.088 | $CH_3$ | 2-chloropyridin-5-yl | H |
| 1.089 | $CH_3$ | 3-chloropyridinyl-5-yl | H |
| 1.090 | $CH_3$ | 2-methylpyridin-5-yl | H |
| 1.091 | $CH_3$ | 3-methylpyridinyl-5-yl | H |
| 1.092 | $CH_3$ | 2-trifluoromethylpyridin-5-yl | H |
| 1.093 | $CH_3$ | 3-trifluoromethylpyridin-5-yl | H |
| 1.094 | $CH_3$ | 2-chloro-3-methylpyridin-5-yl | H |
| 1.095 | $CH_3$ | 2-chloro-4-methylpyridin-5-yl | H |
| 1.096 | $CH_3$ | 6-chloro-2-methylpyridin-3-yl | H |
| 1.097 | $CH_3$ | 2,3-dichloropyridin-5-yl | H |
| 1.098 | $CH_3$ | 2,4-dichloropyridin-5-yl | H |
| 1.099 | $CH_3$ | 2,6-dichloropyridin-3-yl | H |
| 1.100 | $CH_3$ | pyrazin-2-yl | H |
| 1.101 | $CH_3$ | 2-chloropyrazin-5-yl | H |
| 1.102 | $CH_3$ | 2-bromopyrazin-5-yl | H |
| 1.103 | $CH_3$ | pyridazin-3-yl | H |
| 1.104 | $CH_3$ | 6-bromopyridazin-3-yl | H |
| 1.105 | $CH_3$ | 6-chloropyridazin-3-yl | H |
| 1.106 | $CH_3$ | pyrimidin-5-yl | H |
| 1.107 | $CH_3$ | 2-bromopyrimidin-5-yl | H |
| 1.108 | $CH_3$ | 5-bromopyrimidin-2-yl | H |
| 1.109 | $CH_3$ | 2-chloropyrimidin-5-yl | H |
| 1.110 | $CH_3$ | 5-chloropyrimidin-2-yl | H |
| 1.111 | $CH_3$ | 2-furyl | H |
| 1.112 | $CH_3$ | 3-furyl | H |
| 1.113 | $CH_3$ | 2-thienyl | H |
| 1.114 | $CH_3$ | 3-thienyl | H |
| 1.115 | $CH_3$ | 4-bromothien-2-yl | H |
| 1.116 | $CH_3$ | 5-bromothien-2-yl | H |
| 1.117 | $CH_3$ | 4-chlorothien-2-yl | H |
| 1.118 | $CH_3$ | 5-chlorothien-2-yl | H |
| 1.119 | $CH_3$ | pyrazol-1-yl | H |
| 1.120 | $CH_3$ | 3-chloropyrazol-1-yl | H |
| 1.121 | $CH_3$ | 4-chloropyrazol-1-yl | H |
| 1.122 | $CH_3$ | 1-methylpyrazol-4-yl | H |
| 1.123 | $CH_3$ | 1-methyl-3-trifluoromethylpyrazol-5-yl | H |
| 1.124 | $CH_3$ | 2-thiazolyl | H |
| 1.125 | $CH_3$ | 4-methylthiazol-2-yl | H |
| 1.126 | $CH_3$ | 5-methylthiazol-2-yl | H |
| 1.127 | $CH_3CH_2$ | phenyl | H |
| 1.128 | $CH_3CH_2$ | 2-fluorophenyl | H |
| 1.129 | $CH_3CH_2$ | 3-fluorophenyl | H |
| 1.130 | $CH_3CH_2$ | 4-fluorophenyl | H |
| 1.131 | $CH_3CH_2$ | 2-chlorophenyl | H |
| 1.132 | $CH_3CH_2$ | 3-chlorophenyl | H |
| 1.133 | $CH_3CH_2$ | 4-chlorophenyl | H |
| 1.134 | $CH_3CH_2$ | 2-bromophenyl | H |
| 1.135 | $CH_3CH_2$ | 3-bromophenyl | H |
| 1.136 | $CH_3CH_2$ | 4-bromophenyl | H |
| 1.137 | $CH_3CH_2$ | 4-tert-butyl | H |
| 1.138 | $CH_3CH_2$ | 2-iodophenyl | H |
| 1.139 | $CH_3CH_2$ | 3-iodophenyl | H |
| 1.140 | $CH_3CH_2$ | 4-iodophenyl | H |
| 1.141 | $CH_3CH_2$ | 2-methylphenyl | H |
| 1.142 | $CH_3CH_2$ | 3-methylphenyl | H |
| 1.143 | $CH_3CH_2$ | 4-methylphenyl | H |
| 1.144 | $CH_3CH_2$ | 2-cyanophenyl | H |
| 1.145 | $CH_3CH_2$ | 3-cyanophenyl | H |
| 1.146 | $CH_3CH_2$ | 4-cyanophenyl | H |
| 1.147 | $CH_3CH_2$ | 2-methoxyphenyl | H |
| 1.148 | $CH_3CH_2$ | 3-methoxyphenyl | H |
| 1.149 | $CH_3CH_2$ | 4-methoxyphenyl | H |
| 1.150 | $CH_3CH_2$ | 2-difluoromethoxyphenyl | H |
| 1.151 | $CH_3CH_2$ | 3-difluoromethoxyphenyl | H |
| 1.152 | $CH_3CH_2$ | 4-difluoromethoxyphenyl | H |
| 1.153 | $CH_3CH_2$ | 2-difluoromethylphenyl | H |
| 1.154 | $CH_3CH_2$ | 3-difluoromethylphenyl | H |
| 1.155 | $CH_3CH_2$ | 4-difluoromethylphenyl | H |
| 1.156 | $CH_3CH_2$ | 2-trifluoromethylphenyl | H |
| 1.157 | $CH_3CH_2$ | 3-trifluoromethylphenyl | H |
| 1.158 | $CH_3CH_2$ | 4-trifluoromethylphenyl | H |
| 1.159 | $CH_3CH_2$ | 2-trifluoromethoxyphenyl | H |
| 1.160 | $CH_3CH_2$ | 3-trifluoromethoxyphenyl | H |
| 1.161 | $CH_3CH_2$ | 4-trifluoromethoxyphenyl | H |
| 1.162 | $CH_3CH_2$ | 4-methylthiophenyl | H |
| 1.163 | $CH_3CH_2$ | 4-methylsulfinylphenyl | H |
| 1.164 | $CH_3CH_2$ | 4-methylsulfonylphenyl | H |
| 1.165 | $CH_3CH_2$ | 4-trifluoromethylthiophenyl | H |
| 1.166 | $CH_3CH_2$ | 4-trifluoromethylsulfinylphenyl | H |
| 1.167 | $CH_3CH_2$ | 4-trifluoromethylsulfonylphenyl | H |
| 1.168 | $CH_3CH_2$ | 2,3-difluorophenyl | H |
| 1.169 | $CH_3CH_2$ | 2,4-difluorophenyl | H |
| 1.170 | $CH_3CH_2$ | 2,5-difluorophenyl | H |
| 1.171 | $CH_3CH_2$ | 2,6-difluorophenyl | H |
| 1.172 | $CH_3CH_2$ | 3,4-difluorophenyl | H |
| 1.173 | $CH_3CH_2$ | 3,5-difluorophenyl | H |
| 1.174 | $CH_3CH_2$ | 2,3-dichlorophenyl | H |
| 1.175 | $CH_3CH_2$ | 2,4-dichlorophenyl | H |
| 1.176 | $CH_3CH_2$ | 2,5-dichlorophenyl | H |
| 1.177 | $CH_3CH_2$ | 2,6-dichlorophenyl | H |
| 1.178 | $CH_3CH_2$ | 3,4-dichlorophenyl | H |
| 1.179 | $CH_3CH_2$ | 3,5-dichlorophenyl | H |
| 1.180 | $CH_3CH_2$ | 4-chloro-2-cyanophenyl | H |

-continued

| Compound Number | R¹ | R² | R³ |
|---|---|---|---|
| 1.181 | $CH_3CH_2$ | 4-chloro-3-cyanophenyl | H |
| 1.182 | $CH_3CH_2$ | 4-chloro-2-fluorophenyl | H |
| 1.183 | $CH_3CH_2$ | 4-chloro-3-fluorophenyl | H |
| 1.184 | $CH_3CH_2$ | 4-chloro-2-methoxyphenyl | H |
| 1.185 | $CH_3CH_2$ | 4-chloro-3-methoxyphenyl | H |
| 1.186 | $CH_3CH_2$ | 4-chloro-2-methylphenyl | H |
| 1.187 | $CH_3CH_2$ | 4-chloro-3-methylphenyl | H |
| 1.188 | $CH_3CH_2$ | 4-chloro-2-difluoromethoxyphenyl | H |
| 1.189 | $CH_3CH_2$ | 4-chloro-3-difluoromethoxyphenyl | H |
| 1.190 | $CH_3CH_2$ | 4-chloro-2-trifluoromethoxyphenyl | H |
| 1.191 | $CH_3CH_2$ | 4-chloro-3-trifluoromethoxyphenyl | H |
| 1.192 | $CH_3CH_2$ | 4-chloro-2-difluoromethylphenyl | H |
| 1.193 | $CH_3CH_2$ | 4-chloro-3-difluoromethylphenyl | H |
| 1.194 | $CH_3CH_2$ | 4-chloro-2-trifluoromethylphenyl | H |
| 1.195 | $CH_3CH_2$ | 4-chloro-3-trifluoromethylphenyl | H |
| 1.196 | $CH_3CH_2$ | 4-chloro-2,3-difluorophenyl | H |
| 1.197 | $CH_3CH_2$ | 4-chloro-2,5-difluorophenyl | H |
| 1.198 | $CH_3CH_2$ | 4,-chloro-2,6-difluorophenyl | H |
| 1.199 | $CH_3CH_2$ | 2,4-dichloro-3-fluorophenyl | H |
| 1.200 | $CH_3CH_2$ | 2,4-dichloro-5-fluorophenyl | H |
| 1.201 | $CH_3CH_2$ | 2,4-dichloro-6-fluorophenyl | H |
| 1.202 | $CH_3CH_2$ | 2,3,4-trichlorophenyl | H |
| 1.203 | $CH_3CH_2$ | 2,3,5-trichlorophenyl | H |
| 1.204 | $CH_3CH_2$ | 2,3,6-trichlorophenyl | H |
| 1.205 | $CH_3CH_2$ | 2,4,5-trichlorophenyl | H |
| 1.206 | $CH_3CH_2$ | 2,4,6-trichlorophenyl | H |
| 1.207 | $CH_3CH_2$ | 2,3,4-trifluorophenyl | H |
| 1.208 | $CH_3CH_2$ | 2,3,5-trifluorophenyl | H |
| 1.209 | $CH_3CH_2$ | 2,3,6-trifluorophenyl | H |
| 1.210 | $CH_3CH_2$ | 2,4,5-trifluorophenyl | H |
| 1.211 | $CH_3CH_2$ | 2,4,6-trifluorophenyl | H |
| 1.212 | $CH_3CH_2$ | 2-fluoro-4-trifluoromethylphenyl | H |
| 1.213 | $CH_3CH_2$ | 3-fluoro-4-trifluoromethylphenyl | H |
| 1.214 | $CH_3CH_2$ | 2-chloropyridin-5-yl | H |
| 1.215 | $CH_3CH_2$ | 3-chloropyridinyl-5-yl | H |
| 1.216 | $CH_3CH_2$ | 2-methylpyridin-5-yl | H |
| 1.217 | $CH_3CH_2$ | 3-methylpyridinyl-5-yl | H |
| 1.218 | $CH_3CH_2$ | 2-trifluoromethylpyridin-5-yl | H |
| 1.219 | $CH_3CH_2$ | 3-trifluoromethylpyridin-5-yl | H |
| 1.220 | $CH_3CH_2$ | 2-chloro-3-methylpyridin-5-yl | H |
| 1.221 | $CH_3CH_2$ | 2-chloro-4-methylpyridin-5-yl | H |
| 1.222 | $CH_3CH_2$ | 6-chloro-2-methylpyridin-3-yl | H |
| 1.223 | $CH_3CH_2$ | 2,3-dichloropyridin-5-yl | H |
| 1.224 | $CH_3CH_2$ | 2,4-dichloropyridin-5-yl | H |
| 1.225 | $CH_3CH_2$ | 2,6-dichloropyridin-3-yl | H |
| 1.226 | $CH_3CH_2$ | pyrazin-2-yl | H |
| 1.227 | $CH_3CH_2$ | 2-chloropyrazin-5-yl | H |
| 1.228 | $CH_3CH_2$ | 2-bromopyrazin-5-yl | H |
| 1.229 | $CH_3CH_2$ | pyridazin-3-yl | H |
| 1.230 | $CH_3CH_2$ | 6-bromopyridazin-3-yl | H |
| 1.231 | $CH_3CH_2$ | 6-bromopyridazin-3-yl | H |
| 1.232 | $CH_3CH_2$ | pyrimidin-5-yl | H |
| 1.233 | $CH_3CH_2$ | 2-bromopyrimidin-5-yl | H |
| 1.234 | $CH_3CH_2$ | 5-bromopyrimidin-2-yl | H |
| 1.235 | $CH_3CH_2$ | 2-chloropyrimidin-5-yl | H |
| 1.236 | $CH_3CH_2$ | 5-chloropyrimidin-2-yl | H |
| 1.237 | $CH_3CH_2$ | 2-furyl | H |
| 1.238 | $CH_3CH_2$ | 3-furyl | H |
| 1.239 | $CH_3CH_2$ | 2-thienyl | H |
| 1.240 | $CH_3CH_2$ | 3-thienyl | H |
| 1.241 | $CH_3CH_2$ | 4-bromothien-2-yl | H |
| 1.242 | $CH_3CH_2$ | 5-bromothien-2-yl | H |
| 1.243 | $CH_3CH_2$ | 4-chlorothien-2-yl | H |
| 1.244 | $CH_3CH_2$ | 5-chlorothien-2-yl | H |
| 1.245 | $CH_3CH_2$ | pyrazol-1-yl | H |
| 1.246 | $CH_3CH_2$ | 3-chloropyrazol-1-yl | H |
| 1.247 | $CH_3CH_2$ | 4-chloropyrazol-1-yl | H |
| 1.248 | $CH_3CH_2$ | 1-methylpyrazol-4-yl | H |
| 1.249 | $CH_3CH_2$ | 1-methyl-3-trifluoromethylpyrazol-5-yl | H |
| 1.250 | $CH_3CH_2$ | 2-thiazolyl | H |
| 1.251 | $CH_3CH_2$ | 4-methylthiazol-2-yl | H |
| 1.252 | $CH_3CH_2$ | 5-methylthiazol-2-yl | H |
| 1.253 | vinyl | phenyl | H |
| 1.254 | vinyl | 2-fluorophenyl | H |
| 1.255 | vinyl | 3-fluorophenyl | H |
| 1.256 | vinyl | 4-fluorophenyl | H |
| 1.257 | vinyl | 2-chlorophenyl | H |
| 1.258 | vinyl | 3-chlorophenyl | H |
| 1.259 | vinyl | 4-chlorophenyl | H |
| 1.260 | vinyl | 2-bromophenyl | H |
| 1.261 | vinyl | 3-bromophenyl | H |
| 1.262 | vinyl | 4-bromophenyl | H |
| 1.263 | vinyl | 4-tert-butyl | H |
| 1.264 | vinyl | 2-iodophenyl | H |
| 1.265 | vinyl | 3-iodophenyl | H |
| 1.266 | vinyl | 4-iodophenyl | H |
| 1.267 | vinyl | 2-methylphenyl | H |
| 1.268 | vinyl | 3-methylphenyl | H |
| 1.269 | vinyl | 4-methylphenyl | H |
| 1.270 | vinyl | 2-cyanophenyl | H |
| 1.271 | vinyl | 3-cyanophenyl | H |
| 1.272 | vinyl | 4-cyanophenyl | H |
| 1.273 | vinyl | 2-methoxyphenyl | H |
| 1.274 | vinyl | 3-methoxyphenyl | H |
| 1.275 | vinyl | 4-methoxyphenyl | H |
| 1.276 | vinyl | 2-difluoromethoxyphenyl | H |
| 1.277 | vinyl | 3-difluoromethoxyphenyl | H |
| 1.278 | vinyl | 4-difluoromethoxyphenyl | H |
| 1.279 | vinyl | 2-difluoromethylphenyl | H |
| 1.280 | vinyl | 3-difluoromethylphenyl | H |
| 1.281 | vinyl | 4-difluoromethylphenyl | H |
| 1.282 | vinyl | 2-trifluoromethylphenyl | H |
| 1.283 | vinyl | 3-trifluoromethylphenyl | H |
| 1.284 | vinyl | 4-trifluoromethylphenyl | H |
| 1.285 | vinyl | 2-trifluoromethoxyphenyl | H |
| 1.286 | vinyl | 3-trifluoromethoxyphenyl | H |
| 1.287 | vinyl | 4-trifluoromethoxyphenyl | H |
| 1.288 | vinyl | 4-methylthiophenyl | H |
| 1.289 | vinyl | 4-methylsulfinylphenyl | H |
| 1.290 | vinyl | 4-methylsulfonylphenyl | H |
| 1.291 | vinyl | 4-trifluoromethylthiophenyl | H |
| 1.292 | vinyl | 4-trifluoromethylsulfinylphenyl | H |
| 1.293 | vinyl | 4-trifluoromethylsulfonylphenyl | H |
| 1.294 | vinyl | 2,3-difluorophenyl | H |
| 1.295 | vinyl | 2,4-difluorophenyl | H |
| 1.296 | vinyl | 2,5-difluorophenyl | H |
| 1.297 | vinyl | 2,6-difluorophenyl | H |
| 1.298 | vinyl | 3,4-difluorophenyl | H |
| 1.299 | vinyl | 3,5-difluorophenyl | H |
| 1.300 | vinyl | 2,3-dichlorophenyl | H |
| 1.301 | vinyl | 2,4-dichlorophenyl | H |
| 1.302 | vinyl | 2,5-dichlorophenyl | H |
| 1.303 | vinyl | 2,6-dichlorophenyl | H |
| 1.304 | vinyl | 3,4-dichlorophenyl | H |
| 1.305 | vinyl | 3,5-dichlorophenyl | H |
| 1.306 | vinyl | 4-chloro-2-cyanophenyl | H |
| 1.307 | vinyl | 4-chloro-3-cyanophenyl | H |
| 1.308 | vinyl | 4-chloro-2-fluorophenyl | H |
| 1.309 | vinyl | 4-chloro-3-fluorophenyl | H |
| 1.310 | vinyl | 4-chloro-2-methoxyphenyl | H |
| 1.311 | vinyl | 4-chloro-3-methoxyphenyl | H |
| 1.312 | vinyl | 4-chloro-2-methylphenyl | H |
| 1.313 | vinyl | 4-chloro-3-methylphenyl | H |
| 1.314 | vinyl | 4-chloro-2-difluoromethoxyphenyl | H |
| 1.315 | vinyl | 4-chloro-3-difluoromethoxyphenyl | H |
| 1.316 | vinyl | 4-chloro-2-trifluoromethoxyphenyl | H |
| 1.317 | vinyl | 4-chloro-3-trifluoromethoxyphenyl | H |
| 1.318 | vinyl | 4-chloro-2-difluoromethylphenyl | H |
| 1.319 | vinyl | 4-chloro-3-difluoromethylphenyl | H |
| 1.320 | vinyl | 4-chloro-2-trifluoromethylphenyl | H |
| 1.321 | vinyl | 4-chloro-3-trifluoromethylphenyl | H |
| 1.322 | vinyl | 4-chloro-2,3-difluorophenyl | H |
| 1.323 | vinyl | 4-chloro-2,5-difluorophenyl | H |
| 1.324 | vinyl | 4,-chloro-2,6-difluorophenyl | H |
| 1.325 | vinyl | 2,4-dichloro-3-fluorophenyl | H |
| 1.326 | vinyl | 2,4-dichloro-5-fluorophenyl | H |
| 1.327 | vinyl | 2,4-dichloro-6-fluorophenyl | H |
| 1.328 | vinyl | 2,3,4-trichlorophenyl | H |
| 1.329 | vinyl | 2,3,5-trichlorophenyl | H |
| 1.330 | vinyl | 2,3,6-trichlorophenyl | H |

-continued

| Compound Number | R¹ | R² | R³ |
|---|---|---|---|
| 1.331 | vinyl | 2,4,5-trichlorophenyl | H |
| 1.332 | vinyl | 2,4,6-trichlorophenyl | H |
| 1.333 | vinyl | 2,3,4-trifluorophenyl | H |
| 1.334 | vinyl | 2,3,5-trifluorophenyl | H |
| 1.335 | vinyl | 2,3,6-trifluorophenyl | H |
| 1.336 | vinyl | 2,4,5-trifluorophenyl | H |
| 1.337 | vinyl | 2,4,6-trifluorophenyl | H |
| 1.338 | vinyl | 2-fluoro-4-trifluoromethylphenyl | H |
| 1.339 | vinyl | 3-fluoro-4-trifluoromethylphenyl | H |
| 1.340 | vinyl | 2-chloropyridin-5-yl | H |
| 1.341 | vinyl | 3-chloropyridinyl-5-yl | H |
| 1.342 | vinyl | 2-methylpyridin-5-yl | H |
| 1.343 | vinyl | 3-methylpyridinyl-5-yl | H |
| 1.344 | vinyl | 2-trifluoromethylpyridin-5-yl | H |
| 1.345 | vinyl | 3-trifluoromethylpyridin-5-yl | H |
| 1.346 | vinyl | 2-chloro-3-methylpyridin-5-yl | H |
| 1.347 | vinyl | 2-chloro-4-methylpyridin-5-yl | H |
| 1.348 | vinyl | 6-chloro-2-methylpyridin-3-yl | H |
| 1.349 | vinyl | 2,3-dichloropyridin-5-yl | H |
| 1.350 | vinyl | 2,4-dichloropyridin-5-yl | H |
| 1.351 | vinyl | 2,6-dichloropyridin-3-yl | H |
| 1.352 | vinyl | pyrazin-2-yl | H |
| 1.353 | vinyl | 2-chloropyrazin-5-yl | H |
| 1.354 | vinyl | 2-bromopyrazin-5-yl | H |
| 1.355 | vinyl | pyridazin-3-yl | H |
| 1.356 | vinyl | 6-bromopyridazin-3-yl | H |
| 1.357 | vinyl | 6-chloropyridazin-3-yl | H |
| 1.358 | vinyl | pyrimidin-5-yl | H |
| 1.359 | vinyl | 2-bromopyrimidin-5-yl | H |
| 1.360 | vinyl | 5-bromopyrimidin-2-yl | H |
| 1.361 | vinyl | 2-chloropyrimidin-5-yl | H |
| 1.362 | vinyl | 5-chloropyrimidin-2-yl | H |
| 1.363 | vinyl | 2-furyl | H |
| 1.364 | vinyl | 3-furyl | H |
| 1.365 | vinyl | 2-thienyl | H |
| 1.366 | vinyl | 3-thienyl | H |
| 1.367 | vinyl | 4-bromothien-2-yl | H |
| 1.368 | vinyl | 5-bromothien-2-yl | H |
| 1.369 | vinyl | 4-chlorothien-2-yl | H |
| 1.370 | vinyl | 5-chlorothien-2-yl | H |
| 1.371 | vinyl | pyrazol-1-yl | H |
| 1.372 | vinyl | 3-chloropyrazol-1-yl | H |
| 1.373 | vinyl | 4-chloropyrazol-1-yl | H |
| 1.374 | vinyl | 1-methylpyrazol-4-yl | H |
| 1.375 | vinyl | 1-methyl-3-trifluoromethylpyrazol-5-yl | H |
| 1.376 | vinyl | 2-thiazolyl | H |
| 1.377 | vinyl | 4-methylthiazol-2-yl | H |
| 1.378 | vinyl | 5-methylthiazol-2-yl | H |
| 1.379 | ethynyl | phenyl | H |
| 1.380 | ethynyl | 2-fluorophenyl | H |
| 1.381 | ethynyl | 3-fluorophenyl | H |
| 1.382 | ethynyl | 4-fluorophenyl | H |
| 1.383 | ethynyl | 2-chlorophenyl | H |
| 1.384 | ethynyl | 3-chlorophenyl | H |
| 1.385 | ethynyl | 4-chlorophenyl | H |
| 1.386 | ethynyl | 2-bromophenyl | H |
| 1.387 | ethynyl | 3-bromophenyl | H |
| 1.388 | ethynyl | 4-bromophenyl | H |
| 1.389 | ethynyl | 4-tert-butyl | H |
| 1.390 | ethynyl | 2-iodophenyl | H |
| 1.391 | ethynyl | 3-iodophenyl | H |
| 1.392 | ethynyl | 4-iodophenyl | H |
| 1.393 | ethynyl | 2-methylphenyl | H |
| 1.394 | ethynyl | 3-methylphenyl | H |
| 1.395 | ethynyl | 4-methylphenyl | H |
| 1.396 | ethynyl | 2-cyanophenyl | H |
| 1.397 | ethynyl | 3-cyanophenyl | H |
| 1.398 | ethynyl | 4-cyanophenyl | H |
| 1.399 | ethynyl | 2-methoxyphenyl | H |
| 1.400 | ethynyl | 3-methoxyphenyl | H |
| 1.401 | ethynyl | 4-methoxyphenyl | H |
| 1.402 | ethynyl | 2-difluoromethoxyphenyl | H |
| 1.403 | ethynyl | 3-difluoromethoxyphenyl | H |
| 1.404 | ethynyl | 4-difluoromethoxyphenyl | H |
| 1.405 | ethynyl | 2-difluoromethylphenyl | H |
| 1.406 | ethynyl | 3-difluoromethylphenyl | H |
| 1.407 | ethynyl | 4-difluoromethylphenyl | H |
| 1.408 | ethynyl | 2-trifluoromethylphenyl | H |
| 1.409 | ethynyl | 3-trifluoromethylphenyl | H |
| 1.410 | ethynyl | 4-trifluoromethylphenyl | H |
| 1.411 | ethynyl | 2-trifluoromethoxyphenyl | H |
| 1.412 | ethynyl | 3-trifluoromethoxyphenyl | H |
| 1.413 | ethynyl | 4-trifluoromethoxyphenyl | H |
| 1.414 | ethynyl | 4-methylthiophenyl | H |
| 1.415 | ethynyl | 4-methylsulfinylphenyl | H |
| 1.416 | ethynyl | 4-methylsulfonylphenyl | H |
| 1.417 | ethynyl | 4-trifluoromethylthiophenyl | H |
| 1.418 | ethynyl | 4-trifluoromethylsulfinylphenyl | H |
| 1.419 | ethynyl | 4-trifluoromethylsulfonylphenyl | H |
| 1.420 | ethynyl | 2,3-difluorophenyl | H |
| 1.421 | ethynyl | 2,4-difluorophenyl | H |
| 1.422 | ethynyl | 2,5-difluorophenyl | H |
| 1.423 | ethynyl | 2,6-difluorophenyl | H |
| 1.424 | ethynyl | 3,4-difluorophenyl | H |
| 1.425 | ethynyl | 3,5-difluorophenyl | H |
| 1.426 | ethynyl | 2,3-dichlorophenyl | H |
| 1.427 | ethynyl | 2,4-dichlorophenyl | H |
| 1.428 | ethynyl | 2,5-dichlorophenyl | H |
| 1.429 | ethynyl | 2,6-dichlorophenyl | H |
| 1.430 | ethynyl | 3,4-dichlorophenyl | H |
| 1.431 | ethynyl | 3,5-dichlorophenyl | H |
| 1.432 | ethynyl | 4-chloro-2-cyanophenyl | H |
| 1.433 | ethynyl | 4-chloro-3-cyanophenyl | H |
| 1.434 | ethynyl | 4-chloro-2-fluorophenyl | H |
| 1.435 | ethynyl | 4-chloro-3-fluorophenyl | H |
| 1.436 | ethynyl | 4-chloro-2-methoxyphenyl | H |
| 1.437 | ethynyl | 4-chloro-3-methoxyphenyl | H |
| 1.438 | ethynyl | 4-chloro-2-methylphenyl | H |
| 1.439 | ethynyl | 4-chloro-3-methylphenyl | H |
| 1.440 | ethynyl | 4-chloro-2-difluoromethoxyphenyl | H |
| 1.441 | ethynyl | 4-chloro-3-difluoromethoxyphenyl | H |
| 1.442 | ethynyl | 4-chloro-2-trifluoromethoxyphenyl | H |
| 1.443 | ethynyl | 4-chloro-3-trifluoromethoxyphenyl | H |
| 1.444 | ethynyl | 4-chloro-2-difluoromethylphenyl | H |
| 1.445 | ethynyl | 4-chloro-3-difluoromethylphenyl | H |
| 1.446 | ethynyl | 4-chloro-2-trifluoromethylphenyl | H |
| 1.447 | ethynyl | 4-chloro-3-trifluoromethylphenyl | H |
| 1.448 | ethynyl | 4-chloro-2,3-difluorophenyl | H |
| 1.449 | ethynyl | 4-chloro-2,5-difluorophenyl | H |
| 1.450 | ethynyl | 4,-chloro-2,6-difluorophenyl | H |
| 1.451 | ethynyl | 2,4-dichloro-3-fluorophenyl | H |
| 1.452 | ethynyl | 2,4-dichloro-5-fluorophenyl | H |
| 1.453 | ethynyl | 2,4-dichloro-6-fluorophenyl | H |
| 1.454 | ethynyl | 2,3,4-trichlorophenyl | H |
| 1.455 | ethynyl | 2,3,5-trichlorophenyl | H |
| 1.456 | ethynyl | 2,3,6-trichlorophenyl | H |
| 1.457 | ethynyl | 2,4,5-trichlorophenyl | H |
| 1.458 | ethynyl | 2,4,6-trichlorophenyl | H |
| 1.459 | ethynyl | 2,3,4-trifluorophenyl | H |
| 1.460 | ethynyl | 2,3,5-trifluorophenyl | H |
| 1.461 | ethynyl | 2,3,6-trifluorophenyl | H |
| 1.462 | ethynyl | 2,4,5-trifluorophenyl | H |
| 1.463 | ethynyl | 2,4,6-trifluorophenyl | H |
| 1.464 | ethynyl | 2-fluoro-4-trifluoromethylphenyl | H |
| 1.465 | ethynyl | 3-fluoro-4-trifluoromethylphenyl | H |
| 1.466 | ethynyl | 2-chloropyridin-5-yl | H |
| 1.467 | ethynyl | 3-chloropyridinyl-5-yl | H |
| 1.468 | ethynyl | 2-methylpyridin-5-yl | H |
| 1.469 | ethynyl | 3-methylpyridinyl-5-yl | H |
| 1.470 | ethynyl | 2-trifluoromethylpyridin-5-yl | H |
| 1.471 | ethynyl | 3-trifluoromethylpyridin-5-yl | H |
| 1.472 | ethynyl | 2-chloro-3-methylpyridin-5-yl | H |
| 1.473 | ethynyl | 2-chloro-4-methylpyridin-5-yl | H |
| 1.474 | ethynyl | 6-chloro-2-methylpyridin-3-yl | H |
| 1.475 | ethynyl | 2,3-dichloropyridin-5-yl | H |
| 1.476 | ethynyl | 2,4-dichloropyridin-5-yl | H |
| 1.477 | ethynyl | 2,6-dichloropyridin-3-yl | H |
| 1.478 | ethynyl | pyrazin-2-yl | H |
| 1.479 | ethynyl | 2-chloropyrazin-5-yl | H |
| 1.480 | ethynyl | 2-bromopyrazin-5-yl | H |

| Compound Number | R¹ | R² | R³ |
|---|---|---|---|
| 1.481 | ethynyl | pyridazin-3-yl | H |
| 1.482 | ethynyl | 6-bromopyridazin-3-yl | H |
| 1.483 | ethynyl | 6-chloropyridazin-3-yl | H |
| 1.484 | ethynyl | pyrimidin-5-yl | H |
| 1.485 | ethynyl | 2-bromopyrimidin-5-yl | H |
| 1.486 | ethynyl | 5-bromopyrimidin-2-yl | H |
| 1.487 | ethynyl | 2-chloropyrimidin-5-yl | H |
| 1.488 | ethynyl | 5-chloropyrimidin-2-yl | H |
| 1.489 | ethynyl | 2-furyl | H |
| 1.490 | ethynyl | 3-furyl | H |
| 1.491 | ethynyl | 2-thienyl | H |
| 1.492 | ethynyl | 3-thienyl | H |
| 1.493 | ethynyl | 4-bromothien-2-yl | H |
| 1.494 | ethynyl | 5-bromothien-2-yl | H |
| 1.495 | ethynyl | 4-chlorothien-2-yl | H |
| 1.496 | ethynyl | 5-chlorothien-2-yl | H |
| 1.497 | ethynyl | pyrazol-1-yl | H |
| 1.498 | ethynyl | 3-chloropyrazol-1-yl | H |
| 1.499 | ethynyl | 4-chloropyrazol-1-yl | H |
| 1.500 | ethynyl | 1-methylpyrazol-4-yl | H |
| 1.501 | ethynyl | 1-methyl-3-trifluoromethylpyrazol-5-yl | H |
| 1.502 | ethynyl | 2-thiazolyl | H |
| 1.503 | ethynyl | 4-methylthiazol-2-yl | H |
| 1.504 | ethynyl | 5-methylthiazol-2-yl | H |
| 1.505 | Cl | phenyl | H |
| 1.506 | Cl | 2-fluorophenyl | H |
| 1.507 | Cl | 3-fluorophenyl | H |
| 1.508 | Cl | 4-fluorophenyl | H |
| 1.509 | Cl | 2-chlorophenyl | H |
| 1.510 | Cl | 3-chlorophenyl | H |
| 1.511 | Cl | 4-chlorophenyl | H |
| 1.512 | Cl | 2-bromophenyl | H |
| 1.513 | Cl | 3-bromophenyl | H |
| 1.514 | Cl | 4-bromophenyl | H |
| 1.515 | Cl | 4-tert-butyl | H |
| 1.516 | Cl | 2-iodophenyl | H |
| 1.517 | Cl | 3-iodophenyl | H |
| 1.518 | Cl | 4-iodophenyl | H |
| 1.519 | Cl | 2-methylphenyl | H |
| 1.520 | Cl | 3-methylphenyl | H |
| 1.521 | Cl | 4-methylphenyl | H |
| 1.522 | Cl | 2-cyanophenyl | H |
| 1.523 | Cl | 3-cyanophenyl | H |
| 1.524 | Cl | 4-cyanophenyl | H |
| 1.525 | Cl | 2-methoxyphenyl | H |
| 1.526 | Cl | 3-methoxyphenyl | H |
| 1.527 | Cl | 4-methoxyphenyl | H |
| 1.528 | Cl | 2-difluoromethoxyphenyl | H |
| 1.529 | Cl | 3-difluoromethoxyphenyl | H |
| 1.530 | Cl | 4-difluoromethoxyphenyl | H |
| 1.531 | Cl | 2-difluoromethylphenyl | H |
| 1.532 | Cl | 3-difluoromethylphenyl | H |
| 1.533 | Cl | 4-difluoromethylphenyl | H |
| 1.534 | Cl | 2-trifluoromethylphenyl | H |
| 1.535 | Cl | 3-trifluoromethylphenyl | H |
| 1.536 | Cl | 4-trifluoromethylphenyl | H |
| 1.537 | Cl | 2-trifluoromethoxyphenyl | H |
| 1.538 | Cl | 3-trifluoromethoxyphenyl | H |
| 1.539 | Cl | 4-trifluoromethoxyphenyl | H |
| 1.540 | Cl | 4-methylthiophenyl | H |
| 1.541 | Cl | 4-methylsulfinylphenyl | H |
| 1.542 | Cl | 4-methylsulfonylphenyl | H |
| 1.543 | Cl | 4-trifluoromethylthiophenyl | H |
| 1.544 | Cl | 4-trifluoromethylsulfinylphenyl | H |
| 1.545 | Cl | 4-trifluoromethylsulfonylphenyl | H |
| 1.546 | Cl | 2,3-difluorophenyl | H |
| 1.547 | Cl | 2,4-difluorophenyl | H |
| 1.548 | Cl | 2,5-difluorophenyl | H |
| 1.549 | Cl | 2,6-difluorophenyl | H |
| 1.550 | Cl | 3,4-difluorophenyl | H |
| 1.551 | Cl | 3,5-difluorophenyl | H |
| 1.552 | Cl | 2,3-dichlorophenyl | H |
| 1.553 | Cl | 2,4-dichlorophenyl | H |
| 1.554 | Cl | 2,5-dichlorophenyl | H |
| 1.555 | Cl | 2,6-dichlorophenyl | H |
| 1.556 | Cl | 3,4-dichlorophenyl | H |
| 1.557 | Cl | 3,5-dichlorophenyl | H |
| 1.558 | Cl | 4-chloro-2-cyanophenyl | H |
| 1.559 | Cl | 4-chloro-3-cyanophenyl | H |
| 1.560 | Cl | 4-chloro-2-fluorophenyl | H |
| 1.561 | Cl | 4-chloro-3-fluorophenyl | H |
| 1.562 | Cl | 4-chloro-2-methoxyphenyl | H |
| 1.563 | Cl | 4-chloro-3-methoxyphenyl | H |
| 1.564 | Cl | 4-chloro-2-methylphenyl | H |
| 1.565 | Cl | 4-chloro-3-methylphenyl | H |
| 1.566 | Cl | 4-chloro-2-difluoromethoxyphenyl | H |
| 1.567 | Cl | 4-chloro-3-difluoromethoxyphenyl | H |
| 1.568 | Cl | 4-chloro-2-trifluoromethoxyphenyl | H |
| 1.569 | Cl | 4-chloro-3-trifluoromethoxyphenyl | H |
| 1.570 | Cl | 4-chloro-2-difluoromethylphenyl | H |
| 1.571 | Cl | 4-chloro-3-difluoromethylphenyl | H |
| 1.572 | Cl | 4-chloro-2-trifluoromethylphenyl | H |
| 1.573 | Cl | 4-chloro-3-trifluoromethylphenyl | H |
| 1.574 | Cl | 4-chloro-2,3-difluorophenyl | H |
| 1.575 | Cl | 4-chloro-2,5-difluorophenyl | H |
| 1.576 | Cl | 4,-chloro-2,6-difluorophenyl | H |
| 1.577 | Cl | 2,4-dichloro-3-fluorophenyl | H |
| 1.578 | Cl | 2,4-dichloro-5-fluorophenyl | H |
| 1.579 | Cl | 2,4-dichloro-6-fluorophenyl | H |
| 1.580 | Cl | 2,3,4-trichlorophenyl | H |
| 1.581 | Cl | 2,3,5-trichlorophenyl | H |
| 1.582 | Cl | 2,3,6-trichlorophenyl | H |
| 1.583 | Cl | 2,4,5-trichlorophenyl | H |
| 1.584 | Cl | 2,4,6-trichlorophenyl | H |
| 1.585 | Cl | 2,3,4-trifluorophenyl | H |
| 1.586 | Cl | 2,3,5-trifluorophenyl | H |
| 1.587 | Cl | 2,3,6-trifluorophenyl | H |
| 1.588 | Cl | 2,4,5-trifluorophenyl | H |
| 1.589 | Cl | 2,4,6-trifluorophenyl | H |
| 1.590 | Cl | 2-fluoro-4-trifluoromethylphenyl | H |
| 1.591 | Cl | 3-fluoro-4-trifluoromethylphenyl | H |
| 1.592 | Cl | 2-chloropyridin-5-yl | H |
| 1.593 | Cl | 3-chloropyridinyl-5-yl | H |
| 1.594 | Cl | 2-methylpyridin-5-yl | H |
| 1.595 | Cl | 3-methylpyridinyl-5-yl | H |
| 1.596 | Cl | 2-trifluoromethylpyridin-5-yl | H |
| 1.597 | Cl | 3-trifluoromethylpyridin-5-yl | H |
| 1.598 | Cl | 2-chloro-3-methylpyridin-5-yl | H |
| 1.599 | Cl | 2-chloro-4-methylpyridin-5-yl | H |
| 1.600 | Cl | 6-chloro-2-methylpyridin-3-yl | H |
| 1.601 | Cl | 2,3-dichloropyridin-5-yl | H |
| 1.602 | Cl | 2,4-dichloropyridin-5-yl | H |
| 1.603 | Cl | 2,6-dichloropyridin-3-yl | H |
| 1.604 | Cl | pyrazin-2-yl | H |
| 1.605 | Cl | 2-chloropyrazin-5-yl | H |
| 1.606 | Cl | 2-bromopyrazin-5-yl | H |
| 1.607 | Cl | pyridazin-3-yl | H |
| 1.608 | Cl | 6-bromopyridazin-3-yl | H |
| 1.609 | Cl | 6-chloropyridazin-3-yl | H |
| 1.610 | Cl | pyrimidin-5-yl | H |
| 1.611 | Cl | 2-bromopyrimidin-5-yl | H |
| 1.612 | Cl | 5-bromopyrimidin-2-yl | H |
| 1.613 | Cl | 2-chloropyrimidin-5-yl | H |
| 1.614 | Cl | 5-chloropyrimidin-2-yl | H |
| 1.615 | Cl | 2-furyl | H |
| 1.616 | Cl | 3-furyl | H |
| 1.617 | Cl | 2-thienyl | H |
| 1.618 | Cl | 3-thienyl | H |
| 1.619 | Cl | 4-bromothien-2-yl | H |
| 1.620 | Cl | 5-bromothien-2-yl | H |
| 1.621 | Cl | 4-chlorothien-2-yl | H |
| 1.622 | Cl | 5-chlorothien-2-yl | H |
| 1.623 | Cl | pyrazol-1-yl | H |
| 1.624 | Cl | 3-chloropyrazol-1-yl | H |
| 1.625 | Cl | 4-chloropyrazol-1-yl | H |
| 1.626 | Cl | 1-methylpyrazol-4-yl | H |
| 1.627 | Cl | 1-methyl-3-trifluoromethylpyrazol-5-yl | H |
| 1.628 | Cl | 2-thiazolyl | H |
| 1.629 | Cl | 4-methylthiazol-2-yl | H |
| 1.630 | Cl | 5-methylthiazol-2-yl | H |

-continued

| Compound Number | R¹ | R² | R³ |
|---|---|---|---|
| 1.631 | CH₃ | phenyl | CH₃ |
| 1.632 | CH₃ | 2-fluorophenyl | CH₃ |
| 1.633 | CH₃ | 3-fluorophenyl | CH₃ |
| 1.634 | CH₃ | 4-fluorophenyl | CH₃ |
| 1.635 | CH₃ | 2-chlorophenyl | CH₃ |
| 1.636 | CH₃ | 3-chlorophenyl | CH₃ |
| 1.637 | CH₃ | 4-chlorophenyl | CH₃ |
| 1.638 | CH₃ | 2-bromophenyl | CH₃ |
| 1.639 | CH₃ | 3-bromophenyl | CH₃ |
| 1.640 | CH₃ | 4-bromophenyl | CH₃ |
| 1.641 | CH₃ | 4-tert-butyl | CH₃ |
| 1.642 | CH₃ | 2-iodophenyl | CH₃ |
| 1.643 | CH₃ | 3-iodophenyl | CH₃ |
| 1.644 | CH₃ | 4-iodophenyl | CH₃ |
| 1.645 | CH₃ | 2-methylphenyl | CH₃ |
| 1.646 | CH₃ | 3-methylphenyl | CH₃ |
| 1.647 | CH₃ | 4-methylphenyl | CH₃ |
| 1.648 | CH₃ | 2-cyanophenyl | CH₃ |
| 1.649 | CH₃ | 3-cyanophenyl | CH₃ |
| 1.650 | CH₃ | 4-cyanophenyl | CH₃ |
| 1.651 | CH₃ | 2-methoxyphenyl | CH₃ |
| 1.652 | CH₃ | 3-methoxyphenyl | CH₃ |
| 1.653 | CH₃ | 4-methoxyphenyl | CH₃ |
| 1.654 | CH₃ | 2-difluoromethoxyphenyl | CH₃ |
| 1.655 | CH₃ | 3-difluoromethoxyphenyl | CH₃ |
| 1.656 | CH₃ | 4-difluoromethoxyphenyl | CH₃ |
| 1.657 | CH₃ | 2-difluoromethylphenyl | CH₃ |
| 1.658 | CH₃ | 3-difluoromethylphenyl | CH₃ |
| 1.659 | CH₃ | 4-difluoromethylphenyl | CH₃ |
| 1.660 | CH₃ | 2-trifluoromethylphenyl | CH₃ |
| 1.661 | CH₃ | 3-trifluoromethylphenyl | CH₃ |
| 1.662 | CH₃ | 4-trifluoromethylphenyl | CH₃ |
| 1.663 | CH₃ | 2-trifluoromethoxyphenyl | CH₃ |
| 1.664 | CH₃ | 3-trifluoromethoxyphenyl | CH₃ |
| 1.665 | CH₃ | 4-trifluoromethoxyphenyl | CH₃ |
| 1.666 | CH₃ | 4-methylthiophenyl | CH₃ |
| 1.667 | CH₃ | 4-methylsulfinylphenyl | CH₃ |
| 1.668 | CH₃ | 4-methylsulfonylphenyl | CH₃ |
| 1.669 | CH₃ | 4-trifluoromethylthiophenyl | CH₃ |
| 1.670 | CH₃ | 4-trifluoromethylsulfinylphenyl | CH₃ |
| 1.671 | CH₃ | 4-trifluoromethylsulfonylphenyl | CH₃ |
| 1.672 | CH₃ | 2,3-difluorophenyl | CH₃ |
| 1.673 | CH₃ | 2,4-difluorophenyl | CH₃ |
| 1.674 | CH₃ | 2,5-difluorophenyl | CH₃ |
| 1.675 | CH₃ | 2,6-difluorophenyl | CH₃ |
| 1.676 | CH₃ | 3,4-difluorophenyl | CH₃ |
| 1.677 | CH₃ | 3,5-difluorophenyl | CH₃ |
| 1.678 | CH₃ | 2,3-dichlorophenyl | CH₃ |
| 1.679 | CH₃ | 2,4-dichlorophenyl | CH₃ |
| 1.680 | CH₃ | 2,5-dichlorophenyl | CH₃ |
| 1.681 | CH₃ | 2,6-dichlorophenyl | CH₃ |
| 1.682 | CH₃ | 3,4-dichlorophenyl | CH₃ |
| 1.683 | CH₃ | 3,5-dichlorophenyl | CH₃ |
| 1.684 | CH₃ | 4-chloro-2-cyanophenyl | CH₃ |
| 1.685 | CH₃ | 4-chloro-3-cyanophenyl | CH₃ |
| 1.686 | CH₃ | 4-chloro-2-fluorophenyl | CH₃ |
| 1.687 | CH₃ | 4-chloro-3-fluorophenyl | CH₃ |
| 1.688 | CH₃ | 4-chloro-2-methoxyphenyl | CH₃ |
| 1.689 | CH₃ | 4-chloro-3-methoxyphenyl | CH₃ |
| 1.690 | CH₃ | 4-chloro-2-methylphenyl | CH₃ |
| 1.691 | CH₃ | 4-chloro-3-methylphenyl | CH₃ |
| 1.692 | CH₃ | 4-chloro-2-difluoromethoxyphenyl | CH₃ |
| 1.693 | CH₃ | 4-chloro-3-difluoromethoxyphenyl | CH₃ |
| 1.694 | CH₃ | 4-chloro-2-trifluoromethoxyphenyl | CH₃ |
| 1.695 | CH₃ | 4-chloro-3-trifluoromethoxyphenyl | CH₃ |
| 1.696 | CH₃ | 4-chloro-2-difluoromethylphenyl | CH₃ |
| 1.697 | CH₃ | 4-chloro-3-difluoromethylphenyl | CH₃ |
| 1.698 | CH₃ | 4-chloro-2-trifluoromethylphenyl | CH₃ |
| 1.699 | CH₃ | 4-chloro-3-trifluoromethylphenyl | CH₃ |
| 1.700 | CH₃ | 4-chloro-2,3-difluorophenyl | CH₃ |
| 1.701 | CH₃ | 4-chloro-2,5-difluorophenyl | CH₃ |
| 1.702 | CH₃ | 4,-chloro-2,6-difluorophenyl | CH₃ |
| 1.703 | CH₃ | 2,4-dichloro-3-fluorophenyl | CH₃ |
| 1.704 | CH₃ | 2,4-dichloro-5-fluorophenyl | CH₃ |
| 1.705 | CH₃ | 2,4-dichloro-6-fluorophenyl | CH₃ |
| 1.706 | CH₃ | 2,3,4-trichlorophenyl | CH₃ |
| 1.707 | CH₃ | 2,3,5-trichlorophenyl | CH₃ |
| 1.708 | CH₃ | 2,3,6-trichlorophenyl | CH₃ |
| 1.709 | CH₃ | 2,4,5-trichlorophenyl | CH₃ |
| 1.710 | CH₃ | 2,4,6-trichlorophenyl | CH₃ |
| 1.711 | CH₃ | 2,3,4-trifluorophenyl | CH₃ |
| 1.712 | CH₃ | 2,3,5-trifluorophenyl | CH₃ |
| 1.713 | CH₃ | 2,3,6-trifluorophenyl | CH₃ |
| 1.714 | CH₃ | 2,4,5-trifluorophenyl | CH₃ |
| 1.715 | CH₃ | 2,4,6-trifluorophenyl | CH₃ |
| 1.716 | CH₃ | 2-fluoro-4-trifluoromethylphenyl | CH₃ |
| 1.717 | CH₃ | 3-fluoro-4-trifluoromethylphenyl | CH₃ |
| 1.718 | CH₃ | 2-chloropyridin-5-yl | CH₃ |
| 1.719 | CH₃ | 3-chloropyridinyl-5-yl | CH₃ |
| 1.720 | CH₃ | 2-methylpyridin-5-yl | CH₃ |
| 1.721 | CH₃ | 3-methylpyridinyl-5-yl | CH₃ |
| 1.722 | CH₃ | 2-trifluoromethylpyridin-5-yl | CH₃ |
| 1.723 | CH₃ | 3-trifluoromethylpyridin-5-yl | CH₃ |
| 1.724 | CH₃ | 2-chloro-3-methylpyridin-5-yl | CH₃ |
| 1.725 | CH₃ | 2-chloro-4-methylpyridin-5-yl | CH₃ |
| 1.726 | CH₃ | 6-chloro-2-methylpyridin-3-yl | CH₃ |
| 1.727 | CH₃ | 2,3-dichloropyridin-5-yl | CH₃ |
| 1.728 | CH₃ | 2,4-dichloropyridin-5-yl | CH₃ |
| 1.729 | CH₃ | 2,6-dichloropyridin-3-yl | CH₃ |
| 1.730 | CH₃ | pyrazin-2-yl | CH₃ |
| 1.731 | CH₃ | 2-chloropyrazin-5-yl | CH₃ |
| 1.732 | CH₃ | 2-bromopyrazin-5-yl | CH₃ |
| 1.733 | CH₃ | pyridazin-3-yl | CH₃ |
| 1.734 | CH₃ | 6-bromopyridazin-3-yl | CH₃ |
| 1.735 | CH₃ | 6-chloropyridazin-3-yl | CH₃ |
| 1.736 | CH₃ | pyrimidin-5-yl | CH₃ |
| 1.737 | CH₃ | 2-bromopyrimidin-5-yl | CH₃ |
| 1.738 | CH₃ | 5-bromopyrimidin-2-yl | CH₃ |
| 1.739 | CH₃ | 2-chloropyrimidin-5-yl | CH₃ |
| 1.740 | CH₃ | 5-chloropyrimidin-2-yl | CH₃ |
| 1.741 | CH₃ | 2-furyl | CH₃ |
| 1.742 | CH₃ | 3-furyl | CH₃ |
| 1.743 | CH₃ | 2-thienyl | CH₃ |
| 1.744 | CH₃ | 3-thienyl | CH₃ |
| 1.745 | CH₃ | 4-bromothien-2-yl | CH₃ |
| 1.746 | CH₃ | 5-bromothien-2-yl | CH₃ |
| 1.747 | CH₃ | 4-chlorothien-2-yl | CH₃ |
| 1.748 | CH₃ | 5-chlorothien-2-yl | CH₃ |
| 1.749 | CH₃ | pyrazol-1-yl | CH₃ |
| 1.750 | CH₃ | 3-chloropyrazol-1-yl | CH₃ |
| 1.751 | CH₃ | 4-chloropyrazol-1-yl | CH₃ |
| 1.752 | CH₃ | 1-methylpyrazol-4-yl | CH₃ |
| 1.753 | CH₃ | 1-methyl-3-trifluoromethylpyrazol-5-yl | CH₃ |
| 1.754 | CH₃ | 2-thiazolyl | CH₃ |
| 1.755 | CH₃ | 4-methylthiazol-2-yl | CH₃ |
| 1.756 | CH₃ | 5-methylthiazol-2-yl | CH₃ |
| 1.757 | CH₃ | phenyl | CH₃CH₂ |
| 1.758 | CH₃ | 2-fluorophenyl | CH₃CH₂ |
| 1.759 | CH₃ | 3-fluorophenyl | CH₃CH₂ |
| 1.760 | CH₃ | 4-fluorophenyl | CH₃CH₂ |
| 1.761 | CH₃ | 2-chlorophenyl | CH₃CH₂ |
| 1.762 | CH₃ | 3-chlorophenyl | CH₃CH₂ |
| 1.763 | CH₃ | 4-chlorophenyl | CH₃CH₂ |
| 1.764 | CH₃ | 2-bromophenyl | CH₃CH₂ |
| 1.765 | CH₃ | 3-bromophenyl | CH₃CH₂ |
| 1.766 | CH₃ | 4-bromophenyl | CH₃CH₂ |
| 1.767 | CH₃ | 4-tert-butyl | CH₃CH₂ |
| 1.768 | CH₃ | 2-iodophenyl | CH₃CH₂ |
| 1.769 | CH₃ | 3-iodophenyl | CH₃CH₂ |
| 1.770 | CH₃ | 4-iodophenyl | CH₃CH₂ |
| 1.771 | CH₃ | 2-methylphenyl | CH₃CH₂ |
| 1.772 | CH₃ | 3-methylphenyl | CH₃CH₂ |
| 1.773 | CH₃ | 4-methylphenyl | CH₃CH₂ |
| 1.774 | CH₃ | 2-cyanophenyl | CH₃CH₂ |
| 1.775 | CH₃ | 3-cyanophenyl | CH₃CH₂ |
| 1.776 | CH₃ | 4-cyanophenyl | CH₃CH₂ |
| 1.777 | CH₃ | 2-methoxyphenyl | CH₃CH₂ |
| 1.778 | CH₃ | 3-methoxyphenyl | CH₃CH₂ |
| 1.779 | CH₃ | 4-methoxyphenyl | CH₃CH₂ |
| 1.780 | CH₃ | 2-difluoromethoxyphenyl | CH₃CH₂ |

-continued

| Compound Number | R¹ | R² | R³ |
|---|---|---|---|
| 1.781 | CH₃ | 3-difluoromethoxyphenyl | CH₃CH₂ |
| 1.782 | CH₃ | 4-difluoromethoxyphenyl | CH₃CH₂ |
| 1.783 | CH₃ | 2-difluoromethylphenyl | CH₃CH₂ |
| 1.784 | CH₃ | 3-difluoromethylphenyl | CH₃CH₂ |
| 1.785 | CH₃ | 4-difluoromethylphenyl | CH₃CH₂ |
| 1.786 | CH₃ | 2-trifluoromethylphenyl | CH₃CH₂ |
| 1.787 | CH₃ | 3-trifluoromethylphenyl | CH₃CH₂ |
| 1.788 | CH₃ | 4-trifluoromethylphenyl | CH₃CH₂ |
| 1.789 | CH₃ | 2-trifluoromethoxyphenyl | CH₃CH₂ |
| 1.790 | CH₃ | 3-trifluoromethoxyphenyl | CH₃CH₂ |
| 1.791 | CH₃ | 4-trifluoromethoxyphenyl | CH₃CH₂ |
| 1.792 | CH₃ | 4-methylthiophenyl | CH₃CH₂ |
| 1.793 | CH₃ | 4-methylsulfinylphenyl | CH₃CH₂ |
| 1.794 | CH₃ | 4-methylsulfonylphenyl | CH₃CH₂ |
| 1.795 | CH₃ | 4-trifluoromethylthiophenyl | CH₃CH₂ |
| 1.796 | CH₃ | 4-trifluoromethylsulfinylphenyl | CH₃CH₂ |
| 1.797 | CH₃ | 4-trifluoromethylsulfonylphenyl | CH₃CH₂ |
| 1.798 | CH₃ | 2,3-difluorophenyl | CH₃CH₂ |
| 1.799 | CH₃ | 2,4-difluorophenyl | CH₃CH₂ |
| 1.800 | CH₃ | 2,5-difluorophenyl | CH₃CH₂ |
| 1.801 | CH₃ | 2,6-difluorophenyl | CH₃CH₂ |
| 1.802 | CH₃ | 3,4-difluorophenyl | CH₃CH₂ |
| 1.803 | CH₃ | 3,5-difluorophenyl | CH₃CH₂ |
| 1.804 | CH₃ | 2,3-dichlorophenyl | CH₃CH₂ |
| 1.805 | CH₃ | 2,4-dichlorophenyl | CH₃CH₂ |
| 1.806 | CH₃ | 2,5-dichlorophenyl | CH₃CH₂ |
| 1.807 | CH₃ | 2,6-dichlorophenyl | CH₃CH₂ |
| 1.808 | CH₃ | 3,4-dichlorophenyl | CH₃CH₂ |
| 1.809 | CH₃ | 3,5-dichlorophenyl | CH₃CH₂ |
| 1.810 | CH₃ | 4-chloro-2-cyanophenyl | CH₃CH₂ |
| 1.811 | CH₃ | 4-chloro-3-cyanophenyl | CH₃CH₂ |
| 1.812 | CH₃ | 4-chloro-2-fluorophenyl | CH₃CH₂ |
| 1.813 | CH₃ | 4-chloro-3-fluorophenyl | CH₃CH₂ |
| 1.814 | CH₃ | 4-chloro-2-methoxyphenyl | CH₃CH₂ |
| 1.815 | CH₃ | 4-chloro-3-methoxyphenyl | CH₃CH₂ |
| 1.816 | CH₃ | 4-chloro-2-methylphenyl | CH₃CH₂ |
| 1.817 | CH₃ | 4-chloro-3-methylphenyl | CH₃CH₂ |
| 1.818 | CH₃ | 4-chloro-2-difluoromethoxyphenyl | CH₃CH₂ |
| 1.819 | CH₃ | 4-chloro-3-difluoromethoxyphenyl | CH₃CH₂ |
| 1.820 | CH₃ | 4-chloro-2-trifluoromethoxyphenyl | CH₃CH₂ |
| 1.821 | CH₃ | 4-chloro-3-trifluoromethoxyphenyl | CH₃CH₂ |
| 1.822 | CH₃ | 4-chloro-2-difluoromethylphenyl | CH₃CH₂ |
| 1.823 | CH₃ | 4-chloro-3-difluoromethylphenyl | CH₃CH₂ |
| 1.824 | CH₃ | 4-chloro-2-trifluoromethylphenyl | CH₃CH₂ |
| 1.825 | CH₃ | 4-chloro-3-trifluoromethylphenyl | CH₃CH₂ |
| 1.826 | CH₃ | 4-chloro-2,3-difluorophenyl | CH₃CH₂ |
| 1.827 | CH₃ | 4-chloro-2,5-difluorophenyl | CH₃CH₂ |
| 1.828 | CH₃ | 4,-chloro-2,6-difluorophenyl | CH₃CH₂ |
| 1.829 | CH₃ | 2,4-dichloro-3-fluorophenyl | CH₃CH₂ |
| 1.830 | CH₃ | 2,4-dichloro-5-fluorophenyl | CH₃CH₂ |
| 1.831 | CH₃ | 2,4-dichloro-6-fluorophenyl | CH₃CH₂ |
| 1.832 | CH₃ | 2,3,4-trichlorophenyl | CH₃CH₂ |
| 1.833 | CH₃ | 2,3,5-trichlorophenyl | CH₃CH₂ |
| 1.834 | CH₃ | 2,3,6-trichlorophenyl | CH₃CH₂ |
| 1.835 | CH₃ | 2,4,5-trichlorophenyl | CH₃CH₂ |
| 1.836 | CH₃ | 2,4,6-trichlorophenyl | CH₃CH₂ |
| 1.837 | CH₃ | 2,3,4-trifluorophenyl | CH₃CH₂ |
| 1.838 | CH₃ | 2,3,5-trifluorophenyl | CH₃CH₂ |
| 1.839 | CH₃ | 2,3,6-trifluorophenyl | CH₃CH₂ |
| 1.840 | CH₃ | 2,4,5-trifluorophenyl | CH₃CH₂ |
| 1.841 | CH₃ | 2,4,6-trifluorophenyl | CH₃CH₂ |
| 1.842 | CH₃ | 2-fluoro-4-trifluoromethylphenyl | CH₃CH₂ |
| 1.843 | CH₃ | 3-fluoro-4-trifluoromethylphenyl | CH₃CH₂ |
| 1.844 | CH₃ | 2-chloropyridin-5-yl | CH₃CH₂ |
| 1.845 | CH₃ | 3-chloropyridinyl-5-yl | CH₃CH₂ |
| 1.846 | CH₃ | 2-methylpyridin-5-yl | CH₃CH₂ |
| 1.847 | CH₃ | 3-methylpyridinyl-5-yl | CH₃CH₂ |
| 1.848 | CH₃ | 2-trifluoromethylpyridin-5-yl | CH₃CH₂ |
| 1.849 | CH₃ | 3-trifluoromethylpyridin-5-yl | CH₃CH₂ |
| 1.850 | CH₃ | 2-chloro-3-methylpyridin-5-yl | CH₃CH₂ |
| 1.851 | CH₃ | 2-chloro-4-methylpyridin-5-yl | CH₃CH₂ |
| 1.852 | CH₃ | 6-chloro-2-methylpyridin-3-yl | CH₃CH₂ |
| 1.853 | CH₃ | 2,3-dichloropyridin-5-yl | CH₃CH₂ |
| 1.854 | CH₃ | 2,4-dichloropyridin-5-yl | CH₃CH₂ |
| 1.855 | CH₃ | 2,6-dichloropyridin-3-yl | CH₃CH₂ |
| 1.856 | CH₃ | pyrazin-2-yl | CH₃CH₂ |
| 1.857 | CH₃ | 2-chloropyrazin-5-yl | CH₃CH₂ |
| 1.858 | CH₃ | 2-bromopyrazin-5-yl | CH₃CH₂ |
| 1.859 | CH₃ | pyridazin-3-yl | CH₃CH₂ |
| 1.860 | CH₃ | 6-bromopyridazin-3-yl | CH₃CH₂ |
| 1.861 | CH₃ | 6-chloropyridazin-3-yl | CH₃CH₂ |
| 1.862 | CH₃ | pyrimidin-5-yl | CH₃CH₂ |
| 1.863 | CH₃ | 2-bromopyrimidin-5-yl | CH₃CH₂ |
| 1.864 | CH₃ | 5-bromopyrimidin-2-yl | CH₃CH₂ |
| 1.865 | CH₃ | 2-chloropyrimidin-5-yl | CH₃CH₂ |
| 1.866 | CH₃ | 5-chloropyrimidin-2-yl | CH₃CH₂ |
| 1.867 | CH₃ | 2-furyl | CH₃CH₂ |
| 1.868 | CH₃ | 3-furyl | CH₃CH₂ |
| 1.869 | CH₃ | 2-thienyl | CH₃CH₂ |
| 1.870 | CH₃ | 3-thienyl | CH₃CH₂ |
| 1.871 | CH₃ | 4-bromothien-2-yl | CH₃CH₂ |
| 1.872 | CH₃ | 5-bromothien-2-yl | CH₃CH₂ |
| 1.873 | CH₃ | 4-chlorothien-2-yl | CH₃CH₂ |
| 1.874 | CH₃ | 5-chlorothien-2-yl | CH₃CH₂ |
| 1.875 | CH₃ | pyrazol-1-yl | CH₃CH₂ |
| 1.876 | CH₃ | 3-chloropyrazol-1-yl | CH₃CH₂ |
| 1.877 | CH₃ | 4-chloropyrazol-1-yl | CH₃CH₂ |
| 1.878 | CH₃ | 1-methylpyrazol-4-yl | CH₃CH₂ |
| 1.879 | CH₃ | 1-methyl-3-trifluoromethylpyrazol-5-yl | CH₃CH₂ |
| 1.880 | CH₃ | 2-thiazolyl | CH₃CH₂ |
| 1.881 | CH₃ | 4-methylthiazol-2-yl | CH₃CH₂ |
| 1.882 | CH₃ | 5-methylthiazol-2-yl | CH₃CH₂ |
| 1.883 | CH₃CH₂ | phenyl | CH₃CH₂ |
| 1.884 | CH₃CH₂ | 2-fluorophenyl | CH₃CH₂ |
| 1.885 | CH₃CH₂ | 3-fluorophenyl | CH₃CH₂ |
| 1.886 | CH₃CH₂ | 4-fluorophenyl | CH₃CH₂ |
| 1.887 | CH₃CH₂ | 2-chlorophenyl | CH₃CH₂ |
| 1.888 | CH₃CH₂ | 3-chlorophenyl | CH₃CH₂ |
| 1.889 | CH₃CH₂ | 4-chlorophenyl | CH₃CH₂ |
| 1.890 | CH₃CH₂ | 2-bromophenyl | CH₃CH₂ |
| 1.891 | CH₃CH₂ | 3-bromophenyl | CH₃CH₂ |
| 1.892 | CH₃CH₂ | 4-bromophenyl | CH₃CH₂ |
| 1.893 | CH₃CH₂ | 4-tert-butyl | CH₃CH₂ |
| 1.894 | CH₃CH₂ | 2-iodophenyl | CH₃CH₂ |
| 1.895 | CH₃CH₂ | 3-iodophenyl | CH₃CH₂ |
| 1.896 | CH₃CH₂ | 4-iodophenyl | CH₃CH₂ |
| 1.897 | CH₃CH₂ | 2-methylphenyl | CH₃CH₂ |
| 1.898 | CH₃CH₂ | 3-methylphenyl | CH₃CH₂ |
| 1.899 | CH₃CH₂ | 4-methylphenyl | CH₃CH₂ |
| 1.900 | CH₃CH₂ | 2-cyanophenyl | CH₃CH₂ |
| 1.901 | CH₃CH₂ | 3-cyanophenyl | CH₃CH₂ |
| 1.902 | CH₃CH₂ | 4-cyanophenyl | CH₃CH₂ |
| 1.903 | CH₃CH₂ | 2-methoxyphenyl | CH₃CH₂ |
| 1.904 | CH₃CH₂ | 3-methoxyphenyl | CH₃CH₂ |
| 1.905 | CH₃CH₂ | 4-methoxyphenyl | CH₃CH₂ |
| 1.906 | CH₃CH₂ | 2-difluoromethoxyphenyl | CH₃CH₂ |
| 1.907 | CH₃CH₂ | 3-difluoromethoxyphenyl | CH₃CH₂ |
| 1.908 | CH₃CH₂ | 4-difluoromethoxyphenyl | CH₃CH₂ |
| 1.909 | CH₃CH₂ | 2-difluoromethylphenyl | CH₃CH₂ |
| 1.910 | CH₃CH₂ | 3-difluoromethylphenyl | CH₃CH₂ |
| 1.911 | CH₃CH₂ | 4-difluoromethylphenyl | CH₃CH₂ |
| 1.912 | CH₃CH₂ | 2-trifluoromethylphenyl | CH₃CH₂ |
| 1.913 | CH₃CH₂ | 3-trifluoromethylphenyl | CH₃CH₂ |
| 1.914 | CH₃CH₂ | 4-trifluoromethylphenyl | CH₃CH₂ |
| 1.915 | CH₃CH₂ | 2-trifluoromethoxyphenyl | CH₃CH₂ |
| 1.916 | CH₃CH₂ | 3-trifluoromethoxyphenyl | CH₃CH₂ |
| 1.917 | CH₃CH₂ | 4-trifluoromethoxyphenyl | CH₃CH₂ |
| 1.918 | CH₃CH₂ | 4-methylthiophenyl | CH₃CH₂ |
| 1.919 | CH₃CH₂ | 4-methylsulfinylphenyl | CH₃CH₂ |
| 1.920 | CH₃CH₂ | 4-methylsulfonylphenyl | CH₃CH₂ |
| 1.921 | CH₃CH₂ | 4-trifluoromethylthiophenyl | CH₃CH₂ |
| 1.922 | CH₃CH₂ | 4-trifluoromethylsulfinylphenyl | CH₃CH₂ |
| 1.923 | CH₃CH₂ | 4-trifluoromethylsulfonylphenyl | CH₃CH₂ |
| 1.924 | CH₃CH₂ | 2,3-difluorophenyl | CH₃CH₂ |
| 1.925 | CH₃CH₂ | 2,4-difluorophenyl | CH₃CH₂ |
| 1.926 | CH₃CH₂ | 2,5-difluorophenyl | CH₃CH₂ |
| 1.927 | CH₃CH₂ | 2,6-difluorophenyl | CH₃CH₂ |
| 1.928 | CH₃CH₂ | 3,4-difluorophenyl | CH₃CH₂ |
| 1.929 | CH₃CH₂ | 3,5-difluorophenyl | CH₃CH₂ |
| 1.930 | CH₃CH₂ | 2,3-dichlorophenyl | CH₃CH₂ |

| Compound Number | $R^1$ | $R^2$ | $R^3$ |
| --- | --- | --- | --- |
| 1.931 | $CH_3CH_2$ | 2,4-dichlorophenyl | $CH_3CH_2$ |
| 1.932 | $CH_3CH_2$ | 2,5-dichlorophenyl | $CH_3CH_2$ |
| 1.933 | $CH_3CH_2$ | 2,6-dichlorophenyl | $CH_3CH_2$ |
| 1.934 | $CH_3CH_2$ | 3,4-dichlorophenyl | $CH_3CH_2$ |
| 1.935 | $CH_3CH_2$ | 3,5-dichlorophenyl | $CH_3CH_2$ |
| 1.936 | $CH_3CH_2$ | 4-chloro-2-cyanophenyl | $CH_3CH_2$ |
| 1.937 | $CH_3CH_2$ | 4-chloro-3-cyanophenyl | $CH_3CH_2$ |
| 1.938 | $CH_3CH_2$ | 4-chloro-2-fluorophenyl | $CH_3CH_2$ |
| 1.939 | $CH_3CH_2$ | 4-chloro-3-fluorophenyl | $CH_3CH_2$ |
| 1.940 | $CH_3CH_2$ | 4-chloro-2-methoxyphenyl | $CH_3CH_2$ |
| 1.941 | $CH_3CH_2$ | 4-chloro-3-methoxyphenyl | $CH_3CH_2$ |
| 1.942 | $CH_3CH_2$ | 4-chloro-2-methylphenyl | $CH_3CH_2$ |
| 1.943 | $CH_3CH_2$ | 4-chloro-3-methylphenyl | $CH_3CH_2$ |
| 1.944 | $CH_3CH_2$ | 4-chloro-2-difluoromethoxyphenyl | $CH_3CH_2$ |
| 1.945 | $CH_3CH_2$ | 4-chloro-3-difluoromethoxyphenyl | $CH_3CH_2$ |
| 1.946 | $CH_3CH_2$ | 4-chloro-2-trifluoromethoxyphenyl | $CH_3CH_2$ |
| 1.947 | $CH_3CH_2$ | 4-chloro-3-trifluoromethoxyphenyl | $CH_3CH_2$ |
| 1.948 | $CH_3CH_2$ | 4-chloro-2-difluoromethylphenyl | $CH_3CH_2$ |
| 1.949 | $CH_3CH_2$ | 4-chloro-3-difluoromethylphenyl | $CH_3CH_2$ |
| 1.950 | $CH_3CH_2$ | 4-chloro-2-trifluoromethylphenyl | $CH_3CH_2$ |
| 1.951 | $CH_3CH_2$ | 4-chloro-3-trifluoromethylphenyl | $CH_3CH_2$ |
| 1.952 | $CH_3CH_2$ | 4-chloro-2,3-difluorophenyl | $CH_3CH_2$ |
| 1.953 | $CH_3CH_2$ | 4-chloro-2,5-difluorophenyl | $CH_3CH_2$ |
| 1.954 | $CH_3CH_2$ | 4,-chloro-2,6-difluorophenyl | $CH_3CH_2$ |
| 1.955 | $CH_3CH_2$ | 2,4-dichloro-3-fluorophenyl | $CH_3CH_2$ |
| 1.956 | $CH_3CH_2$ | 2,4-dichloro-5-fluorophenyl | $CH_3CH_2$ |
| 1.957 | $CH_3CH_2$ | 2,4-dichloro-6-fluorophenyl | $CH_3CH_2$ |
| 1.958 | $CH_3CH_2$ | 2,3,4-trichlorophenyl | $CH_3CH_2$ |
| 1.959 | $CH_3CH_2$ | 2,3,5-trichlorophenyl | $CH_3CH_2$ |
| 1.960 | $CH_3CH_2$ | 2,3,6-trichlorophenyl | $CH_3CH_2$ |
| 1.961 | $CH_3CH_2$ | 2,4,5-trichlorophenyl | $CH_3CH_2$ |
| 1.962 | $CH_3CH_2$ | 2,4,6-trichlorophenyl | $CH_3CH_2$ |
| 1.963 | $CH_3CH_2$ | 2,3,4-trifluorophenyl | $CH_3CH_2$ |
| 1.964 | $CH_3CH_2$ | 2,3,5-trifluorophenyl | $CH_3CH_2$ |
| 1.965 | $CH_3CH_2$ | 2,3,6-trifluorophenyl | $CH_3CH_2$ |
| 1.966 | $CH_3CH_2$ | 2,4,5-trifluorophenyl | $CH_3CH_2$ |
| 1.967 | $CH_3CH_2$ | 2,4,6-trifluorophenyl | $CH_3CH_2$ |
| 1.968 | $CH_3CH_2$ | 2-fluoro-4-trifluoromethylphenyl | $CH_3CH_2$ |
| 1.969 | $CH_3CH_2$ | 3-fluoro-4-trifluoromethylphenyl | $CH_3CH_2$ |
| 1.970 | $CH_3CH_2$ | 2-chloropyridin-5-yl | $CH_3CH_2$ |
| 1.971 | $CH_3CH_2$ | 3-chloropyridinyl-5-yl | $CH_3CH_2$ |
| 1.972 | $CH_3CH_2$ | 2-methylpyridin-5-yl | $CH_3CH_2$ |
| 1.973 | $CH_3CH_2$ | 3-methylpyridinyl-5-yl | $CH_3CH_2$ |
| 1.974 | $CH_3CH_2$ | 2-trifluoromethylpyridin-5-yl | $CH_3CH_2$ |
| 1.975 | $CH_3CH_2$ | 3-trifluoromethylpyridin-5-yl | $CH_3CH_2$ |
| 1.976 | $CH_3CH_2$ | 2-chloro-3-methylpyridin-5-yl | $CH_3CH_2$ |
| 1.977 | $CH_3CH_2$ | 2-chloro-4-methylpyridin-5-yl | $CH_3CH_2$ |
| 1.978 | $CH_3CH_2$ | 6-chloro-2-methylpyridin-3-yl | $CH_3CH_2$ |
| 1.979 | $CH_3CH_2$ | 2,3-dichloropyridin-5-yl | $CH_3CH_2$ |
| 1.980 | $CH_3CH_2$ | 2,4-dichloropyridin-5-yl | $CH_3CH_2$ |
| 1.981 | $CH_3CH_2$ | 2,6-dichloropyridin-3-yl | $CH_3CH_2$ |
| 1.982 | $CH_3CH_2$ | pyrazin-2-yl | $CH_3CH_2$ |
| 1.983 | $CH_3CH_2$ | 2-chloropyrazin-5-yl | $CH_3CH_2$ |
| 1.984 | $CH_3CH_2$ | 2-bromopyrazin-5-yl | $CH_3CH_2$ |
| 1.985 | $CH_3CH_2$ | pyridazin-3-yl | $CH_3CH_2$ |
| 1.986 | $CH_3CH_2$ | 6-bromopyridazin-3-yl | $CH_3CH_2$ |
| 1.987 | $CH_3CH_2$ | 6-chloropyridazin-3-yl | $CH_3CH_2$ |
| 1.988 | $CH_3CH_2$ | pyrimidin-5-yl | $CH_3CH_2$ |
| 1.989 | $CH_3CH_2$ | 2-bromopyrimidin-5-yl | $CH_3CH_2$ |
| 1.990 | $CH_3CH_2$ | 5-bromopyrimidin-2-yl | $CH_3CH_2$ |
| 1.991 | $CH_3CH_2$ | 2-chloropyrimidin-5-yl | $CH_3CH_2$ |
| 1.992 | $CH_3CH_2$ | 5-chloropyrimidin-2-yl | $CH_3CH_2$ |
| 1.993 | $CH_3CH_2$ | 2-furyl | $CH_3CH_2$ |
| 1.994 | $CH_3CH_2$ | 3-furyl | $CH_3CH_2$ |
| 1.995 | $CH_3CH_2$ | 2-thienyl | $CH_3CH_2$ |
| 1.996 | $CH_3CH_2$ | 3-thienyl | $CH_3CH_2$ |
| 1.997 | $CH_3CH_2$ | 4-bromothien-2-yl | $CH_3CH_2$ |
| 1.998 | $CH_3CH_2$ | 5-bromothien-2-yl | $CH_3CH_2$ |
| 1.999 | $CH_3CH_2$ | 4-chlorothien-2-yl | $CH_3CH_2$ |
| 1.1000 | $CH_3CH_2$ | 5-chlorothien-2-yl | $CH_3CH_2$ |
| 1.1001 | $CH_3CH_2$ | pyrazol-1-yl | $CH_3CH_2$ |
| 1.1002 | $CH_3CH_2$ | 3-chloropyrazol-1-yl | $CH_3CH_2$ |
| 1.1003 | $CH_3CH_2$ | 4-chloropyrazol-1-yl | $CH_3CH_2$ |
| 1.1004 | $CH_3CH_2$ | 1-methylpyrazol-4-yl | $CH_3CH_2$ |
| 1.1005 | $CH_3CH_2$ | 1-methyl-3-trifluoromethylpyrazol-5-yl | $CH_3CH_2$ |
| 1.1006 | $CH_3CH_2$ | 2-thiazolyl | $CH_3CH_2$ |
| 1.1007 | $CH_3CH_2$ | 4-methylthiazol-2-yl | $CH_3CH_2$ |
| 1.1008 | $CH_3CH_2$ | 5-methylthiazol-2-yl | $CH_3CH_2$ |
| 1.1009 | $CH_3CH_2$ | phenyl | $CH_3O$ |
| 1.1010 | $CH_3CH_2$ | 2-fluorophenyl | $CH_3O$ |
| 1.1011 | $CH_3CH_2$ | 3-fluorophenyl | $CH_3O$ |
| 1.1012 | $CH_3CH_2$ | 4-fluorophenyl | $CH_3O$ |
| 1.1013 | $CH_3CH_2$ | 2-chlorophenyl | $CH_3O$ |
| 1.1014 | $CH_3CH_2$ | 3-chlorophenyl | $CH_3O$ |
| 1.1015 | $CH_3CH_2$ | 4-chlorophenyl | $CH_3O$ |
| 1.1016 | $CH_3CH_2$ | 2-bromophenyl | $CH_3O$ |
| 1.1017 | $CH_3CH_2$ | 3-bromophenyl | $CH_3O$ |
| 1.1018 | $CH_3CH_2$ | 4-bromophenyl | $CH_3O$ |
| 1.1019 | $CH_3CH_2$ | 4-tert-butyl | $CH_3O$ |
| 1.1020 | $CH_3CH_2$ | 2-iodophenyl | $CH_3O$ |
| 1.1021 | $CH_3CH_2$ | 3-iodophenyl | $CH_3O$ |
| 1.1022 | $CH_3CH_2$ | 4-iodophenyl | $CH_3O$ |
| 1.1023 | $CH_3CH_2$ | 2-methylphenyl | $CH_3O$ |
| 1.1024 | $CH_3CH_2$ | 3-methylphenyl | $CH_3O$ |
| 1.1025 | $CH_3CH_2$ | 4-methylphenyl | $CH_3O$ |
| 1.1026 | $CH_3CH_2$ | 2-cyanophenyl | $CH_3O$ |
| 1.1027 | $CH_3CH_2$ | 3-cyanophenyl | $CH_3O$ |
| 1.1028 | $CH_3CH_2$ | 4-cyanophenyl | $CH_3O$ |
| 1.1029 | $CH_3CH_2$ | 2-methoxyphenyl | $CH_3O$ |
| 1.1030 | $CH_3CH_2$ | 3-methoxyphenyl | $CH_3O$ |
| 1.1031 | $CH_3CH_2$ | 4-methoxyphenyl | $CH_3O$ |
| 1.1032 | $CH_3CH_2$ | 2-difluoromethoxyphenyl | $CH_3O$ |
| 1.1033 | $CH_3CH_2$ | 3-difluoromethoxyphenyl | $CH_3O$ |
| 1.1034 | $CH_3CH_2$ | 4-difluoromethoxyphenyl | $CH_3O$ |
| 1.1035 | $CH_3CH_2$ | 2-difluoromethylphenyl | $CH_3O$ |
| 1.1036 | $CH_3CH_2$ | 3-difluoromethylphenyl | $CH_3O$ |
| 1.1037 | $CH_3CH_2$ | 4-difluoromethylphenyl | $CH_3O$ |
| 1.1038 | $CH_3CH_2$ | 2-trifluoromethylphenyl | $CH_3O$ |
| 1.1039 | $CH_3CH_2$ | 3-trifluoromethylphenyl | $CH_3O$ |
| 1.1040 | $CH_3CH_2$ | 4-trifluoromethylphenyl | $CH_3O$ |
| 1.1041 | $CH_3CH_2$ | 2-trifluoromethoxyphenyl | $CH_3O$ |
| 1.1042 | $CH_3CH_2$ | 3-trifluoromethoxyphenyl | $CH_3O$ |
| 1.1043 | $CH_3CH_2$ | 4-trifluoromethoxyphenyl | $CH_3O$ |
| 1.1044 | $CH_3CH_2$ | 4-methylthiophenyl | $CH_3O$ |
| 1.1045 | $CH_3CH_2$ | 4-methylsulfinylphenyl | $CH_3O$ |
| 1.1046 | $CH_3CH_2$ | 4-methylsulfonylphenyl | $CH_3O$ |
| 1.1047 | $CH_3CH_2$ | 4-trifluoromethylthiophenyl | $CH_3O$ |
| 1.1048 | $CH_3CH_2$ | 4-trifluoromethylsulfinylphenyl | $CH_3O$ |
| 1.1049 | $CH_3CH_2$ | 4-trifluoromethylsulfonylphenyl | $CH_3O$ |
| 1.1050 | $CH_3CH_2$ | 2,3-difluorophenyl | $CH_3O$ |
| 1.1051 | $CH_3CH_2$ | 2,4-difluorophenyl | $CH_3O$ |
| 1.1052 | $CH_3CH_2$ | 2,5-difluorophenyl | $CH_3O$ |
| 1.1053 | $CH_3CH_2$ | 2,6-difluorophenyl | $CH_3O$ |
| 1.1054 | $CH_3CH_2$ | 3,4-difluorophenyl | $CH_3O$ |
| 1.1055 | $CH_3CH_2$ | 3,5-difluorophenyl | $CH_3O$ |
| 1.1056 | $CH_3CH_2$ | 2,3-dichlorophenyl | $CH_3O$ |
| 1.1057 | $CH_3CH_2$ | 2,4-dichlorophenyl | $CH_3O$ |
| 1.1058 | $CH_3CH_2$ | 2,5-dichlorophenyl | $CH_3O$ |
| 1.1059 | $CH_3CH_2$ | 2,6-dichlorophenyl | $CH_3O$ |
| 1.1060 | $CH_3CH_2$ | 3,4-dichlorophenyl | $CH_3O$ |
| 1.1061 | $CH_3CH_2$ | 3,5-dichlorophenyl | $CH_3O$ |
| 1.1062 | $CH_3CH_2$ | 4-chloro-2-cyanophenyl | $CH_3O$ |
| 1.1063 | $CH_3CH_2$ | 4-chloro-3-cyanophenyl | $CH_3O$ |
| 1.1064 | $CH_3CH_2$ | 4-chloro-2-fluorophenyl | $CH_3O$ |
| 1.1065 | $CH_3CH_2$ | 4-chloro-3-fluorophenyl | $CH_3O$ |
| 1.1066 | $CH_3CH_2$ | 4-chloro-2-methoxyphenyl | $CH_3O$ |
| 1.1067 | $CH_3CH_2$ | 4-chloro-3-methoxyphenyl | $CH_3O$ |
| 1.1068 | $CH_3CH_2$ | 4-chloro-2-methylphenyl | $CH_3O$ |
| 1.1069 | $CH_3CH_2$ | 4-chloro-3-methylphenyl | $CH_3O$ |
| 1.1070 | $CH_3CH_2$ | 4-chloro-2-difluoromethoxyphenyl | $CH_3O$ |
| 1.1071 | $CH_3CH_2$ | 4-chloro-3-difluoromethoxyphenyl | $CH_3O$ |
| 1.1072 | $CH_3CH_2$ | 4-chloro-2-trifluoromethoxyphenyl | $CH_3O$ |
| 1.1073 | $CH_3CH_2$ | 4-chloro-3-trifluoromethoxyphenyl | $CH_3O$ |
| 1.1074 | $CH_3CH_2$ | 4-chloro-2-difluoromethylphenyl | $CH_3O$ |
| 1.1075 | $CH_3CH_2$ | 4-chloro-3-difluoromethylphenyl | $CH_3O$ |
| 1.1076 | $CH_3CH_2$ | 4-chloro-2-trifluoromethylphenyl | $CH_3O$ |
| 1.1077 | $CH_3CH_2$ | 4-chloro-3-trifluoromethylphenyl | $CH_3O$ |
| 1.1078 | $CH_3CH_2$ | 4-chloro-2,3-difluorophenyl | $CH_3O$ |
| 1.1079 | $CH_3CH_2$ | 4-chloro-2,5-difluorophenyl | $CH_3O$ |
| 1.1080 | $CH_3CH_2$ | 4,-chloro-2,6-difluorophenyl | $CH_3O$ |

| Compound Number | R¹ | R² | R³ |
|---|---|---|---|
| 1.1081 | $CH_3CH_2$ | 2,4-dichloro-3-fluorophenyl | $CH_3O$ |
| 1.1082 | $CH_3CH_2$ | 2,4-dichloro-5-fluorophenyl | $CH_3O$ |
| 1.1083 | $CH_3CH_2$ | 2,4-dichloro-6-fluorophenyl | $CH_3O$ |
| 1.1084 | $CH_3CH_2$ | 2,3,4-trichlorophenyl | $CH_3O$ |
| 1.1085 | $CH_3CH_2$ | 2,3,5-trichlorophenyl | $CH_3O$ |
| 1.1086 | $CH_3CH_2$ | 2,3,6-trichlorophenyl | $CH_3O$ |
| 1.1087 | $CH_3CH_2$ | 2,4,5-trichlorophenyl | $CH_3O$ |
| 1.1088 | $CH_3CH_2$ | 2,4,6-trichlorophenyl | $CH_3O$ |
| 1.1089 | $CH_3CH_2$ | 2,3,4-trifluorophenyl | $CH_3O$ |
| 1.1090 | $CH_3CH_2$ | 2,3,5-trifluorophenyl | $CH_3O$ |
| 1.1091 | $CH_3CH_2$ | 2,3,6-trifluorophenyl | $CH_3O$ |
| 1.1092 | $CH_3CH_2$ | 2,4,5-trifluorophenyl | $CH_3O$ |
| 1.1093 | $CH_3CH_2$ | 2,4,6-trifluorophenyl | $CH_3O$ |
| 1.1094 | $CH_3CH_2$ | 2-fluoro-4-trifluoromethylphenyl | $CH_3O$ |
| 1.1095 | $CH_3CH_2$ | 3-fluoro-4-trifluoromethylphenyl | $CH_3O$ |
| 1.1096 | $CH_3CH_2$ | 2-chloropyridin-5-yl | $CH_3O$ |
| 1.1097 | $CH_3CH_2$ | 3-chloropyridinyl-5-yl | $CH_3O$ |
| 1.1098 | $CH_3CH_2$ | 2-methylpyridin-5-yl | $CH_3O$ |
| 1.1099 | $CH_3CH_2$ | 3-methylpyridinyl-5-yl | $CH_3O$ |
| 1.1100 | $CH_3CH_2$ | 2-trifluoromethylpyridin-5-yl | $CH_3O$ |
| 1.1101 | $CH_3CH_2$ | 3-trifluoromethylpyridin-5-yl | $CH_3O$ |
| 1.1102 | $CH_3CH_2$ | 2-chloro-3-methylpyridin-5-yl | $CH_3O$ |
| 1.1103 | $CH_3CH_2$ | 2-chloro-4-methylpyridin-5-yl | $CH_3O$ |
| 1.1104 | $CH_3CH_2$ | 6-chloro-2-methylpyridin-3-yl | $CH_3O$ |
| 1.1105 | $CH_3CH_2$ | 2,3-dichloropyridin-5-yl | $CH_3O$ |
| 1.1106 | $CH_3CH_2$ | 2,4-dichloropyridin-5-yl | $CH_3O$ |
| 1.1107 | $CH_3CH_2$ | 2,6-dichloropyridin-3-yl | $CH_3O$ |
| 1.1108 | $CH_3CH_2$ | pyrazin-2-yl | $CH_3O$ |
| 1.1109 | $CH_3CH_2$ | 2-chloropyrazin-5-yl | $CH_3O$ |
| 1.1110 | $CH_3CH_2$ | 2-bromopyrazin-5-yl | $CH_3O$ |
| 1.1111 | $CH_3CH_2$ | pyridazin-3-yl | $CH_3O$ |
| 1.1112 | $CH_3CH_2$ | 6-bromopyridazin-3-yl | $CH_3O$ |
| 1.1113 | $CH_3CH_2$ | 6-chloropyridazin-3-yl | $CH_3O$ |
| 1.1114 | $CH_3CH_2$ | pyrimidin-5-yl | $CH_3O$ |
| 1.1115 | $CH_3CH_2$ | 2-bromopyrimidin-5-yl | $CH_3O$ |
| 1.1116 | $CH_3CH_2$ | 5-bromopyrimidin-2-yl | $CH_3O$ |
| 1.1117 | $CH_3CH_2$ | 2-chloropyrimidin-5-yl | $CH_3O$ |
| 1.1118 | $CH_3CH_2$ | 5-chloropyrimidin-2-yl | $CH_3O$ |
| 1.1119 | $CH_3CH_2$ | 2-furyl | $CH_3O$ |
| 1.1120 | $CH_3CH_2$ | 3-furyl | $CH_3O$ |
| 1.1121 | $CH_3CH_2$ | 2-thienyl | $CH_3O$ |
| 1.1122 | $CH_3CH_2$ | 3-thienyl | $CH_3O$ |
| 1.1123 | $CH_3CH_2$ | 4-bromothien-2-yl | $CH_3O$ |
| 1.1124 | $CH_3CH_2$ | 5-bromothien-2-yl | $CH_3O$ |
| 1.1125 | $CH_3CH_2$ | 4-chlorothien-2-yl | $CH_3O$ |
| 1.1126 | $CH_3CH_2$ | 5-chlorothien-2-yl | $CH_3O$ |
| 1.1127 | $CH_3CH_2$ | pyrazol-1-yl | $CH_3O$ |
| 1.1128 | $CH_3CH_2$ | 3-chloropyrazol-1-yl | $CH_3O$ |
| 1.1129 | $CH_3CH_2$ | 4-chloropyrazol-1-yl | $CH_3O$ |
| 1.1130 | $CH_3CH_2$ | 1-methylpyrazol-4-yl | $CH_3O$ |
| 1.1131 | $CH_3CH_2$ | 1-methyl-3-trifluoromethylpyrazol-5-yl | $CH_3O$ |
| 1.1132 | $CH_3CH_2$ | 2-thiazolyl | $CH_3O$ |
| 1.1133 | $CH_3CH_2$ | 4-methylthiazol-2-yl | $CH_3O$ |
| 1.1134 | $CH_3CH_2$ | 5-methylthiazol-2-yl | $CH_3O$ |

Table 2:
This table covers 1134 compounds of the type T-1, wherein Y is O, $R^4$ is methyl, $R^5$, $R^6$ and $R^7$ are hydrogen, G is hydrogen and $R^1$, $R^2$ and $R^3$ are as defined in Table 1.

Table 3:
This table covers 1134 compounds of the type T-1, wherein Y is O, $R^4$ and $R^5$ are methyl, $R^6$ and $R^7$ are hydrogen, G is hydrogen and $R^1$, $R^2$ and $R^3$ are as defined in Table 1.

Table 4:
This table covers 1134 compounds of the type T-1, wherein Y is O, $R^4$ and $R^6$ are methyl, $R^5$ and $R^7$ are hydrogen, G is hydrogen and $R^1$, $R^2$ and $R^3$ are as defined in Table 1.

Table 5:
This table covers 1134 compounds of the type T-1, wherein Y is O, $R^4$, $R^5$ and $R^6$ are methyl, $R^7$ is hydrogen, G is hydrogen and $R^1$, $R^2$ and $R^3$ are as defined in Table 1.

Table 6:
This table covers 1134 compounds of the type T-1, wherein Y is O, $R^4$, $R^5$, $R^6$ and $R^7$ are methyl, G is hydrogen and $R^1$, $R^2$ and $R^3$ are as defined in Table 1.

Table 7:
This table covers 1134 compounds of the type T-1, wherein Y is O, $R^4$, $R^5$ and $R^6$ are methyl, $R^7$ is methoxymethyl, G is hydrogen and $R^1$, $R^2$ and $R^3$ are as defined in Table 1.

Table 8:
This table covers 1134 compounds of the type T-1, wherein Y is S, $R^4$, $R^5$, $R^6$ and $R^7$ are hydrogen, G is hydrogen and $R^1$, $R^2$ and $R^3$ are as defined in Table 1.

Table 9:
This table covers 1134 compounds of the type T-1, wherein Y is S, $R^4$ is methyl, $R^5$, $R^6$ and $R^7$ are hydrogen, G is hydrogen and $R^1$, $R^2$ and $R^3$ are as defined in Table 1.

Table 10:
This table covers 1134 compounds of the type T-1, wherein Y is S, $R^4$ and $R^5$ are methyl, $R^6$ and $R^7$ are hydrogen, G is hydrogen and $R^1$, $R^2$ and $R^3$ are as defined in Table 1.

Table 11:
This table covers 1134 compounds of the type T-1, wherein Y is S, $R^4$ and $R^6$ are methyl, $R^5$ and $R^7$ are hydrogen, G is hydrogen and $R^1$, $R^2$ and $R^3$ are as defined in Table 1.

Table 12:
This table covers 1134 compounds of the type T-1, wherein Y is S, $R^4$, $R^5$ and $R^6$ are methyl, $R^7$ is hydrogen, G is hydrogen and $R^1$, $R^2$ and $R^3$ are as defined in Table 1.

Table 13:
This table covers 1134 compounds of the type T-1, wherein Y is S, $R^4$, $R^5$, $R^6$ and $R^7$ are methyl, G is hydrogen and $R^1$, $R^2$ and $R^3$ are as defined in Table 1.

Table 14:
This table covers 1134 compounds of the type T-1, wherein Y is S=O, $R^4$, $R^5$, $R^6$ and $R^7$ are hydrogen, G is hydrogen and $R^1$, $R^2$ and $R^3$ are as defined in Table 1.

Table 15:
This table covers 1134 compounds of the type T-1, wherein Y is S=O, $R^4$ is methyl, $R^5$, $R^6$ and $R^7$ are hydrogen, G is hydrogen and $R^1$, $R^2$ and $R^3$ are as defined in Table 1.

Table 16:
This table covers 1134 compounds of the type T-1, wherein Y is S=O, $R^4$ and $R^5$ are methyl, $R^6$ and $R^7$ are hydrogen, G is hydrogen and $R^1$, $R^2$ and $R^3$ are as defined in Table 1.

Table 17:
This table covers 1134 compounds of the type T-1, wherein Y is S=O, $R^4$ and $R^6$ are methyl, $R^5$ and $R^7$ are hydrogen, G is hydrogen and $R^1$, $R^2$ and $R^3$ are as defined in Table 1.

Table 18:
This table covers 1134 compounds of the type T-1, wherein Y is S=O, $R^4$, $R^5$ and $R^6$ are methyl, $R^7$ is hydrogen, G is hydrogen and $R^1$, $R^2$ and $R^3$ are as defined in Table 1.

Table 19:
This table covers 1134 compounds of the type T-1, wherein Y is S=O, $R^4$, $R^5$, $R^6$ and $R^7$ are methyl, G is hydrogen and $R^1$, $R^2$ and $R^3$ are as defined in Table 1.

Table 20:
This table covers 1134 compounds of the type T-1, wherein Y is $S(=O)_2$, $R^4$, $R^5$, $R^6$ and $R^7$ are hydrogen, G is hydrogen and $R^1$, $R^2$ and $R^3$ are as defined in Table 1.

Table 21:
This table covers 1134 compounds of the type T-1, wherein Y is $S(=O)_2$, $R^4$ is methyl, $R^5$, $R^6$ and $R^7$ are hydrogen, G is hydrogen and $R^1$, $R^2$ and $R^3$ are as defined in Table 1.

Table 22:
This table covers 1134 compounds of the type T-1, wherein Y is $S(=O)_2$, $R^4$ and $R^5$ are methyl, $R^6$ and $R^7$ are hydrogen, G is hydrogen and $R^1$, $R^2$ and $R^3$ are as defined in Table 1.

Table 23:
This table covers 1134 compounds of the type T-1, wherein Y is S(=O)$_2$, R$^4$ and R$^6$ are methyl, R$^5$ and R$^7$ are hydrogen, G is hydrogen and R$^1$, R$^2$ and R$^3$ are as defined in Table 1.

Table 24:
This table covers 1134 compounds of the type T-1, wherein Y is S(=O)$_2$, R$^4$, R$^5$ and R$^6$ are methyl, R$^7$ is hydrogen, G is hydrogen and R$^1$, R$^2$ and R$^3$ are as defined in Table 1.

Table 25:
This table covers 1134 compounds of the type T-1, wherein Y is S(=O)$_2$, R$^4$, R$^5$, R$^6$ and R$^7$ are methyl, G is hydrogen and R$^1$, R$^2$ and R$^3$ are as defined in Table 1.

Table 26:
This table covers 1134 compounds of the type T-1, wherein Y is C=O, R$^4$ and R$^5$ are methyl, R$^6$ and R$^7$ are hydrogen, G is hydrogen and R$^1$, R$^2$ and R$^3$ are as defined in Table 1.

Table 27:
This table covers 1134 compounds of the type T-1, wherein Y is C=O, R$^4$, R$^5$ and R$^6$ are methyl, R$^7$ is hydrogen, G is hydrogen and R$^1$, R$^2$ and R$^3$ are as defined in Table 1.

Table 28:
This table covers 1134 compounds of the type T-1, wherein Y is C=O, R$^4$, R$^5$, R$^6$ and R$^7$ are methyl, G is hydrogen and R$^1$, R$^2$ and R$^3$ are as defined in Table 1.

Table 29:
This table covers 1134 compounds of the type T-2:

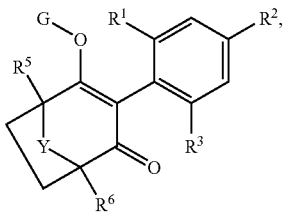

T-2 wherein Y is O, R$^5$ and R$^6$ are hydrogen, G is hydrogen and R$^1$, R$^2$ and R$^3$ are as defined in Table 1.

Table 30:
This table covers 1134 compounds of the type T-2, wherein Y is O, R$^5$ is hydrogen and R$^6$ is methyl, G is hydrogen and R$^1$, R$^2$ and R$^3$ are as defined in Table 1.

Table 31:
This table covers 1134 compounds of the type T-2, wherein Y is O, R$^5$ and R$^6$ are methyl, G is hydrogen and R$^1$, R$^2$ and R$^3$ are as defined in Table 1.

Table 32:
This table covers 1134 compounds of the type T-2, wherein Y is O, R$^5$ is hydrogen and R$^6$ is methoxymethyl, G is hydrogen and R$^1$, R$^2$ and R$^3$ are as defined in Table 1.

Table 33:
This table covers 1134 compounds of the type T-2, wherein Y is O, R$^5$ is hydrogen and R$^6$ is ethoxymethyl, G is hydrogen and R$^1$, R$^2$ and R$^3$ are as defined in Table 1.

Table 34:
This table covers 1134 compounds of the type T-3:

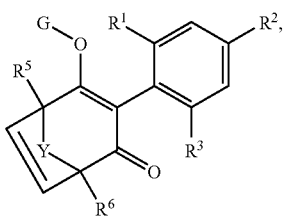

T-3 wherein Y is O, R$^5$ and R$^6$ are hydrogen, G is hydrogen and R$^1$, R$^2$ and R$^3$ are as defined in Table 1.

Table 35:
This table covers 1134 compounds of the type T-3, wherein Y is O, R$^5$ is hydrogen and R$^6$ is methyl, G is hydrogen and R$^1$, R$^2$ and R$^3$ are as defined in Table 1.

Table 36:
This table covers 1134 compounds of the type T-3, wherein Y is O, R$^5$ and R$^6$ are methyl, G is hydrogen and R$^1$, R$^2$ and R$^3$ are as defined in Table 1.

Table 37:
This table covers 1134 compounds of the type T-3, wherein Y is O, R$^5$ is hydrogen and R$^6$ is methoxymethyl, G is hydrogen and R$^1$, R$^2$ and R$^3$ are as defined in Table 1.

Table 38:
This table covers 1134 compounds of the type T-3, wherein Y is O, R$^5$ is hydrogen and R$^6$ is ethoxymethyl, G is hydrogen and R$^1$, R$^2$ and R$^3$ are as defined in Table 1.

Table 39:
This table covers 1134 compounds of the type T-4:

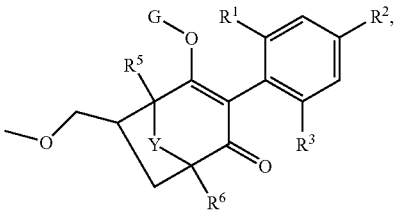

T-4 wherein Y is O, R$^5$ and R$^6$ are hydrogen, G is hydrogen and R$^1$, R$^2$ and R$^3$ are as defined in Table 1.

Table 40:
This table covers 1134 compounds of the type T-4, wherein Y is O, R$^5$ is methyl, R$^6$ is hydrogen, G is hydrogen and R$^1$, R$^2$ and R$^3$ are as defined in Table 1.

Example 21

Preparation of acetic acid (1S*,5R*)-3-(4'-chloro-3-ethylbiphenyl-4-yl)-5-methyl-4-oxo-8-oxabicyclo[3.2.1]oct-2-en-2-yl ester

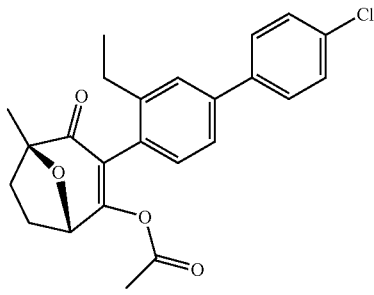 [SMILES: CCc1cc(-c2ccc(Cl)cc2)ccc1C1=C(OC(C)=O)[C@@H]2CC[C@@](C)(O2)C1=O]

Triethylamine (0.12 ml, 0.88 mmol) is added to a solution of (1R*,5S*)-3-(4'-chloro-3-ethylbiphenyl-4-yl)-1-methyl-8-oxabicyclo[3.2.1]octane-2,4-dione (75 mg, 0.20 mmol) in dichloromethane (5 ml) and the mixture is cooled to 0° C. Acetyl chloride (0.07 ml, 0.88 mmol) is added dropwise and the reaction is stirred at 0° C. for 6 hours. The reaction mixture is poured into water and extracted with dichloromethane (3×15 ml). The organic extracts are combined, dried over anhydrous sodium sulfate, filtered and the filtrate is evaporated under reduced pressure to obtain (1S*,5R*)-3-(4'-chloro-3-ethylbiphenyl-4-yl)-5-methyl-4-oxo-8-oxabicyclo[3.2.1]oct-2-en-2-yl ester (83 mg).

Example 22

Preparation of acetic acid 4-(3-ethyl-4'-fluorobiphenyl-4-yl)-2,2,6-trimethyl-5-oxo-5,6-dihydro-2H-pyran-3yl ester

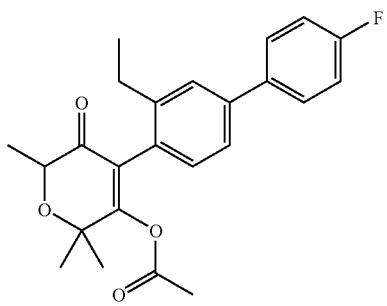 [SMILES: CCc1cc(-c2ccc(F)cc2)ccc1C1=C(OC(C)=O)C(C)(C)OC(C)C1=O]

To a solution of 4-(3-ethyl-4'-fluorobiphenyl-4-yl)-2,2,6-trimethylpyran-3,5-dione (0.125 g, 0.35 mmol) in dichloromethane (5 ml) is added triethylamine (0.2 ml, 1.38 mmol) and the reaction mixture is cooled to 0° C. Acetyl chloride (0.22 g, 2.8 mmol) is added slowly at 0° C. and the mixture is stirred at 0° C. for 5 hours. The reaction mixture is diluted with water and extracted with dichloromethane (3×25 ml). The organic extracts are combined, dried over anhydrous sodium sulphate and concentrated under reduced pressure. The residue is purified by column chromatography on silica gel to afford acetic acid 4-(3-ethyl-4'-fluorobiphenyl-4-yl)-2,2,6-trimethyl-5-oxo-5,6-dihydro-2H-pyran-3yl ester (0.085 g) as a white solid.

Example 23

Preparation of 2,2-dimethyl propionic acid 4-(3-ethyl-4'-fluorobiphenyl-4-yl)-2,2,6-trimethyl-5-oxo-5,6-dihydro-2H pyran-3-yl ester

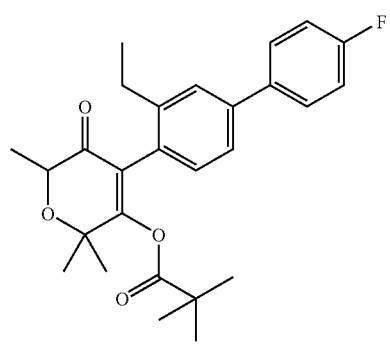 [SMILES: CCc1cc(-c2ccc(F)cc2)ccc1C1=C(OC(=O)C(C)(C)C)C(C)(C)OC(C)C1=O]

To a solution of 4-(3-ethyl-4'-fluoro-biphenyl-4-yl)-2,2,6-trimethylpyran-3,5-dione (0.125 g, 0.35 mmol) in dichloromethane (5 ml) is added triethylamine (0.2 ml, 1.43 mmol) and the reaction mixture is cooled to 0° C. Pivaloyl chloride (0.2 ml, 1.63 mmol) is added slowly at 0° C. and the mixture is stirred at 0° C. for 5 hours. The reaction mixture is diluted with water and extracted with dichloromethane (3×25 ml). The organic extracts are combined, dried over anhydrous sodium sulphate and concentrated under reduced pressure. The residue is purified by column chromatography on silica gel to afford 2,2-dimethyl propionic acid 4-(3-ethyl-4'-fluorobiphenyl-4-yl)-2,2,6-trimethyl-5-oxo-5,6-dihydro-2H pyran-3-yl ester (130 mg) as a white solid.

Additional compounds in Table D below are prepared by similar methods using appropriate starting materials.

TABLE D

| Compound Number | Structure | $^1$H nmr (CDCl$_3$ unless stated) or other physical data |
|---|---|---|
| D-1 | 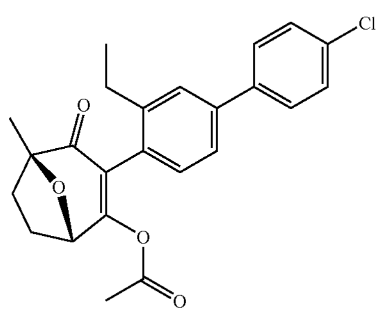 [SMILES: CCc1cc(-c2ccc(Cl)cc2)ccc1C1=C(OC(C)=O)[C@@H]2CC[C@@](C)(O2)C1=O] | $\delta_H$ 7.53-7.33(m, 6H), 7.05 and 6.9(2 × d, 1H), 4.92-4.89(m, 1H), 2.6-2.0(m, 6H), 1.99 and 1.98 (2 × s, 3H), 1.59 and 1.58(2 × s, 3H), 1.19-1.15(m, 3H). |

TABLE D-continued

| Compound Number | Structure | ¹H nmr (CDCl₃ unless stated) or other physical data |
|---|---|---|
| D-2 | 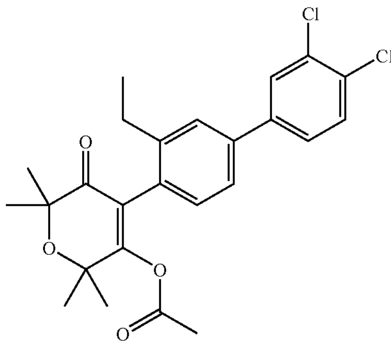 [SMILES: CCc1cc(-c2ccc(Cl)c(Cl)c2)ccc1C1=C(OC(C)=O)C(C)(C)OC(C)(C)C1=O] | $\delta_H$ (DMSO-d₆) 7.99(d, 1H), 7.7(s, 2H), 7.6(d, 1H), 7.53(dd, 1H), 7.0(d, 1H), 2.4(q, 2H), 1.82(s, 3H), 1.44(2 × s, 6H), 1.42(2 × s, 6H), 1.1(t, 3H). |
| D-3 | 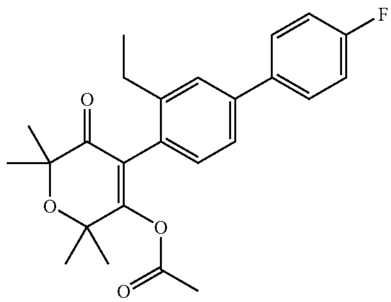 [SMILES: CCc1cc(-c2ccc(F)cc2)ccc1C1=C(OC(C)=O)C(C)(C)OC(C)(C)C1=O] | $\delta_H$ (DMSO-d₆) 7.76-7.72(m, 2H), 7.53(d, 1H), 7.46(dd, 1H), 7.29(t, 2H), 6.97(d, 1H), 2.4(q, 2H), 1.82(s, 3H), 1.5(2 × s, 6H), 1.42(2 × s, 6H), 1.12(t, 3H). |
| D-4 | 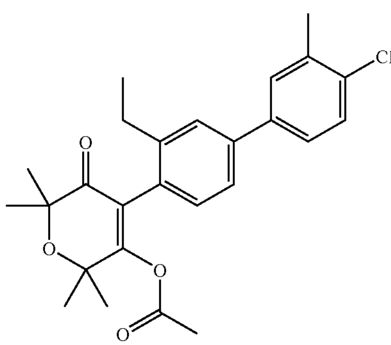 [SMILES: CCc1cc(-c2ccc(Cl)c(C)c2)ccc1C1=C(OC(C)=O)C(C)(C)OC(C)(C)C1=O] | $\delta_H$ (DMSO-d₆) 7.7(d, 1H), 7.55-7.46(m, 4H), 6.97(d, 1H), 2.4(m, 5H), 1.82(s, 3H), 1.5(2 × s, 6H), 1.43(2 × s, 6H), 1.1(t, 3H). |
| D-5 | 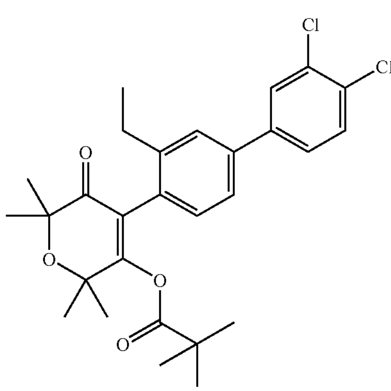 [SMILES: CCc1cc(-c2ccc(Cl)c(Cl)c2)ccc1C1=C(OC(=O)C(C)(C)C)C(C)(C)OC(C)(C)C1=O] | $\delta_H$ (DMSO-d₆) 7.94(d, 1H), 7.72-7.67(m, 2H), 7.6(d, 1H), 7.53-7.51(dd, 1H), 6.95(d, 1H), 2.43(q, 2H), 1.49(s, 3H), 1.46(s, 3H), 1.44(s, 3H), 1.43(s, 3H), 1.11(t, 3H), 0.82(s, 9H). |

TABLE D-continued

| Compound Number | Structure | ¹H nmr (CDCl₃ unless stated) or other physical data |
|---|---|---|
| D-6 | 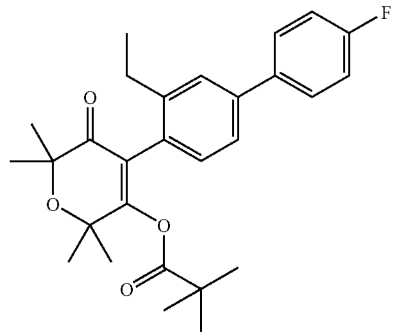 [SMILES: CCc1cc(-c2ccc(F)cc2)ccc1C1=C(OC(=O)C(C)(C)C)C(C)(C)OC(C)(C)C1=O] | $\delta_H$ (DMSO-d₆) 7.68(m, 2H), 7.51(s, 1H), 7.44 (d, 1H), 7.28(t, 2H), 6.93(d, 1H), 2.4(q, 2H), 1.48(s, 3H), 1.46(s, 3H), 1.44(s, 3H), 1.43(s, 3H), 1.11(t, 3H), 0.82(s, 9H). |
| D-7 | 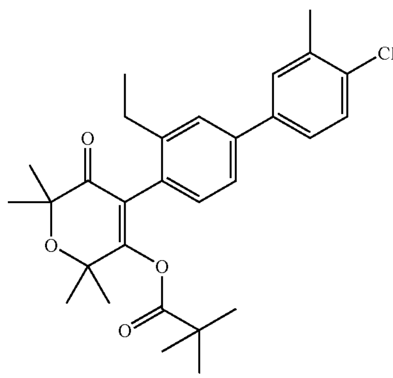 [SMILES: CCc1cc(-c2ccc(Cl)c(C)c2)ccc1C1=C(OC(=O)C(C)(C)C)C(C)(C)OC(C)(C)C1=O] | $\delta_H$ (DMSO-d₆) 7.66(s, 1H), 7.54-7.45(m, 4H), 6.9(d, 1H), 2.44(q, 2H), 2.4(s, 3H), 1.49(s, 3H), 1.46(s, 3H), 1.44(s, 3H), 1.43(s, 3H), 1.11(t, 3H), 0.82(s, 9H). |
| D-8 | 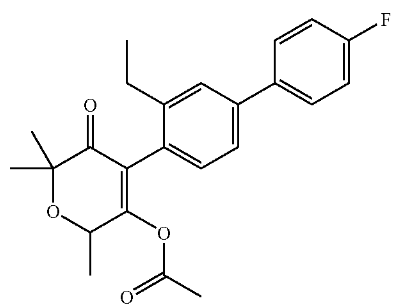 [SMILES: CCc1cc(-c2ccc(F)cc2)ccc1C1=C(OC(C)=O)C(C)OC(C)(C)C1=O] | $\delta_H$ 7.58-7.53(m, 2H), 7.42(d, 1H), 7.33(dt, 1H), 7.12(d,t 2H), 7.06 and 6.94(2 × d, 1H), 4.94-4.9(m, 1H), 2.53-2.48 and 2.4-2.37(2 × m, 2H), 1.93 and 1.89(2 × s, 3H), 1.53(s, 3H), 1.47-1.42(m, 6H), 1.19-1.15(m, 3H). |
| D-9 | 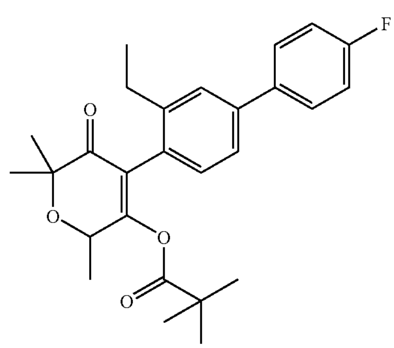 [SMILES: CCc1cc(-c2ccc(F)cc2)ccc1C1=C(OC(=O)C(C)(C)C)C(C)OC(C)(C)C1=O] | $\delta_H$ 7.54-7.49(m, 2H), 7.39((d, 1H), 7.32(dt, 1H), 7.11(dt, 2H), 7.06 and 6.91(2 × d, 1H), 4.93-4.86(m, 1H), 2.58-2.48 and 2.39-2.36(2 × m, 2H), 1.55(s, 3H), 1.46(s, 3H), 1.45 and 1.43(2 × d, 3H), 1.17 and 1.13(2 × t, 3H), 0.92 and 0.90(2 × s, 9H). |

TABLE D-continued

| Compound Number | Structure | ¹H nmr (CDCl₃ unless stated) or other physical data |
|---|---|---|
| D-10 | *(structure shown)* | $\delta_H$ 7.47-7.44(m, 1H), 7.29(d, 1H), 7.27-7.20 (m, 3H), 7.06(d, 1H), 3.5(s, 3H), 2.5(q, 2H), 1.59(2 × s, 6H), 1.53(2 × s, 6H), 1.18(t, 3H). |

Preparation of Intermediates

Example A

Preparation of 4-bromo-4'-chloro-3-methylbiphenyl

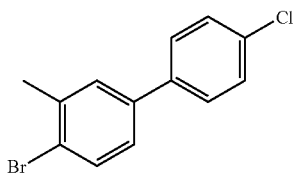

Step 1: Preparation of 4'-chloro-3-methylbiphen-4-ylamine

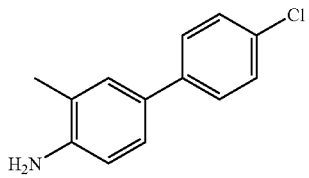

To a stirred, degassed solution of 4-bromo-2-methylaniline (20 g, 0.107 mol) in toluene (1200 ml) and ethanol (400 ml), under an atmosphere of nitrogen, is added 4-chlorophenylboronic acid (20.32 g, 0.13 mol) and the reaction mixture is stirred and heated to 80° C. Tetrakis(triphenylphosphine)palladium(0) (2.48 g, 0.002 mol) is added to the reaction mixture, and to this is added 2M aqueous potassium carbonate solution (160 ml). The reaction mixture is refluxed for 4 hours, then cooled to room temperature. The reaction mixture is filtered through diatomaceous earth, and the filtrate is evaporated under reduced pressure. The residue is partitioned between ethyl acetate and water. The aqueous phase is extracted with ethyl acetate (3×500 ml) and the organic extracts are combined and concentrated under reduced pressure to give 4'-chloro-3-methylbiphen-4-ylamine (16.5 g).

Step 2: Preparation of 4-bromo-4'-chloro-3-methylbiphenyl

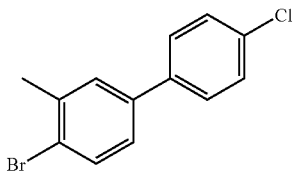

4'-Chloro-3-methylbiphen-4-ylamine (16.5 g, 0.077 mol) is added to acetonitrile (140 ml) and stirred at room temperature until dissolution is complete. The reaction mixture is cooled to between −5° C. and 0° C., tent-butyl nitrite (90%, 12.4 ml, 0.093 mol) is added dropwise and the reaction mixture is maintained at between −5° C. and 0° C. for 30-40 minutes. The mixture is added slowly to a preheated (50° C.) suspension of copper (I) bromide (5.8 g, 0.04 mol) in hydrobromic acid (5.8 ml) and stirred at 50° C. for 10-15 minutes. The reaction mixture is cooled to room temperature, then poured into ice-cold water and extracted with ethyl acetate (3×300 ml). The organic extracts are washed with water, dried over anhydrous sodium sulfate and concentrated under reduced pressure. The residue is purified by column chromatography on silica gel to yield 4-bromo-4'-chloro-3-methylbiphenyl (11.5 g).

Example B

Preparation of 4'-chloro-3-methylbiphen-4-ylboronic acid

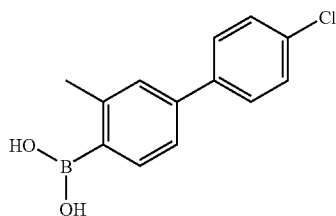 [SMILES: Cc1cc(-c2ccc(Cl)cc2)ccc1B(O)O]

n-Butyl lithium (1.6 M solution in hexanes, 37.5 ml, 0.060 mol) is added dropwise to a solution of 4-bromo-4'-chloro-3-methylbiphenyl (11.5 g, 0.041 mol) in tetrahydrofuran (120 ml) at −78° C., under an atmosphere of nitrogen, and the mixture is stirred at −78° C. for 30 minutes. Trimethyl borate (27.4 ml, 0.245 mol) is added slowly at −78° C. and the mixture is stirred for 1 hr. The reaction mixture is allowed to warm to room temperature over 2-3 hours and then stirred at room temperature for 1 hr. 0.1N Aqueous hydrochloric acid (320 ml) is added and the mixture is stirred at room temperature overnight. The reaction mixture is extracted with ethyl acetate (3×300 ml) and the organic extracts are combined, dried with anhydrous sodium sulfate, filtered and the filtrate is concentrated under reduced pressure. The residue is purified by column chromatography on silica gel to give 4'-chloro-3-methylbiphen-4-ylboronic acid (6.0 g) as white solid.

Example C

Preparation of 4'-chloro-3-methylbiphen-4-yllead triacetate

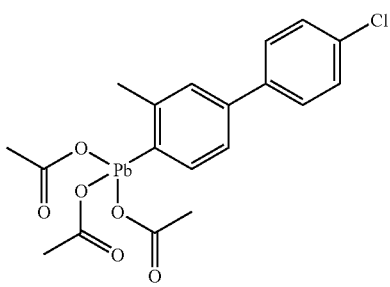

4'-Chloro-3-methylbiphen-4-ylboronic acid (6.0 g, 0.024 mol) is added in one portion to a mixture of lead tetraacetate (13.0 g, 0.029 mol) and mercuric acetate (0.38 g, 5 mol %) in chloroform (50 ml) under an atmosphere of nitrogen. The reaction mixture is stirred at ambient temperature until dissolution is complete, and then heated at 40° C. for 4 hours. The reaction mixture is cooled to ambient temperature, filtered through a plug of diatomaceous earth and the filtrate is concentrated under reduced pressure to give an orange solid. Trituration with hexane (50 ml) affords a yellow solid which is dried under high vacuum. This solid is then dissolved in chloroform (100 ml), anhydrous potassium carbonate (42.5 g, 0.3 mol) is added and the suspension is stirred rapidly for 10 minutes. The mixture is filtered through a plug of diatomaceous earth, and the filtrate is concentrated under reduced pressure to give 4'-chloro-3-methylbiphen-4-yllead triacetate (7.8 g) as a cream solid.

Example D

Preparation of 4-bromo-4'-chloro-3-ethylbiphenyl

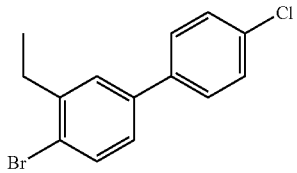 [SMILES: CCc1cc(-c2ccc(Cl)cc2)ccc1Br]

Step 1: Preparation of N-(4-bromo-2-ethylphenyl)acetamide

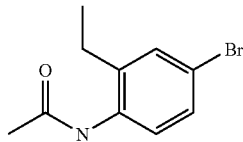

To a solution of 4-bromo-2-ethylaniline (50 g, 0.25 mol) in dichloromethane (250 ml) is added triethylamine (63.24 g, 0.62 mol) and the mixture is stirred at room temperature for 30 minutes. The reaction mixture is cooled to 0° C. and acetyl chloride (39.25 g, 0.5 mol) is added dropwise. The reaction mixture is stirred at 25-30° C. for 60 minutes, then poured into water, and the two phases separated. The organic phase is washed with water, dried over anhydrous sodium sulfate, filtered and the filtrate is evaporated under reduced pressure to yield N-(4-bromo-2-ethylphenyl)acetamide (40 g).

Step 2: Preparation of N-(4'-chloro-3-ethylbiphen-4-yl)acetamide

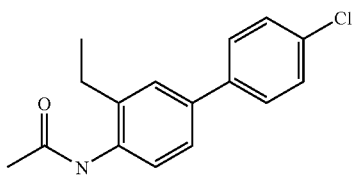 [SMILES: CCc1cc(-c2ccc(Cl)cc2)ccc1NC(C)=O]

To a degassed solution of N-(4-bromo-2-ethylphenyl)acetamide (20 g, 0.082 mol) in toluene (1200 ml) and ethanol (400 ml), 4-chlorobenzene boronic acid (15.5 g, 0.099 mol) is added under an atmosphere of nitrogen, and the reaction mixture is heated to 80° C. Tetrakis(triphenylphosphine)palladium(0) (2.0 g, 0.0017 mol) is added followed by 2M aqueous potassium carbonate solution (160 ml). The reaction mixture is refluxed for 4 hours then cooled to room temperature. The reaction mass is filtered through diatomaceous earth, and the filtrate is evaporated under reduced pressure. The residue is partitioned between ethyl acetate and water. The aqueous phase is extracted with ethyl acetate (3×500 ml) and the organic solutions are combined and concentrated under reduced pressure to give N-(4'-chloro-3-ethylbiphen-4-yl)acetamide (20.5 g).

Step 3: Preparation of 4'-chloro-3-ethylbiphen-4-ylamine

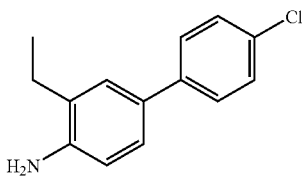 [SMILES: CCc1cc(-c2ccc(Cl)cc2)ccc1N]

To a solution of N-(4'-chloro-3-ethylbiphen-4-yl)acetamide (18 g, 0.06 mol) in dioxane (126 ml), is added concentrated hydrochloric acid (36 ml) and the reaction mixture is refluxed for 2 hours. The dioxane is evaporated under reduced pressure. The residue is diluted with water, the solution made basic by addition of 2N aqueous potassium hydroxide solution and extracted with ethyl acetate (3×500 ml). The organic extracts are combined and concentrated under reduced pressure to give 4'-chloro-3-ethylbiphen-4-ylamine (13.5 g).

Step 4: Preparation of 4-bromo-4'-chloro-3-ethylbiphenyl

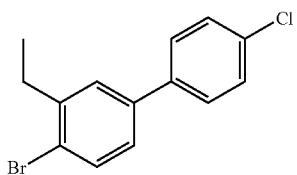 [SMILES: CCc1cc(-c2ccc(Cl)cc2)ccc1Br]

4'-Chloro-3-ethylbiphen-4-ylamine (14.3 g, 0.06 mol) is added to acetonitrile (143 ml) and stirred at room temperature until dissolution is complete. The reaction mixture is cooled to between −5° C. and 0° C., tert-butyl nitrite (90%, 9.8 ml, 0.074 mol) is added dropwise and the reaction mixture is maintained at between −5° C. and 0° C. for 30-40 minutes. The mixture is added slowly to a preheated (50° C.) suspension of copper (I) bromide (4.87 g, 0.034 mol) in hydrobromic acid (4.8 ml) and stirred at 50° C. for 10-15 minutes. The reaction mixture is cooled to room temperature, then poured into ice-cold water and extracted with ethyl acetate (3×500 ml). The organic extracts are washed with water, dried over anhydrous sodium sulfate and concentrated under reduced pressure. The residue is purified by column chromatography on silica gel to yield 4-bromo-4'-chloro-3-ethylbiphenyl (12 g).

Example E

Preparation of 4'-chloro-3-ethylbiphen-4-ylboronic acid

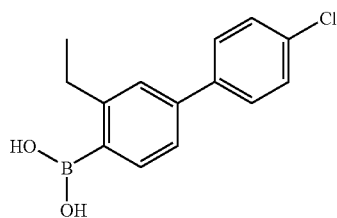 [SMILES: CCc1cc(-c2ccc(Cl)cc2)ccc1B(O)O]

n-Butyl lithium (1.6 M solution in hexanes, 38.75 ml, 0.062 mol) is added dropwise to a solution of 4-bromo-4'-chloro-3-ethylbiphenyl (12.35 g, 0.041 mol) in tetrahydrofuran (125 ml) at −78° C., under an atmosphere of nitrogen, and the mixture is stirred at −78° C. for 30 minutes. Trimethyl borate (27.8 ml, 0.25 mol) is added slowly at −78° C. and the mixture is stirred for 1 hr. The reaction mixture is allowed to warm to room temperature over 2-3 hours and then stirred at room temperature for 1 hr. 0.1N aqueous hydrochloric acid (343 ml) is added and the mixture is stirred at room temperature overnight. The reaction mixture is extracted with ethyl acetate (3×300 ml) and the organic extracts are combined, dried with anhydrous sodium sulfate, filtered and the filtrate is concentrated under reduced pressure. The residue is purified by column chromatography on silica gel to give 4'-chloro-3-ethylbiphen-4-ylboronic acid (4.5 g) as a white solid.

Example F

Preparation of 4'-chloro-3-ethylbiphen-4-yllead triacetate

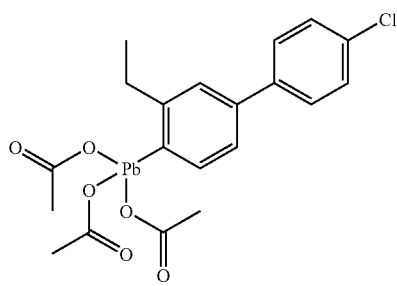

4'-Chloro-3-ethylbiphen-4-ylboronic acid (4.2 g, 0.016 mol) is added in one portion to a mixture of lead tetraacetate (7.86 g, 0.017 mol) and mercuric acetate (0.25 g, 5 mol %) in chloroform (23 ml) under an atmosphere of nitrogen. The reaction mixture is stirred at ambient temperature until dissolution is complete, and then heated at 40° C. for 4 hours. The reaction mixture is cooled to ambient temperature, filtered through a plug of diatomaceous earth and the filtrate is concentrated under reduced pressure to give an orange solid. Trituration with hexane (50 ml) affords a yellow solid which is dried under high vacuum. This solid is then dissolved in chloroform (100 ml), anhydrous potassium carbonate (26.7 g, 0.19 mol) is added and the suspension is stirred rapidly for 10 minutes. The mixture is filtered through a plug of diatomaceous earth, and the filtrate is concentrated under reduced pressure to give 4'-chloro-3-ethylbiphen-4-yllead triacetate (5.6 g) as a cream solid.

Example G

Preparation of 3,5-dimethylbiphen-4-ylboronic acid

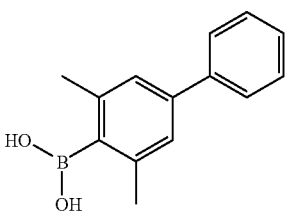 [SMILES: Cc1cc(-c2ccccc2)cc(C)c1B(O)O]

tert-Butyllithium (1.7 M solution in hexane, 36.2 ml, 61.6 mmol) is added dropwise to a solution of 3,5-dimethylbiphenyl (7.27 g, 28 mmol) in dry tetrahydrofuran (150 ml) at −78° C. under an atmosphere of nitrogen. The reaction mixture is stirred at −78° C. for 30 minutes, then trimethylborate (9.54 ml, 84 mmol) is added. The resulting mixture is stirred at −78° C. for 30 minutes and then allowed to warm to room temperature. The reaction mixture is acidified with 10% aqueous hydrochloric acid solution and extracted with diethyl ether (2×150 ml). The organic layers are combined, dried over anhydrous magnesium sulfate, filtered and the filtrate is evaporated under reduced pressure to give a yellow solid. Trituration with isohexane gives 3,5-dimethylbiphen-4-ylboronic acid as a white powder (5.89 g).

Example H

Preparation of 3,5-dimethylbiphen-4-yllead triacetate

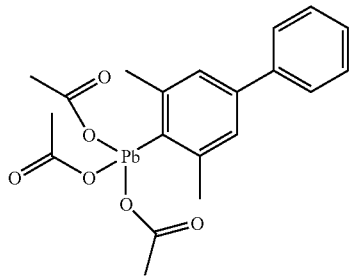

To a solution of lead tetraacetate (4.3 g, 9.7 mmol) in dry chloroform (15 ml) at 40° C. is added 3,5-dimethylbiphen-4-ylboronic acid (2.0 g, 8.8 mmol) in one portion under an atmosphere of nitrogen. The reaction mixture is stirred at 40° C. for 4 hours, and then is cooled to room temperature and filtered, washing the residual solid with chloroform (50 ml). The filtrate is filtered through a plug of potassium carbonate supported on diatomaceous earth and the filtrate is evaporated under reduced pressure to afford 3,5-dimethylbiphen-4-yl-lead triacetate as a brown oil (3.37 g).

Example I

Preparation of 4-bromo-4'-chloro-3,5-diethylbiphenyl

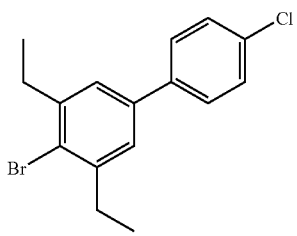 [SMILES: CCc1cc(-c2ccc(Cl)cc2)cc(CC)c1Br]

Step 1: Preparation of (4-bromo-2,6-diethylphenyl)carbamic acid tert-butyl ester

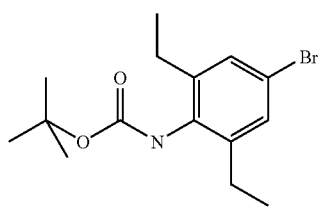 [SMILES: CCc1cc(Br)cc(CC)c1NC(=O)OC(C)(C)C]

Di-tent-butyl dicarbonate (106.13 g, 0.486 mol) is added to a solution of 2,6-diethyl-4-bromoaniline (74 g, 0.324 mol) in ethanol (500 ml) and the reaction mixture is stirred at room temperature for 50 hours. The solvent is evaporated under reduced pressure, the residue dissolved in ethyl acetate and washed with saturated aqueous sodium carbonate solution. The organic phase is dried over anhydrous sodium sulfate, filtered and the filtrate is concentrated under reduced pressure to give (4-bromo-2,6-diethylphenyl)carbamic acid tent-butyl ester (68 gm).

Step 2: Preparation of (4'-chloro-3,5-diethylbiphen-4-yl)carbamic acid tert-butyl ester

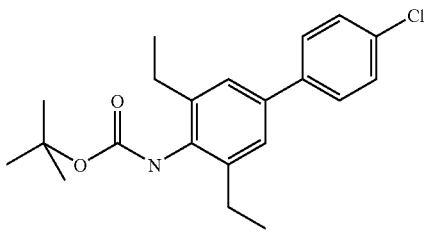 [SMILES: CCc1cc(-c2ccc(Cl)cc2)cc(CC)c1NC(=O)OC(C)(C)C]

A solution of cesium carbonate (89.12 g, 0.27 mol) in water (600 ml) is added to a degassed solution of (4-bromo-2,6-diethylphenyl)carbamic acid tert-butyl ester (30 g, 0.091 mol) and 4-chlorophenylboronic acid (21.54 g, 0.138 mol) in acetone (3000 ml), and the mixture is stirred at room temperature under an atmosphere of nitrogen. Palladium acetate (1.02 g, 0.004 mol) and 2-(dicyclohexylphosphino)-2',4',6'-tri-iso-propyl-1,1'-biphenyl (4.33 g, 0.009 mol) are added and the reaction mixture is stirred at room temperature for 12 hours. The mixture is filtered through diatomaceous earth, and the filtrate is evaporated under reduced pressure to remove most of the acetone. The remaining solution is extracted with ethyl acetate (3×300 ml). The organic extracts are combined and concentrated under reduced pressure to give (4'-chloro-3,5-diethylbiphen-4-yl)carbamic acid tent-butyl ester (22 g).

Step 3: Preparation of 4'-chloro-3,5-diethylbiphen-4-ylamine

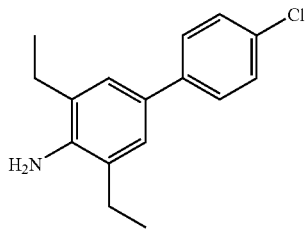 [SMILES: CCc1cc(-c2ccc(Cl)cc2)cc(CC)c1N]

Concentrated hydrochloric acid (22 ml) is added to a solution of (4'-chloro-3,5-diethylbiphen-4-yl)carbamic acid tert-butyl ester (22 g, 0.06 mol) in methanol (110 ml), and the reaction mixture is heated to 60° C. for 2 hours. The mixture is cooled to room temperature and most of the methanol is removed by evaporation under reduced pressure. The mixture is diluted with water, made basic by addition of 2N aqueous potassium hydroxide solution and extracted with ethyl acetate (3×200 ml). The organic extracts are combined and the solvents are removed under reduced pressure to give 4'-chloro-3,5-diethylbiphen-4-ylamine (9.6 g).

Step 4: Preparation of
4-bromo-4'-chloro-3,5-diethylbiphenyl

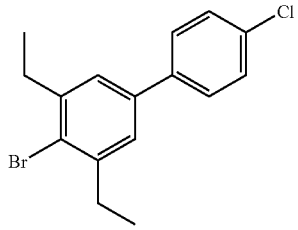 [SMILES: CCc1cc(-c2ccc(Cl)cc2)cc(CC)c1Br]

4'-Chloro-3,5-diethylbiphen-4-ylamine (9.6 g, 0.036 mol) is added to acetonitrile (95 ml) and stirred at room temperature until dissolution is complete. The reaction mixture is cooled to between −5° C. and 0° C., tent-butyl nitrite (5.7 ml, 0.044 mol) is added dropwise and the reaction mixture is maintained at between −5° C. and 0° C. for 30-40 minutes. The mixture is added slowly to a preheated (50° C.) suspension of copper (I) bromide (2.87 g, 0.02 mol) in hydrobromic acid (2.8 ml) and stirred at 50° C. for 10-15 minutes. The reaction mixture is cooled to room temperature, then poured into ice-cold water and extracted with ethyl acetate (3×250 ml). The organic extracts are washed with water, dried over anhydrous sodium sulfate and concentrated under reduced pressure. The residue is purified by column chromatography on silica gel to yield 4-bromo-4'-chloro-3,5-diethylbiphenyl (4.5 g).

Example J

Preparation of
4'-chloro-3,5-diethylbiphen-4-ylboronic acid

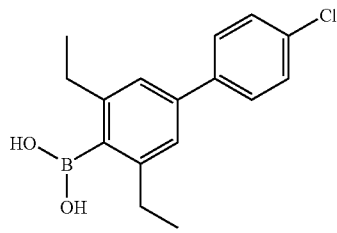 [SMILES: CCc1cc(-c2ccc(Cl)cc2)cc(CC)c1B(O)O]

tert-Butyllithium (1.6 M solution in hexanes, 13 ml, 0.02 mol) is added dropwise to a solution of 4-bromo-4'-chloro-3,5-diethylbiphenyl (4.5 g, 0.0139 mol) in dry tetrahydrofuran (50 ml) at −78° C. under an atmosphere of nitrogen. The reaction mixture is stirred at −78° C. for 30 minutes, then trimethylborate (9.3 ml, 0.083 mol) is added. The resulting mixture is stirred at −78° C. for 1 hour and then allowed to warm to room temperature over 3 hours. The reaction mixture is acidified with 0.1 N aqueous hydrochloric acid solution and the mixture is stirred at room temperature overnight. The mixture is extracted with ethyl acetate (3×100 ml). The organic layers are combined, dried over anhydrous sodium sulfate, filtered and the filtrate is evaporated under reduced pressure. The residue is purified by column chromatography on silica gel to give 4'-chloro-3,5-diethylbiphen-4-ylboronic acid as a white powder (1.8 g).

Example K

Preparation of 4'-chloro-3,5-diethylbiphen-4yllead triacetate

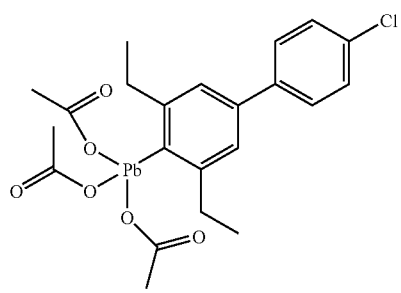

4'-Chloro-3,5-diethylbiphen-4-ylboronic acid (2.1 g, 0.007 mol) is added to a mixture of lead tetraacetate (3.67 g, 0.008 mol) and mercuric acetate (0.12 g, 5 mol %) in chloroform (15 ml) and the reaction mixture is stirred for 15 minutes at room temperature under an atmosphere of nitrogen, then stirred and heated at 40° C. for 4 hours. The reaction mixture is cooled to ambient temperature, filtered through a plug of diatomaceous earth and concentrated under reduced pressure to give an orange solid. Trituration with hexane (20 ml) affords a yellow solid which is dried under high vacuum. The solid is dissolved in chloroform (50 ml) and anhydrous potassium carbonate (11.6 g, 0.084 mol) is added. The suspension is stirred rapidly for 10 minutes, then filtered through plug of diatomaceous earth. The filtrate is concentrated under reduced pressure to give 4'-chloro-3,5-diethylbiphen-4-yl-lead triacetate (2.0 g) as a cream solid.

Example L

Preparation of 4-bromo-2-ethylphenylboronic acid

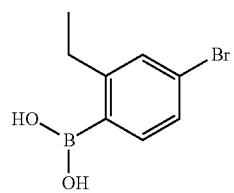

Step 1: Preparation of
4-bromo-2-ethyl-1-iodobenzene

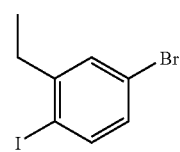

To a stirred mixture of 4-bromo-2-ethylaniline (80 g, 0.4 mol) in distilled water (400 ml) is added concentrated sulphuric acid (80 ml), followed by brief heating to 60° C. for 1 hour until dissolution is complete. The mixture is allowed to cool to room temperature then further cooled to approximately 0° C. in an ice/salt bath. To this slurry is added an aqueous solution of sodium nitrite (28 g, 0.4 mol) in distilled water (140 ml) dropwise over 15 minutes, maintaining the temperature below 5° C., followed by additional stirring for 30 minutes. The reaction mixture is allowed to come to room temperature and then a solution of aqueous potassium iodide (199 g, 1.2 mol) in distilled water (200 ml) is added dropwise at room temperature. After the addition is complete the solution is briefly heated to 80° C. then allowed to cool to room temperature again. The reaction mixture is extracted with ethyl acetate (1000 ml×3) and the organic phase is washed with 1M aqueous hydrochloric acid (500 ml) and aqueous sodium thiosulfate (2×250 ml). The organic phase is dried over anhydrous sodium sulphate, filtered and the filtrate is concentrated under reduced pressure. The residue is purified by column chromatography on silica gel to give 4-bromo-2-ethyl-1-iodobenzene (84.6 g) as an orange liquid.

Step 2: Preparation of 4-bromo-2-ethylphenylboronic acid

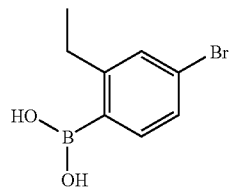

To a solution of 4-bromo-2-ethyl-1-iodobenzene (80 g, 0.25 mol) in tetrahydrofuran (800 ml) at −75° C. is added n-butyl lithium (1.6 M in hexanes, 188 ml, 0.3 mol) dropwise maintaining the temperature of the reaction maixture below −70° C. When the addition is complete the mixture is stirred at −75° C. for an additional 30 minutes and then trimethyl borate (153.7 g, 1.48 mol) is added dropwise. After the addition is complete the reaction is stirred at −75° C. for 1 hour, then allowed to come to room temperature and stirred for 2 hours, followed by cooling in an ice bath and acidification with 0.5 N aqueous hydrochloric acid. The mixture is extracted with ethyl acetate (3×500 ml) and the organic fractions are combined, washed with brine, then dried over anhydrous sodium sulphate. The mixture is filtered and the filtrate is evaporated under reduced pressure. The residue is purified by column chromatography on silica gel to give 4-bromo-2-ethylphenylboronic acid (26 g) as a white solid.

Example M

Preparation of 4-bromo-2-ethylphenyllead triacetate

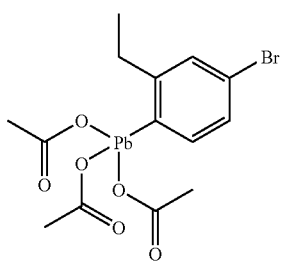

To a mixture of lead tetraacetate (53 g, 0.12 mol) and mercuric diacetate (2.5 g, 0.0078 mol), thoroughly flushed with nitrogen, is added anhydrous chloroform (250 ml). This mixture is warmed to 40° C. and 4-bromo-2-ethylphenylboronic acid (25 g, 0.11 mol) is added in one portion and the mixture is stirred and heated at this temperature for 4 hours. After cooling to room temperature, cooled in an ice bath, filtered through a plug of diatomaceous earth and the filtrate is concentrated to approximately a quarter of its volume. Hexane is added to induce crystallization and the solvents evaporated under reduced pressure. Trituration with hexane gives 4-bromo-2-ethylphenyl lead triacetate (28 g).

Example N

Preparation of 4-bromo-2,6-diethylphenylboronic acid

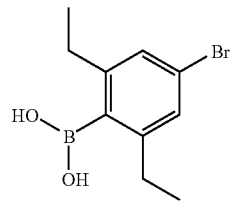

Step 1: Preparation of 4-bromo-2,6-diethyl-1-iodo benzene

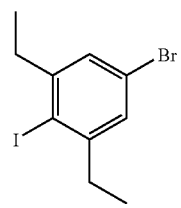

To a stirred mixture of 4-bromo-2,6-diethylaniline (13.6 g, 0.06 mol) in distilled water (14 ml) is added concentrated sulphuric acid (14 ml), followed by brief heating to 60° C. for 1 hour until dissolution is complete. The mixture is allowed to cool to room temperature then further cooled to approximately 0° C. in an ice/salt bath. To this slurry is added an aqueous solution of sodium nitrite (4.1 g, 0.059 mol) in distilled water (20 ml) dropwise over 15 minutes, maintaining the temperature below 5° C., followed by additional stirring for 30 minutes. The reaction mixture is allowed to come to room temperature and then a solution of aqueous potassium iodide (29.8 g, 0.18 mol) in distilled water (30 ml) is added dropwise at room temperature. After the addition is complete the solution is briefly heated to 80° C. then allowed to cool to room temperature again. The reaction mixture is extracted with ethyl acetate (150 ml×3) and the organic phase is washed with 1M aqueous hydrochloric acid (75 ml) and aqueous sodium thiosulfate (2×75 ml). The organic phase is dried over anhydrous sodium sulphate and concentrated under reduced pressure. The residue is purified by column chromatography on silica gel to give 4-bromo-2,6-diethyl-1-iodobenzene (19 g) as an orange liquid.

Step 2: Preparation of 4-bromo-2,6-diethylphenylboronic acid

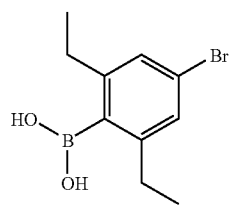

To a solution of 4-bromo-2,6-diethyl-1-iodobenzene (10 g, 0.029 mol) in tetrahydrofuran (100 ml) at −75° C. is added n-butyl lithium (1.6 M in hexanes, 22.2 ml, 0.035 mol) dropwise maintaining the temperature of the reaction mixture below −70° C. When the addition is complete the mixture is stirred at −75° C. for an additional 30 minutes and then trimethyl borate (17.98 g, 0.17 mol) is added dropwise. After the addition is complete the reaction is stirred at −75° C. for 1 hour, then allowed to come to room temperature and stirred for 2 hours, followed by cooling in an ice bath and acidification with 0.5 N aqueous hydrochloric acid. The mixture is extracted with ethyl acetate (3×300 ml) and the organic fractions are combined, washed with brine, dried over anhydrous sodium sulphate. The mixture is filtered and the filtrate is evaporated under reduced pressure. The residue is purified by column chromatography on silica gel to give 4-bromo-2,6-diethylphenylboronic acid (5 g) as a white solid.

Example O

Preparation of 4-bromo-2,6-diethylphenyllead triacetate

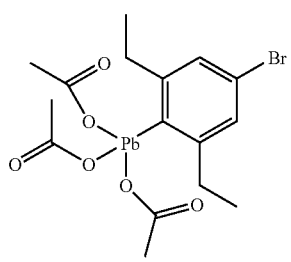

To a mixture of lead tetraacetate (9.5 g, 0.02 mol) and mercuric diacetate (0.25 g, 0.78 mmol), thoroughly flushed with nitrogen, is added anhydrous chloroform (25 ml) and toluene (25 ml). This mixture is warmed to 60° C. and 4-bromo-2,6-diethylphenylboronic acid (5 g, 0.019 mol) is added in one portion and the mixture is stirred and heated at this temperature for 4 hours. After cooling in an ice bath, the mixture is filtered through a plug of diatomaceous earth and the filtrate is concentrated to approximately a quarter of its volume. Hexane is added to induce crystallization and the solvents evaporated under reduced pressure. Trituration with hexane gives 4-bromo-2,6-diethylphenyllead triacetate (5 g).

Example P

Preparation of 4-bromo-2,6-dimethylphenylboronic acid

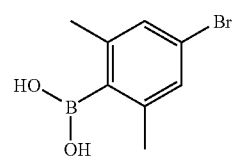

Step 1: Preparation of 4-bromo-2,6-dimethyl-1-iodobenzene

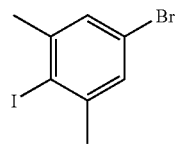

To a stirred mixture of 4-bromo-2,6-dimethylaniline (75 g, 0.37 mol) in distilled water (75 ml) is added concentrated sulphuric acid (75 ml), followed by brief heating to 60° C. for 1 hour until dissolution is complete. The mixture is allowed to cool to room temperature then further cooled to approximately 0° C. in an ice/salt bath. To this slurry is added an aqueous solution of sodium nitrite (25.33 g, 0.36 mol) in distilled water (126 ml) dropwise over 15 minutes, maintaining the temperature below 5° C., followed by additional stirring for 30 minutes. The reaction mixture is allowed to come to room temperature and then a solution of aqueous potassium iodide (187.6 g, 1.13 mol) in distilled water (190 ml) is added dropwise at room temperature. After the addition is complete the solution is briefly heated to 80° C. then allowed to cool to room temperature again. The reaction mixture is extracted with ethyl acetate (750 ml×3) and the organic phase is washed with 1M aqueous hydrochloric acid (200 ml) and aqueous sodium thiosulfate (2×200 ml). The organic phase is dried over anhydrous sodium sulphate and concentrated under reduced pressure. The residue is purified by column chromatography on silica gel to give 4-bromo-2,6-dimethyl-1-iodo benzene (75 g) as an orange liquid.

Step 2: Preparation of 4-bromo-2,6-dimethylphenylboronic acid

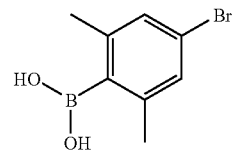

To a solution of 4-bromo-2,6-dimethyl-1-iodobenzene (150 g, 0.48 mol) in tetrahydrofuran (1500 ml) at −75° C. is added n-butyl lithium (1.6 M in hexanes, 364 ml, 0.58 mol) dropwise maintaining the temperature of the reaction mixture below −70° C. When the addition is complete the mixture is stirred at −75° C. for an additional 30 minutes and then trimethyl borate (302 g, 2.9 mol) is added dropwise. After the addition is complete the reaction is stirred at −75° C. for 1 hour, then allowed to come to room temperature and stirred for 2 hours, followed by cooling in an ice bath and acidification with 0.5 N aqueous hydrochloric acid. The mixture is extracted with ethyl acetate (3×1000 ml) and the organic extracts are combined, washed with brine, dried over anhydrous sodium sulphate. The mixture is filtered and the filtrate is evaporated under reduced pressure. The residue is purified by column chromatography on silica gel to give 4-bromo-2,6-dimethylphenylboronic acid (48 g) as a white solid.

Example Q

Preparation of 4-bromo-2,6-dimethylphenyllead triacetate

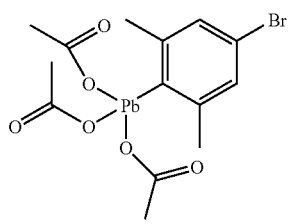

To a mixture of lead tetraacetate (112.16 g, 0.25 mol) and mercuric diacetate (4.8 g, 0.015 mol), thoroughly flushed with nitrogen, is added anhydrous chloroform (480 ml). This mixture is warmed to 40° C. and 4-bromo-2,6-dimethylphenylboronic acid (48 g, 0.21 mol) is added in one portion and the mixture is stirred and heated at this temperature for 4 hours. After cooling in an ice bath, powdered anhydrous potassium carbonate (350 g) is added rapidly followed by rapid stirring for 5 minutes. The solids are removed by filtration and the filtrate is concentrated to approximately a quarter of its volume. Hexane is added to induce crystallization and the solvents evaporated under reduced pressure. Trituration with hexane gives 4-bromo-2,6-dimethylphenyl lead triacetate (30 g).

Example R

Preparation of 4-bromo-2-ethylbenzaldehyde

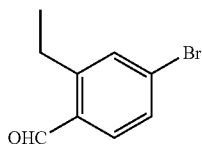

To a solution of 4-bromo-2-ethyl-1-iodobenzene (75 g, 0.24 mol) in tetrahydrofuran (375 ml) at −75° C. is added n-butyl lithium (1.6 M in hexanes, 196 ml, 0.31 mol) dropwise, maintaining the temperature of the reaction mixture below −70° C. When the addition is complete the mixture is stirred at −75° C. for an additional 30 minutes and then N,N-dimethylformamide (70.7 g, 0.97 mol) is added dropwise. After the addition is complete the reaction is stirred at −75° C. for 2 hours, then allowed to warm to room temperature for 2 hours. The mixture is cooled in an ice bath and acidified with 0.5 N aqueous hydrochloric acid. The mixture is extracted with ethyl acetate (3×500 ml) and the organic fractions are combined, washed with brine, and dried over anhydrous sodium sulphate. The mixture is filtered and the filtrate is evaporated under reduced pressure. The residue is purified by column chromatography on silica gel to give 4-bromo-2-ethylbenzaldehyde (48 g) as an oil.

Biological Examples

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100% total damage to plant; 0=no damage to plant).

Test Plants:

*Setaria faberi* (SETFA), *Lolium perenne* (LOLPE), *Alopecurus myosuroides* (ALOMY), *Echinochloa crus-galli* (ECHCG) and *Avena fatua* (AVEFA).

| Compound Number | Rate g/ha | SETFA | LOLPE | ALOMY | ECHCG | AVEFA |
|---|---|---|---|---|---|---|
| PRE-EMERGENCE ACTIVITY | | | | | | |
| A-1 | 250 | 90 | — | 30 | 70 | 40 |
| A-2 | 250 | 60 | — | 50 | 70 | 20 |
| A-3 | 250 | 90 | — | 0 | 70 | 20 |
| A-4 | 250 | 20 | — | 40 | 40 | 0 |
| A-5 | 250 | 70 | — | 30 | 40 | 0 |
| A-6 | 250 | 0 | — | 0 | 0 | 0 |
| A-7 | 250 | 0 | — | 0 | 0 | 0 |
| A-10 | 250 | 0 | — | 0 | 30 | 0 |
| A-11 | 250 | 100 | — | 80 | 100 | 100 |
| A-12 | 250 | 80 | — | 30 | 70 | 20 |
| A-13 | 250 | — | 20 | 0 | 50 | 0 |
| A-14 | 250 | — | 80 | 50 | 80 | 50 |
| A-15 | 250 | 40 | — | 0 | 30 | 40 |
| A-16 | 250 | 50 | — | 0 | 0 | 0 |
| A-17 | 250 | 100 | — | 30 | 100 | 80 |
| A-18 | 250 | 100 | — | 90 | 100 | 70 |
| A-19 | 250 | 0 | — | 0 | 80 | 30 |
| A-20 | 250 | 80 | — | 70 | 70 | 40 |
| A-22 | 250 | 50 | — | 0 | 40 | 50 |
| A-23 | 250 | 60 | — | 60 | 50 | 40 |
| A-24 | 250 | 90 | — | 70 | 100 | 60 |
| A-25 | 250 | 90 | — | 30 | 50 | 20 |
| A-27 | 250 | 30 | — | 20 | 40 | 0 |
| A-29 | 250 | 50 | — | 30 | 40 | 50 |
| A-30 | 250 | 0 | — | 0 | 0 | 0 |
| A-31 | 250 | 60 | — | 30 | 50 | 30 |
| A-33 | 250 | 30 | — | 20 | 60 | 40 |
| A-35 | 250 | — | 80 | 50 | 90 | 40 |
| A-36 | 250 | — | 0 | 0 | 0 | 0 |
| A-38 | 250 | — | 70 | 0 | 50 | 0 |
| A-41 | 250 | — | 20 | 0 | 0 | 30 |
| A-42 | 250 | — | 90 | 10 | 90 | 20 |
| A-43 | 250 | — | 50 | 20 | 70 | 30 |
| A-46 | 250 | — | 40 | 0 | 30 | 0 |
| A-47 | 250 | — | 50 | 0 | 30 | 40 |
| A-48 | 250 | — | 0 | 0 | 0 | 0 |
| A-50 | 250 | — | 100 | 60 | 90 | 60 |

| Compound Number | Rate g/ha | SETFA | LOLPE | ALOMY | ECHCG | AVEFA |
|---|---|---|---|---|---|---|
| A-51 | 250 | — | 0 | 0 | 20 | 0 |
| A-52 | 250 | — | 0 | 0 | 20 | 0 |
| A-53 | 250 | — | 90 | 50 | 100 | 60 |
| A-54 | 250 | — | 0 | 0 | 0 | 0 |
| A-55 | 250 | — | 90 | 70 | 100 | 70 |
| A-60 | 250 | — | 0 | 0 | 0 | 0 |
| A-70 | 250 | — | 0 | 0 | 0 | 0 |
| A-71 | 250 | — | 0 | 0 | 0 | 0 |
| A-72 | 250 | — | 0 | 0 | 0 | 0 |
| A-73 | 250 | — | 0 | 0 | 0 | 0 |
| A-74 | 250 | — | 0 | 0 | 0 | 0 |
| A-75 | 250 | — | 40 | 0 | 0 | 30 |
| A-76 | 250 | — | 0 | 0 | 0 | 0 |
| A-78 | 250 | — | 80 | 20 | 0 | 30 |
| A-82 | 250 | — | 70 | 10 | 30 | 20 |
| A-83 | 250 | — | 0 | 0 | 0 | 0 |
| A-84 | 250 | — | 70 | 30 | 30 | 40 |
| A-85 | 250 | — | 70 | 0 | 20 | 30 |
| A-86 | 250 | — | 0 | 0 | 0 | 0 |
| A-87 | 250 | — | 0 | 0 | 0 | 0 |
| A-95 | 250 | — | 30 | 10 | 30 | 0 |
| A-96 | 250 | — | 0 | 0 | 20 | 10 |
| A-99 | 250 | — | 60 | 10 | 30 | 0 |
| A-101 | 250 | — | 90 | 70 | 50 | 50 |
| A-102 | 250 | — | 70 | 60 | 30 | 10 |
| A-103 | 250 | — | 20 | 20 | 20 | 0 |
| A-104 | 250 | — | 60 | 50 | 40 | 0 |
| A-105 | 250 | — | 40 | 40 | 20 | 0 |
| A-112 | 250 | — | 90 | 80 | 100 | 80 |
| A-113 | 250 | — | 100 | 100 | 100 | 90 |
| A-114 | 250 | — | 100 | 90 | 100 | 90 |
| A-115 | 250 | — | 50 | 60 | 90 | 30 |
| A-116 | 250 | — | 70 | 90 | 100 | 60 |
| A-117 | 250 | — | 60 | 70 | 90 | 40 |
| A-118 | 250 | — | 90 | 20 | 40 | 0 |
| A-119 | 250 | — | 60 | 40 | 30 | 10 |
| A-120 | 250 | — | 90 | 60 | 70 | 40 |
| A-122 | 250 | — | 0 | 20 | 10 | 0 |
| A-123 | 250 | — | 0 | 0 | 0 | 0 |
| A-125 | 250 | — | 0 | 0 | 0 | 0 |
| A-126 | 250 | — | 10 | 10 | 10 | 0 |
| A-128 | 250 | — | 20 | 10 | 40 | 0 |
| A-129 | 250 | — | 30 | 30 | 90 | 10 |
| A-130 | 250 | — | 60 | 50 | 40 | 10 |
| A-132 | 250 | — | 20 | 20 | 10 | 0 |
| A-133 | 250 | — | 30 | 30 | 0 | 0 |
| A-134 | 250 | — | 30 | 40 | 80 | 0 |
| A-135 | 250 | — | 10 | 30 | 30 | 10 |
| B-4 | 250 | — | 0 | 0 | 0 | 0 |
| B-5 | 250 | — | 30 | 50 | 0 | 20 |
| B-6 | 250 | — | 50 | 50 | 0 | 0 |
| B-9 | 250 | — | 10 | 10 | 0 | 0 |
| B-11 | 250 | — | 40 | 50 | 0 | 20 |
| B-12 | 250 | — | 10 | 50 | 0 | 20 |
| B-16 | 250 | — | 40 | 20 | 40 | 30 |
| B-17 | 250 | — | 50 | 50 | 10 | 10 |
| B-18 | 250 | — | 50 | 30 | 30 | 30 |
| C-3 | 250 | — | 10 | 10 | 10 | 0 |
| C-4 | 250 | — | 20 | 20 | 0 | 0 |
| C-5 | 250 | — | 40 | 30 | 0 | 20 |
| C-6 | 250 | — | 70 | 40 | 0 | 10 |
| C-7 | 250 | — | 20 | 30 | 0 | 0 |
| C-8 | 250 | — | 30 | 10 | 30 | 0 |
| D-1 | 250 | 80 | — | 60 | 70 | 40 |
| D-2 | 250 | — | 100 | 30 | 90 | 20 |
| D-3 | 250 | — | 100 | 90 | 100 | 70 |
| D-9 | 250 | — | 90 | 60 | 50 | 0 |

Post-Emergence Activity

| Compound Number | Rate g/ha | SETFA | LOLPE | ALOMY | ECHCG | AVEFA |
|---|---|---|---|---|---|---|
| A-1 | 250 | 80 | — | 50 | 100 | 0 |
| A-2 | 250 | 80 | — | 90 | 100 | 0 |
| A-3 | 250 | 100 | — | 70 | 100 | 0 |
| A-4 | 250 | 60 | — | 80 | 80 | 0 |
| A-5 | 250 | 100 | — | 90 | 100 | 70 |
| A-6 | 250 | 80 | — | 70 | 80 | 30 |
| A-7 | 250 | 100 | — | 60 | 100 | 30 |
| A-10 | 250 | 100 | — | 90 | 100 | 50 |
| A-11 | 250 | 100 | — | 100 | 100 | 100 |
| A-12 | 250 | 100 | — | 70 | 100 | 0 |
| A-13 | 250 | — | 100 | 70 | 100 | 80 |
| A-14 | 250 | — | 100 | 80 | 100 | 100 |
| A-15 | 250 | 100 | — | 100 | 100 | 80 |
| A-16 | 250 | 80 | — | 90 | 20 | 0 |
| A-17 | 250 | 100 | — | 100 | 100 | 100 |
| A-18 | 250 | 100 | — | 100 | 100 | 90 |
| A-19 | 250 | 80 | — | 90 | 90 | 60 |
| A-20 | 250 | 90 | — | 90 | 100 | 70 |
| A-22 | 250 | 100 | — | 100 | 90 | 70 |
| A-23 | 250 | 80 | — | 90 | 100 | 30 |
| A-24 | 250 | 100 | — | 90 | 100 | 80 |
| A-25 | 250 | 100 | — | 90 | 100 | 60 |
| A-27 | 250 | 100 | — | 90 | 100 | 70 |
| A-29 | 250 | 100 | — | 90 | 100 | 60 |
| A-30 | 250 | 90 | — | 30 | 50 | 0 |
| A-31 | 250 | 100 | — | 90 | 100 | 40 |
| A-33 | 250 | 100 | — | 90 | 100 | 80 |
| A-34 | 250 | 90 | — | 30 | 70 | 20 |
| A-35 | 250 | — | 90 | 100 | 100 | 80 |
| A-36 | 250 | — | 40 | 30 | 60 | 20 |
| A-38 | 250 | — | 70 | 80 | 80 | 50 |
| A-41 | 250 | — | 60 | 50 | 70 | 0 |
| A-42 | 250 | — | 90 | 90 | 100 | 80 |
| A-43 | 250 | — | 80 | 80 | 100 | 70 |
| A-46 | 250 | — | 40 | 50 | 80 | 0 |
| A-47 | 250 | — | 60 | 90 | 100 | 70 |
| A-48 | 250 | — | 30 | 50 | 100 | 20 |
| A-50 | 250 | — | 100 | 90 | 100 | 80 |
| A-51 | 250 | — | 50 | 60 | 70 | 60 |
| A-52 | 250 | — | 40 | 40 | 70 | 20 |
| A-53 | 250 | — | 100 | 90 | 100 | 80 |
| A-54 | 250 | — | 40 | 40 | 80 | 30 |
| A-55 | 250 | — | 100 | 100 | 100 | 90 |
| A-60 | 250 | — | 70 | 60 | 90 | 70 |
| A-70 | 250 | — | 50 | 40 | 80 | 0 |
| A-71 | 250 | — | 80 | 30 | 80 | 0 |
| A-72 | 250 | — | 70 | 0 | 80 | 0 |
| A-73 | 250 | — | 60 | 30 | 80 | 0 |
| A-74 | 250 | — | 70 | 80 | 100 | 40 |
| A-75 | 250 | — | 100 | 90 | 100 | 90 |
| A-76 | 250 | — | 80 | 80 | 70 | 40 |
| A-78 | 250 | — | 100 | 80 | 100 | 90 |
| A-82 | 250 | — | 80 | 80 | 80 | 0 |
| A-83 | 250 | — | 70 | 80 | 80 | 50 |
| A-84 | 250 | — | 100 | 80 | 100 | 100 |
| A-85 | 250 | — | 70 | 60 | 80 | 40 |
| A-86 | 250 | — | 90 | 80 | 100 | 70 |
| A-87 | 250 | — | 90 | 70 | 100 | 90 |
| A-95 | 250 | — | 80 | 80 | 80 | 50 |
| A-96 | 250 | — | 80 | 80 | 90 | 10 |
| A-99 | 250 | — | 90 | 90 | 100 | 90 |
| A-101 | 250 | — | 100 | 100 | 100 | 100 |
| A-102 | 250 | — | 90 | 100 | 90 | 80 |
| A-103 | 250 | — | 60 | 60 | 90 | 10 |
| A-104 | 250 | — | 60 | 90 | 90 | 10 |
| A-105 | 250 | — | 90 | 80 | 90 | 30 |
| A-112 | 250 | — | 90 | 80 | 100 | 80 |
| A-113 | 250 | — | 100 | 100 | 100 | 90 |
| A-114 | 250 | — | 100 | 90 | 100 | 90 |
| A-115 | 250 | — | 50 | 60 | 90 | 30 |
| A-116 | 250 | — | 70 | 90 | 100 | 60 |
| A-117 | 250 | — | 80 | 90 | 100 | 80 |
| A-118 | 250 | — | 80 | 60 | 90 | 80 |
| A-119 | 250 | — | 90 | 100 | 100 | 90 |
| A-120 | 250 | — | 100 | 100 | 100 | 100 |
| A-122 | 250 | — | 70 | 90 | 70 | 30 |
| A-123 | 250 | — | 80 | 80 | 90 | 80 |
| A-125 | 250 | — | 30 | 50 | 70 | 10 |
| A-126 | 250 | — | 40 | 40 | 70 | 20 |
| A-128 | 250 | — | 60 | 60 | 80 | 70 |
| A-129 | 250 | — | 80 | 90 | 90 | 70 |
| A-130 | 250 | — | 60 | 90 | 90 | 70 |
| A-132 | 250 | — | 50 | 60 | 80 | 0 |

-continued

| Compound Number | Rate g/ha | SETFA | LOLPE | ALOMY | ECHCG | AVEFA |
|---|---|---|---|---|---|---|
| A-133 | 250 | — | 50 | 60 | 60 | 20 |
| A-134 | 250 | — | 50 | 70 | 100 | 20 |
| A-135 | 250 | — | 60 | 60 | 100 | 10 |
| B-4 | 250 | — | 50 | 40 | 60 | 80 |
| B-5 | 250 | — | 60 | 70 | 60 | 70 |
| B-6 | 250 | — | 80 | 90 | 80 | 90 |
| B-9 | 250 | — | 60 | 60 | 40 | 80 |
| B-11 | 250 | — | 60 | 60 | 40 | 70 |
| B-12 | 250 | — | 50 | 60 | 70 | 90 |
| B-16 | 250 | — | 60 | 50 | 80 | 80 |
| B-17 | 250 | — | 70 | 80 | 50 | 70 |
| B-18 | 250 | — | 80 | 70 | 80 | 90 |
| C-3 | 250 | — | 60 | 30 | 70 | 50 |
| C-4 | 250 | — | 80 | 80 | 70 | 30 |
| C-5 | 250 | — | 70 | 100 | 100 | 90 |
| C-6 | 250 | — | 20 | 20 | 50 | 10 |
| C-7 | 250 | — | 60 | 40 | 40 | 10 |
| C-8 | 250 | — | 60 | 60 | 60 | 10 |
| D-1 | 250 | 100 | — | 90 | 100 | 80 |
| D-2 | 250 | — | 80 | 70 | 90 | 40 |
| D-3 | 250 | — | 100 | 100 | 100 | 80 |
| D-9 | 250 | — | 80 | 70 | 80 | 10 |

What is claimed is:
1. A compound of formula I

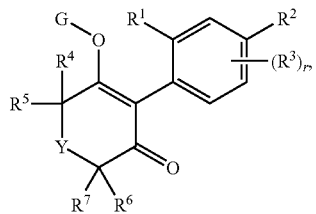

wherein
$R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano;
$R^2$ is aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano;
r is 0, 1, 2 or 3;
$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;
$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; and
Y is O, C=O, $S(O)_m$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;
m is 0 or 1 or 2; and
G is hydrogen, an agriculturally acceptable cation or a latentiating group;
wherein, when G is a latentiating group, then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$ alkenyl, $C_3$ haloalkenyl, $C_3$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;
wherein $X^a$, $X^b$, $X^b$, $X^d$, $X^e$ and $X^f$ are independently of each other oxygen or sulfur;
and wherein $R^a$ is H, $C_1$-$C_{18}$alkyl, $C_2$-$C_{18}$alkenyl, $C_2$-$C_{18}$alkynyl, $C_1$-$C_{10}$ haloalkyl, $C_1$-$C_{10}$cyanoalkyl, $C_1$-$C_{10}$-nitroalkyl, $C_1$-$C_{10}$-aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_8$alkenyloxy$C_1$-$C_8$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$ haloalkyl, $C_1$-$C_{10}$ cyanoalkyl, $C_1$-$C_{10}$nitroalkyl, $C_2$-$C_{10}$ aminoalkyl, $C_1$-$C_5$alkylamino$C_1$-$C_5$alkyl, di($C_2$-$C_5$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_5$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_5$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$-nitroalkyl, $C_1$-$C_{10}$-aminoalkyl, $C_1$-$C_5$alkylamino$C_1$-$C_5$alkyl, di($C_2$-$C_5$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_5$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl;

phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro;

diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; amino, $C_1$-$C_3$alkylamino, di($C_1$-$C_3$alkyl)amino, $C_1$-$C_3$alkoxy, $C_3$-$C_7$cycloalkylamino, di($C_3$-$C_7$cycloalkyl)amino or $C_3$-$C_7$cycloalkoxy;

or $R^c$ and $R^d$ join together to form a 3-7 membered ring, optionally containing one heteroatom selected from O or S and optionally substituted by 1 or 2 $C_1$-$C_3$alkyl groups; and $R^e$ is $C_1$-$C_{10}$ alkyl, $C_2$-$C_{10}$ alkenyl, $C_2$-$C_{10}$ alkynyl, $C_1$-$C_{10}$ haloalkyl, $C_1$-$C_{10}$ cyanoalkyl, $C_1$-$C_{10}$nitroalkyl, $C_1$-$C_{10}$-aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_8$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; amino; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$haloalkoxy, $C_1$-$C_5$alkylamino or di($C_2$-$C_8$alkyl)amino;

$R^f$ and $R^g$ are each independently of each other $C_1$-$C_{10}$ alkyl, $C_2$-$C_{10}$ alkenyl, $C_2$-$C_{10}$alkynyl, $C_1$-$C_{10}$alkoxy, $C_1$-$C_{10}$ haloalkyl, $C_1$-$C_{10}$ cyanoalkyl, $C_1$-$C_{10}$ nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, tri($C_3$-$C_8$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; amino; hydroxyl; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$ haloalkoxy, $C_1$-$C_5$alkylamino or di($C_2$-$C_8$alkyl)amino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_8$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein, in the compound of formula I, "aryl" means phenyl or naphthyl;

and wherein, in the compound of formula I, "heteroaryl" means thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl or pyridazinyl, or, where appropriate, a N-oxide or a salt thereof.

2. A compound according to claim 1, wherein $R^1$ is halogen, $C_1$-$C_4$alkyl, $C_1$-$C_4$haloalkyl, $C_2$-$C_4$alkenyl or $C_2$-$C_4$ alkynyl.

3. A compound according to claim 1, wherein $R^2$ is phenyl or pyridyl; or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

4. A compound according to claim 1, wherein either $R^3$ is hydrogen, halogen or $C_1$-$C_6$alkyl.

5. A compound according to claim 1, wherein $R^4$, $R^5$, $R^6$ and $R^7$, independently of each other, are hydrogen, $C_1$-$C_2$alkyl, $C_1$-$C_2$haloalkyl or $C_1$-$C_2$-alkoxy-$C_1$-$C_2$alkyl.

6. A compound according to claim 1, wherein Y is O, S or C═O.

7. A compound according to claim 1, wherein G is hydrogen.

8. A compound according to claim 1, wherein:
$R^1$ is $C_1$-$C_2$alkyl, $R^2$ is phenyl substituted by halogen, $C_1$-$C_2$alkoxy or $C_1$-$C_2$haloalkyl, $R^3$ is $C_1$-$C_2$alkyl, r is 1, $R^4$, $R^5$, $R^6$ and $R^7$, independently of each other, are hydrogen, $C_1$-$C_2$alkyl, $C_1$-$C_4$haloalkyl or $C_1$-$C_2$alkoxy$C_1$-$C_2$alkyl, Y is O and G is hydrogen.

9. A compound according to claim 1, wherein:
$R^1$ is $C_1$-$C_4$alkyl, $R^2$ is phenyl or phenyl substituted by halogen or $C_1$-$C_2$alkyl, $R^3$ is hydrogen, $R^4$, $R^5$, $R^6$ and $R^7$, independently of each other, are $C_1$-$C_2$alkyl, Y is O and G is hydrogen.

10. A process for the preparation of a compound of formula I according to claim 1, which comprises reacting a compound of the formula (H)

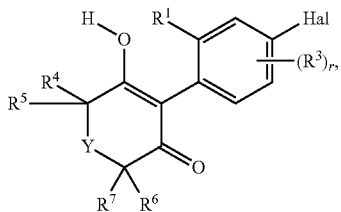

formula (H)

wherein $R^1$, $R^3$, $R^4$, $R^5$, $R^6$, $R^7$, Y and r have the meanings assigned to them in claim 1 and Hal is chlorine, bromine, iodine or trifluoromethanesulfonyloxy, with an aryl- or heteroaryl boronic acid of formula $R^2B(OH)_2$, wherein $R^2$ has the meaning assigned to it in claim 1, or a salt or ester thereof, in the presence of a suitable palladium catalyst, a ligand and a base, and in a suitable solvent.

11. A process for the preparation of a compound of formula I according to claim 1, which is a compound of the formula (A)

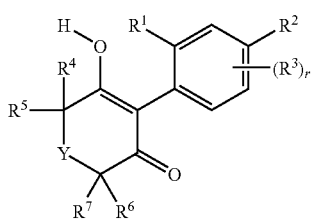

formula (A)

which comprises reacting a compound of the formula (AA)

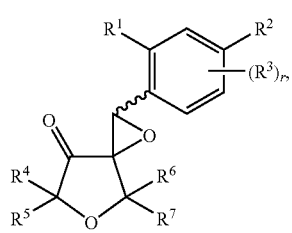

formula (AA)

with a Lewis or Brönsted acid, optionally in the presence of a solvent, where the substituents in the compounds of the formulae (A) and (AA) are as defined in claim 1.

12. A compound of the formula (H)

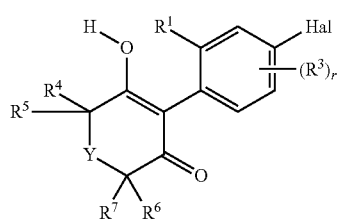

formula (H)

wherein $R^1$, $R^4$, $R^5$, $R^6$, $R^7$ and Y have the meanings assigned to them in claim 1;

Hal is chlorine, bromine, iodine or trifluoromethanesulfonyloxy;
r is 0, 1, 2 or 3;
either $R^3$ is hydrogen, which means that r is 0, or $R^3$ is halogen or $C_1$-$C_6$alkyl;
and wherein, if r is 1, then $R^3$ is halogen or $C_1$-$C_3$alkyl.

13. A compound of the formula (AA)

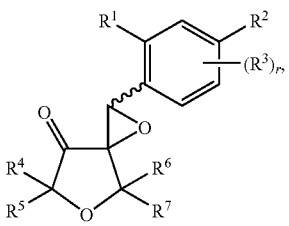

formula (AA)

wherein the substituents are as defined in claim 1.

14. A method of controlling grasses and weeds in crops of useful plants, which comprises applying a herbicidally effective amount of a compound of formula I as defined in claim 1, or of a composition comprising such a compound, to the plants or to the locus thereof.

15. A herbicidal composition, which, in addition to comprising formulation adjuvants, comprises a herbicidally effective amount of a compound of formula I as defined in claim 1.

16. A composition according to claim 15, which, in addition to comprising the compound of formula I, comprises a further herbicide as mixing partner and optionally a safener.

17. A compound according to claim 1, wherein $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl or thiadiazolyl, or an N-oxide or salt thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

18. A compound according to claim 1, wherein $R^2$ is phenyl substituted at the para-position by halogen and is optionally further substituted by halogen, nitro, $C_1$-$C_2$alkyl, $C_1$-$C_2$haloalkyl, $C_1$-$C_2$alkoxy or $C_1$-$C_2$haloalkoxy.

19. A compound according to claim 1, wherein $R^3$ is hydrogen, which means that r is 0.

20. A compound according to claim 1, wherein:
$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$— or $C_2$alkyl or $C_1$- or $C_2$haloalkyl and in which a methylene group is optionally replaced by an oxygen or sulfur atom or a sulfinyl or sulfonyl group; or $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

21. A compound according to claim 1, wherein Y is O.

22. A compound according to claim 1, wherein G denotes $C(X^a)$—$R^a$ or $C(X^b)$—$X^c$—$R^b$, and the meanings of $X^a$, $R^a$, $X^b$, $X^c$ and $R^b$ are as defined in claim 1.

23. A compound according to claim 1, wherein, when G is a latentiating group, then G is selected from the groups $C(X^a)$—$R^a$ and $C(X^b)$—$X^c$—$R^b$, wherein $X^a$, $X^b$ and $X^c$ are oxygen, $R^a$ is $C_1$-$C_6$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl, and $R^b$ is $C_1$-$C_6$alkyl, $C_3$-$C_6$alkenyl, $C_3$-$C_6$alkynyl, $C_3$-$C_6$cycloalkyl or $C_1$-$C_4$alkoxy$C_1$-$C_4$alkyl.

24. A compound of the formula (H) according to claim 12, wherein
either $R^3$ is hydrogen, which means that r is 0;
or r is 1 and $R^3$ is halogen or $C_1$-$C_3$alkyl.

\* \* \* \* \*